US012667606B2

(12) United States Patent
Andersen et al.

(10) Patent No.: US 12,667,606 B2
(45) Date of Patent: Jun. 30, 2026

(54) FORMULATIONS OF PROTEIN MOLECULES COMPRISING IDURONATE 2-SULFATASE

(71) Applicant: DENALI THERAPEUTICS INC., South San Francisco, CA (US)

(72) Inventors: Dana Andersen, South San Francisco, CA (US); Adam Catherman, South San Francisco, CA (US); Tina Giese, South San Francisco, CA (US); Gunasekaran Kannan, South San Francisco, CA (US); Mihalis S. Kariolis, South San Francisco, CA (US); Cathal S. Mahon, South San Francisco, CA (US); Ankit Patel, South San Francisco, CA (US)

(73) Assignee: DENALI THERAPEUTICS INC., South San Francisco, CA (US)

(*) Notice: Subject to any disclaimer, the term of this patent is extended or adjusted under 35 U.S.C. 154(b) by 1124 days.

(21) Appl. No.: 17/600,527

(22) PCT Filed: Apr. 3, 2020

(86) PCT No.: PCT/US2020/026669
§ 371 (c)(1),
(2) Date: Sep. 30, 2021

(87) PCT Pub. No.: WO2020/206320
PCT Pub. Date: Oct. 8, 2020

(65) Prior Publication Data
US 2022/0184186 A1    Jun. 16, 2022

Related U.S. Application Data

(60) Provisional application No. 62/832,032, filed on Apr. 10, 2019, provisional application No. 62/828,859, filed on Apr. 3, 2019.

(51) Int. Cl.
*A61K 38/46* (2006.01)
*A61K 47/18* (2017.01)
*A61K 47/26* (2006.01)

(52) U.S. Cl.
CPC .......... *A61K 38/465* (2013.01); *A61K 47/183* (2013.01); *A61K 47/26* (2013.01); *C12Y 301/06013* (2013.01)

(58) Field of Classification Search
None
See application file for complete search history.

(56) References Cited

U.S. PATENT DOCUMENTS

| | | | |
|---|---|---|---|
| 10,870,837 | B2 | 12/2020 | Henry et al. |
| 10,940,185 | B2 | 3/2021 | Yasukawa et al. |
| 11,795,232 | B2 | 10/2023 | Chen et al. |
| 11,866,742 | B2 | 1/2024 | Henry et al. |
| 11,884,944 | B2 | 1/2024 | Giese et al. |
| 12,178,858 | B2 | 12/2024 | Yasukawa et al. |
| 12,378,540 | B1 | 8/2025 | Kariolis et al. |
| 2020/0230253 | A1* | 7/2020 | Kim ...................... A61K 47/68 |
| 2022/0025065 | A1 | 1/2022 | Arguello et al. |
| 2023/0092681 | A1 | 3/2023 | Arguello et al. |
| 2024/0150736 | A1 | 5/2024 | Giese et al. |
| 2025/0018015 | A1 | 1/2025 | Arguello et al. |
| 2025/0136963 | A1 | 5/2025 | Adusumilli et al. |

FOREIGN PATENT DOCUMENTS

| | | | |
|---|---|---|---|
| EP | 3556399 | A1 | 10/2019 |
| WO | 2011044542 | A1 | 4/2011 |
| WO | 2015009052 | A1 | 1/2015 |
| WO | 2018117613 | A1 | 6/2018 |
| WO | 2018124277 | A1 | 7/2018 |
| WO | 2018152326 | A1 | 8/2018 |
| WO | 2019022563 | A2 | 1/2019 |
| WO | 2019032955 | A1 | 2/2019 |
| WO | WO-2019070577 | A1 * | 4/2019 ............. A61K 38/00 |
| WO | 2019246071 | A1 | 12/2019 |

OTHER PUBLICATIONS

Herold et al (Sci Rep. Sep. 25, 2017;7(1):12276) (Year: 2017).*
Rabia et al (Understanding and overcoming trade-offs between antibody affinity, specificity, stability and solubility. Biochemical engineering journal, 137, 365â374, 2018) (Year: 2018).*
Rudikoff et al (Single amino acid substitution altering antigen-binding specificity. Proc Natl Acad Sci U S A. Mar. 1982;79(6):1979-83) (Year: 1982).*
Vajdos et al.(Comprehensive functional maps of the antigen-binding site of an anti-ErbB2 antibody obtained with shotgun scanning mutagenesis. Journal of molecular biology, 320(2), 415â428, 2022) (Year: 2022).*
Bielicki, et al., "Human liver iduronate-2-sulphatase", Biochem J 271, 75-86 (1990).
Henry, et al., "Improved brain uptake and efficacy of iduronate 2-sulfatase with the enzyme transport vehicle", Molecular Genetics and Metabolism 126, 158, p. S72, (2019).
Liu, et al., "Fc Engineering for Developing Therapeutic Bispecific Antibodies and Novel Scaffolds", Frontiers in Immunology 8 (38), 1-15 (2017).
Lobner, et al., "Engineered IgG1-Fc—one fragment to bind them all", Immunological Reviews 270, 113-131 (2016).
Pardridge, W, "Blood-brain barrier drug delivery of IgG fusion proteins with a transferrin receptor monoclonal antibody", Expert Opinion Drug Delivery 12 (2), 207-222 (2015).

(Continued)

*Primary Examiner* — Zachariah Lucas
*Assistant Examiner* — Sarah A Alsomairy
(74) *Attorney, Agent, or Firm* — Viksnins Harris Padys Malen LLP

(57) ABSTRACT

Certain embodiments provide a pharmaceutical composition comprising: a protein molecule comprising an ERT enzyme-Fc fusion polypeptide and a modified Fc polypeptide; a buffer; an isotonicity agent; a surfactant; and a stabilizer; wherein the pH of the pharmaceutical composition is about 5.5 to 7.0, as well as methods of use thereof.

37 Claims, No Drawings

Specification includes a Sequence Listing.

(56)              References Cited

OTHER PUBLICATIONS

Park, et al., "The Highly Evolvable Antibody Fc Domain", Trends in Biotechnology 34(11), 895-908 (2016).

Patent Cooperation Treaty, International Search Report and Written Opinion for PCT/US2020/026669, 13 pages, Jul. 20, 2020.

NCBI GENBANK, Accession No. NP_000193.1, 4 pages (2019).

* cited by examiner

SEQUENCE LISTING

<160> NUMBER OF SEQ ID NOS: 61

<210> SEQ ID NO 1
<211> LENGTH: 517
<212> TYPE: PRT
<213> ORGANISM: Homo sapiens

<400> SEQUENCE: 1

```
Thr Asp Ala Leu Asn Val Leu Leu Ile Ile Val Asp Asp Leu Arg Pro
1               5                   10                  15

Ser Leu Gly Cys Tyr Gly Asp Lys Leu Val Arg Ser Pro Asn Ile Asp
            20                  25                  30

Gln Leu Ala Ser His Ser Leu Leu Phe Gln Asn Ala Phe Ala Gln Gln
        35                  40                  45

Ala Val Cys Ala Pro Ser Arg Val Ser Phe Leu Thr Gly Arg Arg Pro
    50                  55                  60

Asp Thr Thr Arg Leu Tyr Asp Phe Asn Ser Tyr Trp Arg Val His Ala
65                  70                  75                  80

Gly Asn Phe Ser Thr Ile Pro Gln Tyr Phe Lys Glu Asn Gly Tyr Val
                85                  90                  95

Thr Met Ser Val Gly Lys Val Phe His Pro Gly Ile Ser Ser Asn His
            100                 105                 110

Thr Asp Asp Ser Pro Tyr Ser Trp Ser Phe Pro Pro Tyr His Pro Ser
            115                 120                 125
```

-continued

```
Ser Glu Lys Tyr Glu Asn Thr Lys Thr Cys Arg Gly Pro Asp Gly Glu
    130                 135                 140

Leu His Ala Asn Leu Leu Cys Pro Val Asp Val Leu Asp Val Pro Glu
145                 150                 155                 160

Gly Thr Leu Pro Asp Lys Gln Ser Thr Glu Gln Ala Ile Gln Leu Leu
                165                 170                 175

Glu Lys Met Lys Thr Ser Ala Ser Pro Phe Phe Leu Ala Val Gly Tyr
            180                 185                 190

His Lys Pro His Ile Pro Phe Arg Tyr Pro Lys Glu Phe Gln Lys Leu
            195                 200                 205

Tyr Pro Leu Glu Asn Ile Thr Leu Ala Pro Asp Pro Glu Val Pro Asp
    210                 215                 220

Gly Leu Pro Pro Val Ala Tyr Asn Pro Trp Met Asp Ile Arg Gln Arg
225                 230                 235                 240

Glu Asp Val Gln Ala Leu Asn Ile Ser Val Pro Tyr Gly Pro Ile Pro
            245                 250                 255

Val Asp Phe Gln Arg Lys Ile Arg Gln Ser Tyr Phe Ala Ser Val Ser
            260                 265                 270

Tyr Leu Asp Thr Gln Val Gly Arg Leu Leu Ser Ala Leu Asp Asp Leu
    275                 280                 285

Gln Leu Ala Asn Ser Thr Ile Ile Ala Phe Thr Ser Asp His Gly Trp
    290                 295                 300

Ala Leu Gly Glu His Gly Glu Trp Ala Lys Tyr Ser Asn Phe Asp Val
305                 310                 315                 320

Ala Thr His Val Pro Leu Ile Phe Tyr Val Pro Gly Arg Thr Ala Ser
            325                 330                 335

Leu Pro Glu Ala Gly Glu Lys Leu Phe Pro Tyr Leu Asp Pro Phe Asp
            340                 345                 350

Ser Ala Ser Gln Leu Met Glu Pro Gly Arg Gln Ser Met Asp Leu Val
            355                 360                 365

Glu Leu Val Ser Leu Phe Pro Thr Leu Ala Gly Leu Ala Gly Leu Gln
    370                 375                 380

Val Pro Pro Arg Cys Pro Val Pro Ser Phe His Val Glu Leu Cys Arg
385                 390                 395                 400

Glu Gly Lys Asn Leu Leu Lys His Phe Arg Phe Arg Asp Leu Glu Glu
            405                 410                 415

Asp Pro Tyr Leu Pro Gly Asn Pro Arg Glu Leu Ile Ala Tyr Ser Gln
            420                 425                 430

Tyr Pro Arg Pro Ser Asp Ile Pro Gln Trp Asn Ser Asp Lys Pro Ser
    435                 440                 445

Leu Lys Asp Ile Lys Ile Met Gly Tyr Ser Ile Arg Thr Ile Asp Tyr
    450                 455                 460

Arg Tyr Thr Val Trp Val Gly Phe Asn Pro Asp Glu Phe Leu Ala Asn
465                 470                 475                 480

Phe Ser Asp Ile His Ala Gly Glu Leu Tyr Phe Val Asp Ser Asp Pro
            485                 490                 495

Leu Gln Asp His Asn Met Tyr Asn Asp Ser Gln Gly Gly Asp Leu Phe
            500                 505                 510

Gln Leu Leu Met Pro
            515
```

<210> SEQ ID NO 2
<211> LENGTH: 525

```
<212> TYPE: PRT
<213> ORGANISM: Homo sapiens

<400> SEQUENCE: 2

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
                20                  25                  30

Leu Val Arg Ser Pro Asn Ile Asp Gln Leu Ala Ser His Ser Leu Leu
            35                  40                  45

Phe Gln Asn Ala Phe Ala Gln Gln Ala Val Cys Ala Pro Ser Arg Val
        50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
            130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
            195                 200                 205

Tyr Pro Lys Glu Phe Gln Lys Leu Tyr Pro Leu Glu Asn Ile Thr Leu
            210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
            275                 280                 285

Leu Leu Ser Ala Leu Asp Asp Leu Gln Leu Ala Asn Ser Thr Ile Ile
            290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
            325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
            370                 375                 380

Leu Ala Gly Leu Ala Gly Leu Gln Val Pro Pro Arg Cys Pro Val Pro
385                 390                 395                 400
```

```
Ser Phe His Val Glu Leu Cys Arg Glu Gly Lys Asn Leu Leu Lys His
            405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
            435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
            485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
            515                 520                 525

<210> SEQ ID NO 3
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (59)..(59)
<223> OTHER INFORMATION: formylglycine

<400> SEQUENCE: 3

Ser Glu Thr Gln Ala Asn Ser Thr Thr Asp Ala Leu Asn Val Leu Leu
1                   5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
            35                  40                  45

Phe Gln Asn Ala Phe Ala Gln Gln Ala Val Gly Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
            85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
    130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
            165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
            195                 200                 205
```

```
Tyr Pro Lys Glu Phe Gln Lys Leu Tyr Pro Leu Glu Asn Ile Thr Leu
    210             215             220

Ala Pro Asp Pro Glu Val Pro Asp Gly Leu Pro Pro Val Ala Tyr Asn
225             230             235             240

Pro Trp Met Asp Ile Arg Gln Arg Glu Asp Val Gln Ala Leu Asn Ile
            245             250             255

Ser Val Pro Tyr Gly Pro Ile Pro Val Asp Phe Gln Arg Lys Ile Arg
            260             265             270

Gln Ser Tyr Phe Ala Ser Val Ser Tyr Leu Asp Thr Gln Val Gly Arg
            275             280             285

Leu Leu Ser Ala Leu Asp Asp Leu Gln Leu Ala Asn Ser Thr Ile Ile
    290             295             300

Ala Phe Thr Ser Asp His Gly Trp Ala Leu Gly Glu His Gly Glu Trp
305             310             315             320

Ala Lys Tyr Ser Asn Phe Asp Val Ala Thr His Val Pro Leu Ile Phe
            325             330             335

Tyr Val Pro Gly Arg Thr Ala Ser Leu Pro Glu Ala Gly Glu Lys Leu
            340             345             350

Phe Pro Tyr Leu Asp Pro Phe Asp Ser Ala Ser Gln Leu Met Glu Pro
            355             360             365

Gly Arg Gln Ser Met Asp Leu Val Glu Leu Val Ser Leu Phe Pro Thr
    370             375             380

Leu Ala Gly Leu Ala Gly Leu Gln Val Pro Pro Arg Cys Pro Val Pro
385             390             395             400

Ser Phe His Val Glu Leu Cys Arg Glu Gly Lys Asn Leu Leu Lys His
            405             410             415

Phe Arg Phe Arg Asp Leu Glu Glu Asp Pro Tyr Leu Pro Gly Asn Pro
            420             425             430

Arg Glu Leu Ile Ala Tyr Ser Gln Tyr Pro Arg Pro Ser Asp Ile Pro
            435             440             445

Gln Trp Asn Ser Asp Lys Pro Ser Leu Lys Asp Ile Lys Ile Met Gly
    450             455             460

Tyr Ser Ile Arg Thr Ile Asp Tyr Arg Tyr Thr Val Trp Val Gly Phe
465             470             475             480

Asn Pro Asp Glu Phe Leu Ala Asn Phe Ser Asp Ile His Ala Gly Glu
            485             490             495

Leu Tyr Phe Val Asp Ser Asp Pro Leu Gln Asp His Asn Met Tyr Asn
            500             505             510

Asp Ser Gln Gly Gly Asp Leu Phe Gln Leu Leu Met Pro
    515             520             525
```

<210> SEQ ID NO 4
<211> LENGTH: 757
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 4

```
Ser Glu Thr Gln Ala Asn Ser Thr Thr Asp Ala Leu Asn Val Leu Leu
1               5               10              15

Ile Ile Val Asp Asp Leu Arg Pro Ser Leu Gly Cys Tyr Gly Asp Lys
            20              25              30

Leu Val Arg Ser Pro Asn Ile Asp Gln Leu Ala Ser His Ser Leu Leu
    35              40              45
```

```
Phe Gln Asn Ala Phe Ala Gln Gln Ala Val Cys Ala Pro Ser Arg Val
    50              55              60

Ser Phe Leu Thr Gly Arg Arg Pro Asp Thr Thr Arg Leu Tyr Asp Phe
65              70              75              80

Asn Ser Tyr Trp Arg Val His Ala Gly Asn Phe Ser Thr Ile Pro Gln
                85              90              95

Tyr Phe Lys Glu Asn Gly Tyr Val Thr Met Ser Val Gly Lys Val Phe
            100             105             110

His Pro Gly Ile Ser Ser Asn His Thr Asp Asp Ser Pro Tyr Ser Trp
            115             120             125

Ser Phe Pro Pro Tyr His Pro Ser Ser Glu Lys Tyr Glu Asn Thr Lys
    130             135             140

Thr Cys Arg Gly Pro Asp Gly Glu Leu His Ala Asn Leu Leu Cys Pro
145             150             155             160

Val Asp Val Leu Asp Val Pro Glu Gly Thr Leu Pro Asp Lys Gln Ser
            165             170             175

Thr Glu Gln Ala Ile Gln Leu Leu Glu Lys Met Lys Thr Ser Ala Ser
            180             185             190

Pro Phe Phe Leu Ala Val Gly Tyr His Lys Pro His Ile Pro Phe Arg
            195             200             205

Tyr Pro Lys Glu Phe Gln Lys Leu Tyr Pro Leu Glu Asn Ile Thr Leu
    210             215             220

Ala Pro Asp Pro Glu Val Pro Asp Gly Leu Pro Pro Val Ala Tyr Asn
225             230             235             240

Pro Trp Met Asp Ile Arg Gln Arg Glu Asp Val Gln Ala Leu Asn Ile
            245             250             255

Ser Val Pro Tyr Gly Pro Ile Pro Val Asp Phe Gln Arg Lys Ile Arg
            260             265             270

Gln Ser Tyr Phe Ala Ser Val Ser Tyr Leu Asp Thr Gln Val Gly Arg
    275             280             285

Leu Leu Ser Ala Leu Asp Asp Leu Gln Leu Ala Asn Ser Thr Ile Ile
    290             295             300

Ala Phe Thr Ser Asp His Gly Trp Ala Leu Gly Glu His Gly Glu Trp
305             310             315             320

Ala Lys Tyr Ser Asn Phe Asp Val Ala Thr His Val Pro Leu Ile Phe
            325             330             335

Tyr Val Pro Gly Arg Thr Ala Ser Leu Pro Glu Ala Gly Glu Lys Leu
            340             345             350

Phe Pro Tyr Leu Asp Pro Phe Asp Ser Ala Ser Gln Leu Met Glu Pro
    355             360             365

Gly Arg Gln Ser Met Asp Leu Val Glu Leu Val Ser Leu Phe Pro Thr
    370             375             380

Leu Ala Gly Leu Ala Gly Leu Gln Val Pro Pro Arg Cys Pro Val Pro
385             390             395             400

Ser Phe His Val Glu Leu Cys Arg Glu Gly Lys Asn Leu Leu Lys His
            405             410             415

Phe Arg Phe Arg Asp Leu Glu Glu Asp Pro Tyr Leu Pro Gly Asn Pro
            420             425             430

Arg Glu Leu Ile Ala Tyr Ser Gln Tyr Pro Arg Pro Ser Asp Ile Pro
    435             440             445

Gln Trp Asn Ser Asp Lys Pro Ser Leu Lys Asp Ile Lys Ile Met Gly
    450             455             460
```

-continued

```
Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
                500                 505                 510

Asp Ser Gln Gly Gly Asp Leu Phe Gln Leu Leu Met Pro Gly Gly Gly
                515                 520                 525

Gly Ser Asp Lys Thr His Thr Cys Pro Pro Cys Pro Ala Pro Glu Ala
                530                 535                 540

Ala Gly Gly Pro Ser Val Phe Leu Phe Pro Pro Lys Pro Lys Asp Thr
545                 550                 555                 560

Leu Met Ile Ser Arg Thr Pro Glu Val Thr Cys Val Val Val Asp Val
                565                 570                 575

Ser His Glu Asp Pro Glu Val Lys Phe Asn Trp Tyr Val Asp Gly Val
                580                 585                 590

Glu Val His Asn Ala Lys Thr Lys Pro Arg Glu Glu Gln Tyr Asn Ser
                595                 600                 605

Thr Tyr Arg Val Val Ser Val Leu Thr Val Leu His Gln Asp Trp Leu
                610                 615                 620

Asn Gly Lys Glu Tyr Lys Cys Lys Val Ser Asn Lys Ala Leu Pro Ala
625                 630                 635                 640

Pro Ile Glu Lys Thr Ile Ser Lys Ala Lys Gly Gln Pro Arg Glu Pro
                645                 650                 655

Gln Val Tyr Thr Leu Pro Pro Ser Arg Asp Glu Leu Thr Lys Asn Gln
                660                 665                 670

Val Ser Leu Ser Cys Ala Val Lys Gly Phe Tyr Pro Ser Asp Ile Ala
                675                 680                 685

Val Glu Trp Glu Ser Asn Gly Gln Pro Glu Asn Asn Tyr Lys Thr Thr
                690                 695                 700

Pro Pro Val Leu Asp Ser Asp Gly Ser Phe Phe Leu Val Ser Lys Leu
705                 710                 715                 720

Thr Val Asp Lys Ser Arg Trp Gln Gln Gly Asn Val Phe Ser Cys Ser
                725                 730                 735

Val Met His Glu Ala Leu His Asn His Tyr Thr Gln Lys Ser Leu Ser
                740                 745                 750

Leu Ser Pro Gly Lys
                755
```

```
<210> SEQ ID NO 5
<211> LENGTH: 757
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (59)..(59)
<223> OTHER INFORMATION: formylglycine

<400> SEQUENCE: 5

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
                20                  25                  30

Leu Val Arg Ser Pro Asn Ile Asp Gln Leu Ala Ser His Ser Leu Leu
```

```
                35                  40                  45

Phe Gln Asn Ala Phe Ala Gln Gln Ala Val Gly Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
                100                 105                 110

His Pro Gly Ile Ser Ser Asn His Thr Asp Asp Ser Pro Tyr Ser Trp
                115                 120                 125

Ser Phe Pro Pro Tyr His Pro Ser Ser Glu Lys Tyr Glu Asn Thr Lys
    130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
                180                 185                 190

Pro Phe Phe Leu Ala Val Gly Tyr His Lys Pro His Ile Pro Phe Arg
                195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
                260                 265                 270

Gln Ser Tyr Phe Ala Ser Val Ser Tyr Leu Asp Thr Gln Val Gly Arg
                275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
                340                 345                 350

Phe Pro Tyr Leu Asp Pro Phe Asp Ser Ala Ser Gln Leu Met Glu Pro
                355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
                420                 425                 430

Arg Glu Leu Ile Ala Tyr Ser Gln Tyr Pro Arg Pro Ser Asp Ile Pro
                435                 440                 445

Gln Trp Asn Ser Asp Lys Pro Ser Leu Lys Asp Ile Lys Ile Met Gly
    450                 455                 460
```

```
Tyr Ser Ile Arg Thr Ile Asp Tyr Arg Tyr Thr Val Trp Val Gly Phe
465             470             475             480

Asn Pro Asp Glu Phe Leu Ala Asn Phe Ser Asp Ile His Ala Gly Glu
                485             490             495

Leu Tyr Phe Val Asp Ser Asp Pro Leu Gln Asp His Asn Met Tyr Asn
            500             505             510

Asp Ser Gln Gly Gly Asp Leu Phe Gln Leu Leu Met Pro Gly Gly Gly
            515             520             525

Gly Ser Asp Lys Thr His Thr Cys Pro Pro Cys Pro Ala Pro Glu Ala
        530             535             540

Ala Gly Gly Pro Ser Val Phe Leu Phe Pro Pro Lys Pro Lys Asp Thr
545             550             555             560

Leu Met Ile Ser Arg Thr Pro Glu Val Thr Cys Val Val Val Asp Val
                565             570             575

Ser His Glu Asp Pro Glu Val Lys Phe Asn Trp Tyr Val Asp Gly Val
            580             585             590

Glu Val His Asn Ala Lys Thr Lys Pro Arg Glu Glu Gln Tyr Asn Ser
            595             600             605

Thr Tyr Arg Val Val Ser Val Leu Thr Val Leu His Gln Asp Trp Leu
        610             615             620

Asn Gly Lys Glu Tyr Lys Cys Lys Val Ser Asn Lys Ala Leu Pro Ala
625             630             635             640

Pro Ile Glu Lys Thr Ile Ser Lys Ala Lys Gly Gln Pro Arg Glu Pro
            645             650             655

Gln Val Tyr Thr Leu Pro Pro Ser Arg Asp Glu Leu Thr Lys Asn Gln
            660             665             670

Val Ser Leu Ser Cys Ala Val Lys Gly Phe Tyr Pro Ser Asp Ile Ala
            675             680             685

Val Glu Trp Glu Ser Asn Gly Gln Pro Glu Asn Asn Tyr Lys Thr Thr
        690             695             700

Pro Pro Val Leu Asp Ser Asp Gly Ser Phe Phe Leu Val Ser Lys Leu
705             710             715             720

Thr Val Asp Lys Ser Arg Trp Gln Gln Gly Asn Val Phe Ser Cys Ser
                725             730             735

Val Met His Glu Ala Leu His Asn His Tyr Thr Gln Lys Ser Leu Ser
            740             745             750

Leu Ser Pro Gly Lys
        755
```

<210> SEQ ID NO 6
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Ala Pro Glu Ala Ala Gly Gly Pro Ser Val Phe Leu Phe Pro Pro Lys
1               5               10              15

Pro Lys Asp Thr Leu Met Ile Ser Arg Thr Pro Glu Val Thr Cys Val
            20              25              30

Val Val Asp Val Ser His Glu Asp Pro Glu Val Lys Phe Asn Trp Tyr
            35              40              45

Val Asp Gly Val Glu Val His Asn Ala Lys Thr Lys Pro Arg Glu Glu
```

-continued

```
        50                    55                    60

Gln Tyr Asn Ser Thr Tyr Arg Val Val Ser Val Leu Thr Val Leu His
65                    70                    75                    80

Gln Asp Trp Leu Asn Gly Lys Glu Tyr Lys Cys Lys Val Ser Asn Lys
                85                    90                    95

Ala Leu Pro Ala Pro Ile Glu Lys Thr Ile Ser Lys Ala Lys Gly Gln
            100                   105                   110

Pro Arg Glu Pro Gln Val Tyr Thr Leu Pro Pro Ser Arg Asp Glu Leu
            115                   120                   125

Thr Lys Asn Gln Val Ser Leu Trp Cys Leu Val Lys Gly Phe Tyr Pro
            130                   135                   140

Ser Asp Ile Ala Val Leu Trp Glu Ser Tyr Gly Thr Glu Trp Ser Ser
145                   150                   155                   160

Tyr Lys Thr Thr Pro Pro Val Leu Asp Ser Asp Gly Ser Phe Phe Leu
                165                   170                   175

Tyr Ser Lys Leu Thr Val Thr Lys Glu Glu Trp Gln Gln Gly Phe Val
                180                   185                   190

Phe Ser Cys Ser Val Met His Glu Ala Leu His Asn His Tyr Thr Gln
                195                   200                   205

Lys Ser Leu Ser Leu Ser Pro Gly Lys
            210                   215

<210> SEQ ID NO 7
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Tyr Gly Thr Glu Trp Ala Asn Tyr Lys Thr Thr Pro Pro
                165                 170                 175

Val Leu Asp Ser Asp Gly Ser Phe Phe Leu Tyr Ser Lys Leu Thr Val
                180                 185                 190
```

-continued

```
Thr Lys Glu Glu Trp Gln Gln Gly Phe Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 8
<211> LENGTH: 217
<212> TYPE: PRT
<213> ORGANISM: Homo sapiens

<400> SEQUENCE: 8

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 9
<211> LENGTH: 110
<212> TYPE: PRT
<213> ORGANISM: Homo sapiens

<400> SEQUENCE: 9

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
    50                  55                  60
```

-continued

```
Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 10
<211> LENGTH: 107
<212> TYPE: PRT
<213> ORGANISM: Homo sapiens

<400> SEQUENCE: 10

Gly Gln Pro Arg Glu Pro Gln Val Tyr Thr Leu Pro Pro Ser Arg Asp
1                   5                   10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 11
<211> LENGTH: 550
<212> TYPE: PRT
<213> ORGANISM: Homo sapiens

<400> SEQUENCE: 11

Met Pro Pro Pro Arg Thr Gly Arg Gly Leu Leu Trp Leu Gly Leu Val
1                   5                   10                  15

Leu Ser Ser Val Cys Val Ala Leu Gly Ser Glu Thr Gln Ala Asn Ser
                20                  25                  30

Thr Thr Asp Ala Leu Asn Val Leu Leu Ile Ile Val Asp Asp Leu Arg
            35                  40                  45

Pro Ser Leu Gly Cys Tyr Gly Asp Lys Leu Val Arg Ser Pro Asn Ile
        50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
            115                 120                 125

Val Thr Met Ser Val Gly Lys Val Phe His Pro Gly Ile Ser Ser Asn
        130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
            165                 170                 175
```

```
Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
            195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
            275                 280                 285

Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
            355                 360                 365

Ser Leu Pro Glu Ala Gly Glu Lys Leu Phe Pro Tyr Leu Asp Pro Phe
    370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
            435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
            515                 520                 525

Pro Leu Gln Asp His Asn Met Tyr Asn Asp Ser Gln Gly Gly Asp Leu
    530                 535                 540

Phe Gln Leu Leu Met Pro
545                 550
```

<210> SEQ ID NO 12
<211> LENGTH: 15
<212> TYPE: PRT
<213> ORGANISM: Homo sapiens

<400> SEQUENCE: 12

```
Glu Pro Lys Ser Cys Asp Lys Thr His Thr Cys Pro Pro Cys Pro
1               5                   10                  15

<210> SEQ ID NO 13
<211> LENGTH: 760
<212> TYPE: PRT
<213> ORGANISM: Homo sapiens

<400> SEQUENCE: 13

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
            115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
            195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
            275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
```

-continued

```
          355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
                420                 425                 430

Phe Ser Asp Met Val Leu Lys Asp Gly Phe Gln Pro Ser Arg Ser Ile
                435                 440                 445

Ile Phe Ala Ser Trp Ser Ala Gly Asp Phe Gly Ser Val Gly Ala Thr
            450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
                500                 505                 510

Val Lys His Pro Val Thr Gly Gln Phe Leu Tyr Gln Asp Ser Asn Trp
            515                 520                 525

Ala Ser Lys Val Glu Lys Leu Thr Leu Asp Asn Ala Ala Phe Pro Phe
            530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
            595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
                660                 665                 670

Lys Leu Asn Asp Arg Val Met Arg Val Glu Tyr His Phe Leu Ser Pro
            675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
            755                 760
```

<210> SEQ ID NO 14

```
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
            115                 120                 125

Thr Lys Asn Gln Val Ser Leu Ser Cys Ala Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
    210                 215

<210> SEQ ID NO 15
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

-continued

```
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Ser Cys Ala Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
            210                 215
```

<210> SEQ ID NO 16
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Ser Cys Ala Val Lys Gly Phe Tyr Pro
            130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
            210                 215
```

<210> SEQ ID NO 17
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Ser Cys Ala Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215

<210> SEQ ID NO 18
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys

```
                      85                    90                    95

Ala Leu Pro Ala Pro Ile Glu Lys Thr Ile Ser Lys Ala Lys Gly Gln
            100                    105                    110

Pro Arg Glu Pro Gln Val Tyr Thr Leu Pro Pro Ser Arg Asp Glu Leu
            115                    120                    125

Thr Lys Asn Gln Val Ser Leu Trp Cys Leu Val Lys Gly Phe Tyr Pro
        130                    135                    140

Ser Asp Ile Ala Val Glu Trp Glu Ser Asn Gly Gln Pro Glu Asn Asn
145                    150                    155                    160

Tyr Lys Thr Thr Pro Pro Val Leu Asp Ser Asp Gly Ser Phe Phe Leu
                165                    170                    175

Tyr Ser Lys Leu Thr Val Asp Lys Ser Arg Trp Gln Gln Gly Asn Val
            180                    185                    190

Phe Ser Cys Ser Val Met His Glu Ala Leu His Asn His Tyr Thr Gln
            195                    200                    205

Lys Ser Leu Ser Leu Ser Pro Gly Lys
        210                    215

<210> SEQ ID NO 19
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Pro Glu Ala Ala Gly Gly Pro Ser Val Phe Leu Phe Pro Pro Lys
1                   5                    10                    15

Pro Lys Asp Thr Leu Met Ile Ser Arg Thr Pro Glu Val Thr Cys Val
            20                    25                    30

Val Val Asp Val Ser His Glu Asp Pro Glu Val Lys Phe Asn Trp Tyr
            35                    40                    45

Val Asp Gly Val Glu Val His Asn Ala Lys Thr Lys Pro Arg Glu Glu
        50                    55                    60

Gln Tyr Asn Ser Thr Tyr Arg Val Val Ser Val Leu Thr Val Leu His
65                    70                    75                    80

Gln Asp Trp Leu Asn Gly Lys Glu Tyr Lys Cys Lys Val Ser Asn Lys
                85                    90                    95

Ala Leu Pro Ala Pro Ile Glu Lys Thr Ile Ser Lys Ala Lys Gly Gln
            100                    105                    110

Pro Arg Glu Pro Gln Val Tyr Thr Leu Pro Pro Ser Arg Asp Glu Leu
            115                    120                    125

Thr Lys Asn Gln Val Ser Leu Trp Cys Leu Val Lys Gly Phe Tyr Pro
        130                    135                    140

Ser Asp Ile Ala Val Glu Trp Glu Ser Asn Gly Gln Pro Glu Asn Asn
145                    150                    155                    160

Tyr Lys Thr Thr Pro Pro Val Leu Asp Ser Asp Gly Ser Phe Phe Leu
                165                    170                    175

Tyr Ser Lys Leu Thr Val Asp Lys Ser Arg Trp Gln Gln Gly Asn Val
            180                    185                    190

Phe Ser Cys Ser Val Met His Glu Ala Leu His Asn His Tyr Thr Gln
            195                    200                    205

Lys Ser Leu Ser Leu Ser Pro Gly Lys
        210                    215
```

-continued

```
<210> SEQ ID NO 20
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Trp Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
            195                 200                 205

Lys Ser Leu Ser Leu Ser Pro Gly Lys
        210                 215

<210> SEQ ID NO 21
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80
```

-continued

```
Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215
```

<210> SEQ ID NO 22
<211> LENGTH: 10
<212> TYPE: PRT
<213> ORGANISM: Homo sapiens

<400> SEQUENCE: 22

```
Asp Lys Thr His Thr Cys Pro Pro Cys Pro
1               5                   10
```

<210> SEQ ID NO 23
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
                20                  25                  30

Leu Val Arg Ser Pro Asn Ile Asp Gln Leu Ala Ser His Ser Leu Leu
            35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
    130                 135                 140

Thr Cys Arg Gly Pro Asp Gly Glu Leu His Ala Asn Leu Leu Cys Pro
145                 150                 155                 160
```

```
Val Asp Val Leu Asp Val Pro Glu Gly Thr Leu Pro Asp Lys Gln Ser
            165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
            195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
            245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
    275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
            325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
            405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
            435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
            485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
    515                 520                 525
```

<210> SEQ ID NO 24
<211> LENGTH: 757
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
    130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
            165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
            195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
            245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
    275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
            325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
            405                 410                 415
```

```
Phe Arg Phe Arg Asp Leu Glu Glu Asp Pro Tyr Leu Pro Gly Asn Pro
                420                 425                 430

Arg Glu Leu Ile Ala Tyr Ser Gln Tyr Pro Arg Pro Ser Asp Ile Pro
                435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
                500                 505                 510

Asp Ser Gln Gly Gly Asp Leu Phe Gln Leu Leu Met Pro Gly Gly Gly
    515                 520                 525

Gly Ser Asp Lys Thr His Thr Cys Pro Pro Cys Pro Ala Pro Glu Ala
    530                 535                 540

Ala Gly Gly Pro Ser Val Phe Leu Phe Pro Pro Lys Pro Lys Asp Thr
545                 550                 555                 560

Leu Met Ile Ser Arg Thr Pro Glu Val Thr Cys Val Val Val Asp Val
                565                 570                 575

Ser His Glu Asp Pro Glu Val Lys Phe Asn Trp Tyr Val Asp Gly Val
                580                 585                 590

Glu Val His Asn Ala Lys Thr Lys Pro Arg Glu Glu Gln Tyr Asn Ser
                595                 600                 605

Thr Tyr Arg Val Val Ser Val Leu Thr Val Leu His Gln Asp Trp Leu
    610                 615                 620

Asn Gly Lys Glu Tyr Lys Cys Lys Val Ser Asn Lys Ala Leu Pro Ala
625                 630                 635                 640

Pro Ile Glu Lys Thr Ile Ser Lys Ala Lys Gly Gln Pro Arg Glu Pro
                645                 650                 655

Gln Val Tyr Thr Leu Pro Pro Ser Arg Asp Glu Leu Thr Lys Asn Gln
                660                 665                 670

Val Ser Leu Ser Cys Ala Val Lys Gly Phe Tyr Pro Ser Asp Ile Ala
                675                 680                 685

Val Glu Trp Glu Ser Asn Gly Gln Pro Glu Asn Asn Tyr Lys Thr Thr
    690                 695                 700

Pro Pro Val Leu Asp Ser Asp Gly Ser Phe Phe Leu Val Ser Lys Leu
705                 710                 715                 720

Thr Val Asp Lys Ser Arg Trp Gln Gln Gly Asn Val Phe Ser Cys Ser
                725                 730                 735

Val Met His Glu Ala Leu His Asn His Tyr Thr Gln Lys Ser Leu Ser
                740                 745                 750

Leu Ser Pro Gly Lys
        755
```

<210> SEQ ID NO 25
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Asp Lys Thr His Thr Cys Pro Pro Cys Pro Ala Pro Glu Ala Ala Gly
1                   5                   10                  15
```

```
Gly Pro Ser Val Phe Leu Phe Pro Pro Lys Pro Lys Asp Thr Leu Met
            20              25              30

Ile Ser Arg Thr Pro Glu Val Thr Cys Val Val Val Asp Val Ser His
        35              40              45

Glu Asp Pro Glu Val Lys Phe Asn Trp Tyr Val Asp Gly Val Glu Val
    50              55              60

His Asn Ala Lys Thr Lys Pro Arg Glu Glu Gln Tyr Asn Ser Thr Tyr
65              70              75              80

Arg Val Val Ser Val Leu Thr Val Leu His Gln Asp Trp Leu Asn Gly
                85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Gln Val
            115             120             125

Tyr Thr Leu Pro Pro Ser Arg Asp Glu Leu Thr Lys Asn Gln Val Ser
    130             135             140

Leu Trp Cys Leu Val Lys Gly Phe Tyr Pro Ser Asp Ile Ala Val Trp
145             150             155             160

Trp Glu Ser Tyr Gly Thr Glu Trp Ser Ser Tyr Lys Thr Thr Pro Pro
                165             170             175

Val Leu Asp Ser Asp Gly Ser Phe Phe Leu Tyr Ser Lys Leu Thr Val
            180             185             190

Thr Lys Glu Glu Trp Gln Gln Gly Phe Val Phe Ser Cys Ser Val Met
        195             200             205

His Glu Ala Leu His Asn His Tyr Thr Gln Lys Ser Leu Ser Leu Ser
        210             215             220

Pro Gly Lys
225

<210> SEQ ID NO 26
<211> LENGTH: 757
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser Glu Thr Gln Ala Asn Ser Thr Thr Asp Ala Leu Asn Val Leu Leu
1               5               10              15

Ile Ile Val Asp Asp Leu Arg Pro Ser Leu Gly Cys Tyr Gly Asp Lys
            20              25              30

Leu Val Arg Ser Pro Asn Ile Asp Gln Leu Ala Ser His Ser Leu Leu
        35              40              45

Phe Gln Asn Ala Phe Ala Gln Gln Ala Val Cys Ala Pro Ser Arg Val
    50              55              60

Ser Phe Leu Thr Gly Arg Arg Pro Asp Thr Thr Arg Leu Tyr Asp Phe
65              70              75              80

Asn Ser Tyr Trp Arg Val His Ala Gly Asn Phe Ser Thr Ile Pro Gln
                85              90              95

Tyr Phe Lys Glu Asn Gly Tyr Val Thr Met Ser Val Gly Lys Val Phe
            100             105             110

His Pro Gly Ile Ser Ser Asn His Thr Asp Asp Ser Pro Tyr Ser Trp
        115             120             125

Ser Phe Pro Pro Tyr His Pro Ser Ser Glu Lys Tyr Glu Asn Thr Lys
```

```
        130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
                180                 185                 190

Pro Phe Phe Leu Ala Val Gly Tyr His Lys Pro His Ile Pro Phe Arg
                195                 200                 205

Tyr Pro Lys Glu Phe Gln Lys Leu Tyr Pro Leu Glu Asn Ile Thr Leu
        210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
                260                 265                 270

Gln Ser Tyr Phe Ala Ser Val Ser Tyr Leu Asp Thr Gln Val Gly Arg
                275                 280                 285

Leu Leu Ser Ala Leu Asp Asp Leu Gln Leu Ala Asn Ser Thr Ile Ile
        290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
                340                 345                 350

Phe Pro Tyr Leu Asp Pro Phe Asp Ser Ala Ser Gln Leu Met Glu Pro
                355                 360                 365

Gly Arg Gln Ser Met Asp Leu Val Glu Leu Val Ser Leu Phe Pro Thr
        370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
                420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
        450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
                500                 505                 510

Asp Ser Gln Gly Gly Asp Leu Phe Gln Leu Leu Met Pro Gly Gly Gly
        515                 520                 525

Gly Ser Asp Lys Thr His Thr Cys Pro Pro Cys Pro Ala Pro Glu Leu
        530                 535                 540

Leu Gly Gly Pro Ser Val Phe Leu Phe Pro Pro Lys Pro Lys Asp Thr
545                 550                 555                 560
```

-continued

```
Leu Met Ile Ser Arg Thr Pro Glu Val Thr Cys Val Val Val Asp Val
            565                 570                 575

Ser His Glu Asp Pro Glu Val Lys Phe Asn Trp Tyr Val Asp Gly Val
            580                 585                 590

Glu Val His Asn Ala Lys Thr Lys Pro Arg Glu Glu Gln Tyr Asn Ser
            595                 600                 605

Thr Tyr Arg Val Val Ser Val Leu Thr Val Leu His Gln Asp Trp Leu
            610                 615                 620

Asn Gly Lys Glu Tyr Lys Cys Lys Val Ser Asn Lys Ala Leu Pro Ala
625                 630                 635                 640

Pro Ile Glu Lys Thr Ile Ser Lys Ala Lys Gly Gln Pro Arg Glu Pro
            645                 650                 655

Gln Val Tyr Thr Leu Pro Pro Ser Arg Asp Glu Leu Thr Lys Asn Gln
            660                 665                 670

Val Ser Leu Ser Cys Ala Val Lys Gly Phe Tyr Pro Ser Asp Ile Ala
            675                 680                 685

Val Glu Trp Glu Ser Asn Gly Gln Pro Glu Asn Asn Tyr Lys Thr Thr
            690                 695                 700

Pro Pro Val Leu Asp Ser Asp Gly Ser Phe Phe Leu Val Ser Lys Leu
705                 710                 715                 720

Thr Val Asp Lys Ser Arg Trp Gln Gln Gly Asn Val Phe Ser Cys Ser
            725                 730                 735

Val Met His Glu Ala Leu His Asn His Tyr Thr Gln Lys Ser Leu Ser
            740                 745                 750

Leu Ser Pro Gly Lys
            755

<210> SEQ ID NO 27
<211> LENGTH: 757
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
            35                  40                  45

Phe Gln Asn Ala Phe Ala Gln Gln Ala Val Cys Ala Pro Ser Arg Val
        50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
            130                 135                 140

Thr Cys Arg Gly Pro Asp Gly Glu Leu His Ala Asn Leu Leu Cys Pro
```

```
145              150              155              160

Val Asp Val Leu Asp Val Pro Glu Gly Thr Leu Pro Asp Lys Gln Ser
                165              170              175

Thr Glu Gln Ala Ile Gln Leu Leu Glu Lys Met Lys Thr Ser Ala Ser
            180              185              190

Pro Phe Phe Leu Ala Val Gly Tyr His Lys Pro His Ile Pro Phe Arg
            195              200              205

Tyr Pro Lys Glu Phe Gln Lys Leu Tyr Pro Leu Glu Asn Ile Thr Leu
        210              215              220

Ala Pro Asp Pro Glu Val Pro Asp Gly Leu Pro Pro Val Ala Tyr Asn
225              230              235              240

Pro Trp Met Asp Ile Arg Gln Arg Glu Asp Val Gln Ala Leu Asn Ile
                245              250              255

Ser Val Pro Tyr Gly Pro Ile Pro Val Asp Phe Gln Arg Lys Ile Arg
                260              265              270

Gln Ser Tyr Phe Ala Ser Val Ser Tyr Leu Asp Thr Gln Val Gly Arg
                275              280              285

Leu Leu Ser Ala Leu Asp Asp Leu Gln Leu Ala Asn Ser Thr Ile Ile
        290              295              300

Ala Phe Thr Ser Asp His Gly Trp Ala Leu Gly Glu His Gly Glu Trp
305              310              315              320

Ala Lys Tyr Ser Asn Phe Asp Val Ala Thr His Val Pro Leu Ile Phe
                325              330              335

Tyr Val Pro Gly Arg Thr Ala Ser Leu Pro Glu Ala Gly Glu Lys Leu
            340              345              350

Phe Pro Tyr Leu Asp Pro Phe Asp Ser Ala Ser Gln Leu Met Glu Pro
            355              360              365

Gly Arg Gln Ser Met Asp Leu Val Glu Leu Val Ser Leu Phe Pro Thr
        370              375              380

Leu Ala Gly Leu Ala Gly Leu Gln Val Pro Pro Arg Cys Pro Val Pro
385              390              395              400

Ser Phe His Val Glu Leu Cys Arg Glu Gly Lys Asn Leu Leu Lys His
            405              410              415

Phe Arg Phe Arg Asp Leu Glu Glu Asp Pro Tyr Leu Pro Gly Asn Pro
            420              425              430

Arg Glu Leu Ile Ala Tyr Ser Gln Tyr Pro Arg Pro Ser Asp Ile Pro
        435              440              445

Gln Trp Asn Ser Asp Lys Pro Ser Leu Lys Asp Ile Lys Ile Met Gly
    450              455              460

Tyr Ser Ile Arg Thr Ile Asp Tyr Arg Tyr Thr Val Trp Val Gly Phe
465              470              475              480

Asn Pro Asp Glu Phe Leu Ala Asn Phe Ser Asp Ile His Ala Gly Glu
            485              490              495

Leu Tyr Phe Val Asp Ser Asp Pro Leu Gln Asp His Asn Met Tyr Asn
            500              505              510

Asp Ser Gln Gly Gly Asp Leu Phe Gln Leu Leu Met Pro Gly Gly Gly
        515              520              525

Gly Ser Asp Lys Thr His Thr Cys Pro Pro Cys Pro Ala Pro Glu Leu
        530              535              540

Leu Gly Gly Pro Ser Val Phe Leu Phe Pro Pro Lys Pro Lys Asp Thr
545              550              555              560

Leu Met Ile Ser Arg Thr Pro Glu Val Thr Cys Val Val Val Asp Val
                565              570              575
```

-continued

```
Ser His Glu Asp Pro Glu Val Lys Phe Asn Trp Tyr Val Asp Gly Val
        580             585             590

Glu Val His Asn Ala Lys Thr Lys Pro Arg Glu Glu Gln Tyr Asn Ser
        595             600             605

Thr Tyr Arg Val Val Ser Val Leu Thr Val Leu His Gln Asp Trp Leu
        610             615             620

Asn Gly Lys Glu Tyr Lys Cys Lys Val Ser Asn Lys Ala Leu Pro Ala
625             630             635             640

Pro Ile Glu Lys Thr Ile Ser Lys Ala Lys Gly Gln Pro Arg Glu Pro
            645             650             655

Gln Val Tyr Thr Leu Pro Pro Ser Arg Asp Glu Leu Thr Lys Asn Gln
            660             665             670

Val Ser Leu Trp Cys Leu Val Lys Gly Phe Tyr Pro Ser Asp Ile Ala
            675             680             685

Val Glu Trp Glu Ser Asn Gly Gln Pro Glu Asn Asn Tyr Lys Thr Thr
            690             695             700

Pro Pro Val Leu Asp Ser Asp Gly Ser Phe Phe Leu Tyr Ser Lys Leu
705             710             715             720

Thr Val Asp Lys Ser Arg Trp Gln Gln Gly Asn Val Phe Ser Cys Ser
            725             730             735

Val Met His Glu Ala Leu His Asn His Tyr Thr Gln Lys Ser Leu Ser
            740             745             750

Leu Ser Pro Gly Lys
            755
```

```
<210> SEQ ID NO 28
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ala Pro Glu Ala Ala Gly Gly Pro Ser Val Phe Leu Phe Pro Pro Lys
1               5               10              15

Pro Lys Asp Thr Leu Met Ile Ser Arg Thr Pro Glu Val Thr Cys Val
            20              25              30

Val Val Asp Val Ser His Glu Asp Pro Glu Val Lys Phe Asn Trp Tyr
            35              40              45

Val Asp Gly Val Glu Val His Asn Ala Lys Thr Lys Pro Arg Glu Glu
        50              55              60

Gln Tyr Asn Ser Thr Tyr Arg Val Val Ser Val Leu Thr Val Leu His
65              70              75              80

Gln Asp Trp Leu Asn Gly Lys Glu Tyr Lys Cys Lys Val Ser Asn Lys
            85              90              95

Ala Leu Pro Ala Pro Ile Glu Lys Thr Ile Ser Lys Ala Lys Gly Gln
            100             105             110

Pro Arg Glu Pro Gln Val Tyr Thr Leu Pro Pro Ser Arg Asp Glu Leu
        115             120             125

Thr Lys Asn Gln Val Ser Leu Trp Cys Leu Val Lys Gly Phe Tyr Pro
        130             135             140

Ser Asp Ile Ala Val Glu Trp Glu Ser Tyr Gly Thr Glu Trp Ala Asn
145             150             155             160

Tyr Lys Thr Thr Pro Pro Val Leu Asp Ser Asp Gly Ser Phe Phe Leu
```

```
                    165                     170                     175

Tyr Ser Lys Leu Thr Val Thr Lys Glu Glu Trp Gln Gln Gly Phe Val
            180                     185                     190

Phe Ser Cys Ser Val Met His Glu Ala Leu His Asn His Tyr Thr Gln
        195                     200                     205

Lys Ser Leu Ser Leu Ser Pro Gly Lys
    210                     215
```

```
<210> SEQ ID NO 29
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Trp Cys Leu Val Lys Gly Phe Tyr Pro
    130                 135                 140

Ser Asp Ile Ala Val Leu Trp Glu Ser Tyr Gly Thr Glu Trp Ala Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                     185                     190

Phe Ser Cys Ser Val Met His Glu Ala Leu His Asn His Tyr Thr Gln
        195                     200                     205

Lys Ser Leu Ser Leu Ser Pro Gly Lys
    210                     215
```

```
<210> SEQ ID NO 30
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
```

-continued

```
                20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
             100                 105                 110

Glu Lys Thr Ile Ser Lys Ala Lys Gly Gln Pro Arg Glu Pro Gln Val
         115                 120                 125

Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Leu
145                 150                 155                 160

Trp Glu Ser Tyr Gly Thr Glu Trp Ala Ser Tyr Lys Thr Thr Pro Pro
                 165                 170                 175

Val Leu Asp Ser Asp Gly Ser Phe Phe Leu Tyr Ser Lys Leu Thr Val
             180                 185                 190

Thr Lys Glu Glu Trp Gln Gln Gly Phe Val Phe Ser Cys Ser Val Met
             195                 200                 205

His Glu Ala Leu His Asn His Tyr Thr Gln Lys Ser Leu Ser Leu Ser
    210                 215                 220

Pro Gly Lys
225

<210> SEQ ID NO 31
<211> LENGTH: 757
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser Glu Thr Gln Ala Asn Ser Thr Thr Asp Ala Leu Asn Val Leu Leu
1                   5                  10                  15

Ile Ile Val Asp Asp Leu Arg Pro Ser Leu Gly Cys Tyr Gly Asp Lys
             20                  25                  30

Leu Val Arg Ser Pro Asn Ile Asp Gln Leu Ala Ser His Ser Leu Leu
         35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                 85                  90                  95

Tyr Phe Lys Glu Asn Gly Tyr Val Thr Met Ser Val Gly Lys Val Phe
             100                 105                 110

His Pro Gly Ile Ser Ser Asn His Thr Asp Asp Ser Pro Tyr Ser Trp
         115                 120                 125

Ser Phe Pro Pro Tyr His Pro Ser Ser Glu Lys Tyr Glu Asn Thr Lys
    130                 135                 140
```

-continued

```
Thr Cys Arg Gly Pro Asp Gly Glu Leu His Ala Asn Leu Leu Cys Pro
145             150                 155                 160

Val Asp Val Leu Asp Val Pro Glu Gly Thr Leu Pro Asp Lys Gln Ser
            165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
            195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
            245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
    275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
            325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
            405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
            435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
            485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro Gly Gly Gly
            515                 520                 525

Gly Ser Asp Lys Thr His Thr Cys Pro Pro Cys Pro Ala Pro Glu Leu
    530                 535                 540

Leu Gly Gly Pro Ser Val Phe Leu Phe Pro Pro Lys Pro Lys Asp Thr
545                 550                 555                 560

Leu Met Ile Ser Arg Thr Pro Glu Val Thr Cys Val Val Val Asp Val
```

```
                565               570               575
Ser His Glu Asp Pro Glu Val Lys Phe Asn Trp Tyr Val Asp Gly Val
        580               585               590

Glu Val His Asn Ala Lys Thr Lys Pro Arg Glu Glu Gln Tyr Asn Ser
        595               600               605

Thr Tyr Arg Val Val Ser Val Leu Thr Val Leu His Gln Asp Trp Leu
    610               615               620

Asn Gly Lys Glu Tyr Lys Cys Lys Val Ser Asn Lys Ala Leu Pro Ala
625               630               635               640

Pro Ile Glu Lys Thr Ile Ser Lys Ala Lys Gly Gln Pro Arg Glu Pro
                645               650               655

Gln Val Tyr Thr Leu Pro Pro Ser Arg Asp Glu Leu Thr Lys Asn Gln
        660               665               670

Val Ser Leu Ser Cys Ala Val Lys Gly Phe Tyr Pro Ser Asp Ile Ala
        675               680               685

Val Glu Trp Glu Ser Asn Gly Gln Pro Glu Asn Asn Tyr Lys Thr Thr
    690               695               700

Pro Pro Val Leu Asp Ser Asp Gly Ser Phe Phe Leu Val Ser Lys Leu
705               710               715               720

Thr Val Asp Lys Ser Arg Trp Gln Gln Gly Asn Val Phe Ser Cys Ser
                725               730               735

Val Met His Glu Ala Leu His Asn His Tyr Thr Gln Lys Ser Leu Ser
        740               745               750

Leu Ser Pro Gly Lys
        755

<210> SEQ ID NO 32
<211> LENGTH: 757
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Ser Glu Thr Gln Ala Asn Ser Thr Thr Asp Ala Leu Asn Val Leu Leu
1               5               10               15

Ile Ile Val Asp Asp Leu Arg Pro Ser Leu Gly Cys Tyr Gly Asp Lys
                20               25               30

Leu Val Arg Ser Pro Asn Ile Asp Gln Leu Ala Ser His Ser Leu Leu
        35               40               45

Phe Gln Asn Ala Phe Ala Gln Gln Ala Val Cys Ala Pro Ser Arg Val
        50               55               60

Ser Phe Leu Thr Gly Arg Arg Pro Asp Thr Thr Arg Leu Tyr Asp Phe
65               70               75               80

Asn Ser Tyr Trp Arg Val His Ala Gly Asn Phe Ser Thr Ile Pro Gln
                85               90               95

Tyr Phe Lys Glu Asn Gly Tyr Val Thr Met Ser Val Gly Lys Val Phe
                100               105               110

His Pro Gly Ile Ser Ser Asn His Thr Asp Asp Ser Pro Tyr Ser Trp
        115               120               125

Ser Phe Pro Pro Tyr His Pro Ser Ser Glu Lys Tyr Glu Asn Thr Lys
        130               135               140

Thr Cys Arg Gly Pro Asp Gly Glu Leu His Ala Asn Leu Leu Cys Pro
145               150               155               160
```

-continued

```
Val Asp Val Leu Asp Val Pro Glu Gly Thr Leu Pro Asp Lys Gln Ser
              165             170             175

Thr Glu Gln Ala Ile Gln Leu Leu Glu Lys Met Lys Thr Ser Ala Ser
          180             185             190

Pro Phe Phe Leu Ala Val Gly Tyr His Lys Pro His Ile Pro Phe Arg
          195             200             205

Tyr Pro Lys Glu Phe Gln Lys Leu Tyr Pro Leu Glu Asn Ile Thr Leu
      210             215             220

Ala Pro Asp Pro Glu Val Pro Asp Gly Leu Pro Pro Val Ala Tyr Asn
225             230             235             240

Pro Trp Met Asp Ile Arg Gln Arg Glu Asp Val Gln Ala Leu Asn Ile
              245             250             255

Ser Val Pro Tyr Gly Pro Ile Pro Val Asp Phe Gln Arg Lys Ile Arg
              260             265             270

Gln Ser Tyr Phe Ala Ser Val Ser Tyr Leu Asp Thr Gln Val Gly Arg
      275             280             285

Leu Leu Ser Ala Leu Asp Asp Leu Gln Leu Ala Asn Ser Thr Ile Ile
      290             295             300

Ala Phe Thr Ser Asp His Gly Trp Ala Leu Gly Glu His Gly Glu Trp
305             310             315             320

Ala Lys Tyr Ser Asn Phe Asp Val Ala Thr His Val Pro Leu Ile Phe
              325             330             335

Tyr Val Pro Gly Arg Thr Ala Ser Leu Pro Glu Ala Gly Glu Lys Leu
              340             345             350

Phe Pro Tyr Leu Asp Pro Phe Asp Ser Ala Ser Gln Leu Met Glu Pro
          355             360             365

Gly Arg Gln Ser Met Asp Leu Val Glu Leu Val Ser Leu Phe Pro Thr
      370             375             380

Leu Ala Gly Leu Ala Gly Leu Gln Val Pro Pro Arg Cys Pro Val Pro
385             390             395             400

Ser Phe His Val Glu Leu Cys Arg Glu Gly Lys Asn Leu Leu Lys His
              405             410             415

Phe Arg Phe Arg Asp Leu Glu Glu Asp Pro Tyr Leu Pro Gly Asn Pro
              420             425             430

Arg Glu Leu Ile Ala Tyr Ser Gln Tyr Pro Arg Pro Ser Asp Ile Pro
          435             440             445

Gln Trp Asn Ser Asp Lys Pro Ser Leu Lys Asp Ile Lys Ile Met Gly
      450             455             460

Tyr Ser Ile Arg Thr Ile Asp Tyr Arg Tyr Thr Val Trp Val Gly Phe
465             470             475             480

Asn Pro Asp Glu Phe Leu Ala Asn Phe Ser Asp Ile His Ala Gly Glu
              485             490             495

Leu Tyr Phe Val Asp Ser Asp Pro Leu Gln Asp His Asn Met Tyr Asn
              500             505             510

Asp Ser Gln Gly Gly Asp Leu Phe Gln Leu Leu Met Pro Gly Gly Gly
          515             520             525

Gly Ser Asp Lys Thr His Thr Cys Pro Pro Cys Pro Ala Pro Glu Leu
      530             535             540

Leu Gly Gly Pro Ser Val Phe Leu Phe Pro Pro Lys Pro Lys Asp Thr
545             550             555             560

Leu Met Ile Ser Arg Thr Pro Glu Val Thr Cys Val Val Val Asp Val
              565             570             575

Ser His Glu Asp Pro Glu Val Lys Phe Asn Trp Tyr Val Asp Gly Val
```

-continued

```
                 580                585                590

Glu Val His Asn Ala Lys Thr Lys Pro Arg Glu Glu Gln Tyr Asn Ser
            595                600                605

Thr Tyr Arg Val Val Ser Val Leu Thr Val Leu His Gln Asp Trp Leu
        610                615                620

Asn Gly Lys Glu Tyr Lys Cys Lys Val Ser Asn Lys Ala Leu Pro Ala
625                630                635                640

Pro Ile Glu Lys Thr Ile Ser Lys Ala Lys Gly Gln Pro Arg Glu Pro
                645                650                655

Gln Val Tyr Thr Leu Pro Pro Ser Arg Asp Glu Leu Thr Lys Asn Gln
            660                665                670

Val Ser Leu Trp Cys Leu Val Lys Gly Phe Tyr Pro Ser Asp Ile Ala
            675                680                685

Val Glu Trp Glu Ser Asn Gly Gln Pro Glu Asn Asn Tyr Lys Thr Thr
            690                695                700

Pro Pro Val Leu Asp Ser Asp Gly Ser Phe Phe Leu Tyr Ser Lys Leu
705                710                715                720

Thr Val Asp Lys Ser Arg Trp Gln Gln Gly Asn Val Phe Ser Cys Ser
                725                730                735

Val Met His Glu Ala Leu His Asn His Tyr Thr Gln Lys Ser Leu Ser
                740                745                750

Leu Ser Pro Gly Lys
            755

<210> SEQ ID NO 33
<211> LENGTH: 757
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (59)..(59)
<223> OTHER INFORMATION: formylglycine

<400> SEQUENCE: 33

Ser Glu Thr Gln Ala Asn Ser Thr Thr Asp Ala Leu Asn Val Leu Leu
1               5                10                15

Ile Ile Val Asp Asp Leu Arg Pro Ser Leu Gly Cys Tyr Gly Asp Lys
            20                25                30

Leu Val Arg Ser Pro Asn Ile Asp Gln Leu Ala Ser His Ser Leu Leu
        35                40                45

Phe Gln Asn Ala Phe Ala Gln Gln Ala Val Gly Ala Pro Ser Arg Val
    50                55                60

Ser Phe Leu Thr Gly Arg Arg Pro Asp Thr Thr Arg Leu Tyr Asp Phe
65                70                75                80

Asn Ser Tyr Trp Arg Val His Ala Gly Asn Phe Ser Thr Ile Pro Gln
            85                90                95

Tyr Phe Lys Glu Asn Gly Tyr Val Thr Met Ser Val Gly Lys Val Phe
            100                105                110

His Pro Gly Ile Ser Ser Asn His Thr Asp Asp Ser Pro Tyr Ser Trp
        115                120                125

Ser Phe Pro Pro Tyr His Pro Ser Ser Glu Lys Tyr Glu Asn Thr Lys
        130                135                140

Thr Cys Arg Gly Pro Asp Gly Glu Leu His Ala Asn Leu Leu Cys Pro
145                150                155                160
```

```
Val Asp Val Leu Asp Val Pro Glu Gly Thr Leu Pro Asp Lys Gln Ser
            165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
            195                 200                 205

Tyr Pro Lys Glu Phe Gln Lys Leu Tyr Pro Leu Glu Asn Ile Thr Leu
        210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
                260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
        290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
        370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
            435                 440                 445

Gln Trp Asn Ser Asp Lys Pro Ser Leu Lys Asp Ile Lys Ile Met Gly
        450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro Gly Gly Gly
        515                 520                 525

Gly Ser Asp Lys Thr His Thr Cys Pro Pro Cys Pro Ala Pro Glu Leu
        530                 535                 540

Leu Gly Gly Pro Ser Val Phe Leu Phe Pro Pro Lys Pro Lys Asp Thr
545                 550                 555                 560

Leu Met Ile Ser Arg Thr Pro Glu Val Thr Cys Val Val Val Asp Val
                565                 570                 575
```

-continued

```
Ser His Glu Asp Pro Glu Val Lys Phe Asn Trp Tyr Val Asp Gly Val
            580             585             590

Glu Val His Asn Ala Lys Thr Lys Pro Arg Glu Glu Gln Tyr Asn Ser
            595             600             605

Thr Tyr Arg Val Val Ser Val Leu Thr Val Leu His Gln Asp Trp Leu
            610             615             620

Asn Gly Lys Glu Tyr Lys Cys Lys Val Ser Asn Lys Ala Leu Pro Ala
625             630             635             640

Pro Ile Glu Lys Thr Ile Ser Lys Ala Lys Gly Gln Pro Arg Glu Pro
            645             650             655

Gln Val Tyr Thr Leu Pro Pro Ser Arg Asp Glu Leu Thr Lys Asn Gln
            660             665             670

Val Ser Leu Ser Cys Ala Val Lys Gly Phe Tyr Pro Ser Asp Ile Ala
            675             680             685

Val Glu Trp Glu Ser Asn Gly Gln Pro Glu Asn Asn Tyr Lys Thr Thr
            690             695             700

Pro Pro Val Leu Asp Ser Asp Gly Ser Phe Phe Leu Val Ser Lys Leu
705             710             715             720

Thr Val Asp Lys Ser Arg Trp Gln Gln Gly Asn Val Phe Ser Cys Ser
            725             730             735

Val Met His Glu Ala Leu His Asn His Tyr Thr Gln Lys Ser Leu Ser
            740             745             750

Leu Ser Pro Gly Lys
            755
```

```
<210> SEQ ID NO 34
<211> LENGTH: 757
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (59)..(59)
<223> OTHER INFORMATION: formylglycine

<400> SEQUENCE: 34

Ser Glu Thr Gln Ala Asn Ser Thr Thr Asp Ala Leu Asn Val Leu Leu
1               5               10              15

Ile Ile Val Asp Asp Leu Arg Pro Ser Leu Gly Cys Tyr Gly Asp Lys
            20              25              30

Leu Val Arg Ser Pro Asn Ile Asp Gln Leu Ala Ser His Ser Leu Leu
            35              40              45

Phe Gln Asn Ala Phe Ala Gln Gln Ala Val Gly Ala Pro Ser Arg Val
            50              55              60

Ser Phe Leu Thr Gly Arg Arg Pro Asp Thr Thr Arg Leu Tyr Asp Phe
65              70              75              80

Asn Ser Tyr Trp Arg Val His Ala Gly Asn Phe Ser Thr Ile Pro Gln
                85              90              95

Tyr Phe Lys Glu Asn Gly Tyr Val Thr Met Ser Val Gly Lys Val Phe
            100             105             110

His Pro Gly Ile Ser Ser Asn His Thr Asp Asp Ser Pro Tyr Ser Trp
            115             120             125

Ser Phe Pro Pro Tyr His Pro Ser Ser Glu Lys Tyr Glu Asn Thr Lys
            130             135             140

Thr Cys Arg Gly Pro Asp Gly Glu Leu His Ala Asn Leu Leu Cys Pro
```

```
145                150                155                160

Val Asp Val Leu Asp Val Pro Glu Gly Thr Leu Pro Asp Lys Gln Ser
                 165                170                175

Thr Glu Gln Ala Ile Gln Leu Leu Glu Lys Met Lys Thr Ser Ala Ser
             180                185                190

Pro Phe Phe Leu Ala Val Gly Tyr His Lys Pro His Ile Pro Phe Arg
             195                200                205

Tyr Pro Lys Glu Phe Gln Lys Leu Tyr Pro Leu Glu Asn Ile Thr Leu
     210                215                220

Ala Pro Asp Pro Glu Val Pro Asp Gly Leu Pro Pro Val Ala Tyr Asn
225                230                235                240

Pro Trp Met Asp Ile Arg Gln Arg Glu Asp Val Gln Ala Leu Asn Ile
                 245                250                255

Ser Val Pro Tyr Gly Pro Ile Pro Val Asp Phe Gln Arg Lys Ile Arg
                 260                265                270

Gln Ser Tyr Phe Ala Ser Val Ser Tyr Leu Asp Thr Gln Val Gly Arg
             275                280                285

Leu Leu Ser Ala Leu Asp Asp Leu Gln Leu Ala Asn Ser Thr Ile Ile
     290                295                300

Ala Phe Thr Ser Asp His Gly Trp Ala Leu Gly Glu His Gly Glu Trp
305                310                315                320

Ala Lys Tyr Ser Asn Phe Asp Val Ala Thr His Val Pro Leu Ile Phe
                 325                330                335

Tyr Val Pro Gly Arg Thr Ala Ser Leu Pro Glu Ala Gly Glu Lys Leu
             340                345                350

Phe Pro Tyr Leu Asp Pro Phe Asp Ser Ala Ser Gln Leu Met Glu Pro
             355                360                365

Gly Arg Gln Ser Met Asp Leu Val Glu Leu Val Ser Leu Phe Pro Thr
     370                375                380

Leu Ala Gly Leu Ala Gly Leu Gln Val Pro Pro Arg Cys Pro Val Pro
385                390                395                400

Ser Phe His Val Glu Leu Cys Arg Glu Gly Lys Asn Leu Leu Lys His
                 405                410                415

Phe Arg Phe Arg Asp Leu Glu Glu Asp Pro Tyr Leu Pro Gly Asn Pro
             420                425                430

Arg Glu Leu Ile Ala Tyr Ser Gln Tyr Pro Arg Pro Ser Asp Ile Pro
             435                440                445

Gln Trp Asn Ser Asp Lys Pro Ser Leu Lys Asp Ile Lys Ile Met Gly
     450                455                460

Tyr Ser Ile Arg Thr Ile Asp Tyr Arg Tyr Thr Val Trp Val Gly Phe
465                470                475                480

Asn Pro Asp Glu Phe Leu Ala Asn Phe Ser Asp Ile His Ala Gly Glu
                 485                490                495

Leu Tyr Phe Val Asp Ser Asp Pro Leu Gln Asp His Asn Met Tyr Asn
             500                505                510

Asp Ser Gln Gly Gly Asp Leu Phe Gln Leu Leu Met Pro Gly Gly Gly
             515                520                525

Gly Ser Asp Lys Thr His Thr Cys Pro Pro Cys Pro Ala Pro Glu Leu
     530                535                540

Leu Gly Gly Pro Ser Val Phe Leu Phe Pro Pro Lys Pro Lys Asp Thr
545                550                555                560

Leu Met Ile Ser Arg Thr Pro Glu Val Thr Cys Val Val Val Asp Val
                 565                570                575
```

```
Ser His Glu Asp Pro Glu Val Lys Phe Asn Trp Tyr Val Asp Gly Val
        580                 585                 590

Glu Val His Asn Ala Lys Thr Lys Pro Arg Glu Glu Gln Tyr Asn Ser
        595                 600                 605

Thr Tyr Arg Val Val Ser Val Leu Thr Val Leu His Gln Asp Trp Leu
        610                 615                 620

Asn Gly Lys Glu Tyr Lys Cys Lys Val Ser Asn Lys Ala Leu Pro Ala
625                 630                 635                 640

Pro Ile Glu Lys Thr Ile Ser Lys Ala Lys Gly Gln Pro Arg Glu Pro
                645                 650                 655

Gln Val Tyr Thr Leu Pro Pro Ser Arg Asp Glu Leu Thr Lys Asn Gln
                660                 665                 670

Val Ser Leu Trp Cys Leu Val Lys Gly Phe Tyr Pro Ser Asp Ile Ala
                675                 680                 685

Val Glu Trp Glu Ser Asn Gly Gln Pro Glu Asn Asn Tyr Lys Thr Thr
        690                 695                 700

Pro Pro Val Leu Asp Ser Asp Gly Ser Phe Phe Leu Tyr Ser Lys Leu
705                 710                 715                 720

Thr Val Asp Lys Ser Arg Trp Gln Gln Gly Asn Val Phe Ser Cys Ser
                725                 730                 735

Val Met His Glu Ala Leu His Asn His Tyr Thr Gln Lys Ser Leu Ser
                740                 745                 750

Leu Ser Pro Gly Lys
        755
```

```
<210> SEQ ID NO 35
<211> LENGTH: 181
<212> TYPE: PRT
<213> ORGANISM: Homo sapiens

<400> SEQUENCE: 35

Asn Ser Val Ile Ile Val Asp Lys Asn Gly Arg Leu Val Tyr Leu Val
1                   5                   10                  15

Glu Asn Pro Gly Gly Tyr Val Ala Tyr Ser Lys Ala Ala Thr Val Thr
                20                  25                  30

Gly Lys Leu Val His Ala Asn Phe Gly Thr Lys Lys Asp Phe Glu Asp
        35                  40                  45

Leu Tyr Thr Pro Val Asn Gly Ser Ile Val Ile Val Arg Ala Gly Lys
        50                  55                  60

Ile Thr Phe Ala Glu Lys Val Ala Asn Ala Glu Ser Leu Asn Ala Ile
65                  70                  75                  80

Gly Val Leu Ile Tyr Met Asp Gln Thr Lys Phe Pro Ile Val Asn Ala
                85                  90                  95

Glu Leu Ser Phe Phe Gly His Ala His Leu Gly Thr Gly Asp Pro Tyr
                100                 105                 110

Thr Pro Gly Phe Pro Ser Phe Asn His Thr Gln Phe Pro Pro Ser Arg
        115                 120                 125

Ser Ser Gly Leu Pro Asn Ile Pro Val Gln Thr Ile Ser Arg Ala Ala
        130                 135                 140

Ala Glu Lys Leu Phe Gly Asn Met Glu Gly Asp Cys Pro Ser Asp Trp
145                 150                 155                 160

Lys Thr Asp Ser Thr Cys Arg Met Val Thr Ser Glu Ser Lys Asn Val
                165                 170                 175

Lys Leu Thr Val Ser
```

-continued

```
            180

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Gly Gly Gly Ser
1               5

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Gly Gly Ser Gly Gly Gly Gly Ser
1               5                   10

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 38

His His His His His His
1               5

<210> SEQ ID NO 39
<211> LENGTH: 756
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125
```

```
Ser Phe Pro Pro Tyr His Pro Ser Ser Glu Lys Tyr Glu Asn Thr Lys
    130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
                180                 185                 190

Pro Phe Phe Leu Ala Val Gly Tyr His Lys Pro His Ile Pro Phe Arg
                195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
                260                 265                 270

Gln Ser Tyr Phe Ala Ser Val Ser Tyr Leu Asp Thr Gln Val Gly Arg
    275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
                340                 345                 350

Phe Pro Tyr Leu Asp Pro Phe Asp Ser Ala Ser Gln Leu Met Glu Pro
                355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
                420                 425                 430

Arg Glu Leu Ile Ala Tyr Ser Gln Tyr Pro Arg Pro Ser Asp Ile Pro
    435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
                500                 505                 510

Asp Ser Gln Gly Gly Asp Leu Phe Gln Leu Leu Met Pro Gly Gly Gly
    515                 520                 525

Gly Ser Asp Lys Thr His Thr Cys Pro Pro Cys Pro Ala Pro Glu Ala
    530                 535                 540

Ala Gly Gly Pro Ser Val Phe Leu Phe Pro Pro Lys Pro Lys Asp Thr
```

```
545                 550                 555                 560

Leu Met Ile Ser Arg Thr Pro Glu Val Thr Cys Val Val Val Asp Val
                565                 570                 575

Ser His Glu Asp Pro Glu Val Lys Phe Asn Trp Tyr Val Asp Gly Val
                580                 585                 590

Glu Val His Asn Ala Lys Thr Lys Pro Arg Glu Glu Gln Tyr Asn Ser
                595                 600                 605

Thr Tyr Arg Val Val Ser Val Leu Thr Val Leu His Gln Asp Trp Leu
                610                 615                 620

Asn Gly Lys Glu Tyr Lys Cys Lys Val Ser Asn Lys Ala Leu Pro Ala
625                 630                 635                 640

Pro Ile Glu Lys Thr Ile Ser Lys Ala Lys Gly Gln Pro Arg Glu Pro
                645                 650                 655

Gln Val Tyr Thr Leu Pro Pro Ser Arg Asp Glu Leu Thr Lys Asn Gln
                660                 665                 670

Val Ser Leu Ser Cys Ala Val Lys Gly Phe Tyr Pro Ser Asp Ile Ala
                675                 680                 685

Val Glu Trp Glu Ser Asn Gly Gln Pro Glu Asn Asn Tyr Lys Thr Thr
                690                 695                 700

Pro Pro Val Leu Asp Ser Asp Gly Ser Phe Phe Leu Val Ser Lys Leu
705                 710                 715                 720

Thr Val Asp Lys Ser Arg Trp Gln Gln Gly Asn Val Phe Ser Cys Ser
                725                 730                 735

Val Met His Glu Ala Leu His Asn His Tyr Thr Gln Lys Ser Leu Ser
                740                 745                 750

Leu Ser Pro Gly
                755

<210> SEQ ID NO 40
<211> LENGTH: 756
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (59)..(59)
<223> OTHER INFORMATION: formylglycine

<400> SEQUENCE: 40

Ser Glu Thr Gln Ala Asn Ser Thr Thr Asp Ala Leu Asn Val Leu Leu
1                 5                 10                15

Ile Ile Val Asp Asp Leu Arg Pro Ser Leu Gly Cys Tyr Gly Asp Lys
                20                25                30

Leu Val Arg Ser Pro Asn Ile Asp Gln Leu Ala Ser His Ser Leu Leu
                35                40                45

Phe Gln Asn Ala Phe Ala Gln Gln Ala Val Gly Ala Pro Ser Arg Val
                50                55                60

Ser Phe Leu Thr Gly Arg Arg Pro Asp Thr Thr Arg Leu Tyr Asp Phe
65                70                75                80

Asn Ser Tyr Trp Arg Val His Ala Gly Asn Phe Ser Thr Ile Pro Gln
                85                90                95

Tyr Phe Lys Glu Asn Gly Tyr Val Thr Met Ser Val Gly Lys Val Phe
                100               105               110

His Pro Gly Ile Ser Ser Asn His Thr Asp Asp Ser Pro Tyr Ser Trp
                115               120               125
```

```
Ser Phe Pro Pro Tyr His Pro Ser Ser Glu Lys Tyr Glu Asn Thr Lys
    130             135             140

Thr Cys Arg Gly Pro Asp Gly Glu Leu His Ala Asn Leu Leu Cys Pro
145             150             155             160

Val Asp Val Leu Asp Val Pro Glu Gly Thr Leu Pro Asp Lys Gln Ser
            165             170             175

Thr Glu Gln Ala Ile Gln Leu Leu Glu Lys Met Lys Thr Ser Ala Ser
            180             185             190

Pro Phe Phe Leu Ala Val Gly Tyr His Lys Pro His Ile Pro Phe Arg
            195             200             205

Tyr Pro Lys Glu Phe Gln Lys Leu Tyr Pro Leu Glu Asn Ile Thr Leu
    210             215             220

Ala Pro Asp Pro Glu Val Pro Asp Gly Leu Pro Pro Val Ala Tyr Asn
225             230             235             240

Pro Trp Met Asp Ile Arg Gln Arg Glu Asp Val Gln Ala Leu Asn Ile
            245             250             255

Ser Val Pro Tyr Gly Pro Ile Pro Val Asp Phe Gln Arg Lys Ile Arg
            260             265             270

Gln Ser Tyr Phe Ala Ser Val Ser Tyr Leu Asp Thr Gln Val Gly Arg
    275             280             285

Leu Leu Ser Ala Leu Asp Asp Leu Gln Leu Ala Asn Ser Thr Ile Ile
    290             295             300

Ala Phe Thr Ser Asp His Gly Trp Ala Leu Gly Glu His Gly Glu Trp
305             310             315             320

Ala Lys Tyr Ser Asn Phe Asp Val Ala Thr His Val Pro Leu Ile Phe
            325             330             335

Tyr Val Pro Gly Arg Thr Ala Ser Leu Pro Glu Ala Gly Glu Lys Leu
            340             345             350

Phe Pro Tyr Leu Asp Pro Phe Asp Ser Ala Ser Gln Leu Met Glu Pro
            355             360             365

Gly Arg Gln Ser Met Asp Leu Val Glu Leu Val Ser Leu Phe Pro Thr
    370             375             380

Leu Ala Gly Leu Ala Gly Leu Gln Val Pro Pro Arg Cys Pro Val Pro
385             390             395             400

Ser Phe His Val Glu Leu Cys Arg Glu Gly Lys Asn Leu Leu Lys His
            405             410             415

Phe Arg Phe Arg Asp Leu Glu Glu Asp Pro Tyr Leu Pro Gly Asn Pro
            420             425             430

Arg Glu Leu Ile Ala Tyr Ser Gln Tyr Pro Arg Pro Ser Asp Ile Pro
    435             440             445

Gln Trp Asn Ser Asp Lys Pro Ser Leu Lys Asp Ile Lys Ile Met Gly
    450             455             460

Tyr Ser Ile Arg Thr Ile Asp Tyr Arg Tyr Thr Val Trp Val Gly Phe
465             470             475             480

Asn Pro Asp Glu Phe Leu Ala Asn Phe Ser Asp Ile His Ala Gly Glu
            485             490             495

Leu Tyr Phe Val Asp Ser Asp Pro Leu Gln Asp His Asn Met Tyr Asn
            500             505             510

Asp Ser Gln Gly Gly Asp Leu Phe Gln Leu Leu Met Pro Gly Gly Gly
    515             520             525

Gly Ser Asp Lys Thr His Thr Cys Pro Pro Cys Pro Ala Pro Glu Ala
    530             535             540
```

-continued

```
Ala Gly Gly Pro Ser Val Phe Leu Phe Pro Pro Lys Pro Lys Asp Thr
545             550             555             560

Leu Met Ile Ser Arg Thr Pro Glu Val Thr Cys Val Val Val Asp Val
                565             570             575

Ser His Glu Asp Pro Glu Val Lys Phe Asn Trp Tyr Val Asp Gly Val
            580             585             590

Glu Val His Asn Ala Lys Thr Lys Pro Arg Glu Glu Gln Tyr Asn Ser
        595             600             605

Thr Tyr Arg Val Val Ser Val Leu Thr Val Leu His Gln Asp Trp Leu
    610             615             620

Asn Gly Lys Glu Tyr Lys Cys Lys Val Ser Asn Lys Ala Leu Pro Ala
625             630             635             640

Pro Ile Glu Lys Thr Ile Ser Lys Ala Lys Gly Gln Pro Arg Glu Pro
                645             650             655

Gln Val Tyr Thr Leu Pro Pro Ser Arg Asp Glu Leu Thr Lys Asn Gln
                660             665             670

Val Ser Leu Ser Cys Ala Val Lys Gly Phe Tyr Pro Ser Asp Ile Ala
            675             680             685

Val Glu Trp Glu Ser Asn Gly Gln Pro Glu Asn Asn Tyr Lys Thr Thr
    690             695             700

Pro Pro Val Leu Asp Ser Asp Gly Ser Phe Phe Leu Val Ser Lys Leu
705             710             715             720

Thr Val Asp Lys Ser Arg Trp Gln Gln Gly Asn Val Phe Ser Cys Ser
                725             730             735

Val Met His Glu Ala Leu His Asn His Tyr Thr Gln Lys Ser Leu Ser
            740             745             750

Leu Ser Pro Gly
        755

<210> SEQ ID NO 41
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ala Pro Glu Ala Ala Gly Gly Pro Ser Val Phe Leu Phe Pro Pro Lys
1               5               10              15

Pro Lys Asp Thr Leu Met Ile Ser Arg Thr Pro Glu Val Thr Cys Val
            20              25              30

Val Val Asp Val Ser His Glu Asp Pro Glu Val Lys Phe Asn Trp Tyr
        35              40              45

Val Asp Gly Val Glu Val His Asn Ala Lys Thr Lys Pro Arg Glu Glu
    50              55              60

Gln Tyr Asn Ser Thr Tyr Arg Val Val Ser Val Leu Thr Val Leu His
65              70              75              80

Gln Asp Trp Leu Asn Gly Lys Glu Tyr Lys Cys Lys Val Ser Asn Lys
                85              90              95

Ala Leu Pro Ala Pro Ile Glu Lys Thr Ile Ser Lys Ala Lys Gly Gln
            100             105             110

Pro Arg Glu Pro Gln Val Tyr Thr Leu Pro Pro Ser Arg Asp Glu Leu
        115             120             125

Thr Lys Asn Gln Val Ser Leu Trp Cys Leu Val Lys Gly Phe Tyr Pro
    130             135             140
```

-continued

Ser Asp Ile Ala Val Leu Trp Glu Ser Tyr Gly Thr Glu Trp Ser Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
            180                 185                 190

Phe Ser Cys Ser Val Met His Glu Ala Leu His Asn His Tyr Thr Gln
            195                 200                 205

Lys Ser Leu Ser Leu Ser Pro Gly
        210                 215

<210> SEQ ID NO 42
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Lys Thr His Thr Cys Pro Pro Cys Pro Ala Pro Glu Ala Ala Gly
1                 5                 10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Tyr Gly Thr Glu Trp Ala Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Thr Lys Glu Glu Trp Gln Gln Gly Phe Val Phe Ser Cys Ser Val Met
            195                 200                 205

His Glu Ala Leu His Asn His Tyr Thr Gln Lys Ser Leu Ser Leu Ser
        210                 215                 220

Pro Gly
225

<210> SEQ ID NO 43
<211> LENGTH: 756
<212> TYPE: PRT
<213> ORGANISM: Artificial Sequence
<220> FEATURE:
<223> OTHER INFORMATION: Description of Artificial Sequence: Synthetic -continued

```
      polypeptide

<400> SEQUENCE: 43

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
    130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
            165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
            245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
            325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400
```

```
Ser Phe His Val Glu Leu Cys Arg Glu Gly Lys Asn Leu Leu Lys His
            405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
            435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
            485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro Gly Gly Gly
            515                 520                 525

Gly Ser Asp Lys Thr His Thr Cys Pro Pro Cys Pro Ala Pro Glu Ala
    530                 535                 540

Ala Gly Gly Pro Ser Val Phe Leu Phe Pro Pro Lys Pro Lys Asp Thr
545                 550                 555                 560

Leu Met Ile Ser Arg Thr Pro Glu Val Thr Cys Val Val Val Asp Val
            565                 570                 575

Ser His Glu Asp Pro Glu Val Lys Phe Asn Trp Tyr Val Asp Gly Val
            580                 585                 590

Glu Val His Asn Ala Lys Thr Lys Pro Arg Glu Glu Gln Tyr Asn Ser
            595                 600                 605

Thr Tyr Arg Val Val Ser Val Leu Thr Val Leu His Gln Asp Trp Leu
    610                 615                 620

Asn Gly Lys Glu Tyr Lys Cys Lys Val Ser Asn Lys Ala Leu Pro Ala
625                 630                 635                 640

Pro Ile Glu Lys Thr Ile Ser Lys Ala Lys Gly Gln Pro Arg Glu Pro
            645                 650                 655

Gln Val Tyr Thr Leu Pro Pro Ser Arg Asp Glu Leu Thr Lys Asn Gln
            660                 665                 670

Val Ser Leu Ser Cys Ala Val Lys Gly Phe Tyr Pro Ser Asp Ile Ala
            675                 680                 685

Val Glu Trp Glu Ser Asn Gly Gln Pro Glu Asn Asn Tyr Lys Thr Thr
    690                 695                 700

Pro Pro Val Leu Asp Ser Asp Gly Ser Phe Phe Leu Val Ser Lys Leu
705                 710                 715                 720

Thr Val Asp Lys Ser Arg Trp Gln Gln Gly Asn Val Phe Ser Cys Ser
            725                 730                 735

Val Met His Glu Ala Leu His Asn His Tyr Thr Gln Lys Ser Leu Ser
            740                 745                 750

Leu Ser Pro Gly
        755
```

<210> SEQ ID NO 44
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Trp Cys Leu Val Lys Gly Phe Tyr Pro Ser Asp Ile Ala Val Trp
145                 150                 155                 160

Trp Glu Ser Tyr Gly Thr Glu Trp Ser Ser Tyr Lys Thr Thr Pro Pro
                165                 170                 175

Val Leu Asp Ser Asp Gly Ser Phe Phe Leu Tyr Ser Lys Leu Thr Val
                180                 185                 190

Thr Lys Glu Glu Trp Gln Gln Gly Phe Val Phe Ser Cys Ser Val Met
            195                 200                 205

His Glu Ala Leu His Asn His Tyr Thr Gln Lys Ser Leu Ser Leu Ser
        210                 215                 220

Pro Gly
225
```

```
<210> SEQ ID NO 45
<211> LENGTH: 756
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45
```

```
Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
                20                  25                  30

Leu Val Arg Ser Pro Asn Ile Asp Gln Leu Ala Ser His Ser Leu Leu
            35                  40                  45

Phe Gln Asn Ala Phe Ala Gln Gln Ala Val Cys Ala Pro Ser Arg Val
        50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
                100                 105                 110

His Pro Gly Ile Ser Ser Asn His Thr Asp Asp Ser Pro Tyr Ser Trp
```

```
            115                 120                 125
Ser Phe Pro Pro Tyr His Pro Ser Ser Glu Lys Tyr Glu Asn Thr Lys
    130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
            195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
            245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
    275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
            325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
            405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
            435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro Gly Gly Gly
            515                 520                 525

Gly Ser Asp Lys Thr His Thr Cys Pro Pro Cys Pro Ala Pro Glu Leu
    530                 535                 540
```

```
Leu Gly Gly Pro Ser Val Phe Leu Phe Pro Pro Lys Pro Lys Asp Thr
545             550             555             560

Leu Met Ile Ser Arg Thr Pro Glu Val Thr Cys Val Val Val Asp Val
            565             570             575

Ser His Glu Asp Pro Glu Val Lys Phe Asn Trp Tyr Val Asp Gly Val
            580             585             590

Glu Val His Asn Ala Lys Thr Lys Pro Arg Glu Glu Gln Tyr Asn Ser
            595             600             605

Thr Tyr Arg Val Val Ser Val Leu Thr Val Leu His Gln Asp Trp Leu
            610             615             620

Asn Gly Lys Glu Tyr Lys Cys Lys Val Ser Asn Lys Ala Leu Pro Ala
625             630             635             640

Pro Ile Glu Lys Thr Ile Ser Lys Ala Lys Gly Gln Pro Arg Glu Pro
            645             650             655

Gln Val Tyr Thr Leu Pro Pro Ser Arg Asp Glu Leu Thr Lys Asn Gln
            660             665             670

Val Ser Leu Ser Cys Ala Val Lys Gly Phe Tyr Pro Ser Asp Ile Ala
            675             680             685

Val Glu Trp Glu Ser Asn Gly Gln Pro Glu Asn Asn Tyr Lys Thr Thr
            690             695             700

Pro Pro Val Leu Asp Ser Asp Gly Ser Phe Phe Leu Val Ser Lys Leu
705             710             715             720

Thr Val Asp Lys Ser Arg Trp Gln Gln Gly Asn Val Phe Ser Cys Ser
            725             730             735

Val Met His Glu Ala Leu His Asn His Tyr Thr Gln Lys Ser Leu Ser
            740             745             750

Leu Ser Pro Gly
            755
```

```
<210> SEQ ID NO 46
<211> LENGTH: 756
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ser Glu Thr Gln Ala Asn Ser Thr Thr Asp Ala Leu Asn Val Leu Leu
1               5               10              15

Ile Ile Val Asp Asp Leu Arg Pro Ser Leu Gly Cys Tyr Gly Asp Lys
            20              25              30

Leu Val Arg Ser Pro Asn Ile Asp Gln Leu Ala Ser His Ser Leu Leu
        35              40              45

Phe Gln Asn Ala Phe Ala Gln Gln Ala Val Cys Ala Pro Ser Arg Val
    50              55              60

Ser Phe Leu Thr Gly Arg Arg Pro Asp Thr Thr Arg Leu Tyr Asp Phe
65              70              75              80

Asn Ser Tyr Trp Arg Val His Ala Gly Asn Phe Ser Thr Ile Pro Gln
            85              90              95

Tyr Phe Lys Glu Asn Gly Tyr Val Thr Met Ser Val Gly Lys Val Phe
            100             105             110

His Pro Gly Ile Ser Ser Asn His Thr Asp Asp Ser Pro Tyr Ser Trp
        115             120             125

Ser Phe Pro Pro Tyr His Pro Ser Ser Glu Lys Tyr Glu Asn Thr Lys
```

```
        130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
                180                 185                 190

Pro Phe Phe Leu Ala Val Gly Tyr His Lys Pro His Ile Pro Phe Arg
                195                 200                 205

Tyr Pro Lys Glu Phe Gln Lys Leu Tyr Pro Leu Glu Asn Ile Thr Leu
        210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
                260                 265                 270

Gln Ser Tyr Phe Ala Ser Val Ser Tyr Leu Asp Thr Gln Val Gly Arg
                275                 280                 285

Leu Leu Ser Ala Leu Asp Asp Leu Gln Leu Ala Asn Ser Thr Ile Ile
        290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
                340                 345                 350

Phe Pro Tyr Leu Asp Pro Phe Asp Ser Ala Ser Gln Leu Met Glu Pro
                355                 360                 365

Gly Arg Gln Ser Met Asp Leu Val Glu Leu Val Ser Leu Phe Pro Thr
        370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
                420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
        450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
                500                 505                 510

Asp Ser Gln Gly Gly Asp Leu Phe Gln Leu Leu Met Pro Gly Gly Gly
        515                 520                 525

Gly Ser Asp Lys Thr His Thr Cys Pro Pro Cys Pro Ala Pro Glu Leu
        530                 535                 540

Leu Gly Gly Pro Ser Val Phe Leu Phe Pro Pro Lys Pro Lys Asp Thr
545                 550                 555                 560
```

```
Leu Met Ile Ser Arg Thr Pro Glu Val Thr Cys Val Val Val Asp Val
            565             570             575

Ser His Glu Asp Pro Glu Val Lys Phe Asn Trp Tyr Val Asp Gly Val
            580             585             590

Glu Val His Asn Ala Lys Thr Lys Pro Arg Glu Glu Gln Tyr Asn Ser
            595             600             605

Thr Tyr Arg Val Val Ser Val Leu Thr Val Leu His Gln Asp Trp Leu
            610             615             620

Asn Gly Lys Glu Tyr Lys Cys Lys Val Ser Asn Lys Ala Leu Pro Ala
625             630             635             640

Pro Ile Glu Lys Thr Ile Ser Lys Ala Lys Gly Gln Pro Arg Glu Pro
            645             650             655

Gln Val Tyr Thr Leu Pro Pro Ser Arg Asp Glu Leu Thr Lys Asn Gln
            660             665             670

Val Ser Leu Trp Cys Leu Val Lys Gly Phe Tyr Pro Ser Asp Ile Ala
            675             680             685

Val Glu Trp Glu Ser Asn Gly Gln Pro Glu Asn Asn Tyr Lys Thr Thr
            690             695             700

Pro Pro Val Leu Asp Ser Asp Gly Ser Phe Phe Leu Tyr Ser Lys Leu
705             710             715             720

Thr Val Asp Lys Ser Arg Trp Gln Gln Gly Asn Val Phe Ser Cys Ser
            725             730             735

Val Met His Glu Ala Leu His Asn His Tyr Thr Gln Lys Ser Leu Ser
            740             745             750

Leu Ser Pro Gly
            755

<210> SEQ ID NO 47
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ala Pro Glu Ala Ala Gly Gly Pro Ser Val Phe Leu Phe Pro Pro Lys
1               5               10              15

Pro Lys Asp Thr Leu Met Ile Ser Arg Thr Pro Glu Val Thr Cys Val
            20              25              30

Val Val Asp Val Ser His Glu Asp Pro Glu Val Lys Phe Asn Trp Tyr
            35              40              45

Val Asp Gly Val Glu Val His Asn Ala Lys Thr Lys Pro Arg Glu Glu
            50              55              60

Gln Tyr Asn Ser Thr Tyr Arg Val Val Ser Val Leu Thr Val Leu His
65              70              75              80

Gln Asp Trp Leu Asn Gly Lys Glu Tyr Lys Cys Lys Val Ser Asn Lys
            85              90              95

Ala Leu Pro Ala Pro Ile Glu Lys Thr Ile Ser Lys Ala Lys Gly Gln
            100             105             110

Pro Arg Glu Pro Gln Val Tyr Thr Leu Pro Pro Ser Arg Asp Glu Leu
            115             120             125

Thr Lys Asn Gln Val Ser Leu Trp Cys Leu Val Lys Gly Phe Tyr Pro
            130             135             140

Ser Asp Ile Ala Val Glu Trp Glu Ser Tyr Gly Thr Glu Trp Ala Asn
```

```
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
                180                 185                 190

Phe Ser Cys Ser Val Met His Glu Ala Leu His Asn His Tyr Thr Gln
                195                 200                 205

Lys Ser Leu Ser Leu Ser Pro Gly
    210                 215

<210> SEQ ID NO 48
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
                35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Asp Glu Leu
                115                 120                 125

Thr Lys Asn Gln Val Ser Leu Trp Cys Leu Val Lys Gly Phe Tyr Pro
    130                 135                 140

Ser Asp Ile Ala Val Leu Trp Glu Ser Tyr Gly Thr Glu Trp Ala Ser
145                 150                 155                 160

Tyr Lys Thr Thr Pro Pro Val Leu Asp Ser Asp Gly Ser Phe Phe Leu
                165                 170                 175

Tyr Ser Lys Leu Thr Val Thr Lys Glu Glu Trp Gln Gln Gly Phe Val
                180                 185                 190

Phe Ser Cys Ser Val Met His Glu Ala Leu His Asn His Tyr Thr Gln
                195                 200                 205

Lys Ser Leu Ser Leu Ser Pro Gly
    210                 215

<210> SEQ ID NO 49
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Lys Thr His Thr Cys Pro Pro Cys Pro Ala Pro Glu Ala Ala Gly
```

```
1               5               10              15

Gly Pro Ser Val Phe Leu Phe Pro Pro Lys Pro Lys Asp Thr Leu Met
            20              25              30

Ile Ser Arg Thr Pro Glu Val Thr Cys Val Val Val Asp Val Ser His
            35              40              45

Glu Asp Pro Glu Val Lys Phe Asn Trp Tyr Val Asp Gly Val Glu Val
    50              55              60

His Asn Ala Lys Thr Lys Pro Arg Glu Glu Gln Tyr Asn Ser Thr Tyr
65              70              75              80

Arg Val Val Ser Val Leu Thr Val Leu His Gln Asp Trp Leu Asn Gly
            85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Gln Val
            115             120             125

Tyr Thr Leu Pro Pro Ser Arg Asp Glu Leu Thr Lys Asn Gln Val Ser
    130             135             140

Leu Trp Cys Leu Val Lys Gly Phe Tyr Pro Ser Asp Ile Ala Val Leu
145             150             155             160

Trp Glu Ser Tyr Gly Thr Glu Trp Ala Ser Tyr Lys Thr Thr Pro Pro
            165             170             175

Val Leu Asp Ser Asp Gly Ser Phe Phe Leu Tyr Ser Lys Leu Thr Val
            180             185             190

Thr Lys Glu Glu Trp Gln Gln Gly Phe Val Phe Ser Cys Ser Val Met
            195             200             205

His Glu Ala Leu His Asn His Tyr Thr Gln Lys Ser Leu Ser Leu Ser
    210             215             220

Pro Gly
225

<210> SEQ ID NO 50
<211> LENGTH: 756
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ser Glu Thr Gln Ala Asn Ser Thr Thr Asp Ala Leu Asn Val Leu Leu
1               5               10              15

Ile Ile Val Asp Asp Leu Arg Pro Ser Leu Gly Cys Tyr Gly Asp Lys
            20              25              30

Leu Val Arg Ser Pro Asn Ile Asp Gln Leu Ala Ser His Ser Leu Leu
            35              40              45

Phe Gln Asn Ala Phe Ala Gln Gln Ala Val Cys Ala Pro Ser Arg Val
    50              55              60

Ser Phe Leu Thr Gly Arg Arg Pro Asp Thr Thr Arg Leu Tyr Asp Phe
65              70              75              80

Asn Ser Tyr Trp Arg Val His Ala Gly Asn Phe Ser Thr Ile Pro Gln
            85              90              95

Tyr Phe Lys Glu Asn Gly Tyr Val Thr Met Ser Val Gly Lys Val Phe
            100             105             110

His Pro Gly Ile Ser Ser Asn His Thr Asp Asp Ser Pro Tyr Ser Trp
            115             120             125
```

```
Ser Phe Pro Pro Tyr His Pro Ser Ser Glu Lys Tyr Glu Asn Thr Lys
    130             135             140

Thr Cys Arg Gly Pro Asp Gly Glu Leu His Ala Asn Leu Leu Cys Pro
145             150             155             160

Val Asp Val Leu Asp Val Pro Glu Gly Thr Leu Pro Asp Lys Gln Ser
                165             170             175

Thr Glu Gln Ala Ile Gln Leu Leu Glu Lys Met Lys Thr Ser Ala Ser
            180             185             190

Pro Phe Phe Leu Ala Val Gly Tyr His Lys Pro His Ile Pro Phe Arg
        195             200             205

Tyr Pro Lys Glu Phe Gln Lys Leu Tyr Pro Leu Glu Asn Ile Thr Leu
    210             215             220

Ala Pro Asp Pro Glu Val Pro Asp Gly Leu Pro Pro Val Ala Tyr Asn
225             230             235             240

Pro Trp Met Asp Ile Arg Gln Arg Glu Asp Val Gln Ala Leu Asn Ile
            245             250             255

Ser Val Pro Tyr Gly Pro Ile Pro Val Asp Phe Gln Arg Lys Ile Arg
            260             265             270

Gln Ser Tyr Phe Ala Ser Val Ser Tyr Leu Asp Thr Gln Val Gly Arg
        275             280             285

Leu Leu Ser Ala Leu Asp Asp Leu Gln Leu Ala Asn Ser Thr Ile Ile
    290             295             300

Ala Phe Thr Ser Asp His Gly Trp Ala Leu Gly Glu His Gly Glu Trp
305             310             315             320

Ala Lys Tyr Ser Asn Phe Asp Val Ala Thr His Val Pro Leu Ile Phe
            325             330             335

Tyr Val Pro Gly Arg Thr Ala Ser Leu Pro Glu Ala Gly Glu Lys Leu
            340             345             350

Phe Pro Tyr Leu Asp Pro Phe Asp Ser Ala Ser Gln Leu Met Glu Pro
        355             360             365

Gly Arg Gln Ser Met Asp Leu Val Glu Leu Val Ser Leu Phe Pro Thr
    370             375             380

Leu Ala Gly Leu Ala Gly Leu Gln Val Pro Pro Arg Cys Pro Val Pro
385             390             395             400

Ser Phe His Val Glu Leu Cys Arg Glu Gly Lys Asn Leu Leu Lys His
            405             410             415

Phe Arg Phe Arg Asp Leu Glu Glu Asp Pro Tyr Leu Pro Gly Asn Pro
        420             425             430

Arg Glu Leu Ile Ala Tyr Ser Gln Tyr Pro Arg Pro Ser Asp Ile Pro
    435             440             445

Gln Trp Asn Ser Asp Lys Pro Ser Leu Lys Asp Ile Lys Ile Met Gly
    450             455             460

Tyr Ser Ile Arg Thr Ile Asp Tyr Arg Tyr Thr Val Trp Val Gly Phe
465             470             475             480

Asn Pro Asp Glu Phe Leu Ala Asn Phe Ser Asp Ile His Ala Gly Glu
                485             490             495

Leu Tyr Phe Val Asp Ser Asp Pro Leu Gln Asp His Asn Met Tyr Asn
            500             505             510

Asp Ser Gln Gly Gly Asp Leu Phe Gln Leu Leu Met Pro Gly Gly Gly
        515             520             525

Gly Ser Asp Lys Thr His Thr Cys Pro Pro Cys Pro Ala Pro Glu Leu
    530             535             540

Leu Gly Gly Pro Ser Val Phe Leu Phe Pro Pro Lys Pro Lys Asp Thr
```

```
545               550               555               560

Leu Met Ile Ser Arg Thr Pro Glu Val Thr Cys Val Val Val Asp Val
            565               570               575

Ser His Glu Asp Pro Glu Val Lys Phe Asn Trp Tyr Val Asp Gly Val
            580               585               590

Glu Val His Asn Ala Lys Thr Lys Pro Arg Glu Glu Gln Tyr Asn Ser
            595               600               605

Thr Tyr Arg Val Val Ser Val Leu Thr Val Leu His Gln Asp Trp Leu
            610               615               620

Asn Gly Lys Glu Tyr Lys Cys Lys Val Ser Asn Lys Ala Leu Pro Ala
625               630               635               640

Pro Ile Glu Lys Thr Ile Ser Lys Ala Lys Gly Gln Pro Arg Glu Pro
                645               650               655

Gln Val Tyr Thr Leu Pro Pro Ser Arg Asp Glu Leu Thr Lys Asn Gln
            660               665               670

Val Ser Leu Ser Cys Ala Val Lys Gly Phe Tyr Pro Ser Asp Ile Ala
            675               680               685

Val Glu Trp Glu Ser Asn Gly Gln Pro Glu Asn Asn Tyr Lys Thr Thr
            690               695               700

Pro Pro Val Leu Asp Ser Asp Gly Ser Phe Phe Leu Val Ser Lys Leu
705               710               715               720

Thr Val Asp Lys Ser Arg Trp Gln Gln Gly Asn Val Phe Ser Cys Ser
                725               730               735

Val Met His Glu Ala Leu His Asn His Tyr Thr Gln Lys Ser Leu Ser
                740               745               750

Leu Ser Pro Gly
            755

<210> SEQ ID NO 51
<211> LENGTH: 756
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ser Glu Thr Gln Ala Asn Ser Thr Thr Asp Ala Leu Asn Val Leu Leu
1               5               10               15

Ile Ile Val Asp Asp Leu Arg Pro Ser Leu Gly Cys Tyr Gly Asp Lys
            20               25               30

Leu Val Arg Ser Pro Asn Ile Asp Gln Leu Ala Ser His Ser Leu Leu
            35               40               45

Phe Gln Asn Ala Phe Ala Gln Gln Ala Val Cys Ala Pro Ser Arg Val
            50               55               60

Ser Phe Leu Thr Gly Arg Arg Pro Asp Thr Thr Arg Leu Tyr Asp Phe
65               70               75               80

Asn Ser Tyr Trp Arg Val His Ala Gly Asn Phe Ser Thr Ile Pro Gln
                85               90               95

Tyr Phe Lys Glu Asn Gly Tyr Val Thr Met Ser Val Gly Lys Val Phe
            100               105               110

His Pro Gly Ile Ser Ser Asn His Thr Asp Asp Ser Pro Tyr Ser Trp
            115               120               125

Ser Phe Pro Pro Tyr His Pro Ser Ser Glu Lys Tyr Glu Asn Thr Lys
            130               135               140
```

-continued

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
                180                 185                 190

Pro Phe Phe Leu Ala Val Gly Tyr His Lys Pro His Ile Pro Phe Arg
                195                 200                 205

Tyr Pro Lys Glu Phe Gln Lys Leu Tyr Pro Leu Glu Asn Ile Thr Leu
        210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
                260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
        290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
                340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
        370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
                420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
        450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
                500                 505                 510

Asp Ser Gln Gly Gly Asp Leu Phe Gln Leu Leu Met Pro Gly Gly Gly
        515                 520                 525

Gly Ser Asp Lys Thr His Thr Cys Pro Pro Cys Pro Ala Pro Glu Leu
        530                 535                 540

Leu Gly Gly Pro Ser Val Phe Leu Phe Pro Pro Lys Pro Lys Asp Thr
545                 550                 555                 560

Leu Met Ile Ser Arg Thr Pro Glu Val Thr Cys Val Val Val Asp Val

-continued

```
                    565                     570                     575
Ser His Glu Asp Pro Glu Val Lys Phe Asn Trp Tyr Val Asp Gly Val
            580                     585                     590

Glu Val His Asn Ala Lys Thr Lys Pro Arg Glu Glu Gln Tyr Asn Ser
            595                     600                     605

Thr Tyr Arg Val Val Ser Val Leu Thr Val Leu His Gln Asp Trp Leu
        610                     615                     620

Asn Gly Lys Glu Tyr Lys Cys Lys Val Ser Asn Lys Ala Leu Pro Ala
625                     630                     635                     640

Pro Ile Glu Lys Thr Ile Ser Lys Ala Lys Gly Gln Pro Arg Glu Pro
                    645                     650                     655

Gln Val Tyr Thr Leu Pro Pro Ser Arg Asp Glu Leu Thr Lys Asn Gln
                660                     665                     670

Val Ser Leu Trp Cys Leu Val Lys Gly Phe Tyr Pro Ser Asp Ile Ala
                675                     680                     685

Val Glu Trp Glu Ser Asn Gly Gln Pro Glu Asn Asn Tyr Lys Thr Thr
        690                     695                     700

Pro Pro Val Leu Asp Ser Asp Gly Ser Phe Phe Leu Tyr Ser Lys Leu
705                     710                     715                     720

Thr Val Asp Lys Ser Arg Trp Gln Gln Gly Asn Val Phe Ser Cys Ser
                725                     730                     735

Val Met His Glu Ala Leu His Asn His Tyr Thr Gln Lys Ser Leu Ser
                740                     745                     750

Leu Ser Pro Gly
            755
```

<210> SEQ ID NO 52
<211> LENGTH: 756
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (59)..(59)
<223> OTHER INFORMATION: formylglycine

<400> SEQUENCE: 52

```
Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Gly Ala Pro Ser Arg Val
        50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
        130                 135                 140
```

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
            195                 200                 205

Tyr Pro Lys Glu Phe Gln Lys Leu Tyr Pro Leu Glu Asn Ile Thr Leu
        210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
            245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
        290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
            325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
        370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
            405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
        450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
            485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro Gly Gly Gly
        515                 520                 525

Gly Ser Asp Lys Thr His Thr Cys Pro Pro Cys Pro Ala Pro Glu Leu
        530                 535                 540

Leu Gly Gly Pro Ser Val Phe Leu Phe Pro Pro Lys Pro Lys Asp Thr
545                 550                 555                 560

-continued

```
Leu Met Ile Ser Arg Thr Pro Glu Val Thr Cys Val Val Val Asp Val
            565             570             575

Ser His Glu Asp Pro Glu Val Lys Phe Asn Trp Tyr Val Asp Gly Val
        580             585             590

Glu Val His Asn Ala Lys Thr Lys Pro Arg Glu Glu Gln Tyr Asn Ser
        595             600             605

Thr Tyr Arg Val Val Ser Val Leu Thr Val Leu His Gln Asp Trp Leu
        610             615             620

Asn Gly Lys Glu Tyr Lys Cys Lys Val Ser Asn Lys Ala Leu Pro Ala
625             630             635             640

Pro Ile Glu Lys Thr Ile Ser Lys Ala Lys Gly Gln Pro Arg Glu Pro
            645             650             655

Gln Val Tyr Thr Leu Pro Pro Ser Arg Asp Glu Leu Thr Lys Asn Gln
            660             665             670

Val Ser Leu Ser Cys Ala Val Lys Gly Phe Tyr Pro Ser Asp Ile Ala
            675             680             685

Val Glu Trp Glu Ser Asn Gly Gln Pro Glu Asn Asn Tyr Lys Thr Thr
            690             695             700

Pro Pro Val Leu Asp Ser Asp Gly Ser Phe Phe Leu Val Ser Lys Leu
705             710             715             720

Thr Val Asp Lys Ser Arg Trp Gln Gln Gly Asn Val Phe Ser Cys Ser
            725             730             735

Val Met His Glu Ala Leu His Asn His Tyr Thr Gln Lys Ser Leu Ser
            740             745             750

Leu Ser Pro Gly
            755
```

```
<210> SEQ ID NO 53
<211> LENGTH: 756
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (59)..(59)
<223> OTHER INFORMATION: formylglycine

<400> SEQUENCE: 53
```

```
Ser Glu Thr Gln Ala Asn Ser Thr Thr Asp Ala Leu Asn Val Leu Leu
1               5               10              15

Ile Ile Val Asp Asp Leu Arg Pro Ser Leu Gly Cys Tyr Gly Asp Lys
            20              25              30

Leu Val Arg Ser Pro Asn Ile Asp Gln Leu Ala Ser His Ser Leu Leu
        35              40              45

Phe Gln Asn Ala Phe Ala Gln Gln Ala Val Gly Ala Pro Ser Arg Val
        50              55              60

Ser Phe Leu Thr Gly Arg Arg Pro Asp Thr Thr Arg Leu Tyr Asp Phe
65              70              75              80

Asn Ser Tyr Trp Arg Val His Ala Gly Asn Phe Ser Thr Ile Pro Gln
            85              90              95

Tyr Phe Lys Glu Asn Gly Tyr Val Thr Met Ser Val Gly Lys Val Phe
            100             105             110

His Pro Gly Ile Ser Ser Asn His Thr Asp Asp Ser Pro Tyr Ser Trp
            115             120             125

Ser Phe Pro Pro Tyr His Pro Ser Ser Glu Lys Tyr Glu Asn Thr Lys
```

```
                 130                    135                    140

Thr Cys Arg Gly Pro Asp Gly Glu Leu His Ala Asn Leu Leu Cys Pro
145                 150                    155                    160

Val Asp Val Leu Asp Val Pro Glu Gly Thr Leu Pro Asp Lys Gln Ser
                 165                    170                    175

Thr Glu Gln Ala Ile Gln Leu Leu Glu Lys Met Lys Thr Ser Ala Ser
                 180                    185                    190

Pro Phe Phe Leu Ala Val Gly Tyr His Lys Pro His Ile Pro Phe Arg
                 195                    200                    205

Tyr Pro Lys Glu Phe Gln Lys Leu Tyr Pro Leu Glu Asn Ile Thr Leu
                 210                    215                    220

Ala Pro Asp Pro Glu Val Pro Asp Gly Leu Pro Pro Val Ala Tyr Asn
225                 230                    235                    240

Pro Trp Met Asp Ile Arg Gln Arg Glu Asp Val Gln Ala Leu Asn Ile
                 245                    250                    255

Ser Val Pro Tyr Gly Pro Ile Pro Val Asp Phe Gln Arg Lys Ile Arg
                 260                    265                    270

Gln Ser Tyr Phe Ala Ser Val Ser Tyr Leu Asp Thr Gln Val Gly Arg
                 275                    280                    285

Leu Leu Ser Ala Leu Asp Asp Leu Gln Leu Ala Asn Ser Thr Ile Ile
                 290                    295                    300

Ala Phe Thr Ser Asp His Gly Trp Ala Leu Gly Glu His Gly Glu Trp
305                 310                    315                    320

Ala Lys Tyr Ser Asn Phe Asp Val Ala Thr His Val Pro Leu Ile Phe
                 325                    330                    335

Tyr Val Pro Gly Arg Thr Ala Ser Leu Pro Glu Ala Gly Glu Lys Leu
                 340                    345                    350

Phe Pro Tyr Leu Asp Pro Phe Asp Ser Ala Ser Gln Leu Met Glu Pro
                 355                    360                    365

Gly Arg Gln Ser Met Asp Leu Val Glu Leu Val Ser Leu Phe Pro Thr
                 370                    375                    380

Leu Ala Gly Leu Ala Gly Leu Gln Val Pro Pro Arg Cys Pro Val Pro
385                 390                    395                    400

Ser Phe His Val Glu Leu Cys Arg Glu Gly Lys Asn Leu Leu Lys His
                 405                    410                    415

Phe Arg Phe Arg Asp Leu Glu Glu Asp Pro Tyr Leu Pro Gly Asn Pro
                 420                    425                    430

Arg Glu Leu Ile Ala Tyr Ser Gln Tyr Pro Arg Pro Ser Asp Ile Pro
                 435                    440                    445

Gln Trp Asn Ser Asp Lys Pro Ser Leu Lys Asp Ile Lys Ile Met Gly
                 450                    455                    460

Tyr Ser Ile Arg Thr Ile Asp Tyr Arg Tyr Thr Val Trp Val Gly Phe
465                 470                    475                    480

Asn Pro Asp Glu Phe Leu Ala Asn Phe Ser Asp Ile His Ala Gly Glu
                 485                    490                    495

Leu Tyr Phe Val Asp Ser Asp Pro Leu Gln Asp His Asn Met Tyr Asn
                 500                    505                    510

Asp Ser Gln Gly Gly Asp Leu Phe Gln Leu Leu Met Pro Gly Gly Gly
                 515                    520                    525

Gly Ser Asp Lys Thr His Thr Cys Pro Pro Cys Pro Ala Pro Glu Leu
                 530                    535                    540

Leu Gly Gly Pro Ser Val Phe Leu Phe Pro Pro Lys Pro Lys Asp Thr
545                 550                    555                    560
```

```
Leu Met Ile Ser Arg Thr Pro Glu Val Thr Cys Val Val Val Asp Val
            565             570             575

Ser His Glu Asp Pro Glu Val Lys Phe Asn Trp Tyr Val Asp Gly Val
            580             585             590

Glu Val His Asn Ala Lys Thr Lys Pro Arg Glu Glu Gln Tyr Asn Ser
        595             600             605

Thr Tyr Arg Val Val Ser Val Leu Thr Val Leu His Gln Asp Trp Leu
        610             615             620

Asn Gly Lys Glu Tyr Lys Cys Lys Val Ser Asn Lys Ala Leu Pro Ala
625             630             635             640

Pro Ile Glu Lys Thr Ile Ser Lys Ala Lys Gly Gln Pro Arg Glu Pro
            645             650             655

Gln Val Tyr Thr Leu Pro Pro Ser Arg Asp Glu Leu Thr Lys Asn Gln
            660             665             670

Val Ser Leu Trp Cys Leu Val Lys Gly Phe Tyr Pro Ser Asp Ile Ala
            675             680             685

Val Glu Trp Glu Ser Asn Gly Gln Pro Glu Asn Asn Tyr Lys Thr Thr
        690             695             700

Pro Pro Val Leu Asp Ser Asp Gly Ser Phe Phe Leu Tyr Ser Lys Leu
705             710             715             720

Thr Val Asp Lys Ser Arg Trp Gln Gln Gly Asn Val Phe Ser Cys Ser
            725             730             735

Val Met His Glu Ala Leu His Asn His Tyr Thr Gln Lys Ser Leu Ser
            740             745             750

Leu Ser Pro Gly
        755
```

```
<210> SEQ ID NO 54
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54
```

```
Ala Pro Glu Leu Leu Gly Gly Pro Ser Val Phe Leu Phe Pro Pro Lys
1               5               10              15

Pro Lys Asp Thr Leu Met Ile Ser Arg Thr Pro Glu Val Thr Cys Val
            20              25              30

Val Val Asp Val Ser His Glu Asp Pro Glu Val Lys Phe Asn Trp Tyr
        35              40              45

Val Asp Gly Val Glu Val His Asn Ala Lys Thr Lys Pro Arg Glu Glu
        50              55              60

Gln Tyr Asn Ser Thr Tyr Arg Val Val Ser Val Leu Thr Val Leu His
65              70              75              80

Gln Asp Trp Leu Asn Gly Lys Glu Tyr Lys Cys Lys Val Ser Asn Lys
            85              90              95

Ala Leu Pro Ala Pro Ile Glu Lys Thr Ile Ser Lys Ala Lys Gly Gln
            100             105             110

Pro Arg Glu Pro Gln Val Tyr Thr Leu Pro Pro Ser Arg Asp Glu Leu
            115             120             125

Thr Lys Asn Gln Val Ser Leu Ser Cys Ala Val Lys Gly Phe Tyr Pro
        130             135             140

Ser Asp Ile Ala Val Glu Trp Glu Ser Asn Gly Gln Pro Glu Asn Asn
```

```
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 55
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Ser Cys Ala Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 56
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Ala Pro Glu Leu Leu Gly Gly Pro Ser Val Phe Leu Phe Pro Pro Lys
```

-continued

```
1               5               10              15

Pro Lys Asp Thr Leu Tyr Ile Thr Arg Glu Pro Glu Val Thr Cys Val
                20              25              30

Val Val Asp Val Ser His Glu Asp Pro Glu Val Lys Phe Asn Trp Tyr
                35              40              45

Val Asp Gly Val Glu Val His Asn Ala Lys Thr Lys Pro Arg Glu Glu
    50              55              60

Gln Tyr Asn Ser Thr Tyr Arg Val Val Ser Val Leu Thr Val Leu His
65              70              75              80

Gln Asp Trp Leu Asn Gly Lys Glu Tyr Lys Cys Lys Val Ser Asn Lys
                85              90              95

Ala Leu Pro Ala Pro Ile Glu Lys Thr Ile Ser Lys Ala Lys Gly Gln
                100             105             110

Pro Arg Glu Pro Gln Val Tyr Thr Leu Pro Pro Ser Arg Asp Glu Leu
                115             120             125

Thr Lys Asn Gln Val Ser Leu Ser Cys Ala Val Lys Gly Phe Tyr Pro
    130             135             140

Ser Asp Ile Ala Val Glu Trp Glu Ser Asn Gly Gln Pro Glu Asn Asn
145             150             155             160

Tyr Lys Thr Thr Pro Pro Val Leu Asp Ser Asp Gly Ser Phe Phe Leu
                165             170             175

Val Ser Lys Leu Thr Val Asp Lys Ser Arg Trp Gln Gln Gly Asn Val
                180             185             190

Phe Ser Cys Ser Val Met His Glu Ala Leu His Asn His Tyr Thr Gln
                195             200             205

Lys Ser Leu Ser Leu Ser Pro Gly
    210             215
```

```
<210> SEQ ID NO 57
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57
```

```
Ala Pro Glu Ala Ala Gly Gly Pro Ser Val Phe Leu Phe Pro Pro Lys
1               5               10              15

Pro Lys Asp Thr Leu Tyr Ile Thr Arg Glu Pro Glu Val Thr Cys Val
                20              25              30

Val Val Asp Val Ser His Glu Asp Pro Glu Val Lys Phe Asn Trp Tyr
                35              40              45

Val Asp Gly Val Glu Val His Asn Ala Lys Thr Lys Pro Arg Glu Glu
    50              55              60

Gln Tyr Asn Ser Thr Tyr Arg Val Val Ser Val Leu Thr Val Leu His
65              70              75              80

Gln Asp Trp Leu Asn Gly Lys Glu Tyr Lys Cys Lys Val Ser Asn Lys
                85              90              95

Ala Leu Pro Ala Pro Ile Glu Lys Thr Ile Ser Lys Ala Lys Gly Gln
                100             105             110

Pro Arg Glu Pro Gln Val Tyr Thr Leu Pro Pro Ser Arg Asp Glu Leu
                115             120             125

Thr Lys Asn Gln Val Ser Leu Ser Cys Ala Val Lys Gly Phe Tyr Pro
    130             135             140
```

```
Ser Asp Ile Ala Val Glu Trp Glu Ser Asn Gly Gln Pro Glu Asn Asn
145             150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 58
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145             150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 59
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59
```

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Trp Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly
        210                 215

<210> SEQ ID NO 60
<211> LENGTH: 216
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 60

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Trp Cys Leu Val Lys Gly Phe Tyr Pro
        130                 135                 140
```

-continued

```
Ser Asp Ile Ala Val Glu Trp Glu Ser Asn Gly Gln Pro Glu Asn Asn
145             150             155             160

Tyr Lys Thr Thr Pro Pro Val Leu Asp Ser Asp Gly Ser Phe Phe Leu
                165             170             175

Tyr Ser Lys Leu Thr Val Asp Lys Ser Arg Trp Gln Gln Gly Asn Val
            180             185             190

Phe Ser Cys Ser Val Met His Glu Ala Leu His Asn His Tyr Thr Gln
            195             200             205

Lys Ser Leu Ser Leu Ser Pro Gly
        210             215
```

```
<210> SEQ ID NO 61
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61
```

```
Ala Pro Glu Ala Ala Gly Gly Pro Ser Val Phe Leu Phe Pro Pro Lys
1               5               10              15

Pro Lys Asp Thr Leu Tyr Ile Thr Arg Glu Pro Glu Val Thr Cys Val
            20              25              30

Val Val Asp Val Ser His Glu Asp Pro Glu Val Lys Phe Asn Trp Tyr
            35              40              45

Val Asp Gly Val Glu Val His Asn Ala Lys Thr Lys Pro Arg Glu Glu
        50              55              60

Gln Tyr Asn Ser Thr Tyr Arg Val Val Ser Val Leu Thr Val Leu His
65              70              75              80

Gln Asp Trp Leu Asn Gly Lys Glu Tyr Lys Cys Lys Val Ser Asn Lys
            85              90              95

Ala Leu Pro Ala Pro Ile Glu Lys Thr Ile Ser Lys Ala Lys Gly Gln
            100             105             110

Pro Arg Glu Pro Gln Val Tyr Thr Leu Pro Pro Ser Arg Asp Glu Leu
            115             120             125

Thr Lys Asn Gln Val Ser Leu Trp Cys Leu Val Lys Gly Phe Tyr Pro
        130             135             140

Ser Asp Ile Ala Val Glu Trp Glu Ser Asn Gly Gln Pro Glu Asn Asn
145             150             155             160

Tyr Lys Thr Thr Pro Pro Val Leu Asp Ser Asp Gly Ser Phe Phe Leu
                165             170             175

Tyr Ser Lys Leu Thr Val Asp Lys Ser Arg Trp Gln Gln Gly Asn Val
            180             185             190

Phe Ser Cys Ser Val Met His Glu Ala Leu His Asn His Tyr Thr Gln
            195             200             205

Lys Ser Leu Ser Leu Ser Pro Gly
        210             215
```

FORMULATIONS OF PROTEIN MOLECULES COMPRISING IDURONATE 2-SULFATASE

CROSS-REFERENCE TO RELATED APPLICATIONS

This application claims priority to U.S. Provisional Application Ser. No. 62/828,859, filed Apr. 3, 2019, and U.S. Provisional Application Ser. No. 62/832,032, filed Apr. 10, 2019. The entire content of the applications referenced above are hereby incorporated by reference herein.

SEQUENCE LISTING

The instant application contains a Sequence Listing which has been submitted electronically in ASCII format and is hereby incorporated by reference in its entirety. Said ASCII copy, created on May 5, 2022, is named 02900_018US1_SL.txt and is 211,801 bytes in size.

BACKGROUND

Lysosomal storage disorders (LSDs) are relatively rare inherited metabolic diseases that result from defects in lysosomal function. LSDs are typically caused by the deficiency of a single enzyme that participates in the breakdown of metabolic products in the lysosome. The buildup of the product resulting from lack of the enzymatic activity affects various organ systems and can lead to severe symptoms and premature death. The majority of LSDs also have a significant neurological component, which ranges from progressive neurodegeneration and severe cognitive impairment to epileptic, behavioral, and psychiatric disorders. A recombinant form of an enzyme that is deficient in an LSD can be used to treat the disorder, but such therapies may have little effect on the brain due to difficulties in delivering the recombinant enzyme across the blood-brain barrier (BBB). Accordingly, there is a need for new compositions for treating these disorders. In particular, new compositions for treating Hunter syndrome are needed.

SUMMARY

Certain embodiments provide a pharmaceutical composition comprising:
- a. a protein molecule comprising:
  - i. a first Fc polypeptide; and
  - ii. a second Fc polypeptide linked to an enzyme replacement therapy (ERT) enzyme, an ERT enzyme variant, or a catalytically active fragment thereof;
- b. a buffer; and
- c. a salt;
- wherein the pH of the pharmaceutical composition is about 5.5 to 7.0.

In certain embodiments, the buffer is selected from the group consisting of: a phosphate buffer, an acetate buffer, an arginine buffer, and a histidine buffer. In certain embodiments, the phosphate buffer is a sodium phosphate buffer or a potassium phosphate buffer.

In certain embodiments, the salt is a sodium salt. In certain embodiments, the sodium salt is selected from the group consisting of: sodium chloride, sodium sulfate, and sodium phosphate.

In certain embodiments, the pharmaceutical composition further comprises a surfactant.

In certain embodiments, the pharmaceutical composition further comprises a stabilizer comprising a sugar.

In some embodiments, the pharmaceutical composition further comprises methionine.

In some embodiments, the ERT enzyme is iduronate 2-sulfatase (IDS), or a catalytically active variant or fragment of a wild-type IDS, e.g., a wild-type human IDS.

In some embodiments, the ERT enzyme is iduronate 2-sulfatase (IDS), an IDS variant, or a catalytically active fragment thereof. In some embodiments, the ERT enzyme comprises an amino acid sequence having at least 80%, 85%, 90%, or 95% identity to the amino acid sequence of any one of SEQ ID NOS:1, 2, 3, 11 and 23. In some embodiments, the ERT enzyme comprises the amino acid sequence of any one of SEQ ID NOS: 1, 2, 3, 11 and 23.

In some embodiments, the first or the second Fc polypeptide comprises substitutions at at least nine amino acid residue positions selected from the group consisting of 380, 384, 386, 387, 388, 389, 390, 413, 415, 416, and 421, according to EU numbering.

Certain embodiments also provide a pharmaceutical composition comprising:
- a. a protein molecule comprising:
  - i. a first Fc polypeptide comprising substitutions at at least nine amino acid residue positions selected from the group consisting of 380, 384, 386, 387, 388, 389, 390, 413, 415, 416, and 421, according to EU numbering; and
  - ii. a second Fc polypeptide linked to an iduronate 2-sulfatase (IDS) amino acid sequence, wherein the IDS amino acid sequence comprises a sequence having at least 90% identity to SEQ ID NO:1;
- b. a buffer; and
- c. a salt;
- wherein the pH of the pharmaceutical composition is about 5.5 to 7.0.

In certain embodiments, the buffer is selected from the group consisting of: a phosphate buffer, an acetate buffer, an arginine buffer, and a histidine buffer. In certain embodiments, the phosphate buffer is a sodium phosphate buffer or a potassium phosphate buffer.

In certain embodiments, the salt is a sodium salt. In certain embodiments, the sodium salt is selected from the group consisting of: sodium chloride, sodium sulfate, and sodium phosphate.

In certain embodiments, the pharmaceutical composition further comprises a surfactant.

In certain embodiments, the pharmaceutical composition further comprises a stabilizer comprising a sugar.

In certain embodiments, the pharmaceutical composition further comprises methionine.

In certain embodiments, the IDS amino acid sequence comprises a sequence selected from the group consisting of SEQ ID NOs:1, 2, and 3. In certain embodiments, the IDS amino acid sequence is linked to the N-terminus of the second Fc polypeptide. In certain embodiments, the second Fc polypeptide linked to the IDS amino acid sequence comprises the amino acid sequence of SEQ ID NO:4 or 5.

In certain embodiments, the first Fc polypeptide comprises substitutions at amino acid residue positions 384, 386, 387, 388, 389, 413, 415, 416, and 421, according to EU numbering. In certain embodiments, the first Fc polypeptide comprises a sequence having at least 90% identity to SEQ ID NO:6. In certain embodiments, the first Fc polypeptide comprises: Trp, Leu, or Glu at position 380; Tyr at position 384; Thr at position 386; Glu at position 387; Trp at position 388; Ser or Ala at position 389; Ser or Asn at position 390; Thr at position 413; Glu at position 415; Glu at position 416; and Phe at position 421.

In certain embodiments, the first Fc polypeptide and the second Fc polypeptide dimerize.

In certain embodiments, the first Fc polypeptide comprises an amino acid sequence having at least 90% identity to SEQ ID NO:6, and the second Fc polypeptide linked to the IDS amino acid sequence comprises the sequence of SEQ ID NO:4 or 5.

In certain embodiments, the pharmaceutical composition is a liquid composition. In certain embodiments, the pharmaceutical composition is a lyophilized composition.

Certain embodiments also provide a method of treating a LSD (e.g., Hunter syndrome) in a subject in need thereof, comprising providing and administering the pharmaceutical composition described herein to the subject.

Certain embodiments provide a pharmaceutical composition described herein for use in treating a LSD (e.g., Hunter syndrome) in a subject in need thereof.

DETAILED DESCRIPTION

Certain embodiments provide a pharmaceutical composition comprising: (a) a protein molecule comprising an ERT enzyme-Fc fusion polypeptide and an Fc polypeptide (e.g., a modified Fc polypeptide); (b) a buffer; and (c) an isotonicity agent, such as a salt, as well as methods of using such compositions. In certain embodiments, the pharmaceutical composition further comprises one or more additional components described herein. For example, in certain embodiments, the pharmaceutical composition further comprises a surfactant; and/or one or more stabilizers. Thus, certain embodiments provide a pharmaceutical composition comprising: (a) a protein molecule comprising an ERT enzyme-Fc fusion polypeptide and an Fc polypeptide (e.g., a modified Fc polypeptide); (b) a buffer (e.g., comprising sodium phosphate or potassium phosphate); (c) an isotonicity agent (e.g., sodium chloride, sodium sulfate or sodium phosphate); (d) a surfactant; and (e) one or more stabilizers (e.g., a stabilizer comprising a sugar). In some embodiments, the pharmaceutical composition further comprises methionine. In certain embodiments, the pharmaceutical composition comprises a plurality of protein molecules, which may be the same or different. In some embodiments, pharmaceutical compositions have been formulated such that they are capable of stabilizing, or alternatively slowing or preventing the degradation, of a protein molecule described herein. In particular, formulations have been developed, wherein the protein molecule retains its physical and/or chemical integrity and biological activity upon storage and during certain processes (such as freeze/thaw, mechanical mixing and lyophilization) (see, the Examples).

Protein Molecules Comprising an ERT Enzyme-Fc Fusion Polypeptide

As described herein, certain embodiments provide pharmaceutical compositions comprising a protein molecule comprising an ERT enzyme-Fc fusion polypeptide. The ERT enzyme may be any enzyme that is deficient in an LSD. An ERT enzyme incorporated into the fusion protein is catalytically active, i.e., it retains the enzymatic activity that is deficient in the LSD. In some embodiments, the ERT enzyme is iduronate 2-sulfatase (IDS), which is deficient in Hunter syndrome.

Described below are certain embodiments of protein molecules comprising fusion proteins that include an ERT enzyme linked to an Fc polypeptide; these fusion proteins may be used in certain methods described herein as a treatment for a LSD. In certain embodiments, the protein molecule includes a dimeric Fc polypeptide, where at least one of the Fc polypeptide monomers is linked to the ERT enzyme. The Fc polypeptides can increase enzyme half-life and, in some cases, can be modified to confer additional functional properties onto the protein. Also described herein are protein molecules comprising fusion proteins that facilitate delivery of an ERT enzyme across the blood-brain barrier (BBB). These protein molecules comprise an Fc polypeptide and a modified Fc polypeptide that form a dimer, and an ERT enzyme linked to the Fc region and/or the modified Fc region. The modified Fc region can specifically bind to a BBB receptor such as a transferrin receptor (TfR). In some embodiments, the ERT amino acid sequence is a full length ERT sequence. In other embodiments, the ERT amino acid sequence is a catalytically active variant or fragment of a wild-type ERT, e.g., a wild-type human IDS. Certain embodiments of these protein molecules may be referenced herein as an enzyme transport vehicle (ETV) in conjunction with an ERT enzyme, for example ETV:IDS.

In some embodiments, the ERT enzyme is iduronate 2-sulfatase (IDS), an IDS variant, or a catalytically active fragment thereof. In some embodiments, the IDS enzyme comprises an amino acid sequence having at least 80%, 85%, 90%, or 95% identity, or at least 96%, 97%, 98%, or 99% identity to the amino acid sequence of any one of SEQ ID NOS:1, 2, 3, 11 and 23. In some embodiments, the IDS enzyme comprises the amino acid sequence of any one of SEQ ID NOS:1, 2, 3, 11, and 23.

In some embodiments, the IDS enzyme comprises an amino acid sequence having at least 80%, 85%, 90%, or 95% identity, or at least 96%, 97%, 98%, or 99% identity to the amino acid sequence of any one of SEQ ID NOS:1, 2 and 3. In some embodiments, the IDS enzyme comprises the amino acid sequence of any one of SEQ ID NOS:1, 2 and 3.

In some embodiments, the IDS enzyme comprises an amino acid sequence having at least 80%, 85%, 90%, 91%, 92%, 93%, 94%, 95%, 96%, 97%, 98% or 99% identity to the amino acid sequence of SEQ ID NO:1. In some embodiments, the IDS enzyme comprises the amino acid sequence of SEQ ID NO:1.

In some embodiments, the IDS enzyme comprises an amino acid sequence having at least 80%, 85%, 90%, 91%, 92%, 93%, 94%, 95%, 96%, 97%, 98% or 99% identity to the amino acid sequence of SEQ ID NO:2. In some embodiments, the IDS enzyme comprises the amino acid sequence of SEQ ID NO:2.

In some embodiments, the IDS enzyme comprises an amino acid sequence having at least 80%, 85%, 90%, 91%, 92%, 93%, 94%, 95%, 96%, 97%, 98% or 99% identity to the amino acid sequence of SEQ ID NO:3. In some embodiments, the IDS enzyme comprises the amino acid sequence of SEQ ID NO:3.

In some aspects, a protein molecule described herein comprises: (i) an Fc polypeptide, which may contain modifications (e.g., one or more modifications that promote heterodimerization) or may be a wild-type Fc polypeptide; and an ERT enzyme amino acid sequence; and (ii) an Fc polypeptide, which may contain modifications (e.g., one or more modifications that promote heterodimerization) or may be a wild-type Fc polypeptide; and optionally an ERT enzyme amino acid sequence. In some embodiments, one or both Fc polypeptides may contain modifications that result in binding to a blood-brain barrier (BBB) receptor, e.g., a TfR. The ERT enzyme may be any enzyme that is deficient in an LSD. An ERT enzyme incorporated into the fusion protein is catalytically active, i.e., it retains the enzymatic activity that is deficient in the LSD. In some embodiments, the ERT enzyme is IDS, which is deficient in Hunter syndrome.

In some embodiments, a protein molecule described herein comprises an IDS enzyme and optionally a modified Fc polypeptide that binds to a BBB receptor, e.g., a TfR-binding Fc polypeptide comprising a catalytically active fragment or variant of a wild-type IDS. In some embodiments, the IDS enzyme is a variant or a catalytically active fragment of an IDS protein that comprises the amino acid sequence of any one of SEQ ID NOS:1, 2, 3, 11 and 23. In some embodiments, a catalytically active variant or fragment of an IDS enzyme has at least 50%, at least 55%, at least 60%, at least 65%, at least 70%, at least 75%, at least 80%, at least 85%, at least 90%, at least 95%, or greater of the activity of the wild-type IDS enzyme.

In some embodiments, an ERT enzyme, e.g., IDS, or a catalytically active variant or fragment thereof, that is present in a fusion protein described herein, retains at least 25% of its activity compared to its activity when not joined to an Fc polypeptide or a TfR-binding Fc polypeptide. In some embodiments, an ERT enzyme, or a catalytically active variant or fragment thereof, retains at least 10%, or at least 15%, 20%, 25%, 30%, 35%, 40%, 45%, 50%, 55%, 60%, 65%, 70%, 75%, 80%, 85%, 90%, or 95%, of its activity compared to its activity when not joined to an Fc polypeptide or a TfR-binding Fc polypeptide. In some embodiments, an ERT enzyme, or a catalytically active variant or fragment thereof, retains at least 80%, 85%, 90%, or 95% of its activity compared to its activity when not joined to an Fc polypeptide or a TfR-binding Fc polypeptide. In some embodiments, fusion to an Fc polypeptide does not decrease the activity of the ERT enzyme, or catalytically active variant or fragment thereof. In some embodiments, fusion to a TfR-binding Fc polypeptide does not decrease the activity of the ERT enzyme.

Fc Polypeptide Modifications for Blood-Brain Barrier (BBB) Receptor Binding

In some aspects, the molecules are capable of being transported across the blood-brain barrier (BBB). Such a protein comprises a modified Fc polypeptide that binds to a BBB receptor. BBB receptors are expressed on BBB endothelia, as well as other cell and tissue types. In some embodiments, the BBB receptor is transferrin receptor (TfR).

Amino acid residues designated in various Fc modifications, including those introduced in a modified Fc polypeptide that binds to a BBB receptor, e.g., TfR, are numbered herein using EU index numbering. Any Fc polypeptide, e.g., an IgG1, IgG2, IgG3, or IgG4 Fc polypeptide, may have modifications, e.g., amino acid substitutions, in one or more positions as described herein.

A modified (e.g., enhancing heterodimerization and/or BBB receptor-binding) Fc polypeptide present in a protein molecule described herein can have at least 70% identity, at least 75% identity, at least 80% identity, at least 85% identity, at least 90% identity, at least 95% identity to a native Fc region sequence or a fragment thereof, e.g., a fragment of at least 50 amino acids or at least 100 amino acids, or greater in length. In some embodiments, the native Fc amino acid sequence is the Fc region sequence of SEQ ID NO:8. In some embodiments, the modified Fc polypeptide has at least 70% identity, at least 75% identity, at least 80% identity, at least 85% identity, at least 90% identity, at least 95% identity, at least 96% identity, at least 97% identity, at least 98% identity, or at least 99% identity to amino acids 1-110 of SEQ ID NO:8, or to amino acids 111-217 of SEQ ID NO:8, or a fragment thereof, e.g., a fragment of at least 50 amino acids or at least 100 amino acids, or greater in length. In some embodiments, the modified Fc polypeptide has at least 70% identity, at least 75% identity, at least 80% identity, at least 85% identity, at least 90% identity, at least 95% identity, at least 96% identity, at least 97% identity, at least 98% identity, or at least 99% identity to amino acids 1-216 of SEQ ID NO:8, or a fragment thereof, e.g., a fragment of at least 50 amino acids or at least 100 amino acids, or greater in length.

In some embodiments, a modified (e.g., enhancing heterodimerization and/or BBB receptor-binding) Fc polypeptide comprises at least 50 amino acids, or at least 60, 65, 70, 75, 80, 85, 90, or 95 or more, or at least 100 amino acids, or more, that correspond to a native Fc region amino acid sequence. In some embodiments, the modified Fc polypeptide comprises at least 25 contiguous amino acids, or at least 30, 35, 40, or 45 contiguous amino acids, or 50 contiguous amino acids, or at least 60, 65, 70, 75, 80 85, 90, or 95 or more contiguous amino acids, or 100 or more contiguous amino acids, that correspond to a native Fc region amino acid sequence, such as SEQ ID NO:8.

In some embodiments, the domain that is modified for BBB receptor-binding activity is a human Ig CH3 domain, such as an IgG1 CH3 domain. The CH3 domain can be of any IgG subtype, i.e., from IgG1, IgG2, IgG3, or IgG4. In the context of IgG1 antibodies, a CH3 domain refers to the segment of amino acids from about position 341 to about position 447 as numbered according to the EU numbering scheme.

In some embodiments, a modified (e.g., BBB receptor-binding) Fc polypeptide present in a protein molecule described herein comprises at least one, two, or three substitutions; and in some embodiments, at least four, five, six, seven, eight, or nine substitutions at amino acid positions 384, 386, 387, 388, 389, 390, 413, 416, and 421, according to the EU numbering scheme. In some embodiments, a modified (e.g., BBB receptor-binding) Fc polypeptide present in a protein molecule described herein comprises at least one, two, or three substitutions; and in some embodiments, at least four, five, six, seven, eight, or nine substitutions at amino acid positions 384, 386, 387, 388, 389, 390, 413, 416, and 421, according to the EU numbering scheme, in a reference sequence, e.g., SEQ ID NO:8.

FcRn Binding Sites

In certain aspects, modified (e.g., BBB receptor-binding) Fc polypeptides, or Fc polypeptides present in a protein molecule described herein that do not specifically bind to a BBB receptor, can also comprise an FcRn binding site. In some embodiments, the FcRn binding site is within the Fc polypeptide or a fragment thereof.

In some embodiments, the FcRn binding site comprises a native FcRn binding site. In some embodiments, the FcRn binding site does not comprise amino acid changes relative to the amino acid sequence of a native FcRn binding site. In some embodiments, the native FcRn binding site is an IgG binding site, e.g., a human IgG binding site. In some embodiments, the FcRn binding site comprises a modification that alters FcRn binding.

In some embodiments, an FcRn binding site has one or more amino acid residues that are mutated, e.g., substituted, wherein the mutation(s) increase serum half-life or do not substantially reduce serum half-life (i.e., reduce serum half-life by no more than 25% compared to a counterpart modified Fc polypeptide having the wild-type residues at the mutated positions when assayed under the same conditions).

In some embodiments, an FcRn binding site has one or more amino acid residues that are substituted at positions 250-256, 307, 380, 428, and 433-436, according to the EU numbering scheme.

In some embodiments, one or more residues at or near an FcRn binding site are mutated, relative to a native human IgG sequence, to extend serum half-life of the modified polypeptide. In some embodiments, mutations are introduced into one, two, or three of positions 252, 254, and 256, according to the EU numbering scheme. In some embodiments, the mutations are M252Y, S254T, and T256E. In some embodiments, a modified Fc polypeptide further comprises the mutations M252Y, S254T, and T256E. In some embodiments, a modified Fc polypeptide comprises a substitution at one, two, or all three of positions T307, E380, and N434, according to the EU numbering scheme. In some embodiments, the mutations are T307Q and N434A. In some embodiments, a modified Fc polypeptide comprises mutations T307A, E380A, and N434A. In some embodiments, a modified Fc polypeptide comprises substitutions at positions T250 and M428, according to the EU numbering scheme. In some embodiments, the modified Fc polypeptide comprises mutations T250Q and/or M428L. In some embodiments, a modified Fc polypeptide comprises substitutions at positions M428 and N434, according to the EU numbering scheme. In some embodiments, the modified Fc polypeptide comprises mutations M428L and N434S. In some embodiments, a modified Fc polypeptide comprises an N434S or N434A mutation.

Transferrin Receptor-Binding Fc Polypeptides

This section describes generation of modified Fc polypeptides described herein that bind to transferrin receptor (TfR) and are capable of being transported across the blood-brain barrier (BBB).

TfR-Binding Fc Polypeptides Comprising Mutations in the CH3 Domain

In some embodiments, a modified Fc polypeptide that specifically binds to TfR comprises substitutions in a CH3 domain. In some embodiments, a modified Fc polypeptide comprises a human Ig CH3 domain, such as an IgG CH3 domain, that is modified for TfR-binding activity. The CH3 domain can be of any IgG subtype, i.e., from IgG1, IgG2, IgG3, or IgG4. In the context of IgG antibodies, a CH3 domain refers to the segment of amino acids from about position 341 to about position 447 as numbered according to the EU numbering scheme.

In some embodiments, a modified Fc polypeptide that specifically binds to TfR binds to the apical domain of TfR and may bind to TfR without blocking or otherwise inhibiting binding of transferrin to TfR. In some embodiments, binding of transferrin to TfR is not substantially inhibited. In some embodiments, binding of transferrin to TfR is inhibited by less than about 50% (e.g., less than about 45%, 40%, 35%, 30%, 25%, 20%, 15%, 10%, or 5%). In some embodiments, binding of transferrin to TfR is inhibited by less than about 20% (e.g., less than about 19%, 18%, 17%, 16%, 15%, 14%, 13%, 12%, 11%, 10%, 9%, 8%, 7%, 6%, 5%, 4%, 3%, 2%, or 1%).

In some embodiments, a modified Fc polypeptide that specifically binds to TfR comprises at least two, three, four, five, six, seven, eight, or nine substitutions at positions 384, 386, 387, 388, 389, 390, 413, 416, and 421, according to the EU numbering scheme. In some embodiments, a modified Fc polypeptide that specifically binds to TfR comprises at least two, three, four, five, six, seven, eight, or nine substitutions at positions 384, 386, 387, 388, 389, 390, 413, 416, and 421, according to the EU numbering scheme, in a reference sequence, e.g., SEQ ID NO:8. In some embodiments, the amino acid at position 388 and/or 421 is an aromatic amino acid, e.g., Trp, Phe, or Tyr. In some embodiments, the amino acid at position 388 is Trp. In some embodiments, the aromatic amino acid at position 421 is Trp or Phe.

In some embodiments, at least one position as follows is substituted: Leu, Tyr, Met, or Val at position 384; Leu, Thr, His, or Pro at position 386; Val, Pro, or an acidic amino acid at position 387; an aromatic amino acid, e.g., Trp at position 388; Val, Ser, or Ala at position 389; an acidic amino acid, Ala, Ser, Leu, Thr, or Pro at position 413; Thr or an acidic amino acid at position 416; or Trp, Tyr, His, or Phe at position 421. In some embodiments, the modified Fc polypeptide may comprise a conservative substitution, e.g., an amino acid in the same charge grouping, hydrophobicity grouping, side chain ring structure grouping (e.g., aromatic amino acids), or size grouping, and/or polar or non-polar grouping, of a specified amino acid at one or more of the positions in the set. Thus, for example, Ile may be present at position 384, 386, and/or position 413. In some embodiments, the acidic amino acid at position one, two, or each of positions 387, 413, and 416 is Glu. In other embodiments, the acidic amino acid at one, two or each of positions 387, 413, and 416 is Asp. In some embodiments, two, three, four, five, six, seven, or all eight of positions 384, 386, 387, 388, 389, 413, 416, and 421 have an amino acid substitution as specified in this paragraph.

In some embodiments, an Fc polypeptide that is modified as described in the preceding two paragraphs comprises a native Asn at position 390. In some embodiments, the modified Fc polypeptide comprises Gly, His, Gln, Leu, Lys, Val, Phe, Ser, Ala, or Asp at position 390. In some embodiments, the modified Fc polypeptide further comprises one, two, three, or four substitutions at positions comprising 380, 391, 392, and 415, according to the EU numbering scheme. In some embodiments, Trp, Tyr, Leu, or Gln may be present at position 380. In some embodiments, Ser, Thr, Gln, or Phe may be present at position 391. In some embodiments, Gln, Phe, or His may be present at position 392. In some embodiments, Glu may be present at position 415.

In certain embodiments, the modified Fc polypeptide comprises at least two, three, four, five, six, seven, eight, nine, ten, or eleven substitutions at positions selected from the group consisting of 380, 384, 386, 387, 388, 389, 390, 413, 415, 416, and 421, according to EU numbering. In certain embodiments, the modified Fc polypeptide comprises at least eight substitutions at positions selected from the group consisting of 380, 384, 386, 387, 388, 389, 390, 413, 415, 416, and 421, according to EU numbering. In certain embodiments, the modified Fc polypeptide comprises at least nine substitutions at positions selected from the group consisting of 380, 384, 386, 387, 388, 389, 390, 413, 415, 416, and 421, according to EU numbering. In certain embodiments, the modified Fc polypeptide comprises at least ten substitutions at positions selected from the group consisting of 380, 384, 386, 387, 388, 389, 390, 413, 415, 416, and 421, according to EU numbering. In certain embodiments, the modified Fc polypeptide comprises eleven substitutions at positions selected from the group consisting of 380, 384, 386, 387, 388, 389, 390, 413, 415, 416, and 421, according to EU numbering. In certain embodiments, the modified Fc polypeptide comprises substitutions at positions 384, 386, 387, 388, 389, 413, 415, 416, and 421, according to EU numbering.

In certain embodiments, the modified Fc polypeptide comprises two, three, four, five, six, seven, eight, nine, ten, or eleven positions selected from the following: Trp, Leu, or Glu at position 380; Tyr or Phe at position 384; Thr at position 386; Glu at position 387; Trp at position 388; Ser, Ala, Val, or Asn at position 389; Ser or Asn at position 390; Thr or Ser at position 413; Glu or Ser at position 415; Glu at position 416; and/or Phe at position 421, wherein the positions are according to EU numbering. In some embodiments, the modified Fc polypeptide comprises: Trp, Leu, or Glu at position 380; Tyr or Phe at position 384; Thr at position 386; Glu at position 387; Trp at position 388; Ser, Ala, Val, or Asn at position 389; Ser or Asn at position 390; Thr or Ser at position 413; Glu or Ser at position 415; Glu at position 416; and Phe at position 421, wherein the positions are according to EU numbering.

In certain embodiments, the modified Fc polypeptide comprises two, three, four, five, six, seven, eight, nine, ten, or eleven positions selected from the following: Trp, Leu, or Glu at position 380; Tyr at position 384; Thr at position 386; Glu at position 387; Trp at position 388; Ser or Ala at position 389; Ser or Asn at position 390; Thr at position 413; Glu at position 415; Glu at position 416; and/or Phe at position 421, wherein the positions are according to EU numbering. In some embodiments, the modified Fc polypeptide comprises: Trp, Leu, or Glu at position 380; Tyr at position 384; Thr at position 386; Glu at position 387; Trp at position 388; Ser or Ala at position 389; Ser or Asn at position 390; Thr at position 413; Glu at position 415; Glu at position 416; and Phe at position 421, wherein the positions are according to EU numbering.

In certain embodiments, the modified Fc polypeptide comprises two, three, four, five, six, seven, eight, nine, ten, or eleven positions selected from the following: Trp at position 380; Tyr at position 384; Thr at position 386; Glu at position 387; Trp at position 388; Ser at position 389; Ser at position 390; Thr at position 413; Glu at position 415; Glu at position 416; and/or Phe at position 421, wherein the positions are according to EU numbering. In some embodiments, the modified Fc polypeptide comprises: Trp at position 380; Tyr at position 384; Thr at position 386; Glu at position 387; Trp at position 388; Ser at position 389; Ser at position 390; Thr at position 413; Glu at position 415; Glu at position 416; and Phe at position 421, wherein the positions are according to EU numbering.

In certain embodiments, the modified Fc polypeptide comprises two, three, four, five, six, seven, eight, nine, ten, or eleven positions selected from the following: Leu at position 380; Tyr at position 384; Thr at position 386; Glu at position 387; Trp at position 388; Ala at position 389; Ser at position 390; Thr at position 413; Glu at position 415; Glu at position 416; and/or Phe at position 421, wherein the positions are according to EU numbering. In some embodiments, the modified Fc polypeptide comprises: Leu at position 380; Tyr at position 384; Thr at position 386; Glu at position 387; Trp at position 388; Ala at position 389; Ser at position 390; Thr at position 413; Glu at position 415; Glu at position 416; and Phe at position 421, wherein the positions are according to EU numbering.

In certain embodiments, the modified Fc polypeptide comprises two, three, four, five, six, seven, eight, nine, ten, or eleven positions selected from the following: Glu at position 380; Tyr at position 384; Thr at position 386; Glu at position 387; Trp at position 388; Ala at position 389; Asn at position 390; Thr at position 413; Glu at position 415; Glu at position 416; and/or Phe at position 421, wherein the positions are according to EU numbering. In some embodiments, the modified Fc polypeptide comprises: Glu at position 380; Tyr at position 384; Thr at position 386; Glu at position 387; Trp at position 388; Ala at position 389; Asn at position 390; Thr at position 413; Glu at position 415; Glu at position 416; and Phe at position 421, wherein the positions are according to EU numbering.

In certain embodiments, the modified Fc polypeptide comprises two, three, four, five, six, seven, eight, nine, ten, or eleven positions selected from the following: Leu at position 380; Tyr at position 384; Thr at position 386; Glu at position 387; Trp at position 388; Ser at position 389; Ser at position 390; Thr at position 413; Glu at position 415; Glu at position 416; and/or Phe at position 421, wherein the positions are according to EU numbering. In some embodiments, the modified Fc polypeptide comprises: Leu at position 380; Tyr at position 384; Thr at position 386; Glu at position 387; Trp at position 388; Ser at position 389; Ser at position 390; Thr at position 413; Glu at position 415; Glu at position 416; and Phe at position 421, wherein the positions are according to EU numbering.

In certain embodiments, the modified Fc polypeptide comprises Leu or Met at position 384; Leu, His, or Pro at position 386; Val at position 387; Trp at position 388; Val or Ala at position 389; Pro at position 413; Thr at position 416; and/or Trp at position 421, wherein the positions are according to EU numbering. In some embodiments, the modified Fc polypeptide further comprises Ser, Thr, Gln, or Phe at position 391, according to EU numbering. In some embodiments, the modified Fc polypeptide further comprises Trp, Tyr, Leu, or Gln at position 380 and/or Gln, Phe, or His at position 392, wherein the positions are according to EU numbering. In some embodiments, Trp is present at position 380 and/or Gln is present at position 392, according to EU numbering. In some embodiments, the modified Fc polypeptide does not have a Trp at position 380, according to EU numbering.

In other embodiments, the modified Fc polypeptide comprises Tyr at position 384; Thr at position 386; Glu or Val and position 387; Trp at position 388; Ser at position 389; Ser or Thr at position 413; Glu at position 416; and/or Phe at position 421, wherein the positions are according to EU numbering. In some embodiments, the modified Fc polypeptide comprises a native Asn at position 390, according to EU numbering. In certain embodiments, the modified Fc polypeptide further comprises Trp, Tyr, Leu, or Gln at position 380; and/or Glu at position 415, wherein the positions are according to EU numbering. In some embodiments, the modified Fc polypeptide further comprises Trp at position 380 and/or Glu at position 415, wherein the positions are according to EU numbering.

In additional embodiments, the modified Fc polypeptide further comprises one, two, or three substitutions at positions comprising 414, 424, and 426, according to the EU numbering scheme. In some embodiments, position 414 is Lys, Arg, Gly, or Pro; position 424 is Ser, Thr, Glu, or Lys; and/or position 426 is Ser, Trp, or Gly.

In some embodiments, the modified Fc polypeptide comprises one or more of the following substitutions: Trp at position 380; Thr at position 386; Trp at position 388; Val at position 389; Thr or Ser at position 413; Glu at position 415; and/or Phe at position 421, according to the EU numbering scheme.

In some embodiments, the modified Fc polypeptide comprises additional mutations such as the mutations described below, including, but not limited to, a knob mutation (e.g., T366W as numbered with reference to EU numbering), hole mutations (e.g., T366S, L368A, and Y407V as numbered with reference to EU numbering), mutations that modulate effector function (e.g., L234A, L235A, and/or P329G (e.g., L234A and L235A) as numbered with reference to EU numbering), and/or mutations that increase serum stability or serum half-life (e.g., (i) M252Y, S254T, and T256E as numbered with reference to EU numbering, or (ii) N434S with or without M428L as numbered according to the EU numbering scheme). By way of illustration, SEQ ID NOs:6, 7, 25, 28, 29, 30, 41, 42, 44, 47, 48 and 49 provide non-limiting examples of a modified Fc polypeptide with mutations in the CH3 domain comprising one or more of these additional mutations.

In some embodiments, the modified Fc polypeptide comprises a knob mutation (e.g., T366W as numbered with reference to EU numbering). In some embodiments, the modified Fc polypeptide comprises a knob mutation (e.g., T366W as numbered with reference to EU numbering) and mutations that modulate effector function (e.g., L234A, L235A, and/or P329G (e.g., L234A and L235A) as numbered with reference to EU numbering). In some embodiments, the modified Fc polypeptide has at least 85% identity, at least 90% identity, at least 95% identity, at least 96% identity, at least 97% identity, at least 98% identity, or at least 99% identity to the sequence of SEQ ID NOS:6, 7, 25, 28, 29, 30, 41, 42, 44, 47, 48 or 49. In certain embodiments, the modified Fc polypeptide has at least 85% identity, at least 90% identity, at least 95% identity, at least 96% identity, at least 97% identity, at least 98% identity, or at least 99% identity to the sequence of SEQ ID NOS:6, 7, 25, 28, 29 or 30. In certain embodiments, the modified Fc polypeptide has at least 85% identity, at least 90% identity, at least 95% identity, at least 96% identity, at least 97% identity, at least 98% identity, or at least 99% identity to the sequence of SEQ ID NOS: 41, 42, 44, 47, 48 or 49.

In some embodiments, the modified Fc polypeptide comprises a knob mutation (e.g., T366W as numbered with reference to EU numbering) and mutations that increase serum stability or serum half-life (e.g., (i) M252Y, S254T, and T256E as numbered with reference to EU numbering, or (ii) N4345 with or without M428L as numbered according to the EU numbering scheme).

In some embodiments, the modified Fc polypeptide comprises a knob mutation (e.g., T366W as numbered with reference to EU numbering), mutations that modulate effector function (e.g., L234A, L235A, and/or P329G (e.g., L234A and L235A) as numbered with reference to EU numbering), and mutations that increase serum stability or serum half-life (e.g., (i) M252Y, S254T, and T256E as numbered with reference to EU numbering, or (ii) N434S with or without M428L as numbered according to the EU numbering scheme).

In some embodiments, the modified Fc polypeptide comprises hole mutations (e.g., T366S, L368A, and Y407V as numbered with reference to EU numbering).

In some embodiments, the modified Fc polypeptide comprises hole mutations (e.g., T366S, L368A, and Y407V as numbered with reference to EU numbering) and mutations that modulate effector function (e.g., L234A, L235A, and/or P329G (e.g., L234A and L235A) as numbered with reference to EU numbering).

In some embodiments, the modified Fc polypeptide comprises hole mutations (e.g., T366S, L368A, and Y407V as numbered with reference to EU numbering) and mutations that increase serum stability or serum half-life (e.g., (i) M252Y, S254T, and T256E as numbered with reference to EU numbering, or (ii) N434S with or without M428L as numbered according to the EU numbering scheme).

In some embodiments, the modified Fc polypeptide comprises hole mutations (e.g., T366S, L368A, and Y407V as numbered with reference to EU numbering), mutations that modulate effector function (e.g., L234A, L235A, and/or P329G (e.g., L234A and L235A) as numbered with reference to EU numbering), and mutations that increase serum stability or serum half-life (e.g., (i) M252Y, S254T, and T256E as numbered with reference to EU numbering, or (ii) N434S with or without M428L as numbered according to the EU numbering scheme).

In some embodiments, a modified Fc polypeptide that specifically binds to TfR comprises at least two, three, four, five, six, seven, or eight substitutions at positions 345, 346, 347, 349, 437, 438, 439, and 440, according to the EU numbering scheme. In some embodiments, the modified Fc polypeptide comprises Gly at position 437; Phe at position 438; and/or Asp at position 440. In some embodiments, Glu is present at position 440. In certain embodiments, the modified Fc polypeptide comprises at least one substitution at a position as follows: Phe or Ile at position 345; Asp, Glu, Gly, Ala, or Lys at position 346; Tyr, Met, Leu, Ile, or Asp at position 347; Thr or Ala at position 349; Gly at position 437; Phe at position 438; His Tyr, Ser, or Phe at position 439; or Asp at position 440. In some embodiments, two, three, four, five, six, seven, or all eight of positions 345, 346, 347, 349, 437, 438, 439, and 440 have a substitution as specified in this paragraph. In some embodiments, the modified Fc polypeptide may comprise a conservative substitution, e.g., an amino acid in the same charge grouping, hydrophobicity grouping, side chain ring structure grouping (e.g., aromatic amino acids), or size grouping, and/or polar or non-polar grouping, of a specified amino acid at one or more of the positions in the set.

Additional Fc Polypeptide Mutations

In some aspects, a protein molecule described herein comprises two Fc polypeptides that may each comprise independently selected modifications or may be a wild-type Fc polypeptide, e.g., a human IgG1 Fc polypeptide. In some embodiments, one or both Fc polypeptides contains one or more modifications that confer binding to a blood-brain barrier (BBB) receptor, e.g., transferrin receptor (TfR). Non-limiting examples of other mutations that can be introduced into one or both Fc polypeptides include, e.g., mutations to increase serum stability or serum half-life, to modulate effector function, to influence glycosylation, to reduce immunogenicity in humans, and/or to provide for knob and hole heterodimerization of the Fc polypeptides.

In some embodiments, the Fc polypeptides present in the protein molecule independently have an amino acid sequence identity of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% to a corresponding wild-type Fc polypeptide (e.g., a human IgG1, IgG2, IgG3, or IgG4 Fc polypeptide).

In some embodiments, the Fc polypeptides present in the protein molecule include knob and hole mutations to promote heterodimer formation and hinder homodimer formation. Generally, the modifications introduce a protuberance ("knob") at the interface of a first polypeptide and a corresponding cavity ("hole") in the interface of a second polypeptide, such that the protuberance can be positioned in the cavity so as to promote heterodimer formation and thus hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine). In some embodiments, such additional mutations are at a position in the Fc polypeptide that does not have a negative effect on binding of the polypeptide to a BBB receptor, e.g., TfR.

In one illustrative embodiment of a knob and hole approach for dimerization, position 366 (numbered according to the EU numbering scheme) of one of the Fc polypeptides present in the protein molecule comprises a tryptophan in place of a native threonine. The other Fc polypeptide in the dimer has a valine at position 407 (numbered according to the EU numbering scheme) in place of the native tyrosine. The other Fc polypeptide may further comprise a substitution in which the native threonine at position 366 (numbered according to the EU numbering scheme) is substituted with a serine and a native leucine at position 368 (numbered according to the EU numbering scheme) is substituted with an alanine. Thus, one of the Fc polypeptides of a protein molecule described herein has the T366W knob mutation and the other Fc polypeptide has the Y407V mutation, which is typically accompanied by the T366S and L368A hole mutations.

In some embodiments, modifications to enhance serum half-life may be introduced. For example, in some embodiments, one or both Fc polypeptides present in a protein molecule described herein may comprise a tyrosine at position 252, a threonine at position 254, and a glutamic acid at position 256, as numbered according to the EU numbering scheme. Thus, one or both Fc polypeptides may have M252Y, S254T, and T256E substitutions. Alternatively, one or both Fc polypeptides may have M428L and N434S substitutions, as numbered according to the EU numbering scheme. Alternatively, one or both Fc polypeptides may have an N434S or N434A substitution.

In some embodiments, one or both Fc polypeptides present in a protein molecule described herein may comprise modifications that reduce effector function, i.e., having a reduced ability to induce certain biological functions upon binding to an Fc receptor expressed on an effector cell that mediates the effector function. Examples of antibody effector functions include, but are not limited to, C1q binding and complement dependent cytotoxicity (CDC), Fc receptor binding, antibody-dependent cell-mediated cytotoxicity (ADCC), antibody-dependent cell-mediated phagocytosis (ADCP), down-regulation of cell surface receptors (e.g., B cell receptor), and B-cell activation. Effector functions may vary with the antibody class. For example, native human IgG1 and IgG3 antibodies can elicit ADCC and CDC activities upon binding to an appropriate Fc receptor present on an immune system cell; and native human IgG1, IgG2, IgG3, and IgG4 can elicit ADCP functions upon binding to the appropriate Fc receptor present on an immune cell.

In some embodiments, one or both Fc polypeptides present in a protein molecule described herein may also be engineered to contain other modifications for heterodimerization, e.g., electrostatic engineering of contact residues within a CH3-CH3 interface that are naturally charged or hydrophobic patch modifications.

In some embodiments, one or both Fc polypeptides present in a protein molecule described herein may include additional modifications that modulate effector function.

In some embodiments, one or both Fc polypeptides present in a protein molecule described herein may comprise modifications that reduce or eliminate effector function. Illustrative Fc polypeptide mutations that reduce effector function include, but are not limited to, substitutions in a CH2 domain, e.g., at positions 234 and 235, according to the EU numbering scheme. For example, in some embodiments, one or both Fc polypeptides can comprise alanine residues at positions 234 and 235. Thus, one or both Fc polypeptides may have L234A and L235A (LALA) substitutions.

Additional Fc polypeptide mutations that modulate an effector function include, but are not limited to, the following: position 329 may have a mutation in which proline is substituted with a glycine or arginine or an amino acid residue large enough to destroy the Fc/Fcγ receptor interface that is formed between proline 329 of the Fc and tryptophan residues Trp 87 and Trp 110 of FcγRIII. Additional illustrative substitutions include S228P, E233P, L235E, N297A, N297D, and P331S, according to the EU numbering scheme. Multiple substitutions may also be present, e.g., L234A and L235A of a human IgG1 Fc region; L234A, L235A, and P329G of a human IgG1 Fc region; S228P and L235E of a human IgG4 Fc region; L234A and G237A of a human IgG1 Fc region; L234A, L235A, and G237A of a human IgG1 Fc region; V234A and G237A of a human IgG2 Fc region; L235A, G237A, and E318A of a human IgG4 Fc region; and S228P and L236E of a human IgG4 Fc region, according to the EU numbering scheme. In some embodiments, one or both Fc polypeptides may have one or more amino acid substitutions that modulate ADCC, e.g., substitutions at positions 298, 333, and/or 334, according to the EU numbering scheme.

Illustrative Fc Polypeptides Comprising Additional Mutations

By way of non-limiting example, one or both Fc polypeptides present in a protein molecule described herein may comprise additional mutations including a knob mutation (e.g., T366W as numbered according to the EU numbering scheme), hole mutations (e.g., T366S, L368A, and Y407V as numbered according to the EU numbering scheme), mutations that modulate effector function (e.g., L234A, L235A, and/or P329G (e.g., L234A and L235A) as numbered according to the EU numbering scheme), and/or mutations that increase serum stability or serum half-life (e.g., (i) M252Y, S254T, and T256E as numbered with reference to EU numbering, or (ii) N4345 with or without M428L as numbered according to the EU numbering scheme).

In some embodiments, an Fc polypeptide may have a knob mutation (e.g., T366W as numbered according to the EU numbering scheme) (e.g., having at least 85% identity, at least 90% identity, or at least 95% identity to the sequence of SEQ ID NO:8).

In some embodiments, an Fc polypeptide may have a knob mutation (e.g., T366W as numbered according to the EU numbering scheme), mutations that modulate effector function (e.g., L234A, L235A, and/or P329G (e.g., L234A and L235A) as numbered according to the EU numbering scheme). In some embodiments, an Fc polypeptide may have a knob mutation (e.g., T366W as numbered according to the EU numbering scheme), mutations that modulate effector function (e.g., L234A, L235A, and/or P329G (e.g., L234A and L235A) as numbered according to the EU numbering scheme) (e.g., having at least 85% identity, at least 90% identity, or at least 95% identity to the sequence of SEQ ID NO:8).

In some embodiments, an Fc polypeptide may have a knob mutation (e.g., T366W as numbered according to the EU numbering scheme), mutations that increase serum stability or serum half-life (e.g., (i) M252Y, S254T, and T256E as numbered with reference to EU numbering, or (ii) N434S with or without M428L as numbered according to the EU numbering scheme) (e.g., having at least 85% identity, at least 90% identity, or at least 95% identity to the sequence of SEQ ID NO:8).

In some embodiments, an Fc polypeptide may have a knob mutation (e.g., T366W as numbered according to the EU numbering scheme), mutations that modulate effector function (e.g., L234A, L235A, and/or P329G (e.g., L234A and L235A) as numbered according to the EU numbering scheme), mutations that increase serum stability or serum half-life (e.g., (i) M252Y, S254T, and T256E as numbered with reference to EU numbering, or (ii) N434S with or without M428L as numbered according to the EU numbering scheme) (e.g., having at least 85% identity, at least 90% identity, or at least 95% identity to the sequence of SEQ ID NO:8).

In some embodiments, an Fc polypeptide may have hole mutations (e.g., T366S, L368A, and Y407V as numbered according to the EU numbering scheme) (e.g., having at least 85% identity, at least 90% identity, or at least 95% identity to the sequence of SEQ ID NO:8).

In some embodiments, an Fc polypeptide may have hole mutations (e.g., T366S, L368A, and Y407V as numbered according to the EU numbering scheme), mutations that modulate effector function (e.g., L234A, L235A, and/or P329G (e.g., L234A and L235A) as numbered according to the EU numbering scheme) (e.g., having at least 85% identity, at least 90% identity, or at least 95% identity to the sequence of SEQ ID NO:8).

In some embodiments, an Fc polypeptide may have hole mutations (e.g., T366S, L368A, and Y407V as numbered according to the EU numbering scheme), mutations that increase serum or serum half-life (e.g., (i) M252Y, S254T, and T256E as numbered with reference to EU numbering, or (ii) N434S with or without M428L as numbered according to the EU numbering scheme) (e.g., having at least 85% identity, at least 90% identity, or at least 95% identity to the sequence of SEQ ID NO:8).

In some embodiments, an Fc polypeptide may have hole mutations (e.g., T366S, L368A, and Y407V as numbered according to the EU numbering scheme), mutations that modulate effector function (e.g., L234A, L235A, and/or P329G (e.g., L234A and L235A) as numbered according to the EU numbering scheme), mutations that increase serum stability or serum half-life (e.g., (i) M252Y, S254T, and T256E as numbered with reference to EU numbering, or (ii) N434S with or without M428L as numbered according to the EU numbering scheme) (e.g., having at least 85% identity, at least 90% identity, or at least 95% identity to the sequence of SEQ ID NO:8).

Illustrative Protein Molecules Comprising an ERT Enzyme

In some aspects, a protein molecule described herein comprises a first Fc polypeptide and a second Fc polypeptide, which is linked to an ERT enzyme, an ERT enzyme variant, or a catalytically active fragment thereof, wherein the first Fc polypeptide forms an Fc dimer with the second Fc polypeptide. In some embodiments, the first Fc polypeptide and/or the second Fc polypeptide does not include an immunoglobulin heavy and/or light chain variable region sequence or an antigen-binding portion thereof. In some embodiments, the first Fc polypeptide is a modified Fc polypeptide and/or the second Fc polypeptide is a modified Fc polypeptide. In some embodiments, the first Fc polypeptide is a modified Fc polypeptide. In some embodiments, the second Fc polypeptide is a modified Fc polypeptide. In some embodiments, the modified Fc polypeptide contains one or more modifications that promote its heterodimerization to the other Fc polypeptide. In some embodiments, the modified Fc polypeptide contains one or more modifications that reduce effector function. In some embodiments, the modified Fc polypeptide contains one or more modifications that extend serum half-life. In some embodiments, the modified Fc polypeptide contains one or more modifications that confer binding to a blood-brain barrier (BBB) receptor, e.g., transferrin receptor (TfR).

In other aspects, a protein molecule described herein comprises a first polypeptide chain that comprises a modified Fc polypeptide that specifically binds to a BBB receptor, e.g., TfR, and a second polypeptide chain that comprises an Fc polypeptide which dimerizes with the modified Fc polypeptide to form an Fc dimer. An ERT enzyme may be linked to either the first or the second polypeptide chain. In some embodiments, the ERT enzyme is linked to the second polypeptide chain. In some embodiments, the protein comprises two ERT enzymes, each linked to one of the polypeptide chains. In some embodiments, the Fc polypeptide in the second polypeptide chain may be a BBB receptor-binding polypeptide that specifically binds to the same BBB receptor as the modified Fc polypeptide in the first polypeptide chain. In some embodiments, the Fc polypeptide in the second polypeptide chain does not specifically bind to a BBB receptor.

In some embodiments, a protein molecule described herein comprises a first polypeptide chain comprising a modified Fc polypeptide that specifically binds to TfR and a second polypeptide chain that comprises an Fc polypeptide, wherein the modified Fc polypeptide and the Fc polypeptide dimerize to from an Fc dimer. In some embodiments, the ERT enzyme is linked to the first polypeptide chain. In some embodiments, the ERT enzyme is linked to the second polypeptide chain. In some embodiments, the Fc polypeptide of the second polypeptide chain does not specifically bind to a BBB receptor, e.g., TfR.

In some embodiments, a protein molecule described herein comprises a first polypeptide chain that comprises a modified Fc polypeptide that binds to TfR and comprises a T366W (knob) substitution; and a second polypeptide chain that comprises an Fc polypeptide comprising T366S, L368A, and Y407V (hole) substitutions, as numbered according to the EU numbering scheme. In some embodiments, the modified Fc polypeptide and/or the Fc polypeptide further comprises L234A and L235A (LALA) substitutions, as numbered according to the EU numbering scheme. In some embodiments, the modified Fc polypeptide and/or the Fc polypeptide further comprises M252Y, S254T, and T256E (YTE) substitutions, as numbered according to the EU numbering scheme. In some embodiments, the modified Fc polypeptide and/or the Fc polypeptide further comprises L234A and L235A (LALA) substitutions and M252Y, S254T, and T256E (YTE) substitutions, as numbered according to the EU numbering scheme. In some embodiments, the modified Fc polypeptide and/or the Fc polypeptide comprises human IgG1 wild-type residues at positions 234, 235, 252, 254, 256, and 366, as numbered according to the EU numbering scheme.

In some embodiments, the modified Fc polypeptide comprises the knob and LALA mutations as specified for any one of SEQ ID NOS:6, 28, 29, 41, 47 and 48, and has at least 85% identity, at least 90% identity, at least 95% identity, at least 96% identity, at least 97% identity, at least 98% identity, or at least 99% identity to the respective sequence; or comprises the sequence of any one of SEQ ID NOS:6, 28, 29, 41, 47 and 48. In some embodiments, the modified Fc polypeptide comprises the knob and LALA mutations as specified for any one of SEQ ID NOS:6, 28 and 29, and has at least 85% identity, at least 90% identity, at least 95% identity, at least 96% identity, at least 97% identity, at least 98% identity, or at least 99% identity to the respective sequence; or comprises the sequence of any one of SEQ ID NOS:6, 28 and 29. In some embodiments, the modified Fc polypeptide comprises the knob and LALA mutations as specified for any one of SEQ ID NOS: 41, 47 and 48, and has at least 85% identity, at least 90% identity, at least 95% identity, at least 96% identity, at least 97% identity, at least 98% identity, or at least 99% identity to the respective sequence; or comprises the sequence of any one of SEQ ID NOS: 41, 47 and 48. In some embodiments, the Fc polypeptide comprises the hole, LALA, and/or YTE mutations as specified for any one of SEQ ID NOS:14-17 and has at least 85% identity, at least 90% identity, at least 95% identity, at least 96% identity, at least 97% identity, at least 98% identity, or at least 99% identity to the respective sequence; or comprises the sequence of any one of SEQ ID NOS:14-17. In some embodiments, the Fc polypeptide comprises the hole, LALA, and/or YTE mutations as specified for any one of SEQ ID NOS:54-57 and has at least 85% identity, at least 90% identity, at least 95% identity, at least 96% identity, at least 97% identity, at least 98% identity, or at least 99% identity to the respective sequence; or comprises the sequence of any one of SEQ ID NOS:54-57. In some embodiments, the modified Fc polypeptide comprises any one of SEQ ID NOS:6, 28, 29, 41, 47 and 48 and the Fc polypeptide comprises any one of SEQ ID NOS:14, 15, 16, 17, 54, 55, 56 and 57. In some embodiments, the modified Fc polypeptide comprises any one of SEQ ID NOS:6, 28 and 29, and the Fc polypeptide comprises any one of SEQ ID NOS:14-17. In some embodiments, the modified Fc polypeptide comprises any one of SEQ ID NOS:41, 47 and 48 and the Fc polypeptide comprises any one of SEQ ID NOS:54, 55, 56 and 57. In some embodiments, the N-terminus of the modified Fc polypeptide and/or the Fc polypeptide includes a portion of an IgG1 hinge region (e.g., DKTHTCPPCP; SEQ ID NO:22). In some embodiments, the modified Fc polypeptide has at least 85%, at least 90%, at least 95%, at least 96%, at least 97%, at least 98%, or at least 99% identity to any one of SEQ ID NOS:7, 25, 30, 42, 44 and 49, or comprises the sequence of any one of SEQ ID NOS:7, 25, 30, 42, 44 and 49. In some embodiments, the modified Fc polypeptide has at least 85%, at least 90%, at least 95%, at least 96%, at least 97%, at least 98%, or at least 99% identity to any one of SEQ ID NOS:7, 25 and 30, or comprises the sequence of any one of SEQ ID NOS:7, 25 and 30. In some embodiments, the modified Fc polypeptide has at least 85%, at least 90%, at least 95%, at least 96%, at least 97%, at least 98%, or at least 99% identity to any one of SEQ ID NOS:42, 44 and 49, or comprises the sequence of any one of SEQ ID NOS: 42, 44 and 49.

In some embodiments, a protein molecule described herein comprises a first polypeptide chain that comprises a modified Fc polypeptide that binds to TfR and comprises T366S, L368A, and Y407V (hole) substitutions; and a second polypeptide chain that comprises an Fc polypeptide comprising a T366W (knob) substitution, as numbered according to the EU numbering scheme. In some embodiments, the modified Fc polypeptide and/or the Fc polypeptide further comprises L234A and L235A (LALA) substitutions, as numbered according to the EU numbering scheme. In some embodiments, the modified Fc polypeptide and/or the Fc polypeptide further comprises M252Y, S254T, and T256E (YTE) substitutions, as numbered according to the EU numbering scheme. In some embodiments, the modified Fc polypeptide and/or the Fc polypeptide further comprises L234A and L235A (LALA) substitutions and M252Y, S254T, and T256E (YTE) substitutions, as numbered according to the EU numbering scheme. In some embodiments, the modified Fc polypeptide and/or the Fc polypeptide comprises human IgG1 wild-type residues at positions 234, 235, 252, 254, 256, and 366, as numbered according to the EU numbering scheme.

In some embodiments, the modified Fc polypeptide comprises the hole, LALA, and YTE mutations. In some embodiments, the Fc polypeptide comprises the knob, LALA, and YTE mutations as specified for any one of SEQ ID NOS:18-21 and has at least 85% identity, at least 90% identity, at least 95%, at least 96%, at least 97%, at least 98%, or at least 99% identity to the respective sequence; or comprises the sequence of any one of SEQ ID NOS:18-21. In some embodiments, the Fc polypeptide comprises the knob, LALA, and YTE mutations as specified for any one of SEQ ID NOS:58-61 and has at least 85% identity, at least 90% identity, at least 95%, at least 96%, at least 97%, at least 98%, or at least 99% identity to the respective sequence; or comprises the sequence of any one of SEQ ID NOS:58-61. In some embodiments, the N-terminus of the modified Fc polypeptide and/or the Fc polypeptide includes a portion of an IgG1 hinge region (e.g., DKTHTCPPCP; SEQ ID NO:22).

In some embodiments, an IDS enzyme present in a protein molecule described herein is linked to a polypeptide chain that comprises an Fc polypeptide having at least 85%, at least 90%, at least 95%, at least 96%, at least 97%, at least 98%, or at least 99% identity to any one of SEQ ID NOS:14-17, or comprises the sequence of any one of SEQ ID NOS:14-17 (e.g., as a fusion polypeptide). In some embodiments, an IDS enzyme present in a protein molecule described herein is linked to a polypeptide chain that comprises an Fc polypeptide having at least 85%, at least 90%, at least 95%, at least 96%, at least 97%, at least 98%, or at least 99% identity to any one of SEQ ID NOS:14-17 and SEQ ID NOs:54-57, or comprises the sequence of any one of SEQ ID NOS:14-17 and SEQ ID NOs:54-57 (e.g., as a fusion polypeptide). In some embodiments, the IDS enzyme is linked to the N-terminus of the Fc polypeptide. In some embodiments, the IDS enzyme is linked to the Fc polypeptide by a linker, such as a flexible linker, and/or a hinge region or portion thereof (e.g., DKTHTCPPCP; SEQ ID NO:22). In some embodiments, the IDS sequence having at least 85%, at least 90%, at least 95%, at least 96%, at least 97%, at least 98%, or at least 99% identity to any one of SEQ ID NOS:1, 2, 3 and 23 or comprises the sequence of any one of SEQ ID NOS:1, 2, 3 and 23. In some embodiments, the IDS sequence linked to the Fc polypeptide has at least 85%, at least 90%, at least 95%, at least 96%, at least 97%, at least 98%, or at least 99% identity to any one of SEQ ID NOS:4, 5, 24, 26, 31, 33, 39, 40, 43, 45, 50 and 52 or comprises the sequence of any one of SEQ ID NOS:4, 5, 24, 26, 31, 33, 39, 40, 43, 45, 50 and 52. In some embodiments, the IDS sequence linked to the Fc polypeptide has at least 85%, at least 90%, at least 95%, at least 96%, at least 97%, at least 98%, or at least 99% identity to any one of SEQ ID NOS:4, 5, 24, 26, 31 and 33, or comprises the sequence of any one of SEQ ID NOS:4, 5, 24, 26, 31 and 33. In some embodiments, the IDS sequence linked to the Fc polypeptide has at least 85%, at least 90%, at least 95%, at least 96%, at least 97%, at least 98%, or at least 99% identity to any one of SEQ ID NOS:39, 40, 43, 45, 50 and 52 or comprises the sequence of any one of SEQ ID NOS: 39, 40, 43, 45, 50 and 52. In some embodiments, the protein molecule comprises a modified Fc polypeptide having at least 85%, at least 90%, at least 95%, at least 96%, at least 97%, at least 98%, or at least 99% identity to any one of SEQ ID NOS:6, 28, 29, 41, 47 and 48 or comprises the sequence of any one of SEQ ID NOS: 6, 28, 29, 41, 47 and 48. In some embodiments, the protein molecule comprises a modified Fc polypeptide having at least 85%, at least 90%, at least 95%, at least 96%, at least 97%, at least 98%, or at least 99% identity to any one of SEQ ID NOS:6, 28 and 29, or comprises the sequence of any one of SEQ ID NOS: 6, 28 and 29. In some embodiments, the protein molecule comprises a modified Fc polypeptide having at least 85%, at least 90%, at least 95%, at least 96%, at least 97%, at least 98%, or at least 99% identity to any one of SEQ ID NOS:41, 47 and 48 or comprises the sequence of any one of SEQ ID NOS:41, 47 and 48. In some embodiments, the N-terminus of the Fc polypeptide and/or the modified Fc polypeptide includes a portion of an IgG1 hinge region (e.g., DKTHTCPPCP; SEQ ID NO:22). In some embodiments, the modified Fc polypeptide has at least 85%, at least 90%, at least 95%, at least 96%, at least 97%, at least 98%, or at least 99% identity to any one of SEQ ID NOS:7, 25, 30, 42, 49 and 50 or comprises the sequence of any one of SEQ ID NOS:7, 25, 30, 42, 49 and 50. In some embodiments, the modified Fc polypeptide has at least 85%, at least 90%, at least 95%, at least 96%, at least 97%, at least 98%, or at least 99% identity to any one of SEQ ID NOS:7, 25 and 30, or comprises the sequence of any one of SEQ ID NOS:7, 25 and 30. In some embodiments, the modified Fc polypeptide has at least 85%, at least 90%, at least 95%, at least 96%, at least 97%, at least 98%, or at least 99% identity to any one of SEQ ID NOS:42, 49 and 50 or comprises the sequence of any one of SEQ ID NOS:42, 49 and 50.

In some embodiments, an IDS enzyme present in a protein molecule described herein is linked to a polypeptide chain that comprises an Fc polypeptide having at least 85%, at least 90%, at least 95%, at least 96%, at least 97%, at least 98%, or at least 99% identity to any one of SEQ ID NOS:14-17, or comprises the sequence of any one of SEQ ID NOS:14-17 (e.g., as a fusion polypeptide). In some embodiments, an IDS enzyme present in a protein molecule described herein is linked to a polypeptide chain that comprises an Fc polypeptide having at least 85%, at least 90%, at least 95%, at least 96%, at least 97%, at least 98%, or at least 99% identity to any one of SEQ ID NOS:54-57, or comprises the sequence of any one of SEQ ID NOS:54-57 (e.g., as a fusion polypeptide). In some embodiments, the IDS enzyme is linked to the N-terminus of the Fc polypeptide. In some embodiments, the IDS enzyme is linked to the Fc polypeptide by a linker, such as a flexible linker, and/or a hinge region or portion thereof (e.g., DKTHTCPPCP; SEQ ID NO:22). In some embodiments, the IDS sequence having at least 85%, at least 90%, at least 95%, at least 96%, at least 97%, at least 98%, or at least 99% identity to any one of SEQ ID NOS:1, 2 and 3, or comprises the sequence of any one of SEQ ID NOS:1, 2 and 3. In some embodiments, the IDS sequence linked to the Fc polypeptide has at least 85%, at least 90%, at least 95%, at least 96%, at least 97%, at least 98%, or at least 99% identity to any one of SEQ ID NOS:4, 5, 39 and 40 or comprises the sequence of any one of SEQ ID NOS:4, 5, 39 and 40. In some embodiments, the IDS sequence linked to the Fc polypeptide has at least 85%, at least 90%, at least 95%, at least 96%, at least 97%, at least 98%, or at least 99% identity to any one of SEQ ID NOS:4 and 5, or comprises the sequence of any one of SEQ ID NOS:4 and 5. In some embodiments, the IDS sequence linked to the Fc polypeptide has at least 85%, at least 90%, at least 95%, at least 96%, at least 97%, at least 98%, or at least 99% identity to any one of SEQ ID NOS:39 and 40 or comprises the sequence of any one of SEQ ID NOS:39 and 40. In some embodiments, the protein molecule comprises a modified Fc polypeptide having at least 85%, at least 90%, at least 95%, at least 96%, at least 97%, at least 98%, or at least 99% identity to SEQ ID NO:6, or comprises the sequence of SEQ ID NO:6. In some embodiments, the protein molecule comprises a modified Fc polypeptide having at least 85%, at least 90%, at least 95%, at least 96%, at least 97%, at least 98%, or at least 99% identity to SEQ ID NO:41, or comprises the sequence of SEQ ID NO:41. In some embodiments, the N-terminus of the Fc polypeptide and/or the modified Fc polypeptide includes a portion of an IgG1 hinge region (e.g., DKTHTCPPCP; SEQ ID NO:22). In some embodiments, the modified Fc polypeptide has at least 85%, at least 90%, at least 95%, at least 96%, at least 97%, at least 98%, or at least 99% identity to SEQ ID NO:7, or comprises the sequence of SEQ ID NO:7. In some embodiments, the modified Fc polypeptide has at least 85%, at least 90%, at least 95%, at least 96%, at least 97%, at least 98%, or at least 99% identity to SEQ ID NO:42, or comprises the sequence of SEQ ID NO:42. In some embodiments, the modified Fc polypeptide has at least 85%, at least 90%, at least 95%, at least 96%, at least 97%, at least 98%, or at least 99% identity to SEQ ID NO:25, or comprises the sequence of SEQ ID NO:25. In some embodiments, the modified Fc polypeptide has at least 85%, at least 90%, at least 95%, at least 96%, at least 97%, at least 98%, or at least 99% identity to SEQ ID NO:44, or comprises the sequence of SEQ ID NO:44. In some embodiments, the modified Fc polypeptide has at least 85%, at least 90%, at least 95%, at least 96%, at least 97%, at least 98%, or at least 99% identity to SEQ ID NO:30, or comprises the sequence of SEQ ID NO:30. In some embodiments, the modified Fc polypeptide has at least 85%, at least 90%, at least 95%, at least 96%, at least 97%, at least 98%, or at least 99% identity to SEQ ID NO:49, or comprises the sequence of SEQ ID NO:49.

In some embodiments, the IDS sequence linked to the Fc polypeptide has at least 85%, at least 90%, at least 95%, at least 96%, at least 97%, at least 98%, or at least 99% identity to any one of SEQ ID NOS:4 and 5, or comprises the sequence of any one of SEQ ID NOS:4 and 5; and the modified Fc polypeptide has at least 85%, at least 90%, at least 95%, at least 96%, at least 97%, at least 98%, or at least 99% identity to SEQ ID NO:6, or comprises the sequence of SEQ ID NO:6.

In some embodiments, the IDS sequence linked to the Fc polypeptide comprises the sequence of any one of SEQ ID NOS:4 and 5; and the modified Fc polypeptide comprises the sequence of SEQ ID NO:6.

In some embodiments, the IDS sequence linked to the Fc polypeptide has at least 85%, at least 90%, at least 95%, at least 96%, at least 97%, at least 98%, or at least 99% identity to any one of SEQ ID NOS:39 and 40, or comprises the sequence of any one of SEQ ID NOS:39 and 40; and the modified Fc polypeptide has at least 85%, at least 90%, at least 95%, at least 96%, at least 97%, at least 98%, or at least 99% identity to SEQ ID NO:41, or comprises the sequence of SEQ ID NO:41.

In some embodiments, the IDS sequence linked to the Fc polypeptide comprises the sequence of any one of SEQ ID NOS:39 and 40; and the modified Fc polypeptide comprises the sequence of SEQ ID NO:41.

In some embodiments, the IDS sequence linked to the Fc polypeptide has at least 85%, at least 90%, at least 95%, at least 96%, at least 97%, at least 98%, or at least 99% identity to any one of SEQ ID NOS:4 and 5, or comprises the sequence of any one of SEQ ID NOS:4 and 5; and the modified Fc polypeptide has at least 85%, at least 90%, at least 95%, at least 96%, at least 97%, at least 98%, or at least 99% identity to SEQ ID NO:7, or comprises the sequence of SEQ ID NO:7.

In some embodiments, the IDS sequence linked to the Fc polypeptide comprises the sequence of any one of SEQ ID NOS:4 and 5; and the modified Fc polypeptide comprises the sequence of SEQ ID NO:7.

In some embodiments, the IDS sequence linked to the Fc polypeptide has at least 85%, at least 90%, at least 95%, at least 96%, at least 97%, at least 98%, or at least 99% identity to any one of SEQ ID NOS:39 and 40, or comprises the sequence of any one of SEQ ID NOS:39 and 40; and the modified Fc polypeptide has at least 85%, at least 90%, at least 95%, at least 96%, at least 97%, at least 98%, or at least 99% identity to SEQ ID NO:42, or comprises the sequence of SEQ ID NO:42.

In some embodiments, the IDS sequence linked to the Fc polypeptide comprises the sequence of any one of SEQ ID NOS:39 and 40; and the modified Fc polypeptide comprises the sequence of SEQ ID NO:42.

In some embodiments, the IDS sequence linked to the Fc polypeptide has at least 85%, at least 90%, at least 95%, at least 96%, at least 97%, at least 98%, or at least 99% identity to any one of SEQ ID NOS:4 and 5, or comprises the sequence of any one of SEQ ID NOS:4 and 5; and the modified Fc polypeptide has at least 85%, at least 90%, at least 95%, at least 96%, at least 97%, at least 98%, or at least 99% identity to SEQ ID NO:25, or comprises the sequence of SEQ ID NO:25.

In some embodiments, the IDS sequence linked to the Fc polypeptide comprises the sequence of any one of SEQ ID NOS:4 and 5; and the modified Fc polypeptide comprises the sequence of SEQ ID NO:25.

In some embodiments, the IDS sequence linked to the Fc polypeptide has at least 85%, at least 90%, at least 95%, at least 96%, at least 97%, at least 98%, or at least 99% identity to any one of SEQ ID NOS:39 and 40, or comprises the sequence of any one of SEQ ID NOS:39 and 40; and the modified Fc polypeptide has at least 85%, at least 90%, at least 95%, at least 96%, at least 97%, at least 98%, or at least 99% identity to SEQ ID NO:44, or comprises the sequence of SEQ ID NO:44.

In some embodiments, the IDS sequence linked to the Fc polypeptide comprises the sequence of any one of SEQ ID NOS:39 and 40; and the modified Fc polypeptide comprises the sequence of SEQ ID NO:44.

In some embodiments, the IDS sequence linked to the Fc polypeptide has at least 85%, at least 90%, at least 95%, at least 96%, at least 97%, at least 98%, or at least 99% identity to any one of SEQ ID NOS:4 and 5, or comprises the sequence of any one of SEQ ID NOS:4 and 5; and the modified Fc polypeptide has at least 85%, at least 90%, at least 95%, at least 96%, at least 97%, at least 98%, or at least 99% identity to SEQ ID NO:30, or comprises the sequence of SEQ ID NO:30.

In some embodiments, the IDS sequence linked to the Fc polypeptide comprises the sequence of any one of SEQ ID NOS:4 and 5; and the modified Fc polypeptide comprises the sequence of SEQ ID NO:30.

In some embodiments, the IDS sequence linked to the Fc polypeptide has at least 85%, at least 90%, at least 95%, at least 96%, at least 97%, at least 98%, or at least 99% identity to any one of SEQ ID NOS:39 and 40, or comprises the sequence of any one of SEQ ID NOS:39 and 40; and the modified Fc polypeptide has at least 85%, at least 90%, at least 95%, at least 96%, at least 97%, at least 98%, or at least 99% identity to SEQ ID NO:49, or comprises the sequence of SEQ ID NO:49.

In some embodiments, the IDS sequence linked to the Fc polypeptide comprises the sequence of any one of SEQ ID NOS:39 and 40; and the modified Fc polypeptide comprises the sequence of SEQ ID NO:49.

In some embodiments, the protein molecule comprises an IDS-Fc fusion polypeptide comprising the sequence of SEQ ID NO:24, and a modified Fc polypeptide comprising the sequence of any one of SEQ ID NOS:29 and 30 (e.g., SEQ ID NO:30). In other embodiments, the protein molecule comprises an IDS-Fc fusion polypeptide comprising the sequence of SEQ ID NO:24, and a modified Fc polypeptide comprising the sequence of any one of SEQ ID NOS:7 and 28 (e.g., SEQ ID NO:7). In some embodiments, the protein molecule comprises an IDS-Fc fusion polypeptide comprising the sequence of SEQ ID NO:24, and a modified Fc polypeptide comprising the sequence of SEQ ID NO:6, wherein the N-terminus of the modified Fc polypeptide optionally includes a portion of an IgG1 hinge region (e.g., DKTHTCPPCP; SEQ ID NO:22). In some embodiments, the protein molecule comprises an IDS-Fc fusion polypeptide comprising the sequence of SEQ ID NO:24, and a modified Fc polypeptide comprising the sequence of SEQ ID NO:25.

In some embodiments, the protein molecule comprises an IDS-Fc fusion polypeptide comprising the sequence of SEQ ID NO:43, and a modified Fc polypeptide comprising the sequence of any one of SEQ ID NOS:48 and 49 (e.g., SEQ ID NO:49). In other embodiments, the protein molecule comprises an IDS-Fc fusion polypeptide comprising the sequence of SEQ ID NO:43, and a modified Fc polypeptide comprising the sequence of any one of SEQ ID NOS:42 and 47 (e.g., SEQ ID NO:42). In some embodiments, the protein molecule comprises an IDS-Fc fusion polypeptide comprising the sequence of SEQ ID NO:43, and a modified Fc polypeptide comprising the sequence of SEQ ID NO:41, wherein the N-terminus of the modified Fc polypeptide optionally includes a portion of an IgG1 hinge region (e.g., DKTHTCPPCP; SEQ ID NO:22). In some embodiments, the protein molecule comprises an IDS-Fc fusion polypeptide comprising the sequence of SEQ ID NO:43, and a modified Fc polypeptide comprising the sequence of SEQ ID NO:44

In some embodiments, the protein molecule comprises an IDS-Fc fusion polypeptide comprising the sequence of SEQ ID NO:4, and a modified Fc polypeptide comprising the sequence of any one of SEQ ID NOS:29 and 30 (e.g., SEQ ID NO:30). In other embodiments, the protein molecule comprises an IDS-Fc fusion polypeptide comprising the sequence of SEQ ID NO:4, and a modified Fc polypeptide comprising the sequence of any one of SEQ ID NOS:7 and 28 (e.g., SEQ ID NO:7). In some embodiments, the protein molecule comprises an IDS-Fc fusion polypeptide comprising the sequence of SEQ ID NO:4, and a modified Fc polypeptide comprising the sequence of SEQ ID NO:6, wherein the N-terminus of the modified Fc polypeptide optionally includes a portion of an IgG1 hinge region (e.g., DKTHTCPPCP; SEQ ID NO:22). In some embodiments, the protein molecule comprises an IDS-Fc fusion polypeptide comprising the sequence of SEQ ID NO:4, and a modified Fc polypeptide comprising the sequence of SEQ ID NO:25.

In some embodiments, the protein molecule comprises an IDS-Fc fusion polypeptide comprising the sequence of SEQ ID NO:39, and a modified Fc polypeptide comprising the sequence of any one of SEQ ID NOS:48 and 49 (e.g., SEQ ID NO:49). In other embodiments, the protein molecule comprises an IDS-Fc fusion polypeptide comprising the sequence of SEQ ID NO:39, and a modified Fc polypeptide comprising the sequence of any one of SEQ ID NOS:42 and 47 (e.g., SEQ ID NO:42). In some embodiments, the protein molecule comprises an IDS-Fc fusion polypeptide comprising the sequence of SEQ ID NO:39, and a modified Fc polypeptide comprising the sequence of SEQ ID NO:41, wherein the N-terminus of the modified Fc polypeptide optionally includes a portion of an IgG1 hinge region (e.g., DKTHTCPPCP; SEQ ID NO:22). In some embodiments, the protein molecule comprises an IDS-Fc fusion polypeptide comprising the sequence of SEQ ID NO:39, and a modified Fc polypeptide comprising the sequence of SEQ ID NO:44

In some embodiments, the protein molecule comprises an IDS-Fc fusion polypeptide comprising the sequence of SEQ ID NO:5, and a modified Fc polypeptide comprising the sequence of any one of SEQ ID NOS:29 and 30 (e.g., SEQ ID NO:30). In other embodiments, the protein molecule comprises an IDS-Fc fusion polypeptide comprising the sequence of SEQ ID NO:5, and a modified Fc polypeptide comprising the sequence of any one of SEQ ID NOS:7 and 28 (e.g., SEQ ID NO:7). In some embodiments, the protein molecule comprises an IDS-Fc fusion polypeptide comprising the sequence of SEQ ID NO:5, and a modified Fc polypeptide comprising the sequence of SEQ ID NO:6, wherein the N-terminus of the modified Fc polypeptide optionally includes a portion of an IgG1 hinge region (e.g., DKTHTCPPCP; SEQ ID NO:22). In some embodiments, the protein molecule comprises an IDS-Fc fusion polypeptide comprising the sequence of SEQ ID NO:5, and a modified Fc polypeptide comprising the sequence of SEQ ID NO:25.

In some embodiments, the protein molecule comprises an IDS-Fc fusion polypeptide comprising the sequence of SEQ ID NO:40, and a modified Fc polypeptide comprising the sequence of any one of SEQ ID NOS:48 and 49 (e.g., SEQ ID NO:49). In other embodiments, the protein molecule comprises an IDS-Fc fusion polypeptide comprising the sequence of SEQ ID NO:40, and a modified Fc polypeptide comprising the sequence of any one of SEQ ID NOS:42 and 47 (e.g., SEQ ID NO:42). In some embodiments, the protein molecule comprises an IDS-Fc fusion polypeptide comprising the sequence of SEQ ID NO:40, and a modified Fc polypeptide comprising the sequence of SEQ ID NO:41, wherein the N-terminus of the modified Fc polypeptide optionally includes a portion of an IgG1 hinge region (e.g., DKTHTCPPCP; SEQ ID NO:22). In some embodiments, the protein molecule comprises an IDS-Fc fusion polypeptide comprising the sequence of SEQ ID NO:40, and a modified Fc polypeptide comprising the sequence of SEQ ID NO:44

In some embodiments, an IDS enzyme present in a protein molecule described herein is linked to a polypeptide chain that comprises an Fc polypeptide having at least 85%, at least 90%, at least 95%, at least 96%, at least 97%, at least 98%, or at least 99% identity to any one of SEQ ID NOS:18-21, or comprises the sequence of any one of SEQ ID NOS:18-21 (e.g., as a fusion polypeptide). In some embodiments, an IDS enzyme present in a protein molecule described herein is linked to a polypeptide chain that comprises an Fc polypeptide having at least 85%, at least 90%, at least 95%, at least 96%, at least 97%, at least 98%, or at least 99% identity to any one of SEQ ID NOS:58-61, or comprises the sequence of any one of SEQ ID NOS:58-61

(e.g., as a fusion polypeptide). In some embodiments, the IDS enzyme is linked to the Fc polypeptide by a linker, such as a flexible linker, and/or a hinge region or portion thereof (e.g., DKTHTCPPCP; SEQ ID NO:22). In some embodiments, the IDS enzyme comprises a sequence having at least 85%, at least 90%, at least 95%, at least 96%, at least 97%, at least 98%, or at least 99% identity to any one of SEQ ID NOS: 2, 3 and 23, or comprises the sequence of any one of SEQ ID NOS:2, 3 and 23. In some embodiments, the IDS sequence linked to the Fc polypeptide has at least 85%, at least 90%, at least 95%, at least 96%, at least 97%, at least 98%, or at least 99% identity to any one of SEQ ID NOS:27, 32, and 34, or comprises the sequence of any one of SEQ ID NOS:27, 32, and 34. In some embodiments, the IDS sequence linked to the Fc polypeptide has at least 85%, at least 90%, at least 95%, at least 96%, at least 97%, at least 98%, or at least 99% identity to any one of SEQ ID NOS:46, 51, and 53, or comprises the sequence of any one of SEQ ID NOS:46, 51, and 53. In some embodiments, the N-terminus of the Fc polypeptide and/or the modified Fc polypeptide includes a portion of an IgG1 hinge region (e.g., DKTH-TCPPCP; SEQ ID NO:22).

In some embodiments, an IDS enzyme present in a protein molecule described herein is linked to a polypeptide chain that comprises a modified Fc polypeptide having at least 85%, at least 90%, at least 95%, at least 96%, at least 97%, at least 98%, or at least 99% identity to any one of SEQ ID NOS:6, 28 and 29, or comprises the sequence of any one of SEQ ID NOS: 6, 28 and 29 (e.g., as a fusion polypeptide). In some embodiments, an IDS enzyme present in a protein molecule described herein is linked to a polypeptide chain that comprises a modified Fc polypeptide having at least 85%, at least 90%, at least 95%, at least 96%, at least 97%, at least 98%, or at least 99% identity to any one of SEQ ID NOS:41, 47 and 48, or comprises the sequence of any one of SEQ ID NOS: 41, 47 and 48 (e.g., as a fusion polypeptide). In some embodiments, the IDS enzyme is linked to the modified Fc polypeptide by a linker, such as a flexible linker, and/or a hinge region or portion thereof (e.g., DKTH-TCPPCP; SEQ ID NO:22). In some embodiments, the IDS enzyme comprises an IDS sequence having at least 85%, at least 90%, at least 95%, at least 96%, at least 97%, at least 98%, or at least 99% identity to any one of SEQ ID NOS: 2, 3 and 23, or comprises the sequence of any one of SEQ ID NOS: 2, 3 and 23. In some embodiments, the protein molecule comprises an Fc polypeptide having at least 85%, at least 90%, at least 95%, at least 96%, at least 97%, at least 98%, or at least 99% identity to any one of SEQ ID NOS:14-17, or comprises the sequence of any one of SEQ ID NOS:14-17. In some embodiments, the protein molecule comprises an Fc polypeptide having at least 85%, at least 90%, at least 95%, at least 96%, at least 97%, at least 98%, or at least 99% identity to any one of SEQ ID NOS:54-57, or comprises the sequence of any one of SEQ ID NOS:54-57. In some embodiments, the N-terminus of the modified Fc polypeptide and/or the Fc polypeptide includes a portion of an IgG1 hinge region (e.g., DKTHTCPPCP; SEQ ID NO:22).

ERT Enzymes Linked To Fc Polypeptides

In some embodiments, a protein molecule described herein comprises two Fc polypeptides as described herein and one or both of the Fc polypeptides may further comprise a partial or full hinge region. The hinge region can be from any immunoglobulin subclass or isotype. An illustrative immunoglobulin hinge is an IgG hinge region, such as an IgG1 hinge region, e.g., human IgG1 hinge amino acid sequence EPKSCDKTHTCPPCP (SEQ ID NO:12) or a portion thereof (e.g., DKTHTCPPCP; SEQ ID NO:22). In some embodiments, the hinge region is at the N-terminal region of the Fc polypeptide.

In some embodiments, an Fc polypeptide is joined to the ERT enzyme by a linker, e.g., a peptide linker. In some embodiments, the Fc polypeptide is joined to the ERT enzyme by a peptide bond or by a peptide linker, e.g., is a fusion polypeptide. The peptide linker may be configured such that it allows for the rotation of the ERT enzyme relative to the Fc polypeptide to which it is joined; and/or is resistant to digestion by proteases. Peptide linkers may contain natural amino acids, unnatural amino acids, or a combination thereof. In some embodiments, the peptide linker may be a flexible linker, e.g., containing amino acids such as Gly, Asn, Ser, Thr, Ala, and the like. Such linkers are designed using known parameters and may be of any length and contain any number of repeat units of any length (e.g., repeat units of Gly and Ser residues). For example, the linker may have repeats, such as two, three, four, five, or more $Gly_4$-Ser (SEQ ID NO:36) repeats or a single $Gly_4$-Ser (SEQ ID NO:36). In some embodiments, the peptide linker may include a protease cleavage site, e.g., that is cleavable by an enzyme present in the central nervous system.

In some embodiments, the ERT enzyme is joined to the N-terminus of the Fc polypeptide, e.g., by a $Gly_4$-Ser linker (SEQ ID NO:36) or a ($Gly_4$-Ser)$_2$ linker (SEQ ID NO:37).G In some embodiments, the Fc polypeptide may comprise a hinge sequence or partial hinge sequence at the N-terminus that is joined to the linker or directly joined to the ERT enzyme.

In some embodiments, the ERT enzyme is joined to the C-terminus of the Fc polypeptide, e.g., by a $Gly_4$-Ser linker (SEQ ID NO:36) or a ($Gly_4$-Ser)$_2$ linker (SEQ ID NO:37). In some embodiments, the C-terminus of the Fc polypeptide is directly joined to the ERT enzyme.

In some embodiments, the ERT enzyme is joined to the Fc polypeptide by a chemical cross-linking agent. Such conjugates can be generated using well-known chemical cross-linking reagents and protocols. For example, there are a large number of chemical cross-linking agents that are known to those skilled in the art and useful for cross-linking the polypeptide with an agent of interest. For example, the cross-linking agents are heterobifunctional cross-linkers, which can be used to link molecules in a stepwise manner. Heterobifunctional cross-linkers provide the ability to design more specific coupling methods for conjugating proteins, thereby reducing the occurrences of unwanted side reactions such as homo-protein polymers. A wide variety of heterobifunctional cross-linkers are known in the art, including N-hydroxysuccinimide (NHS) or its water soluble analog N-hydroxysulfosuccinimide (sulfo-NHS), succinimidyl 4-(N-maleimidomethyl)cyclohexane-1-carboxylate (SMCC), m-maleimidobenzoyl-N-hydroxysuccinimide ester (MBS); N-succinimidyl (4-iodoacetyl) aminobenzoate (SIAB), succinimidyl 4-(p-maleimidophenyl)butyrate (SMPB), 1-ethyl-3-(3-dimethylaminopropyl)carbodiimide hydrochloride (EDC); 4-succinimidyloxycarbonyl-a-methyl-a-(2-pyridyldithio)-toluene (SMPT), N-succinimidyl 3-(2-pyridyldithio)propionate (SPDP), and succinimidyl 6-[3-(2-pyridyldithio)propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo. In addition to the heterobifunctional cross-linkers, there exist a number of other cross-linking agents including homobifunctional and photoreactive cross-linkers. Di succinimidyl subcrate (DSS), bismaleimidohexane (BMH) and dimethylpimelimidate. 2HCl (DMP) are examples of useful homobifunctional cross-linking agents, and bis-[B-(4-azidosalicylamido) ethyl]disulfide (BASED) and N-succinimidyl-6(4'-azido-2'-nitrophenylamino)hexanoate (SANPAH) are examples of useful photoreactive cross-linkers.

Concentration of the Protein Molecule

In certain embodiments, the concentration of the protein molecule in a pharmaceutical composition described herein (e.g., in aqueous, pre-lyophilized, lyophilized or reconstituted form), is about 5-50 mg/mL, 5-45 mg/mL, 5-40 mg/mL, 5-35 mg/mL, 5-30 mg/mL, 10-40 mg/mL or 10-30 mg/mL. In certain embodiments, the concentration of the protein molecule in an aqueous/liquid pharmaceutical composition described herein is about 5-50 mg/mL, 5-45 mg/mL, 5-40 mg/mL, 5-35 mg/mL, 5-30 mg/mL, 10-40 mg/mL or 10-30 mg/mL.

In certain embodiments, the protein molecule concentration is about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, or 50 mg/mL±2 mg/mL. In certain embodiments, the protein molecule concentration is about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, or 50 mg/mL.

In certain embodiments, the protein molecule concentration is about 10 mg/mL±2 mg/mL. In certain embodiments, the protein molecule concentration is about 15 mg/mL±2 mg/mL. In certain embodiments, the protein molecule concentration is about 20 mg/mL±2 mg/mL. In certain embodiments, the protein molecule concentration is about 25 mg/mL±2 mg/mL. In certain embodiments, the protein molecule concentration is about 30 mg/mL±2 mg/mL. In certain embodiments, the protein molecule concentration is about 35 mg/mL±2 mg/mL. In certain embodiments, the protein molecule concentration is about 40 mg/mL±2 mg/mL.

In certain embodiments, the protein molecule concentration is about 10 mg/mL. In certain embodiments, the protein molecule concentration is about 15 mg/mL. In certain embodiments, the protein molecule concentration is about 20 mg/mL. In certain embodiments, the protein molecule concentration is about 25 mg/mL. In certain embodiments, the protein molecule concentration is about 30 mg/mL. In certain embodiments, the protein molecule concentration is about 35 mg/mL. In certain embodiments, the protein molecule concentration is about 40 mg/mL.

Buffers

The pH of a pharmaceutical composition is capable of altering the solubility of a therapeutic agent (e.g., an enzyme or protein) in an aqueous formulation or in a pre-lyophilization or reconstituted formulation. Accordingly, in certain embodiments, a pharmaceutical composition described herein comprises one or more buffers. In some embodiments, a pharmaceutical composition described herein comprises an amount of buffer sufficient to maintain the optimal pH of said composition between about 5.0-7.5.

Thus, in certain embodiments, the pH of a pharmaceutical composition described herein is about 5.0 to 7.5, or about 5.0 to 7.0, or about 5.5 to 7.0.

In certain embodiments, the pH of a pharmaceutical composition described herein is about 5.0, 5.5, 6.0, 6.5, or 7.0±0.5. In certain embodiments, the pH of a pharmaceutical composition described herein is about 5.5, 6.0, 6.5, or 7.0±0.3.

In certain embodiments, the pH of a pharmaceutical composition described herein is about 5.5, 5.6, 5.7, 5.8, 5.9, 6.0, 6.1, 6.2, 6.3, 6.4, 6.5, 6.6, 6.7, 6.8, 6.9 or 7.0±0.2. In certain embodiments, the pH of a pharmaceutical composition described herein is about 5.5, 5.6, 5.7, 5.8, 5.9, 6.0, 6.1, 6.2, 6.3, 6.4, 6.5, 6.6, 6.7, 6.8, 6.9 or 7.0.

In certain embodiments, the pH of a pharmaceutical composition described herein is about 5.5±0.5, 5.8±0.5, 6.0±0.5, 6.2±0.5, 6.5±0.5, or 6.8±0.5.

In certain embodiments, the pH of a pharmaceutical composition described herein is about 5.5±0.3, 5.8±0.3, 6.0±0.3, 6.2±0.3, 6.5±0.3, or 6.8±0.3.

In certain embodiments, the pH of a pharmaceutical composition described herein is about 5.5±0.2, 5.8±0.2, 6.0±0.2, 6.2±0.2, 6.5±0.2, or 6.8±0.2.

In certain embodiments, the pH of a pharmaceutical composition described herein is about 5.0. In certain embodiments, the pH of a pharmaceutical composition described herein is about 5.5. In certain embodiments, the pH of a pharmaceutical composition described herein is about 5.8. In certain embodiments, the pH of a pharmaceutical composition described herein is about 6.0. In certain embodiments, the pH of a pharmaceutical composition described herein is about 6.2. In certain embodiments, the pH of a pharmaceutical composition described herein is about 6.5. In certain embodiments, the pH of a pharmaceutical composition described herein is about 6.8. In certain embodiments, the pH of a pharmaceutical composition described herein is about 7.0.

Suitable buffers include, for example acetate, arginine, citrate, histidine, phosphate, succinate, tris(hydroxymethyl) aminomethane ("Tris") and other organic acids. In certain embodiments, the buffer is selected from the group consisting of a phosphate buffer, an acetate buffer, an arginine buffer and a histidine buffer. In some embodiments, a buffering agent is present at a concentration ranging between about 1 mM to about 150 mM, or between about 10 mM to about 50 mM, or between about 5 mM to about 50 mM, or between about 15 mM to about 50 mM, or between about 20 mM to about 50 mM, or between about 25 mM to about 50 mM, or between about 10 mM to about 30 mM. In some embodiments, a suitable buffering agent is present at a concentration of approximately 1 mM, 5 mM, 10 mM, 15 mM, 20 mM, 25 mM, 30 mM, 35 mM, 40 mM, 45 mM, 50 mM, 75 mM, 100 mM, 125 mM or 150 mM.

Sodium phosphate and other phosphate-based buffers, such as a potassium phosphate buffer, can be useful in keeping IDS enzyme in a reversible inactive state, thereby preserving the stability of the enzyme under appropriate storage conditions (e.g., at a pH range as disclosed herein, at temperatures ranging from 2° C. to 25° C.). Thus, in certain embodiments, a pharmaceutical composition described herein comprises a buffer comprising phosphate (i.e., a phosphate buffer).

In certain embodiments, a pharmaceutical composition described herein comprises a buffer comprising sodium phosphate. In certain embodiments, the concentration of the sodium phosphate buffer in a pharmaceutical composition described herein is about 5-50 mM. In certain embodiments, the sodium phosphate buffer concentration is about 10-50 mM, 5-45 mM, 5-40 mM, 5-35 mM, 5-30 mM, 10-40 mM, 10-30 mM, 10-25 mM or 15-25 mM. In certain embodiments, the sodium phosphate buffer concentration is about 10-50 mM. In certain embodiments, the sodium phosphate buffer concentration is about 10-40 mM. In certain embodiments, the sodium phosphate buffer concentration is about 10-30 mM. In certain embodiments, the sodium phosphate buffer concentration is about 15-25 mM. In certain embodiments, the sodium phosphate buffer concentration in a pharmaceutical composition described herein is about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, or 50 mM±3 mM. In certain embodiments, the sodium phosphate buffer concentration is about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, or 50 mM.

In certain embodiments, the sodium phosphate buffer concentration is about 5 mM±3 mM. In certain embodiments, the sodium phosphate buffer concentration is about 10 mM±3 mM. In certain embodiments, the sodium phosphate buffer concentration is about 15 mM±3 mM. In certain embodiments, the sodium phosphate buffer concentration is about 20 mM±3 mM. In certain embodiments, the sodium phosphate buffer concentration is about 25 mM±3 mM. In certain embodiments, the sodium phosphate buffer concentration is about 30 mM±3 mM. In certain embodiments, the sodium phosphate buffer concentration is about 35 mM±3 mM. In certain embodiments, the sodium phosphate buffer concentration is about 40 mM±3 mM. In certain embodiments, the sodium phosphate buffer concentration is about 45 mM±3 mM. In certain embodiments, the sodium phosphate buffer concentration is about 50 mM±3 mM. In certain embodiments, the sodium phosphate buffer concentration is about 5 mM. In certain embodiments, the sodium phosphate buffer concentration is about 10 mM. In certain embodiments, the sodium phosphate buffer concentration is about 15 mM. In certain embodiments, the sodium phosphate buffer concentration is about 20 mM. In certain embodiments, the sodium phosphate buffer concentration is about 25 mM. In certain embodiments, the sodium phosphate buffer concentration is about 30 mM. In certain embodiments, the sodium phosphate buffer concentration is about 35 mM. In certain embodiments, the sodium phosphate buffer concentration is about 40 mM. In certain embodiments, the sodium phosphate buffer concentration is about 45 mM. In certain embodiments, the sodium phosphate buffer concentration is about 50 mM.

In certain embodiments, a pharmaceutical composition described herein comprises a buffer comprising potassium phosphate. In certain embodiments, the concentration of the potassium phosphate buffer in a pharmaceutical composition described herein is about 5-50 mM. In certain embodiments, the potassium phosphate buffer concentration is about 10-50 mM, 5-45 mM, 5-40 mM, 5-35 mM, 5-30 mM, 10-40 mM, 10-30 mM, 10-25 mM or 15-25 mM. In certain embodiments, the potassium phosphate buffer concentration is about 10-50 mM. In certain embodiments, the potassium phosphate buffer concentration is about 10-40 mM. In certain embodiments, the potassium phosphate buffer concentration is about 10-30 mM. In certain embodiments, the potassium phosphate buffer concentration is about 15-25 mM.

In certain embodiments, the potassium phosphate buffer concentration in a pharmaceutical composition described herein is about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, or 50 mM±3 mM. In certain embodiments, the potassium phosphate buffer concentration is about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, or 50 mM.

In certain embodiments, the potassium phosphate buffer concentration is about 5 mM±3 mM. In certain embodiments, the potassium phosphate buffer concentration is about 10 mM±3 mM. In certain embodiments, the potassium phosphate buffer concentration is about 15 mM±3 mM. In certain embodiments, the potassium phosphate buffer concentration is about 20 mM±3 mM. In certain embodiments, the potassium phosphate buffer concentration is about 25 mM±3 mM. In certain embodiments, the potassium phosphate buffer concentration is about 30 mM±3 mM. In certain embodiments, the potassium phosphate buffer concentration is about 35 mM±3 mM. In certain embodiments, the potassium phosphate buffer concentration is about 40 mM±3 mM. In certain embodiments, the potassium phosphate buffer concentration is about 45 mM±3 mM. In certain embodiments, the potassium phosphate buffer concentration is about 50 mM±3 mM. In certain embodiments, the potassium phosphate buffer concentration is about 5 mM. In certain embodiments, the potassium phosphate buffer concentration is about 10 mM. In certain embodiments, the potassium phosphate buffer concentration is about 15 mM. In certain embodiments, the potassium phosphate buffer concentration is about 20 mM. In certain embodiments, the potassium phosphate buffer concentration is about 25 mM. In certain embodiments, the potassium phosphate buffer concentration is about 30 mM. In certain embodiments, the potassium phosphate buffer concentration is about 35 mM. In certain embodiments, the potassium phosphate buffer concentration is about 40 mM. In certain embodiments, the potassium phosphate buffer concentration is about 45 mM. In certain embodiments, the potassium phosphate buffer concentration is about 50 mM.

Isotonicity Agent

In some embodiments, a pharmaceutical composition described herein, in either aqueous, pre-lyophilized, lyophilized or reconstituted form, comprises one or more isotonicity agents to keep the composition isotonic. Typically, by "isotonic" is meant that the formulation of interest has essentially the same osmotic pressure as human blood. Isotonic formulations will generally have an osmotic pressure from about 240 mOsm/kg to about 350 mOsm/kg. Isotonicity can be measured using, for example, a vapor pressure or freezing point type osmometers. Exemplary isotonicity agents include, but are not limited to, glycine, sorbitol, mannitol, sodium chloride and arginine. In some embodiments, suitable isotonic agents may be present in aqueous and/or pre-lyophilized formulations at a concentration from about 0.01-5% (e.g., 0.05, 0.1, 0.15, 0.2, 0.3, 0.4, 0.5, 0.75, 1.0, 1.25, 1.5, 2.0, 2.5, 3.0, 4.0 or 5.0%) by weight. In some embodiments, formulations for lyophilization contain an isotonicity agent to keep the pre-lyophilization formulations or the reconstituted formulations isotonic.

Similar to sodium phosphate and other phosphate-based buffers, certain salts can be useful in keeping IDS enzyme in a reversible inactive state, thereby preserving the stability of the enzyme under appropriate storage conditions (e.g., at a pH range as disclosed herein, at temperatures ranging from 2° C. to 25° C.). In certain embodiments, a pharmaceutical composition described herein comprises a salt, such as a sodium salt. In certain embodiments, the concentration of the salt (e.g., sodium salt) is about 20-175 mM, 20-170 mM, 20-165 mM, 20-160 mM, 20-155 mM, 25-150 mM, 30-150 mM, 30-145 mM, 30-140 mM, 30-135 mM, 30-130 mM, 30-125 mM, 30-120 mM, 30-115 mM, 30-110 mM, 30-105 mM, 30-100 mM, 30-95 mM, 30-90 mM, 30-85 mM, 30-80 mM, 30-75 mM, 30-70 mM, 30-65 mM, 30-60 mM or 40-60 mM. In certain embodiments, the salt (e.g., sodium salt) concentration is about 40-150 mM, 40-145 mM, 40-140 mM, 40-135 mM, 40-130 mM, 40-125 mM, 40-120 mM, 40-115 mM, 40-110 mM, 40-105 mM, 40-100 mM, 40-95 mM, 40-90 mM, 40-85 mM, 40-80 mM, 40-75 mM, 40-70 mM or 40-65 mM. In certain embodiments, the salt (e.g., sodium salt) concentration is about 30-150 mM. In certain embodiments, the salt (e.g., sodium salt) concentration is about 40-140 mM. In certain embodiments, the salt (e.g., sodium salt) concentration is about 50-137 mM. In certain embodiments, the salt (e.g., sodium salt) concentration is about 40-100 mM. In certain embodiments, the salt (e.g., sodium salt) concentration is about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139 or 140 mM±2 mM. In certain embodiments, the salt (e.g., sodium salt) concentration is about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139 or 140 mM.

In certain embodiments, the salt may be one selected from the group consisting of: sodium chloride, sodium sulfate, sodium phosphate, and cupric acetate. In certain embodiments, a pharmaceutical composition described herein comprises a sodium salt, such as sodium chloride, sodium sulfate or sodium phosphate.

In certain embodiments, a pharmaceutical composition described herein comprises sodium chloride. In certain embodiments, the sodium chloride concentration in a pharmaceutical composition described herein is about 20-175 mM, 20-170 mM, 20-165 mM, 20-160 mM, 20-155 mM, 25-150 mM, 30-150 mM, 30-145 mM, 30-140 mM, 30-135 mM, 30-130 mM, 30-125 mM, 30-120 mM, 30-115 mM, 30-110 mM, 30-105 mM, 30-100 mM, 30-95 mM, 30-90 mM, 30-85 mM, 30-80 mM, 30-75 mM, 30-70 mM, 30-65 mM, 30-60 mM or 40-60 mM.

In certain embodiments, the sodium chloride concentration is about 40-150 mM, 40-145 mM, 40-140 mM, 40-135 mM, 40-130 mM, 40-125 mM, 40-120 mM, 40-115 mM, 40-110 mM, 40-105 mM, 40-100 mM, 40-95 mM, 40-90 mM, 40-85 mM, 40-80 mM, 40-75 mM, 40-70 mM or 40-65 mM.

In certain embodiments, the sodium chloride concentration is about 30-150 mM. In certain embodiments, the sodium chloride concentration is about 40-140 mM. In certain embodiments, the sodium chloride concentration is about 50-137 mM. In certain embodiments, the sodium chloride concentration is about 40-100 mM.

In certain embodiments, the sodium chloride concentration is about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139 or 140 mM±2 mM. In certain embodiments, the sodium chloride concentration is about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139 or 140 mM.

In certain embodiments, the sodium chloride concentration is about 40 mM±2 mM. In certain embodiments, the sodium chloride concentration is about 45 mM±2 mM. In certain embodiments, the sodium chloride concentration is about 50 mM±2 mM. In certain embodiments, the sodium chloride concentration is about 55 mM±2 mM. In certain embodiments, the sodium chloride concentration is about 40 mM. In certain embodiments, the sodium chloride concentration is about 45 mM. In certain embodiments, the sodium chloride concentration is about 50 mM. In certain embodiments, the sodium chloride concentration is about 55 mM.

In certain embodiments, the sodium chloride concentration is about 130 mM±2 mM. In certain embodiments, the sodium chloride concentration is about 135 mM±2 mM. In certain embodiments, the sodium chloride concentration is about 137 mM±2 mM. In certain embodiments, the sodium chloride concentration is about 140 mM±2 mM. In certain embodiments, the sodium chloride concentration is about 145 mM±2 mM. In certain embodiments, the sodium chloride concentration is about 130 mM. In certain embodiments, the sodium chloride concentration is about 135 mM. In certain embodiments, the sodium chloride concentration is about 137 mM. In certain embodiments, the sodium chloride concentration is about 140 mM. In certain embodiments, the sodium chloride concentration is about 145 mM.

Surfactants

In certain embodiments, a pharmaceutical composition described herein comprises one or more surfactants. Exemplary surfactants include nonionic surfactants such as Polysorbates (e.g., polysorbate 20, polysorbate 40, polysorbate 60, polysorbate 80 and combination thereof); poloxamers (e.g., poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristarnidopropyl-, palmidopropyl-, or isostearamidopropyl-dimethylamine; sodium methyl cocoyl-, or di sodium methyl ofeyl-taurate; and the MONAQUAT™ series (Mona Industries, Inc., Paterson, N.J.), polyethyl glycol, polypropyl glycol, and copolymers of ethylene and propylene glycol (e.g., Pluronics, PF68, etc).

In certain embodiments, the surfactant comprises polysorbate. In certain embodiments, the surfactant is selected from the group consisting of: polysorbate-20 (PS-20) and polysorbate-80 (PS-80). In certain embodiments, the surfactant is polysorbate-20 (PS-20). In certain embodiments, the surfactant is polysorbate-80 (PS-80).

In certain embodiments, the surfactant comprises poloxamer.

Typically, the amount of surfactant added is such that it reduces aggregation of the protein and minimizes the formation of particulates or effervescences. For example, a surfactant may be present in a pharmaceutical composition at a concentration from about 0.01-5 mg/mL, (e.g., about 0.05-0.5 mg/mL, or about 0.05-0.1 mg/mL). In particular, a surfactant may be present in a pharmaceutical composition at a concentration of approximately 0.05 mg/mL, 0.1 mg/mL, 0.2 mg/mL, 1.0 mg/mL, 2.0 mg/mL, 3.0 mg/mL, 4 mg/mL, or 5.0 mg/mL, etc. Alternatively, or in addition, the surfactant may be added to a lyophilized formulation, pre-lyophilized formulation and/or the reconstituted formulation.

In certain embodiments, the surfactant concentration in a pharmaceutical composition described herein is about 0.1-1.0 mg/mL, 0.1-0.9 mg/mL, 0.1-0.8 mg/mL, 0.1-0.7 mg/mL, 0.1-0.6 mg/mL, 0.1-0.5 mg/mL, 0.2-1.0 mg/mL, 0.2-0.9 mg/mL, 0.2-0.8 mg/mL, 0.2-0.7 mg/mL, 0.2-0.6 mg/mL, 0.3-0.8 mg/mL, 0.3-0.7 mg/mL, 0.3-0.6 mg/mL, 0.3-0.5 mg/mL, 0.4-0.8 mg/mL, 0.4-0.7 mg/mL, 0.5-0.8 mg/mL or 0.5-0.7 mg/mL.

In certain embodiments, the surfactant concentration is about 0.1, 0.2, 0.3, 0.4, 0.5, 0.6, 0.7, 0.8, 0.9 or 1.0 mg/mL±0.1 mg/mL. In certain embodiments, the surfactant concentration is about 0.1, 0.2, 0.3, 0.4, 0.5, 0.6, 0.7, 0.8, 0.9 or 1.0 mg/mL.

In certain embodiments, the surfactant concentration is about 0.2 mg/mL±0.1 mg/mL. In certain embodiments, the surfactant concentration is about 0.3 mg/mL±0.1 mg/mL. In certain embodiments, the surfactant concentration is about 0.4 mg/mL±0.1 mg/mL. In certain embodiments, the surfactant concentration is about 0.5 mg/mL±0.1 mg/mL. In certain embodiments, the surfactant concentration is about 0.6 mg/mL±0.1 mg/mL. In certain embodiments, the surfactant concentration is about 0.7 mg/mL±0.1 mg/mL.

In certain embodiments, the surfactant concentration is about 0.2 mg/mL. In certain embodiments, the surfactant concentration is about 0.3 mg/mL. In certain embodiments, the surfactant concentration is about 0.4 mg/mL. In certain embodiments, the surfactant concentration is about 0.5 mg/mL. In certain embodiments, the surfactant concentration is about 0.6 mg/mL. In certain embodiments, the surfactant concentration is about 0.7 mg/mL.

In certain embodiments the surfactant is a polysorbate surfactant and the concentration of the polysorbate surfactant in a pharmaceutical composition described herein is about 0.4-0.7 mg/mL. In certain embodiments, the polysorbate surfactant concentration is about 0.4 mg/mL. In certain embodiments, the polysorbate surfactant concentration is about 0.5 mg/mL. In certain embodiments, the polysorbate surfactant concentration is about 0.6 mg/mL. In certain embodiments, the polysorbate surfactant concentration is about 0.7 mg/mL.

Stabilizers

In some embodiments, a pharmaceutical composition described herein may contain one or more stabilizing agents, cryoprotectants, or lyoprotectants, or combinations thereof, to protect the protein. Typically, a suitable stabilizing agent is a sugar, a non-reducing sugar and/or an amino acid. Exemplary sugars include, but are not limited to, dextran, lactose, mannitol, mannose, sorbitol, raffinose, sucrose and trehalose. Exemplary amino acids include, but are not limited to, arginine, glycine and methionine. Additional stabilizing agents may include sodium chloride, hydroxyethyl starch and polyvinylpyrolidone.

In some embodiments, liquid formulations contain amorphous materials. In some embodiments, liquid formulations contain a substantial amount of amorphous materials (e.g., sucrose-based formulations). In some embodiments, liquid formulations contain partly crystalline/partly amorphous materials.

In some embodiments, a pharmaceutical composition described herein comprises sodium chloride. In certain embodiments, the sodium chloride concentration in a pharmaceutical composition described herein is as disclosed supra. For example, the sodium chloride concentration can be about 20-175 mM, 20-170 mM, 20-165 mM, 20-160 mM, 20-155 mM, 25-150 mM, 30-150 mM, 30-145 mM, 30-140 mM, 30-135 mM, 30-130 mM, 30-125 mM, 30-120 mM, 30-115 mM, 30-110 mM, 30-105 mM, 30-100 mM, 30-95 mM, 30-90 mM, 30-85 mM, 30-80 mM, 30-75 mM, 30-70 mM, 30-65 mM, 30-60 mM 40-60 mM, or any other range or concentration as disclosed herein.

In certain embodiments, a pharmaceutical composition described herein comprises a sugar. In certain embodiments, the sugar is sucrose or trehalose. In certain embodiments, the sugar is sucrose. In certain embodiments, a pharmaceutical composition described herein comprises methionine.

The amount of stabilizing agent in a lyophilized formulation is generally such that the formulation will be isotonic. However, hypertonic reconstituted formulations may also be suitable. In addition, the amount of stabilizing agent should not be too low such that an unacceptable amount of degradation/aggregation of the therapeutic agent occurs. Exemplary stabilizing agent concentrations in the formulation may range from about 1 mM to about 400 mM (e.g., from about 30 mM to about 300 mM, and from about 50 mM to about 100 mM), or alternatively, from 0.1% to 15% (e.g., from 1% to 10%, from 5% to 15%, from 5% to 10%) by weight. In some embodiments, the ratio of the mass amount of the stabilizing agent and the therapeutic agent is about 1:1. In other embodiments, the ratio of the mass amount of the stabilizing agent and the therapeutic agent can be about 0.1:1, 0.2:1, 0.25:1, 0.4:1, 0.5:1, 1:1, 2:1, 2.6:1, 3:1, 4:1, 5:1, 10:1, or 20:1. In some embodiments, suitable for lyophilization, the stabilizing agent is also a lyoprotectant.

In certain embodiments, a pharmaceutical composition described herein comprises a sugar (e.g., sucrose or trehalose). In certain embodiments, the sugar concentration in a pharmaceutical composition described herein is about 30-300 mM, 50-300 mM, 75-300 mM, 100-300 mM, 100-275 mM, 100-250 mM, 125-250 mM, 150-250 mM, 150-225 mM or 150-200 mM. In certain embodiments, the sugar concentration in a pharmaceutical composition described herein is about 100-250 mM. In certain embodiments, the sugar concentration in a pharmaceutical composition described herein is about 150-200 mM.

In certain embodiments, the sugar concentration is about 170±2 mM. In certain embodiments, the sugar concentration is about 175±2 mM. In certain embodiments, the sugar concentration is about 180±2 mM. In certain embodiments, the sugar concentration is about 170 mM. In certain embodiments, the sugar concentration is about 175 mM. In certain embodiments, the sugar concentration is about 180 mM.

In certain embodiments, a pharmaceutical composition described herein comprises sucrose. In certain embodiments, the sucrose concentration in a pharmaceutical composition described herein is about 30-300 mM, 50-300 mM, 75-300 mM, 100-300 mM, 100-275 mM, 100-250 mM, 125-250 mM, 150-250 mM, 150-225 mM or 150-200 mM.

In certain embodiments, the sucrose concentration is about 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 mM±2 mM. In certain embodiments, the sucrose concentration is about 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 mM.

In certain embodiments, the sucrose concentration is about 170±2 mM. In certain embodiments, the sucrose concentration is about 175±2 mM. In certain embodiments, the sucrose concentration is about 180±2 mM. In certain embodiments, the sucrose concentration is about 170 mM. In certain embodiments, the sucrose concentration is about 175 mM. In certain embodiments, the sucrose concentration is about 180 mM.

In certain embodiments, a pharmaceutical composition described herein comprises methionine. In certain embodiments, the methionine concentration in a pharmaceutical composition described herein is about 2-50 mM. In certain embodiments, the methionine concentration in a pharmaceutical composition described herein is about 5-50 mM, 5-45 mM, 5-40 mM, 5-35 mM, 5-30 mM, 5-25 mM, 5-20 mM or 5-15 mM.

In certain embodiments, the methionine concentration is about 5, 6, 7, 8, 9, 10, 11, 12, 13, 14 or 15 mM±2 mM. In certain embodiments, the methionine concentration is about 5, 6, 7, 8, 9, 10, 11, 12, 13, 14 or 15 mM.

In certain embodiments, the methionine concentration is about 8 mM±2 mM. In certain embodiments, the methionine concentration is about 9 mM±2 mM. In certain embodiments, the methionine concentration is about 10 mM±2 mM. In certain embodiments, the methionine concentration is about 11 mM±2 mM. In certain embodiments, the methionine concentration is about 12 mM±2 mM. In certain embodiments, the methionine concentration is about 8 mM. In certain embodiments, the methionine concentration is about 9 mM. In certain embodiments, the methionine concentration is about 10 mM. In certain embodiments, the methionine concentration is about 11 mM. In certain embodiments, the methionine concentration is about 12 mM.

Bulking Agents

In some embodiments, suitable formulations for lyophilization may further include one or more bulking agents. A "bulking agent" is a compound that adds mass to the lyophilized mixture and contributes to the physical structure of the lyophilized cake. For example, a bulking agent may improve the appearance of lyophilized cake (e.g., essentially uniform lyophilized cake). Suitable bulking agents include, but are not limited to, sodium chloride, lactose, mannitol, glycine, sucrose, trehalose, hydroxyethyl starch. Exemplary concentrations of bulking agents are from about 1% to about 10% (e.g., 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0%).

Additional Agents

Other pharmaceutically acceptable carriers, excipients or stabilizers such as those described in Remington's Pharmaceutical Sciences 16th edition, Osol, A. Ed. (1980) may be included in a pharmaceutical composition described herein (and/or a lyophilized formulation and/or a reconstituted formulation) provided that they do not adversely affect the desired characteristics of the composition. Acceptable carriers, excipients or stabilizers are nontoxic to recipients at the dosages and concentrations employed and include, but are not limited to, additional buffering agents; preservatives; co-solvents; antioxidants including ascorbic acid and methionine; chelating agents such as EDTA; metal complexes (e.g., Zn-protein complexes); biodegradable polymers such as polyesters; and/or salt-forming counterions such as sodium.

Liquid and Lyophilized Formulations

In certain embodiments, a pharmaceutical composition described herein is a liquid formulation. In certain embodiments, a pharmaceutical composition described herein is formulated as lyophilized dry powder.

Lyophilization

Typically, a pre-lyophilization formulation further contains an appropriate choice of excipients or other components such as stabilizers, buffering agents, bulking agents, and surfactants to prevent a compound of interest from degradation (e.g., protein aggregation, deamidation, and/or oxidation) during freeze-drying and storage. The formulation for lyophilization can include one or more additional ingredients including lyoprotectants or stabilizing agents, buffers, bulking agents, isotonicity agents and surfactants.

After the substance of interest and any additional components are mixed together, the formulation is lyophilized. Lyophilization generally includes three main stages: freezing, primary drying and secondary drying. Freezing is necessary to convert water to ice or some amorphous formulation components to the crystalline form. Primary drying is the process step when ice is removed from the frozen product by direct sublimation at low pressure and temperature. Secondary drying is the process step when bounded water is removed from the product matrix utilizing the diffusion of residual water to the evaporation surface. Product temperature during secondary drying is normally higher than during primary drying. See, Tang X. et al. (2004) "Design of freeze-drying processes for pharmaceuticals: Practical advice," *Pharm. Res.,* 21:191-200; Nail S. L. et al. (2002) "Fundamentals of freeze-drying," in Development and manufacture of protein pharmaceuticals. Nail S. L. editor New York: Kluwer Academic/Plenum Publishers, pp 281-353; Wang et al. (2000) "Lyophilization and development of solid protein pharmaceuticals," *Int. J Pharm.,* 203:1-60; Williams N. A. et al. (1984) "The lyophilization of pharmaceuticals; A literature review." *J Parenteral Sci. Technol.,* 38:48-59.

In some embodiments, an annealing step may be introduced during the initial freezing of the product. The annealing step may reduce the overall cycle time. Without wishing to be bound by any theories, it is contemplated that the annealing step can help promote excipient crystallization and formation of larger ice crystals due to re-crystallization of small crystals formed during supercooling, which, in turn, improves reconstitution. Typically, an annealing step includes an interval or oscillation in the temperature during freezing. For example, the freeze temperature may be −40° C., and the annealing step will increase the temperature to, for example, −10° C. and maintain this temperature for a set period of time. The annealing step time may range from 0.5 hours to 8 hours (e.g., 0.5, 1.0 1.5, 2.0, 2.5, 3, 4, 6, and 8 hours). The annealing temperature may be between the freezing temperature and 0° C.

Lyophilization may be performed in a container, such as a tube, a bag, a bottle, a tray, a vial (e.g., a glass vial), syringe or any other suitable containers. The containers may be disposable. Lyophilization may also be performed in a large scale or small scale. In some instances, it may be desirable to lyophilize the protein formulation in the container in which reconstitution of the protein is to be carried out in order to avoid a transfer step. The container in this instance may, for example, be a 3, 4, 5, 10, 20, 50 or 100 cc vial.

Many different freeze-dryers are available for this purpose such as Hull pilot scale dryer (SP Industries, USA), Genesis (SP Industries) laboratory freeze-dryers, or any freeze-dryers capable of controlling the given lyophilization process parameters. Freeze-drying is accomplished by freezing the formulation and subsequently subliming ice from the frozen content at a temperature suitable for primary drying. Initial freezing brings the formulation to a temperature below about −20° C. (e.g., −50° C., −45° C., −40° C., −35° C., −30° C., −25° C., etc.) in typically not more than about 4 hours (e.g., not more than about 3 hours, not more than about 2.5 hours, not more than about 2 hours). Under this condition, the product temperature is typically below the eutectic point or the collapse temperature of the formulation. Typically, the shelf temperature for the primary drying will range from about −30 to 25° C. (provided the product remains below the melting point during primary drying) at a suitable pressure, ranging typically from about 20 to 250 mTorr. The formulation, size and type of the container holding the sample (e.g., glass vial) and the volume of liquid will mainly dictate the time required for drying, which can range from a few hours to several days. A secondary drying stage is carried out at about 0-60° C., depending primarily on the type and size of container and the type of therapeutic protein employed. Again, volume of liquid will mainly dictate the time required for drying, which can range from a few hours to several days.

As a general proposition, lyophilization will result in a lyophilized formulation in which the moisture content thereof is less than about 5%, less than about 4%, less than about 3%, less than about 2%, less than about 1%, and less than about 0.5%.

Reconstitution

While pharmaceutical compositions described herein are generally in an aqueous form upon administration to a subject, in some embodiments the pharmaceutical compositions described herein are lyophilized. Such compositions must be reconstituted by adding one or more diluents thereto prior to administration to a subject. At the desired stage, typically at an appropriate time prior to administration to the patient, the lyophilized formulation may be reconstituted with a diluent such that the protein concentration in the reconstituted formulation is desirable.

Various diluents may be used as described herein. In some embodiments, a suitable diluent for reconstitution is water. The water used as the diluent can be treated in a variety of ways including reverse osmosis, distillation, deionization, filtrations (e.g., activated carbon, microfiltration, nanofiltration) and combinations of these treatment methods. In general, the water should be suitable for injection including, but not limited to, sterile water or bacteriostatic water for injection.

Additional exemplary diluents include a pH buffered solution (e.g., phosphate-buffered saline), sterile saline solution, Elliot's solution, Ringer's solution or dextrose solution. Suitable diluents may optionally contain a preservative. Exemplary preservatives include aromatic alcohols such as benzyl or phenol alcohol. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0%, from about 0.5-1.5%, or about 1.0-1.2%.

Suitable diluents may include a variety of additives, including, but not limited to, pH buffering agents, (e.g. Tris, histidine) salts (e.g., sodium chloride) and other additives (e.g., sucrose) including those described above (e.g. stabilizing agents, isotonicity agents).

As described herein, a lyophilized substance (e.g., protein) can be reconstituted to a concentration of, e.g., at least 5 mg/ml (e.g., at least 10 mg/ml, at least 15 mg/ml, at least 20 mg/ml, at least 25 mg/ml, at least 30 mg/ml, at least 50 mg/ml, at least 75 mg/ml, at least 100 mg/ml) and in any ranges there between. In some embodiments, a lyophilized substance (e.g., protein) may be reconstituted to a concentration ranging from about 1 mg/ml to 100 mg/ml (e.g., from about 1 mg/ml to 50 mg/ml, from 1 mg/ml to 100 mg/ml, from about 1 mg/ml to about 5 mg/ml, from about 1 mg/ml to about 10 mg/ml, from about 1 mg/ml to about 25 mg/ml, from about 1 mg/ml to about 75 mg/ml, from about 10 mg/ml to about 30 mg/ml, from about 10 mg/ml to about 50 mg/ml, from about 10 mg/ml to about 75 mg/ml, from about 10 mg/ml to about 100 mg/ml, from about 25 mg/ml to about 50 mg/ml, from about 25 mg/ml to about 75 mg/ml, from about 25 mg/ml to about 100 mg/ml, from about 50 mg/ml to about 75 mg/ml, from about 50 mg/ml to about 100 mg/ml). In some embodiments, the concentration of protein in the reconstituted formulation may be higher than the concentration in the pre-lyophilization formulation. In some embodiments, the protein concentration in the reconstituted formulation may be about 2-50 times (e.g., about 2-20, about 2-10 times, or about 2-5 times) of the pre-lyophilized formulation. In some embodiments, the protein concentration in the reconstituted formulation may be at least about 2 times (e.g., at least about 3, 4, 5, 10, 20, 40 times) of the pre-lyophilized formulation.

Reconstitution may be performed in any container. Exemplary containers include, but are not limited to, such as tubes, vials, syringes (e.g., single-chamber or dual-chamber), bags, bottles, and trays. Suitable containers may be made of any materials such as glass, plastics, metal. The containers may be disposable or reusable. Reconstitution may also be performed in a large scale or small scale.

In some instances, it may be desirable to lyophilize the protein formulation in the container in which reconstitution of the protein is to be carried out in order to avoid a transfer step. The container in this instance may, for example, be a 3, 4, 5, 10, 20, 50 or 100 cc vial. In some embodiments, a suitable container for lyophilization and reconstitution is a dual chamber syringe (e.g., Lyo-Ject,® (Vetter) syringes). For example, a dual chamber syringe may contain both the lyophilized substance and the diluent, each in a separate chamber, separated by a stopper. To reconstitute, a plunger can be attached to the stopper at the diluent side and pressed to move diluent into the product chamber so that the diluent can contact the lyophilized substance and reconstitution may take place as described herein.

Stability

In some embodiments, pharmaceutical compositions described herein have been formulated such that they are capable of stabilizing, or alternatively slowing or preventing the degradation, of a therapeutic agent formulated therewith (i.e., a protein molecule described herein). As used herein, the term "stable" refers to the ability of a protein molecule described herein to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In the context of a formulation, a stable formulation is one in which the therapeutic agent therein essentially retains its physical and/or chemical integrity and biological activity upon storage and during processes (such as freeze/thaw, mechanical mixing and lyophilization). For protein stability, it can be measured by, e.g., formation of high molecular weight (HMW) aggregates, loss of enzyme activity, generation of peptide fragments and shift of charge profiles. In certain embodiments, the stability of a pharmaceutical composition is assessed using an assay or set of conditions described herein (see, e.g., the Examples).

Stability of the therapeutic agent may be further assessed relative to the biological activity or physiochemical integrity of the therapeutic agent over extended periods of time. For example, stability at a given time point may be compared against stability at an earlier time point (e.g., upon formulation day 0) or against unformulated therapeutic agent and the results of this comparison expressed as a percentage. In certain embodiments, pharmaceutical compositions maintain at least 100%, at least 99%, at least 98%, at least 97% at least 95%, at least 90%, at least 85%, at least 80%, at least 75%, at least 70%, at least 65%, at least 60%, at least 55% or at least 50% of the therapeutic agent's biological activity or physiochemical integrity over an extended period of time (e.g., as measured over at least about 6-12 months, at room temperature or under accelerated storage conditions).

In certain embodiments, a pharmaceutical composition described herein is stable under a variety of conditions (e.g., normal storage conditions or stress conditions). For example, the stability of the pharmaceutical composition may be assessed over time, at a range of temperatures, or during freeze/thaw cycles by examining a variety of factors, such as pH, turbidity or cleavage/clipping of a protein molecule described herein. Additionally, compositions can be assessed based on product quality analysis, reconstitution time (if lyophilized), quality of reconstitution (if lyophilized), quantity of high molecular weight content (indicative of molecule aggregation), quantity of low molecular weight content (indicative of molecule stability) moisture, and glass transition temperature. Typically, protein quality and product analysis include product degradation rate analysis using methods including, but not limited to, size exclusion HPLC (SE-HPLC), cation exchange-HPLC (CEX-HPLC), X-ray diffraction (XRD), modulated differential scanning calorimetry (mDSC), reversed phase HPLC (RP-HPLC), multi-angle light scattering (MALS), fluorescence, ultraviolet absorption, nephelometry, capillary electrophoresis (CE), SDS-PAGE, and combinations thereof. In some embodiments, evaluation of product may include a step of evaluating appearance (either liquid or cake appearance).

In certain embodiments, the pH of the pharmaceutical composition remains stable at a temperature range of about 2-8° C. (e.g., 2, 3, 4, 5, 6, 7 or 8° C.) for a period of time (e.g., for about one month, three months, six months, 12 months, etc.). In certain embodiments, the pH of the pharmaceutical composition remains stable at a temperature range of about 2-8° C. (e.g., 2, 3, 4, 5, 6, 7 or 8° C.) for a period of time (e.g., for about one month, three months, six months, 12 months, etc.).

In certain embodiments, the pH of the pharmaceutical composition remains stable at a temperature range of about 20-40° C. for a period of time (e.g., for about 1 week, two weeks, three weeks, four weeks, etc.). In certain embodiments, the pH of the pharmaceutical composition remains stable at a temperature range of about 25-40° C.

In certain embodiments, the pH of the pharmaceutical composition remains stable at a temperature of about 25, 26, 27, 28, 29, 30, 31, 32, 33, 34, 35, 36, 37, 38, 39 or 40° C. In certain embodiments, the pH of the pharmaceutical composition remains stable at a temperature of about 25, 26, 27, 28, 29, 30, 31, 32, 33, 34, 35, 36, 37, 38, 39 or 40° C. for about 1 week. In certain embodiments, the pH of the pharmaceutical composition remains stable at a temperature of about 25, 26, 27, 28, 29, 30, 31, 32, 33, 34, 35, 36, 37, 38, 39 or 40° C. for about 2 weeks. In certain embodiments, the pH of the pharmaceutical composition remains stable at a temperature of about 25, 26, 27, 28, 29, 30, 31, 32, 33, 34, 35, 36, 37, 38, 39 or 40° C. for about 3 weeks. In certain embodiments, the pH of the pharmaceutical composition remains stable at a temperature of about 25, 26, 27, 28, 29, 30, 31, 32, 33, 34, 35, 36, 37, 38, 39 or 40° C. for about 4 weeks.

In certain embodiments, the pH of the pharmaceutical composition remains stable at a temperature of about 25° C. In certain embodiments, the pH of the pharmaceutical composition remains stable at a temperature of about 30° C. In certain embodiments, the pH of the pharmaceutical composition remains stable at a temperature of about 35° C. In certain embodiments, the pH of the pharmaceutical composition remains stable at a temperature of about 40° C.

In certain embodiments, the pH of the pharmaceutical composition remains stable at a temperature of about 25° C. for about 1 week. In certain embodiments, the pH of the pharmaceutical composition remains stable at a temperature of about 30° C. for about 1 week. In certain embodiments, the pH of the pharmaceutical composition remains stable at a temperature of about 35° C. for about 1 week. In certain embodiments, the pH of the pharmaceutical composition remains stable at a temperature of about 40° C. for about 1 week.

In certain embodiments, the pH of the pharmaceutical composition remains stable at a temperature of about 25° C. for about 2 weeks. In certain embodiments, the pH of the pharmaceutical composition remains stable at a temperature of about 30° C. for about 2 weeks.

In certain embodiments, the pH of the pharmaceutical composition remains stable at a temperature of about 35° C. for about 2 weeks. In certain embodiments, the pH of the pharmaceutical composition remains stable at a temperature of about 40° C. for about 2 weeks.

In certain embodiments, the turbidity of the pharmaceutical composition remains stable, e.g., over time and/or at a variety of temperatures. Methods of evaluating turbidity are known in the art and described herein (see, e.g., the Examples).

In certain embodiments, the turbidity of the pharmaceutical composition remains stable at a temperature range of about 2-40° C. In certain embodiments, the turbidity of the pharmaceutical composition remains stable at a temperature range of about 2-40° C. for a period of time (e.g., for about 1 week, two weeks, three weeks, four weeks, etc.).

In certain embodiments, the turbidity of the pharmaceutical composition remains stable at a temperature of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40° C. In certain embodiments, the turbidity of the pharmaceutical composition remains stable at a temperature of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40° C. for about 1 week. In certain embodiments, the turbidity of the pharmaceutical composition remains stable at a temperature of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40° C. for about 2 weeks. In certain embodiments, the turbidity of the pharmaceutical composition remains stable at a temperature of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40° C. for about 3 weeks. In certain embodiments, the turbidity of the pharmaceutical composition remains stable at a temperature of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40° C. for about 4 weeks.

In certain embodiments, a protein molecule described herein remains intact (i.e., is not cleaved or "clipped"), e.g., over time, over a range of temperatures, over a range of pH values and/or during freeze-thaw cycles. Methods of evaluating protein cleavage or clipping are known in the art and described herein (see, e.g., the Examples).

In certain embodiments, a protein molecule described herein remains intact over a temperature range of about 2-40° C. In certain embodiments, the protein molecule remains intact over a temperature range of about 2-40° C. for a period of time (e.g., for about 1 week, two weeks, three weeks, four weeks, etc.). In certain embodiments, a protein molecule described herein remains intact over a temperature range of about 2-8° C. In certain embodiments, the protein molecule remains intact over a temperature range of about 2-8° C. for a period of time (e.g., for about 1 month, three months, six months, 12 months, etc.).

In certain embodiments, a protein molecule described herein remains intact at a temperature of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40° C. In certain embodiments, the protein molecule remains intact at a temperature of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40° C. for about 1 week. In certain embodiments, the protein molecule remains intact at a temperature of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40° C. for about 2 weeks. In certain embodiments, the protein molecule remains intact at a temperature of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40° C. for about 3 weeks. In certain embodiments, a protein molecule remains intact at a temperature of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40° C. for about 4 weeks.

In certain embodiments, a protein molecule described herein remains intact during freeze-thaw cycles. For example, in certain embodiments, the protein molecule remains intact during 1, 2, 3, 4, 5, 6, 7, 8, 9, 10, 11, 12, 13, 14, 15, 16, 17, 18, 19 or 20 or more freeze-thaw cycles. In certain embodiments, the protein molecule remains intact during 5 or more freeze-thaw cycles.

In certain embodiments, a protein molecule described herein remains intact over a range of pH values. In certain embodiments, the protein molecule remains intact over a pH range of about 5.0 to about 7.5. In certain embodiments, the protein molecule remains intact over a pH range of about 5.0 to 7.0. In certain embodiments, the protein molecule remains intact over a pH range of about 5.5 to 7.0.

In certain embodiments, a protein molecule described herein remains intact over a pH of about 5.5, 5.6, 5.7, 5.8, 5.9, 6.0, 6.1, 6.2, 6.3, 6.4, 6.5, 6.6, 6.7, 6.8, 6.9 or 7.0±0.2. In certain embodiments, the protein molecule remains intact over a pH of about 5.5, 5.6, 5.7, 5.8, 5.9, 6.0, 6.1, 6.2, 6.3, 6.4, 6.5, 6.6, 6.7, 6.8, 6.9 or 7.0.

In certain embodiments, a protein molecule described herein is colloidally stable over a range of pH values. Methods of measuring colloidal stability are known in the art and described herein (see, e.g., the Examples).

In certain embodiments, a protein molecule described herein is colloidally stable over a pH range of about 5.5 to about 7.5. In certain embodiments, the protein molecule is colloidally stable over a pH range of about 5.5 to 7.0. In certain embodiments, the protein molecule is colloidally stable over a pH range of about 6.0 to 7.0. In certain embodiments, the protein molecule is colloidally stable over a pH range of about 6.5 to 7.0.

In certain embodiments, a protein molecule described herein is colloidally stable over a pH of about 6.0, 6.1, 6.2, 6.3, 6.4, 6.5, 6.6, 6.7, 6.8, 6.9 or 7.0±0.2. In certain embodiments, the protein molecule is colloidally stable over a pH of about 6.0, 6.1, 6.2, 6.3, 6.4, 6.5, 6.6, 6.7, 6.8, 6.9 or 7.0.

In certain embodiments, a protein molecule described herein is conformationally stable over a range of pH values. Methods of measuring conformational stability are known in the art and described herein (see, e.g., the Examples).

In certain embodiments, a protein molecule described herein is conformationally stable over a pH range of about 5.5 to about 7.5. In certain embodiments, the protein molecule is conformationally stable over a pH range of about 5.5 to 7.0. In certain embodiments, the protein molecule is conformationally stable over a pH range of about 6.0 to 7.0. In certain embodiments, the protein molecule is conformationally stable over a pH range of about 6.5 to 7.0.

In certain embodiments, a protein molecule described herein is conformationally stable over a pH of about 6.0, 6.1, 6.2, 6.3, 6.4, 6.5, 6.6, 6.7, 6.8, 6.9 or 7.0±0.2. In certain embodiments, the protein molecule is conformationally stable over a pH of about 6.0, 6.1, 6.2, 6.3, 6.4, 6.5, 6.6, 6.7, 6.8, 6.9 or 7.0.

In certain embodiments, a protein molecule described herein does not aggregate or has limited aggregation (e.g., compared to a control protein or reference value) over a range of pH values. Methods of measuring aggregation are known in the art and described herein (see, e.g., the Examples).

In certain embodiments, a protein molecule described herein does not aggregate or has limited aggregation over a pH range of about 5.5 to about 7.5. In certain embodiments, the protein molecule does not aggregate or has limited aggregation over a pH range of about 5.5 to 7.0. In certain embodiments, the protein molecule does not aggregate or has limited aggregation over a pH range of about 6.0 to 7.0.

In certain embodiments, a protein molecule described herein does not aggregate or has limited aggregation over a pH of about 6.0, 6.1, 6.2, 6.3, 6.4, 6.5, 6.6, 6.7, 6.8, 6.9 or 7.0±0.2. In certain embodiments, the protein molecule does not aggregate or has limited aggregation over a pH of about 6.0, 6.1, 6.2, 6.3, 6.4, 6.5, 6.6, 6.7, 6.8, 6.9 or 7.0.

Methods of Treatment

LSDs are inherited metabolic diseases characterized by the accumulation of undigested or partially digested macromolecules, which ultimately results in cellular dysfunction and clinical abnormalities. Classically, LSDs have been defined as deficiencies in lysosomal function generally classified by the accumulated substrate and include sphingolipidoses, oligosaccharidoses, mucolipidoses, mucopolysaccharidoses, lipoprotein storage disorders, neuronal ceroid lipofuscinoses, and others. The classification of these disorders has recently been expanded to include other deficiencies or defects in proteins that result in accumulation of macromolecules, such as proteins necessary for normal post-translational modification of lysosomal enzymes, or proteins important for proper lysosomal trafficking.

Pharmaceutical compositions described herein may be used to treat individuals suffering from or susceptible to a LSD. Accordingly, certain embodiments provide a method of treating a LSD in a subject in need thereof, comprising administering a pharmaceutical composition described herein to the subject. Certain embodiments also provide a method of treating a LSD in a subject in need thereof, comprising providing and administering a pharmaceutical composition described herein to the subject.

In certain embodiments, the pharmaceutical composition is provided as a liquid composition.

In certain embodiments, the pharmaceutical composition is provided as a lyophilized composition. In such an embodiment, the pharmaceutical composition is reconstituted prior to administration.

In certain embodiments, the method further comprises administering a second therapeutic agent.

Certain embodiments also provide a pharmaceutical composition described herein for treating a LSD in a subject in need thereof. Certain embodiments provide the use of a pharmaceutical composition described herein in the preparation of a medicament for treating a LSD in a subject in need thereof.

In certain embodiments, the LSD is Hunter syndrome.

The terms, "treat" or "treatment," as used herein, includes the amelioration of one or more symptoms associated with the disease, prevention or delay of the onset of one or more symptoms of the disease, and/or lessening of the severity or frequency of one or more symptoms of the disease.

In some embodiments, treatment refers to partially or complete alleviation, amelioration, relief, inhibition, delaying onset, reducing severity and/or incidence of neurological impairment in a patient having a LSD. As used herein, the term "neurological impairment" includes various symptoms associated with impairment of the central nervous system (e.g., the brain and spinal cord). Symptoms of neurological impairment may include, for example, e.g., cognitive impairment; white matter lesions; dilated perivascular spaces in the brain parenchyma, ganglia, corpus callosum, and/or brainstem; atrophy; and/or ventriculomegaly, among others.

In some embodiments, treatment refers to decreased lysosomal storage (e.g., of GAG) in various tissues. In some embodiments, treatment refers to decreased lysosomal storage in brain target tissues, spinal cord neurons, and/or peripheral target tissues. In certain embodiments, lysosomal storage is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, lysosomal storage is decreased by at least 1-fold, 2-fold, 3-fold, 4-fold, 5-fold, 6-fold, 7-fold, 8-fold, 9-fold or 10-fold as compared to a control. In some embodiments, lysosomal storage is measured by the presence of lysosomal storage granules (e.g., zebra-striped morphology). The presence of lysosomal storage granules can be measured by various means known in the art, such as by histological analysis.

In some embodiments, treatment refers to reduced vacuolization in neurons (e.g., neurons containing Purkinje cells). In certain embodiments, vacuolization in neurons is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, vacuolization is decreased by at least 1-fold, 2-fold, 3-fold, 4-fold, 5-fold, 6-fold, 7-fold, 8-fold, 9-fold or 10-fold as compared to a control. The presence of and reduction of vacuolization can be measured by various means known in the art, such as by histological analysis In some embodiments, treatment refers to increased ERT enzyme activity in various tissues. In some embodiments, ERT enzyme activity is increased by about 5% to about 100%, or about 10% to about 100%, or about 20% to about 100%, or about 30% to about 100%, or about 40% to about 100%, or about 50% to about 100%, or about 60% to about 100%, or about 70% to about 100%, or about 80% to about 100% as compared to a control. In some embodiments, ERT enzyme activity is increased by about 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900% 1000% or more as compared to a control. In some embodiments, ERT enzyme activity is increased by at least 1-fold, 2-fold, 3-fold, 4-fold, 5-fold, 6-fold, 7-fold, 8-fold, 9-fold or 10-fold as compared to a control. In some embodiments, increased ERT enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg, 600 nmol/hr/mg or more.

In some embodiments, treatment refers to decreased progression of loss of cognitive ability. In certain embodiments, progression of loss of cognitive ability is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control (e.g., an untreated subject). In some embodiments, treatment refers to decreased developmental delay. In certain embodiments, developmental delay is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control (e.g., an untreated subject).

In some embodiments, treatment refers to increased survival (e.g. survival time). For example, treatment can result in an increased life expectancy of a patient. In some embodiments, treatment according to the present invention results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with similar disease without treatment. In some embodiments, treatment according to the present invention results in an increased life expectancy of a patient by more than about 6 month, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with similar disease without treatment. In some embodiments, treatment according to the present invention results in long-term survival of a patient. As used herein, the term "long term survival" refers to a survival time or life expectancy longer than about 40 years, 45 years, 50 years, 55 years, 60 years, or longer.

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with a LSD (e.g., Hunter's syndrome), who is about the same age and/or gender as the individual being treated (to ensure that the stages of the disease in the treated individual and the control individual(s) are comparable).

Administration

A pharmaceutical composition described herein may be administered to a subject at a therapeutically effective amount or dose. Illustrative dosages include a daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. In some embodiments, the pharmaceutical composition is administered in a weekly dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg. In some embodiments, a protein molecule described herein has an enzymatic activity of at least about 500 units (U)/mg, about 1,000 U/mg, or at least about 1,500, 2,000, 2,500, 3,000, 3,500, 4,000, 4,500, 5,000, 6,000, 7,000, 8,000, 9,000, or 10,000 U/mg. In some embodiments, the enzymatic activity is at least about 11,000 U/mg, or at least about 12,000, 13,000, 14,000, 15,000, 16,000, 17,000, 18,000, 19,000, 20,000, 25,000, 30,000, 35,000, 40,000, 45000, or 50,000 U/mg; or anywhere in a range of about 500 U/mg to about 50,000 U/mg. The dosages, however, may be varied according to several factors, including the chosen route of administration, the formulation of the composition, patient response, the severity of the condition, the subject's weight, the subject's age, the subject's head size and/or ratio of head size to height, and the judgment of the prescribing physician. The dosage can be increased or decreased over time, as required by an individual patient. In some embodiments, a patient initially is given a low dose, which is then increased to an efficacious dosage tolerable to the patient. Determination of an effective amount is well within the capability of those skilled in the art.

In various embodiments, a protein molecule described herein (e.g., present in a pharmaceutical composition described herein) is administered parenterally. In some embodiments, the protein molecule (e.g., present in a pharmaceutical composition described herein) is administered intravenously. Intravenous administration can be by infusion, e.g., over a period of from about 10 to about 30 minutes, or over a period of at least 1 hour, 2 hours, 3 hours, 4 hours, 6 hours, 8 hours, or 10 hours. In some embodiments, the protein molecule is administered intravenously over a period of from about 20 minute to 6 hours, or from about 30 minutes to 4 hours. In some embodiments, the protein molecule is administered as an intravenous bolus. Combinations of infusion and bolus administration may also be used.

In some parenteral embodiments, a pharmaceutical composition described herein is administered intraperitoneally, subcutaneously, intradermally, or intramuscularly. In some embodiments, a pharmaceutical composition described herein is administered intradermally or intramuscularly. In some embodiments, a pharmaceutical composition described herein is administered intrathecally, such as by epidural administration, or intracerebroventricularly.

Kits and Packages

A kit for use in treating a LSD (e.g. Hunter syndrome), comprising a pharmaceutical composition as described herein is also provided. A package for use in treating a LSD (e.g. Hunter syndrome), comprising a pharmaceutical composition as described herein is also provided.

In certain embodiments, the kit/package comprises a container (e.g., an ampule or a vial, such as a 6R glass vial) which holds a pharmaceutical composition described herein. Typically, the pharmaceutical composition is provided either as a liquid solution or in dehydrated form. In certain embodiments, the pharmaceutical composition comprised within the kit/package is provided in a liquid form, wherein the protein molecule is present in a concentration described herein, such as 30 mg/ml. In certain embodiments, 0.5 ml, 1.0 ml, 1.5ml, 2.0 ml, 2.5 ml, 3.0 ml, 3.5 ml, 4.0 ml, 4.5 ml, 5.0 ml, 5.5 ml, 6.0 ml, 6.5 ml, 7.0 ml, 7.5 ml, 8.0 ml, 8.5 ml, 9.0 ml, 9.5 ml, 10 ml, 15 ml, 20 ml, 25 ml, 30 ml, 35 ml, 40 ml, 45 ml, 50 ml or more of the pharmaceutical composition is provided. In certain embodiments, 5 ml of a pharmaceutical composition described herein is provided (e.g., comprising 150 mg of the protein molecule in the 5 ml of liquid).

In some embodiments, the kit/package further comprises one or more additional therapeutic agents. For example, in some embodiments, the kit/package comprises a pharmaceutical composition as described herein and further comprises one or more additional therapeutic agents for use in the treatment of neurological symptoms of a LSD (e.g., Hunter Syndrome). In certain embodiments, the one or more additional therapeutic agents are provided in a separate container.

In some embodiments, the kit/package further comprises instructional materials containing directions (i.e., protocols) for the practice of the methods described herein (e.g., instructions for using the kit/package for administering a composition described herein). In certain embodiments, the instructions comprise directions for rehydration if the pharmaceutical composition is lyophilized. Additionally, in certain embodiments, the instructions comprise directions for diluting the pharmaceutical composition to an appropriate dosage prior to administration. For example, the pharmaceutical composition may be diluted in saline (e.g., a 100 ml of saline). While the instructional materials typically comprise written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD-ROM), and the like. Such media may include addresses to internet sites that provide such instructional materials.

CERTAIN EMBODIMENTS

Embodiment 1. A pharmaceutical composition comprising:
  a. a protein molecule comprising:
    i. a first Fc polypeptide; and
    ii. a second Fc polypeptide linked to an enzyme replacement therapy (ERT) enzyme, an ERT enzyme variant, or a catalytically active fragment thereof;
  b. a buffer; and
  c. a salt;
  wherein the pH of the pharmaceutical composition is about 5.5 to 7.0.

Embodiment 2. The pharmaceutical composition of embodiment 1, wherein the buffer is selected from the group consisting of: a phosphate buffer, an acetate buffer, an arginine buffer, and a histidine buffer.

Embodiment 3. The pharmaceutical composition of embodiment 2, wherein the phosphate buffer is a sodium phosphate buffer or a potassium phosphate buffer.

Embodiment 4. The pharmaceutical composition of any one of embodiments 1 to 3, wherein the salt is a sodium salt.

Embodiment 5. The pharmaceutical composition of embodiment 4, wherein the sodium salt is selected from the group consisting of: sodium chloride, sodium sulfate, and sodium phosphate.

Embodiment 6. The pharmaceutical composition of any one of embodiments 1 to 5, wherein the pharmaceutical composition further comprises a surfactant.

Embodiment 7. The pharmaceutical composition of any one of embodiments 1 to 6, wherein the pharmaceutical composition further comprises a stabilizer comprising a sugar.

Embodiment 8. The pharmaceutical composition of any one of embodiments 1 to 7, wherein the pharmaceutical composition further comprises methionine.

Embodiment 9. A pharmaceutical composition comprising:
  a. a protein molecule comprising:
    i. a first Fc polypeptide; and
    ii. a second Fc polypeptide linked to an enzyme replacement therapy (ERT) enzyme, an ERT enzyme variant, or a catalytically active fragment thereof;
  b. a buffer comprising sodium phosphate;
  c. sodium chloride;
  d. a surfactant; and
  e. a stabilizer comprising a sugar;
  wherein the pH of the pharmaceutical composition is about 5.5 to 7.0.

Embodiment 10. A pharmaceutical composition comprising:
  a. a protein molecule comprising:
    i. a first Fc polypeptide; and
    ii. a second Fc polypeptide linked to an enzyme replacement therapy (ERT) enzyme, an ERT enzyme variant, or a catalytically active fragment thereof;
  b. a buffer comprising sodium phosphate;
  c. sodium chloride;
  d. a surfactant;
  e. a stabilizer comprising a sugar; and
  f. methionine;
  wherein the pH of the pharmaceutical composition is about 5.5 to 7.0.

Embodiment 11. The pharmaceutical composition of any one of embodiments 1-10, wherein the ERT enzyme is iduronate 2-sulfatase (IDS), and IDS variant, or a catalytically active fragment thereof.

Embodiment 12. The pharmaceutical composition of any one of embodiments 1-11, wherein the ERT enzyme comprises an IDS amino acid sequence, and wherein the IDS amino acid sequence comprises a sequence having at least 90% identity to SEQ ID NO:1.

Embodiment 13. The pharmaceutical composition of embodiment 12, wherein the IDS amino acid sequence comprises a sequence selected from the group consisting of SEQ ID NOs:1, 2 and 3.

Embodiment 14. The pharmaceutical composition of any one of embodiments 1-13, wherein the first or second Fc polypeptide comprises substitutions at at least nine amino acid residue positions selected from the group consisting of 380, 384, 386, 387, 388, 389, 390, 413, 415, 416, and 421, according to EU numbering.

Embodiment 15. The pharmaceutical composition of embodiment 14, wherein the first Fc polypeptide comprises substitutions at at least nine amino acid residue positions selected from the group consisting of 380, 384, 386, 387, 388, 389, 390, 413, 415, 416, and 421, according to EU numbering.

Embodiment 16. A pharmaceutical composition comprising:

a. a protein molecule comprising:

i. a first Fc polypeptide comprising substitutions at at least nine amino acid residue positions selected from the group consisting of 380, 384, 386, 387, 388, 389, 390, 413, 415, 416, and 421, according to EU numbering; and ii. a second Fc polypeptide linked to an iduronate-2-sulfatase (IDS) enzyme, wherein the IDS amino sequence comprises a sequence having at least 90% identity to SEQ ID NO:1;

b. a buffer; and c. a salt;

wherein the pH of the pharmaceutical composition is about 5.5 to 7.0.

Embodiment 17. The pharmaceutical composition of embodiment 16, wherein the buffer is selected from the group consisting of: a phosphate buffer, an acetate buffer, an arginine buffer, and a histidine buffer.

Embodiment 18. The pharmaceutical composition of embodiment 17, wherein the phosphate buffer is a sodium phosphate buffer or a potassium phosphate buffer.

Embodiment 19. The pharmaceutical composition of any one of embodiments 16 to 18, wherein the salt is a sodium salt.

Embodiment 20. The pharmaceutical composition of embodiment 19, wherein the sodium salt is selected from the group consisting of: sodium chloride, sodium sulfate, and sodium phosphate.

Embodiment 21. The pharmaceutical composition of any one of embodiments 16 to 20, wherein the pharmaceutical composition further comprises a surfactant.

Embodiment 22. The pharmaceutical composition of any one of embodiments 16 to 21, wherein the pharmaceutical composition further comprises a stabilizer comprising a sugar.

Embodiment 23. The pharmaceutical composition of any one of embodiments 16 to 22, wherein the pharmaceutical composition further comprises methionine.

Embodiment 24. A pharmaceutical composition comprising:

a. a protein molecule comprising:

i. a first Fc polypeptide comprising substitutions at at least nine amino acid residue positions selected from the group consisting of 380, 384, 386, 387, 388, 389, 390, 413, 415, 416, and 421, according to EU numbering; and ii. a second Fc polypeptide linked to iduronate-2-sulfatase (IDS) enzyme, wherein the IDS amino sequence comprises a sequence having at least 90% identity to SEQ ID NO:1;

b. a buffer comprising sodium phosphate;

c. sodium chloride;

d. a surfactant; and e. a stabilizer comprising a sugar;

wherein the pH of the pharmaceutical composition is about 5.5 to 7.0.

Embodiment 25. The pharmaceutical composition of embodiment 24, further comprising methionine. Embodiment 26. The pharmaceutical composition of any one of embodiments 15-25, wherein the first Fc polypeptide comprises substitutions at amino acid residue positions 384, 386, 387, 388, 389, 413, 415, 416, and 421, according to EU numbering.

Embodiment 27. The pharmaceutical composition of any one of embodiments 11-26, wherein the IDS amino acid sequence is linked to the N-terminus of the second Fc polypeptide.

Embodiment 28. The pharmaceutical composition of any one of embodiments 11-27, wherein the second Fc polypeptide linked to the IDS amino acid sequence comprises an amino acid sequence having at least 95% identity to SEQ ID NO:4, 5, 39 or 40.

Embodiment 29. The pharmaceutical composition of any one of embodiments 11-28, wherein the second Fc polypeptide linked to the IDS amino acid sequence comprises the amino acid sequence of SEQ ID NO:4, 5, 39 or 40.

Embodiment 30. The pharmaceutical composition of any one of embodiments 11-29, wherein the second Fc polypeptide linked to the IDS amino acid sequence comprises the amino acid sequence of SEQ ID NO:4 or 5.

Embodiment 31. The pharmaceutical composition of any one of embodiments 11-29, wherein the second Fc polypeptide linked to the IDS amino acid sequence comprises the amino acid sequence of SEQ ID NO:39 or 40.

Embodiment 32. The pharmaceutical composition of any one of embodiments 1-31, wherein the first Fc polypeptide comprises a sequence having at least 90% identity (e.g., 95% identity) to SEQ ID NO:6 or 41.

Embodiment 33. The pharmaceutical composition of any one of embodiments 1-32, wherein the first Fc polypeptide comprises a sequence having at least 90% identity to SEQ ID NO:6.

Embodiment 34. The pharmaceutical composition of any one of embodiments 1-32, wherein the first Fc polypeptide comprises a sequence having at least 90% identity to SEQ ID NO:41.

Embodiment 35. The pharmaceutical composition of any one of embodiments 1-34, wherein the first Fc polypeptide comprises:

a. Trp, Leu, or Glu at position 380;

b. Tyr at position 384;

c. Thr at position 386;

d. Glu at position 387;

e. Trp at position 388;

f. Ser or Ala at position 389;

g. Ser or Asn at position 390;

h. Thr at position 413;

i. Glu at position 415;

j. Glu at position 416; and k. Phe at position 421.

Embodiment 36. The pharmaceutical composition of any one of embodiments 1-35, wherein the first Fc polypeptide and the second Fc polypeptide dimerize.

Embodiment 37. The pharmaceutical composition of any one of embodiments 11-36, wherein the first Fc polypeptide comprises an amino acid sequence having at least 95% identity to any one of SEQ ID NOs:6, 7, 25 and 30 and the second Fc polypeptide linked to the IDS amino acid sequence comprises an amino acid sequence having at least 95% identity to SEQ ID NO:4 or 5.

Embodiment 38. The pharmaceutical composition of embodiment 37, wherein the first Fc polypeptide comprises the amino acid sequence of SEQ ID NO:6, and the second Fc polypeptide linked to the IDS amino acid sequence comprises the sequence of SEQ ID NO:4 or 5.

Embodiment 39. The pharmaceutical composition of embodiment 37, wherein the first Fc polypeptide comprises the amino acid sequence of SEQ ID NO:7, and the second Fc polypeptide linked to the IDS amino acid sequence comprises the sequence of SEQ ID NO:4 or 5.

Embodiment 40. The pharmaceutical composition of embodiment 37, wherein the first Fc polypeptide comprises the amino acid sequence of SEQ ID NO:25, and the second Fc polypeptide linked to the IDS amino acid sequence comprises the sequence of SEQ ID NO:4 or 5.

Embodiment 41. The pharmaceutical composition of embodiment 37, wherein the first Fc polypeptide comprises the amino acid sequence of SEQ ID NO:30, and the second Fc polypeptide linked to the IDS amino acid sequence comprises the sequence of SEQ ID NO:4 or 5.

Embodiment 42. The pharmaceutical composition of any one of embodiments 11-36, wherein the first Fc polypeptide comprises an amino acid sequence having at least 95% identity to any one of SEQ ID NOs:41, 42, 44 and 49 and the second Fc polypeptide linked to the IDS amino acid sequence comprises an amino acid sequence having at least 95% identity to SEQ ID NO:39 or 40.

Embodiment 43. The pharmaceutical composition of embodiment 42, wherein the first Fc polypeptide comprises the amino acid sequence of SEQ ID NO:41, and the second Fc polypeptide linked to the IDS amino acid sequence comprises the sequence of SEQ ID NO:39 or 40.

Embodiment 44. The pharmaceutical composition of embodiment 42, wherein the first Fc polypeptide comprises the amino acid sequence of SEQ ID NO:42, and the second Fc polypeptide linked to the IDS amino acid sequence comprises the sequence of SEQ ID NO:39 or 40.

Embodiment 45. The pharmaceutical composition of embodiment 42, wherein the first Fc polypeptide comprises the amino acid sequence of SEQ ID NO:44, and the second Fc polypeptide linked to the IDS amino acid sequence comprises the sequence of SEQ ID NO:39 or 40.

Embodiment 46. The pharmaceutical composition of embodiment 42, wherein the first Fc polypeptide comprises the amino acid sequence of SEQ ID NO:49, and the second Fc polypeptide linked to the IDS amino acid sequence comprises the sequence of SEQ ID NO:39 or 40.

Embodiment 47. The pharmaceutical composition of any one of embodiments 1 to 46, wherein the protein molecule concentration is about 5-50 mg/mL.

Embodiment 48. The pharmaceutical composition of any one of embodiments 1 to 47, wherein the protein molecule concentration is about 10-40 mg/mL.

Embodiment 49. The pharmaceutical composition of any one of embodiments 1 to 48, wherein the protein molecule concentration is about 10-30 mg/mL.

Embodiment 50. The pharmaceutical composition of any one of embodiments 1 to 49, wherein the protein molecule concentration is about 10 mg/mL.

Embodiment 51. The pharmaceutical composition of any one of embodiments 1 to 49, wherein the protein molecule concentration is about 20 mg/mL.

Embodiment 52. The pharmaceutical composition of any one of embodiments 1 to 49, wherein the protein molecule concentration is about 30 mg/mL.

Embodiment 53. The pharmaceutical composition of any one of embodiments 1 to 52, wherein buffer concentration is about 5-50 mM.

Embodiment 54. The pharmaceutical composition of any one of embodiments 1 to 53, wherein the buffer concentration is about 10-50 mM.

Embodiment 55. The pharmaceutical composition of any one of embodiments 1 to 54, wherein the buffer concentration is about 10-40 mM.

Embodiment 56. The pharmaceutical composition of any one of embodiments 1 to 55, wherein the buffer concentration is about 10-30 mM.

Embodiment 57. The pharmaceutical composition of any one of embodiments 1 to 56, wherein the buffer concentration is about 15-25 mM.

Embodiment 58. The pharmaceutical composition of any one of embodiments 1 to 57, wherein the buffer concentration is about 20 mM.

Embodiment 59. The pharmaceutical composition of any one of embodiments 1 to 52, wherein the buffer is a sodium phosphate buffer having a concentration of about 5-50 mM.

Embodiment 60. The pharmaceutical composition of any one of embodiments 1 to 52 and 59, wherein the buffer is a sodium phosphate buffer having a concentration of about 10-50 mM.

Embodiment 61. The pharmaceutical composition of any one of embodiments 1 to 52 and 59 to 60, wherein the buffer is a sodium phosphate buffer having a concentration of about 10-40 mM.

Embodiment 62. The pharmaceutical composition of any one of embodiments 1 to 52 and 59 to 61, wherein the buffer is a sodium phosphate buffer having a concentration of about 10-30 mM.

Embodiment 63. The pharmaceutical composition of any one of embodiments 1 to 52 and 59 to 62, wherein the buffer is a sodium phosphate buffer having a concentration of about 15-25 mM.

Embodiment 64. The pharmaceutical composition of any one of embodiments 1 to 52 and 59 to 63, wherein the buffer is a sodium phosphate buffer having a concentration of about 20 mM.

Embodiment 65. The pharmaceutical composition of any one of embodiments 1 to 64, wherein the salt (e.g., sodium salt) concentration is about 30-150 mM.

Embodiment 66. The pharmaceutical composition of any one of embodiments 1 to 65, wherein the salt (e.g., sodium salt) concentration is about 40-140 mM.

Embodiment 67. The pharmaceutical composition of any one of embodiments 1 to 66, wherein the salt (e.g., sodium salt) concentration is about 50-137 mM.

Embodiment 68. The pharmaceutical composition of any one of embodiments 1 to 66, wherein the salt (e.g., sodium salt) concentration is about 40-100 mM.

Embodiment 69. The pharmaceutical composition of any one of embodiments 1 to 68, wherein the salt (e.g., sodium salt) concentration is about 50 mM.

Embodiment 70. The pharmaceutical composition of any one of embodiments 1 to 67, wherein the salt (e.g., sodium salt) concentration is about 137 mM.

Embodiment 71. The pharmaceutical composition of any one of embodiments 1 to 64, wherein the salt is sodium chloride having a concentration of about 30-150 mM.

Embodiment 72. The pharmaceutical composition of any one of embodiments 1 to 64 and 71, wherein the salt is sodium chloride having a concentration of about 40-140 mM.

Embodiment 73. The pharmaceutical composition of any one of embodiments 1 to 64 and 71 to 72, wherein the salt is sodium chloride having a concentration of about 50-137 mM.

Embodiment 74. The pharmaceutical composition of any one of embodiments 1 to 64 and 71 to 72, wherein the salt is sodium chloride having a concentration of about 40-100 mM.

Embodiment 75. The pharmaceutical composition of any one of embodiments 1 to 64 and 71 to 74, wherein the salt is sodium chloride having a concentration of about 50 mM.

Embodiment 76. The pharmaceutical composition of any one of embodiments 1 to 64 and 71-73, wherein the salt is sodium chloride having a concentration of about 137 mM.

Embodiment 77. The pharmaceutical composition of any one of embodiments 6 to 15 and 21 to 76, wherein the surfactant concentration is about 0.1-1.0 mg/mL.

Embodiment 78. The pharmaceutical composition of any one of embodiments 6 to 15 and 21 to 77, wherein the surfactant concentration is about 0.2-0.8 mg/mL.

Embodiment 79. The pharmaceutical composition of any one of embodiments 6 to 15 and 21 to 78, wherein the surfactant concentration is about 0.2-0.6 mg/mL.

Embodiment 80. The pharmaceutical composition of any one of embodiments 6 to 15 and 21 to 79, wherein the surfactant concentration is about 0.2 mg/mL.

Embodiment 81. The pharmaceutical composition of any one of embodiments 6 to 15 and 21 to 79, wherein the surfactant concentration is about 0.4 mg/mL.

Embodiment 82. The pharmaceutical composition of any one of embodiments 6 to 15 and 21 to 79, wherein the surfactant concentration is about 0.5 mg/mL.

Embodiment 83. The pharmaceutical composition of any one of embodiments 6 to 15 and 21 to 79, wherein the surfactant concentration is about 0.6 mg/mL.

Embodiment 84. The pharmaceutical composition of any one of embodiments 6 to 15 and 21 to 83, wherein the surfactant comprises polysorbate.

Embodiment 85. The pharmaceutical composition of embodiment 84, wherein the surfactant is selected from the group consisting of: polysorbate-20 (PS-20) and polysorbate-80 (PS-80).

Embodiment 86. The pharmaceutical composition of embodiment 85, wherein the surfactant is polysorbate-20 (PS-20).

Embodiment 87. The pharmaceutical composition of embodiment 85, wherein the surfactant is polysorbate-80 (PS-80).

Embodiment 88. The pharmaceutical composition of any one of embodiments 6 to 15 and 21 to 83, wherein the surfactant comprises poloxamer.

Embodiment 89. The pharmaceutical composition of any one of embodiments 7 to 15 and 22 to 88, wherein the stabilizer comprises a sugar selected from sucrose or trehalose.

Embodiment 90. The pharmaceutical composition of any one of embodiments 7 to 15 and 22 to 89, wherein the sugar concentration is about 50-300 mM.

Embodiment 91. The pharmaceutical composition of any one of embodiments 7 to 15 and 22 to 90, wherein the sugar concentration is about 100-250 mM.

Embodiment 92. The pharmaceutical composition of any one of embodiments 7 to 15 and 22 to 91, wherein the sugar concentration is about 150-200 mM.

Embodiment 93. The pharmaceutical composition of any one of embodiments 7 to 15 and 22 to 92, wherein the sugar concentration is about 175 mM.

Embodiment 94. The pharmaceutical composition of any one of embodiments 7 to 15 and 22 to 93, wherein the stabilizer comprises sucrose.

Embodiment 95. The pharmaceutical composition of any one of embodiments 8 to 15, 23 and 25 to 94, wherein the methionine concentration is about 5-25 mM.

Embodiment 96. The pharmaceutical composition of any one of embodiments 8 to 15, 23 and 25 to 95, wherein the methionine concentration is about 5-20 mM.

Embodiment 97. The pharmaceutical composition of any one of embodiments 8 to 15, 23 and 25 to 96, wherein the methionine concentration is about 5-15 mM.

Embodiment 98. The pharmaceutical composition of any one of embodiments 8 to 15, 23 and 25 to 97, wherein the methionine concentration is about 10 mM.

Embodiment 99. The pharmaceutical composition of any one of embodiments 1 to 98, wherein the pH of the pharmaceutical composition is from about 5.5 to 6.5.

Embodiment 100. The pharmaceutical composition of any one of embodiments 1 to 99, wherein the pH of the pharmaceutical composition is about 5.5±0.5.

Embodiment 101. The pharmaceutical composition of embodiment 100, wherein the pH of the pharmaceutical composition is about 5.5.

Embodiment 102. The pharmaceutical composition of any one of embodiments 1 to 99, wherein the pH of the pharmaceutical composition is about 6.0±0.5.

Embodiment 103. The pharmaceutical composition of embodiment 102, wherein the pH of the pharmaceutical composition is about 6.0.

Embodiment 104. The pharmaceutical composition of any one of embodiments 1 to 99, wherein the pH of the pharmaceutical composition is about 6.5±0.5.

Embodiment 105. The pharmaceutical composition of embodiment 104, wherein the pH of the pharmaceutical composition is about 6.5. Embodiment 106. A pharmaceutical composition, comprising:

a. a protein molecule comprising:

i. a first polypeptide comprising an amino acid sequence having at least 95% identity to any one of SEQ ID NOs:6, 7, 25 and 30; and ii. a fusion polypeptide comprising iduronate-2-sulfatase (IDS) comprising an amino acid sequence having at least 95% identity to SEQ ID NO:4 or 5;

b. about 10-30 mM of sodium phosphate buffer;

c. about 30-100 mM sodium chloride;

d. about 0.4-0.7 mg/mL of a polysorbate surfactant; and e. about 150-200 mM of sucrose;

wherein the pH of the pharmaceutical composition is about 6.5±0.5

Embodiment 107. The pharmaceutical composition of embodiment 106, wherein the protein molecule comprises:

i. a first polypeptide comprising the amino acid sequence of SEQ ID NO:6 and ii. a fusion polypeptide comprising iduronate-2-sulfatase (IDS) comprising the amino acid sequence of SEQ ID NO:4 or 5.

Embodiment 108. The pharmaceutical composition of embodiment 106, wherein the protein molecule comprises:

i. a first polypeptide comprising the amino acid sequence of SEQ ID NO:7; and ii. a fusion polypeptide comprising iduronate-2-sulfatase (IDS) comprising the amino acid sequence of SEQ ID NO:4 or 5.

Embodiment 109. The pharmaceutical composition of embodiment 106, wherein the protein molecule comprises:

i. a first polypeptide comprising the amino acid sequence of SEQ ID NO:25; and ii. a fusion polypeptide comprising iduronate-2-sulfatase (IDS) comprising the amino acid sequence of SEQ ID NO:4 or 5.

Embodiment 110. The pharmaceutical composition of embodiment 106, wherein the protein molecule comprises:
  i. a first polypeptide comprising the amino acid sequence of SEQ ID NO:30; and
  ii. a fusion polypeptide comprising iduronate-2-sulfatase (IDS) comprising the amino acid sequence of SEQ ID NO:4 or 5.

Embodiment 111. A pharmaceutical composition, comprising:
  a. a protein molecule comprising:
    i. a first polypeptide comprising an amino acid sequence having at least 95% identity to any one of SEQ ID NO:41, 42, 44 and 49; and
    ii. a fusion polypeptide comprising iduronate-2-sulfatase (IDS) comprising an amino acid sequence having at least 95% identity to SEQ ID NO:39 or 40;
  b. about 10-30 mM of sodium phosphate buffer;
  c. about 30-100 mM sodium chloride;
  d. about 0.4-0.7 mg/mL of a polysorbate surfactant; and
  e. about 150-200 mM of sucrose;
  wherein the pH of the pharmaceutical composition is about 6.5±0.5.

Embodiment 112. The pharmaceutical composition of embodiment 111, wherein the protein molecule comprises:
  i. a first polypeptide comprising the amino acid sequence of SEQ ID NO:41; and
  ii. a fusion polypeptide comprising iduronate-2-sulfatase (IDS) comprising the amino acid sequence of SEQ ID NO:39 or 40.

Embodiment 113. The pharmaceutical composition of embodiment 111, wherein the protein molecule comprises:
  i. a first polypeptide comprising the amino acid sequence of SEQ ID NO:42; and
  ii. a fusion polypeptide comprising iduronate-2-sulfatase (IDS) comprising the amino acid sequence of SEQ ID NO:39 or 40.

Embodiment 114. The pharmaceutical composition of embodiment 111, wherein the protein molecule comprises:
  i. a first polypeptide comprising the amino acid sequence of SEQ ID NO:44; and
  ii. a fusion polypeptide comprising iduronate-2-sulfatase (IDS) comprising the amino acid sequence of SEQ ID NO:39 or 40.

Embodiment 115. The pharmaceutical composition of embodiment 111, wherein the protein molecule comprises:
  i. a first polypeptide comprising the amino acid sequence of SEQ ID NO:49; and
  ii. a fusion polypeptide comprising iduronate-2-sulfatase (IDS) comprising the amino acid sequence of SEQ ID NO:39 or 40.

Embodiment 116. A pharmaceutical composition, comprising:
  a. a protein molecule comprising:
    i. a first polypeptide comprising an amino acid sequence having at least 95% identity to any one of SEQ ID NOs:6, 7, 25 and 30; and
    ii. a fusion polypeptide comprising iduronate-2-sulfatase (IDS) comprising an amino acid sequence having at least 95% identity to SEQ ID NO:4 or 5;
  b. about 10-30 mM of sodium phosphate buffer;
  c. about 30-100 mM sodium chloride;
  d. about 0.4-0.7 mg/mL of a polysorbate surfactant;
  e. about 150-200 mM of sucrose; and
  f. about 5-25 mM methionine;

wherein the pH of the pharmaceutical composition is about 6.5±0.5.

Embodiment 117. The pharmaceutical composition of embodiment 116, wherein the protein molecule comprises:
  i. a first polypeptide comprising the amino acid sequence of SEQ ID NO:6; and
  ii. a fusion polypeptide comprising iduronate-2-sulfatase (IDS) comprising the amino acid sequence of SEQ ID NO:4 or 5.

Embodiment 118. The pharmaceutical composition of embodiment 116, wherein the protein molecule comprises:
  i. a first polypeptide comprising the amino acid sequence of SEQ ID NO:7; and
  ii. a fusion polypeptide comprising iduronate-2-sulfatase (IDS) comprising the amino acid sequence of SEQ ID NO:4 or 5.

Embodiment 119. The pharmaceutical composition of embodiment 116, wherein the protein molecule comprises:
  i. a first polypeptide comprising the amino acid sequence of SEQ ID NO:25; and
  ii. a fusion polypeptide comprising iduronate-2-sulfatase (IDS) comprising the amino acid sequence of SEQ ID NO:4 or 5.

Embodiment 120. The pharmaceutical composition of embodiment 116, wherein the protein molecule comprises:
  i. a first polypeptide comprising the amino acid sequence of SEQ ID NO:30; and
  ii. a fusion polypeptide comprising iduronate-2-sulfatase (IDS) comprising the amino acid sequence of SEQ ID NO:4 or 5.

Embodiment 121. A pharmaceutical composition, comprising:
  a. a protein molecule comprising:
    i. a first polypeptide comprising an amino acid sequence having at least 95% identity to any one of SEQ ID NO:41, 42, 44 and 49; and
    ii. a fusion polypeptide comprising iduronate-2-sulfatase (IDS) comprising an amino acid sequence having at least 95% identity to SEQ ID NO:39 or 40;
  b. about 10-30 mM of sodium phosphate buffer;
  c. about 30-100 mM sodium chloride;
  d. about 0.4-0.7 mg/mL of a polysorbate surfactant;
  e. about 150-200 mM of sucrose; and
  f. about 5-25 mM methionine;
  wherein the pH of the pharmaceutical composition is about 6.5±0.5.

Embodiment 122. The pharmaceutical composition of embodiment 121, wherein the protein molecule comprises:
  i. a first polypeptide comprising the amino acid sequence of SEQ ID NO:41; and
  ii. a fusion polypeptide comprising iduronate-2-sulfatase (IDS) comprising the amino acid sequence of SEQ ID NO:39 or 40.

Embodiment 123. The pharmaceutical composition of embodiment 121, wherein the protein molecule comprises:
  i. a first polypeptide comprising the amino acid sequence of SEQ ID NO:42; and
  ii. a fusion polypeptide comprising iduronate-2-sulfatase (IDS) comprising the amino acid sequence of SEQ ID NO:39 or 40.

Embodiment 124. The pharmaceutical composition of embodiment 121, wherein the protein molecule comprises:
  i. a first polypeptide comprising the amino acid sequence of SEQ ID NO:44; and
  ii. a fusion polypeptide comprising iduronate-2-sulfatase (IDS) comprising the amino acid sequence of SEQ ID NO:39 or 40.

Embodiment 125. The pharmaceutical composition of embodiment 121, wherein the protein molecule comprises:

i. a first polypeptide comprising the amino acid sequence of SEQ ID NO:49; and ii. a fusion polypeptide comprising iduronate-2-sulfatase (IDS) comprising the amino acid sequence of SEQ ID NO:39 or 40.

Embodiment 126. The pharmaceutical composition of any one of embodiments 106 to 125, wherein the pH of the pharmaceutical composition is about 6.5±0.2.

Embodiment 127. The pharmaceutical composition of any one of embodiments of 106 to 126, wherein the protein molecule is present in the composition at about 5-50 mg/mL.

Embodiment 128. The pharmaceutical composition of any one of embodiments 106 to 127, wherein the protein molecule is present in the composition at about 10-40 mg/mL.

Embodiment 129. The pharmaceutical composition of any one of embodiments 106 to 128, wherein the protein molecule is present in the composition at about 10-30 mg/mL.

Embodiment 130. The pharmaceutical composition of any one of embodiments 106 to 129, wherein the sodium phosphate buffer concentration is about 15-25 mM.

Embodiment 131. The pharmaceutical composition of any one of embodiments 106 to 130, wherein the sodium phosphate buffer concentration is about 20 mM.

Embodiment 132. The pharmaceutical composition of any one of embodiments 106 to 131, wherein the sodium chloride concentration is about 40-100 mM.

Embodiment 133. The pharmaceutical composition of any one of embodiments 106 to 132, wherein the sodium chloride concentration is about 50 mM.

Embodiment 134. The pharmaceutical composition of any one of embodiments 106 to 133, wherein the polysorbate surfactant concentration is about 0.4 mg/mL.

Embodiment 135. The pharmaceutical composition of any one of embodiments 106 to 133, wherein the polysorbate surfactant concentration is about 0.5 mg/mL.

Embodiment 136. The pharmaceutical composition of any one of embodiments 106 to 133, wherein the polysorbate surfactant concentration is about 0.6 mg/mL.

Embodiment 137. The pharmaceutical composition of any one of embodiments 106 to 136, wherein the polysorbate surfactant is selected from the group consisting of: polysorbate-20 (PS-20) and polysorbate-80 (PS-80).

Embodiment 138. The pharmaceutical composition of embodiment 137, wherein the polysorbate surfactant is polysorbate-20 (PS-20).

Embodiment 139. The pharmaceutical composition of embodiment 137, wherein the polysorbate surfactant is polysorbate-80 (PS-80).

Embodiment 140. The pharmaceutical composition of any one of embodiments 106 to 139, wherein the sucrose concentration is about 175 mM.

Embodiment 141. The pharmaceutical composition of any one of embodiments 116 to 140, wherein the methionine concentration is about 5-20 mM.

Embodiment 142. The pharmaceutical composition of any one of embodiments 116 to 141, wherein the methionine concentration is about 5-15 mM.

Embodiment 143. The pharmaceutical composition of any one of embodiments 116 to 142, wherein the methionine concentration is about 10 mM.

Embodiment 144. The pharmaceutical composition of any one of embodiments 116 to 125, comprising:

a. about 5-50 mg/mL of the protein molecule;

b. about 20 mM of sodium phosphate buffer;

c. about 50 mM sodium chloride;

d. about 0.4-0.7 mg/mL (e.g., 0.6 mg/mL) of polysorbate-20 (PS-20);

e. about 175 mM of sucrose; and f. about 10 mM methionine;

wherein the pH of the pharmaceutical composition is about 6.5±0.2.

Embodiment 145. The pharmaceutical composition of any one of embodiments 1-144, wherein the pH is maintained at 25° C. for two weeks.

Embodiment 146. The pharmaceutical composition of any one of embodiments 1-144, wherein the pH is maintained at 40° C. for two weeks.

Embodiment 147. The pharmaceutical composition of any one of embodiments 1-146, wherein the pH is maintained at a temperature of about 2-8° C. for about 1 month.

Embodiment 148. The pharmaceutical composition of any one of embodiments 1-147, wherein turbidity remains stable at a temperature of about 2-40° C.

Embodiment 149. The pharmaceutical composition of embodiment 148, wherein turbidity remains stable at a temperature of about 2-8° C.

Embodiment 150. The pharmaceutical composition of any one of embodiments 1-149, wherein the protein molecule is remains intact at a temperature of about 2-40° C.

Embodiment 151. The pharmaceutical composition of embodiment 150, wherein the protein molecule is remains intact at a temperature of about 2-8° C.

Embodiment 152. The pharmaceutical composition of any one of embodiments 1-151, wherein the protein molecule is remains intact during freeze-thaw cycles.

Embodiment 153. The pharmaceutical composition of any one of embodiments 1-152, wherein the protein molecule remains intact at a pH of about 5.5-7.0.

Embodiment 154. The pharmaceutical composition of any one of embodiments 1-153, wherein the protein molecule is colloidally and/or conformationally stable at a pH of about 6.0-7.0.

Embodiment 155. The pharmaceutical composition of any one of embodiments 1-154, wherein the pharmaceutical composition is provided as a liquid composition.

Embodiment 156. The pharmaceutical composition of any one of embodiments 1-154, wherein the pharmaceutical composition is provided as a lyophilized composition.

Embodiment 157. A method of treating a lysosomal storage disorder (LSD) (e.g., Hunter syndrome) in a subject in need thereof, comprising administering the pharmaceutical composition of any one of embodiments 1 to 156 to the subject.

Embodiment 158. A method of treating a lysosomal storage disorder (LSD) (e.g., Hunter syndrome) in a subject in need thereof, comprising providing and administering the pharmaceutical composition of any one of embodiments 1 to 156 to the subject.

Embodiment 159. The method of embodiment 157 or 158, wherein the pharmaceutical composition is administered intravenously.

Embodiment 160. The pharmaceutical composition of any one of embodiments 1 to 156 for use in treating a lysosomal storage disorder (LSD) (e.g., Hunter syndrome) in a subject in need thereof.

Embodiment 161. The use of a pharmaceutical composition as described in any one of embodiments 1 to 156 in the preparation of a medicament for treating a lysosomal storage disorder (LSD) (e.g., Hunter Syndrome) in a subject in need thereof.

Embodiment 162. The method, pharmaceutical composition or use of any one of embodiments 157 to 161, wherein the LSD is Hunter syndrome.

Certain Definitions

The term "subject," "individual," and "patient," as used interchangeably herein, refer to a mammal, including but not limited to humans, non-human primates, rodents (e.g., rats, mice, and guinea pigs), rabbits, cows, pigs, horses, and other mammalian species. In one embodiment, the patient is a human.

The term "pharmaceutically acceptable excipient" refers to a non-active pharmaceutical ingredient that is biologically or pharmacologically compatible for use in humans or animals, such as but not limited to a buffer, carrier, or preservative.

The term "administer" refers to a method of delivering agents (e.g., a protein molecule described herein), compounds, or compositions (e.g., pharmaceutical composition) to the desired site of biological action. These methods include, but are not limited to, oral, topical delivery, parenteral delivery, intravenous delivery, intradermal delivery, intramuscular delivery, intrathecal delivery, colonic delivery, rectal delivery, or intraperitoneal delivery. In one embodiment, the pharmaceutical compositions described herein are administered intravenously.

The terms "treatment," "treating," and the like are used herein to generally mean obtaining a desired pharmacologic and/or physiologic effect. "Treating" or "treatment" may refer to any indicia of success in the treatment or amelioration of a lysosomal storage disorder, e.g., Hunter syndrome, including any objective or subjective parameter such as abatement, remission, improvement in patient survival, increase in survival time or rate, diminishing of symptoms or making the disorder more tolerable to the patient, slowing in the rate of degeneration or decline, or improving a patient's physical or mental well-being. The treatment or amelioration of symptoms can be based on objective or subjective parameters. The effect of treatment can be compared to an individual or pool of individuals not receiving the treatment, or to the same patient prior to treatment or at a different time during treatment.

The phrase "effective amount" means an amount of a compound described herein that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

A "therapeutically effective amount" of a substance/molecule disclosed herein may vary according to factors such as the disease state, age, sex, and weight of the individual, and the ability of the substance/molecule, to elicit a desired response in the individual. A therapeutically effective amount encompasses an amount in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount would be less than the therapeutically effective amount.

An "enzyme replacement therapy enzyme" or "ERT enzyme" refers to an enzyme that is deficient in a lysosomal storage disorder. An "ERT enzyme variant" refers to a functional variant, including allelic and splice variants, of a wild-type ERT enzyme or a fragment thereof, where the ERT enzyme variant has at least 50%, at least 55%, at least 60%, at least 65%, at least 70%, at least 75%, at least 80%, at least 85%, at least 90%, or at least 95% of the activity of the corresponding wild-type ERT enzyme or fragment thereof, e.g., when assayed under identical conditions. A "catalytically active fragment" of an ERT enzyme refers to a portion of a full-length ERT enzyme or a variant thereof, where the catalytically active fragment has at least 50%, at least 55%, at least 60%, at least 65%, at least 70%, at least 75%, at least 80%, at least 85%, at least 90%, or at least 95% of the activity of the corresponding full-length ERT enzyme or variant thereof, e.g., when assayed under identical conditions.

An "iduronate sulfatase," "iduronate-2-sulfatase," or "IDS" as used herein refers to iduronate 2-sulfatase (EC 3.1.6.13), which is an enzyme involved in the lysosomal degradation of the glycosaminoglycans heparan sulfate and dermatan sulfate. Deficiency of IDS is associated with Mucopolysaccharidosis II, also known as Hunter syndrome. The term "IDS" as used herein as a component of a protein that comprises an Fc polypeptide is catalytically active and encompasses functional variants, including allelic and splice variants, of a wild-type IDS or a fragment thereof. The sequence of human IDS isoform I, which is the human sequence designated as the canonical sequence, is available under UniProt entry P22304 and is encoded by the human IDS gene at Xq28. The full-length sequence is provided as SEQ ID NO:11. A "mature" IDS sequence as used herein refers to a form of a polypeptide chain that lacks the signal and propeptide sequences of the naturally occurring full-length polypeptide chain. The amino acid sequence of a mature human IDS polypeptide is provided as SEQ ID NO:1, which corresponds to amino acids 34-550 of the full-length human sequence. A "truncated" IDS sequence as used herein refers to a catalytically active fragment of the naturally occurring full-length polypeptide chain. The amino acid sequence of an exemplary truncated human IDS polypeptide is provided as SEQ ID NO:23, which corresponds to amino acids 26-550 of the full-length human sequence. The structure of human IDS has been well-characterized. An illustrative structure is available under PDB accession code 5FQL. The structure is also described in Nat. Comm. 8:15786 doi: 10.1038/ ncomms15786, 2017. Non-human primate IDS sequences have also been described, including chimpanzee (UniProt entry K7BKV4) and rhesus macaque (UniProt entry H9FTX2). A mouse IDS sequence is available under Uniprot entry Q08890. An IDS variant has at least 50%, at least 55%, at least 60%, at least 65%, at least 70%, at least 75%, at least 80%, at least 85%, at least 90%, or at least 95% of the activity of the corresponding wild-type IDS or fragment thereof, e.g., when assayed under identical conditions. A catalytically active IDS fragment has at least 50%, at least 55%, at least 60%, at least 65%, at least 70%, at least 75%, at least 80%, at least 85%, at least 90%, or at least 95% of the activity of the corresponding full-length IDS or variant thereof, e.g., when assayed under identical conditions.

A "transferrin receptor" or "TfR" as used herein refers to transferrin receptor protein 1. The human transferrin receptor 1 polypeptide sequence is set forth in SEQ ID NO:13. Transferrin receptor protein 1 sequences from other species are also known (e.g., chimpanzee, accession number XP_003310238.1; rhesus monkey, NP_001244232.1; dog, NP_001003111.1; cattle, NP_001193506.1; mouse, NP_035768.1; rat, NP_073203.1; and chicken, NP_990587.1). The term "transferrin receptor" also encompasses allelic variants of exemplary reference sequences, e.g., human sequences, that are encoded by a gene at a transferrin receptor protein 1 chromosomal locus. Full-length transferrin receptor protein includes a short N-terminal intracellular region, a transmembrane region, and a large extracellular domain. The extracellular domain is characterized by three domains: a protease-like domain, a helical domain, and an apical domain. The apical domain sequence of human transferrin receptor 1 is set forth in SEQ ID NO:35.

An "[ERT enzyme]-Fc fusion protein," "ETV:[ERT enzyme] protein molecule," or "protein molecule" as used herein refers to a dimeric protein comprising a first Fc polypeptide and a second Fc polypeptide, which is linked (e.g., fused) to an ERT enzyme, an ERT enzyme variant, or a catalytically active fragment thereof (e.g., an "IDS-Fc fusion polypeptide"), wherein the first Fc polypeptide forms an Fc dimer with the second Fc polypeptide. The first Fc polypeptide may also be linked (e.g., fused) to an ERT enzyme, an ERT enzyme variant, or a catalytically active fragment thereof. The first Fc polypeptide and/or the second Fc polypeptide may be linked to the ERT enzyme, ERT enzyme variant, or catalytically active fragment thereof by a peptide bond or by a polypeptide linker. The first Fc polypeptide and/or the second Fc polypeptide may be a modified Fc polypeptide that contains one or more modifications that promote its heterodimerization to the other Fc polypeptide. The first Fc polypeptide and/or the second Fc polypeptide may be a modified Fc polypeptide that contains one or more modifications that confer binding to a transferrin receptor. The first Fc polypeptide and/or the second Fc polypeptide may be a modified Fc polypeptide that contains one or more modifications that reduce effector function. The first Fc polypeptide and/or the second Fc polypeptide may be a modified Fc polypeptide that contains one or more modifications that extend serum half-life. The terms "[ERT enzyme]-Fc fusion protein," "ETV:[ERT enzyme] protein molecule," or "protein molecule" may refer to a single protein molecule or to a plurality of protein molecules.

A "fusion polypeptide" or "[ERT enzyme]-Fc fusion polypeptide" as used herein refers to an Fc polypeptide that is linked (e.g., fused) to an ERT enzyme, an ERT enzyme variant, or a catalytically active fragment thereof. The Fc polypeptide may be linked to the ERT enzyme, ERT enzyme variant, or catalytically active fragment thereof by a peptide bond or by a polypeptide linker. The Fc polypeptide may be a modified Fc polypeptide that contains one or more modifications that promote its heterodimerization to another Fc polypeptide. The Fc polypeptide may be a modified Fc polypeptide that contains one or more modifications that confer binding to a transferrin receptor. The Fc polypeptide may be a modified Fc polypeptide that contains one or more modifications that reduce effector function. The Fc polypeptide may be a modified Fc polypeptide that contains one or more modifications that extend serum half-life.

As used herein, the term "Fc polypeptide" refers to the C-terminal region of a naturally occurring immunoglobulin heavy chain polypeptide that is characterized by an Ig fold as a structural domain. An Fc polypeptide contains constant region sequences including at least the CH2 domain and/or the CH3 domain and may contain at least part of the hinge region. In general, an Fc polypeptide does not contain a variable region.

A "modified Fc polypeptide" refers to an Fc polypeptide that has at least one mutation, e.g., a substitution, deletion or insertion, as compared to a wild-type immunoglobulin heavy chain Fc polypeptide sequence, but retains the overall Ig fold or structure of the native Fc polypeptide.

The term "FcRn" refers to the neonatal Fc receptor. Binding of Fc polypeptides to FcRn reduces clearance and increases serum half-life of the Fc polypeptide. The human FcRn protein is a heterodimer that is composed of a protein of about 50 kDa in size that is similar to a major histocompatibility (MHC) class I protein and a β2-microglobulin of about 15 kDa in size.

As used herein, an "FcRn binding site" refers to the region of an Fc polypeptide that binds to FcRn. In human IgG, the FcRn binding site, as numbered using the EU index, includes T250, L251, M252, 1253, S254, R255, T256, T307, E380, M428, H433, N434, H435, and Y436. These positions correspond to positions 20 to 26, 77, 150, 198, and 203 to 206 of SEQ ID NO:8.

As used herein, a "native FcRn binding site" refers to a region of an Fc polypeptide that binds to FcRn and that has the same amino acid sequence as the region of a naturally occurring Fc polypeptide that binds to FcRn.

The terms "CH3 domain" and "CH2 domain" as used herein refer to immunoglobulin constant region domain polypeptides. For purposes of this application, a CH3 domain polypeptide refers to the segment of amino acids from about position 341 to about position 447 as numbered according to EU, and a CH2 domain polypeptide refers to the segment of amino acids from about position 231 to about position 340 as numbered according to the EU numbering scheme and does not include hinge region sequences. CH2 and CH3 domain polypeptides may also be numbered by the IMGT (ImMunoGeneTics) numbering scheme in which the CH2 domain numbering is 1-110 and the CH3 domain numbering is 1-107, according to the IMGT Scientific chart numbering (IMGT website). CH2 and CH3 domains are part of the Fc region of an immunoglobulin. An Fc region refers to the segment of amino acids from about position 231 to about position 447 as numbered according to the EU numbering scheme, but as used herein, can include at least a part of a hinge region of an antibody. An illustrative hinge region sequence is the human IgG1 hinge sequence EPKSCDKTH-TCPPCP (SEQ ID NO:12).

"Naturally occurring," "native" or "wild type" is used to describe an object that can be found in nature as distinct from being artificially produced. For example, a nucleotide sequence present in an organism (including a virus), which can be isolated from a source in nature and which has not been intentionally modified in the laboratory, is naturally occurring. Furthermore, "wild-type" refers to the normal gene, or organism found in nature without any known mutation. For example, the terms "wild-type," "native," and "naturally occurring" with respect to a CH3 or CH2 domain are used herein to refer to a domain that has a sequence that occurs in nature.

As used herein, the term "mutant" with respect to a mutant polypeptide or mutant polynucleotide is used interchangeably with "variant." A variant with respect to a given wild-type CH3 or CH2 domain reference sequence can include naturally occurring allelic variants. A "non-naturally" occurring CH3 or CH2 domain refers to a variant or mutant domain that is not present in a cell in nature and that is produced by genetic modification, e.g., using genetic engineering technology or mutagenesis techniques, of a native CH3 domain or CH2 domain polynucleotide or polypeptide. A "variant" includes any domain comprising at least one amino acid mutation with respect to wild-type. Mutations may include substitutions, insertions, and deletions.

The term "amino acid" refers to naturally occurring and synthetic amino acids, as well as amino acid analogs and amino acid mimetics that function in a manner similar to the naturally occurring amino acids.

Naturally occurring amino acids are those encoded by the genetic code, as well as those amino acids that are later modified, e.g., hydroxyproline, γ-carboxyglutamate and O-phosphoserine. "Amino acid analogs" refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that function in a manner similar to a naturally occurring amino acid.

Naturally occurring a-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring a-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Amino acids may be referred to herein by either their commonly known three letter symbols or by the one-letter symbols recommended by the IUPAC-IUB Biochemical Nomenclature Commission.

The terms "polypeptide" and "peptide" are used interchangeably herein to refer to a polymer of amino acid residues in a single chain. The terms apply to amino acid polymers in which one or more amino acid residue is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or a mixture of L and D amino acids.

The term "protein" as used herein refers to either a polypeptide or a dimer (i.e, two) or multimer (i.e., three or more) of single chain polypeptides. The single chain polypeptides of a protein may be joined by a covalent bond, e.g., a disulfide bond, or non-covalent interactions.

The term "conservative substitution," "conservative mutation," or "conservatively modified variant" refers to an alteration that results in the substitution of an amino acid with another amino acid that can be categorized as having a similar feature. Examples of categories of conservative amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R), and His (Histidine or H); an "aromatic group" including Phe (Phenylalanine or F), Tyr (Tyrosine or Y), Trp (Tryptophan or W), and (Histidine or H); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T), and Cys (Cysteine or C). Within each group, subgroups can also be identified. For example, the group of charged or polar amino acids can be sub-divided into sub-groups including: a "positively-charged sub-group" comprising Lys, Arg and His; a "negatively-charged sub-group" comprising Glu and Asp; and a "polar sub-group" comprising Asn and Gln. In another example, the aromatic or cyclic group can be sub-divided into sub-groups including: a "nitrogen ring sub-group" comprising Pro, His and Trp; and a "phenyl sub-group" comprising Phe and Tyr. In another further example, the aliphatic group can be sub-divided into sub-groups, e.g., an "aliphatic non-polar sub-group" comprising Val, Leu, Gly, and Ala; and an "aliphatic slightly-polar sub-group" comprising Met, Ser, Thr, and Cys. Examples of categories of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH$_2$ can be maintained. In some embodiments, hydrophobic amino acids are substituted for naturally occurring hydrophobic amino acid, e.g., in the active site, to preserve hydrophobicity.

The terms "identical" or percent "identity," in the context of two or more polypeptide sequences, refer to two or more sequences or subsequences that are the same or have a specified percentage of amino acid residues, e.g., at least 60% identity, at least 65%, at least 70%, at least 75%, at least 80%, at least 85%, at least 90%, or at least 95% or greater, that are identical over a specified region when compared and aligned for maximum correspondence over a comparison window, or designated region, as measured using a sequence comparison algorithm or by manual alignment and visual inspection.

For sequence comparison of polypeptides, typically one amino acid sequence acts as a reference sequence, to which a candidate sequence is compared. Alignment can be performed using various methods available to one of skill in the art, e.g., visual alignment or using publicly available software using known algorithms to achieve maximal alignment. Such programs include the BLAST programs, ALIGN, ALIGN-2 (Genentech, South San Francisco, Calif.) or Megalign (DNASTAR). The parameters employed for an alignment to achieve maximal alignment can be determined by one of skill in the art. For sequence comparison of polypeptide sequences for purposes of this application, the BLASTP algorithm standard protein BLAST for aligning two proteins sequence with the default parameters is used.

The terms "corresponding to," "determined with reference to," or "numbered with reference to" when used in the context of the identification of a given amino acid residue in a polypeptide sequence, refers to the position of the residue of a specified reference sequence when the given amino acid sequence is maximally aligned and compared to the reference sequence. Thus, for example, an amino acid residue in a modified Fc polypeptide "corresponds to" an amino acid in SEQ ID NO:8, when the residue aligns with the amino acid in SEQ ID NO:8 when optimally aligned to SEQ ID NO:8.

The polypeptide that is aligned to the reference sequence need not be the same length as the reference sequence.

A "binding affinity" as used herein refers to the strength of the non-covalent interaction between two molecules, e.g., a single binding site on a polypeptide and a target, e.g., transferrin receptor, to which it binds. Thus, for example, the term may refer to 1:1 interactions between a polypeptide and its target, unless otherwise indicated or clear from context. Binding affinity may be quantified by measuring an equilibrium dissociation constant ($K_D$), which refers to the dissociation rate constant ($k_d$, time$^{-1}$) divided by the association rate constant ($k_a$, time$^{-1}$ M$^{-1}$). $K_D$ can be determined by measurement of the kinetics of complex formation and dissociation, e.g., using Surface Plasmon Resonance (SPR) methods, e.g., a Biacore™ system; kinetic exclusion assays such as KinExA®; and BioLayer interferometry (e.g., using the ForteBio® Octet® platform). As used herein, "binding affinity" includes not only formal binding affinities, such as those reflecting 1:1 interactions between a polypeptide and its target, but also apparent affinities for which $K_D$'s are calculated that may reflect avid binding.

As used herein, the term "specifically binds" or "selectively binds" to a target, e.g., TfR, when referring to an engineered TfR-binding polypeptide or TfR-binding peptide as described herein, refers to a binding reaction whereby the engineered TfR-binding polypeptide or TfR-binding peptide binds to the target with greater affinity, greater avidity, and/or greater duration than it binds to a structurally different target. In typical embodiments, the engineered TfR-binding polypeptide or TfR-binding peptide has at least 5-fold, 10-fold, 50-fold, 100-fold, 1,000-fold, 10,000-fold, or greater affinity for a specific target, e.g., TfR, compared to an unrelated target when assayed under the same affinity assay conditions. The term "specific binding," "specifically binds to," or "is specific for" a particular target (e.g., TfR), as used herein, can be exhibited, for example, by a molecule having an equilibrium dissociation constant $K_D$ for the target to which it binds of, e.g., 10$^{-4}$ M or smaller, e.g., 10$^{-5}$ M, 10$^{-6}$ M, 10$^{-7}$ M, 10$^{-8}$ M, 10$^{-9}$ M, 10$^{-10}$ M, 10$^{-11}$ M, or 10$^{-12}$ M. In some embodiments, an engineered TfR-binding polypeptide or TfR-binding peptide specifically binds to an epitope on TfR that is conserved among species, (e.g., structurally conserved among species), e.g., conserved between non-human primate and human species (e.g., structurally conserved between non-human primate and human species). In some embodiments, an engineered TfR-binding polypeptide or TfR-binding peptide may bind exclusively to a human TfR.

The term "variable region" or "variable domain" refers to a domain in an antibody heavy chain or light chain that is derived from a germline Variable (V) gene, Diversity (D) gene, or Joining (J) gene (and not derived from a Constant (Cμ and Cδ gene segment), and that gives an antibody its specificity for binding to an antigen. Typically, an antibody variable region comprises four conserved "framework" regions interspersed with three hypervariable "complementarity determining regions."

The terms "antigen-binding portion" and "antigen-binding fragment" are used interchangeably herein and refer to one or more fragments of an antibody that retains the ability to specifically bind to an antigen via its variable region. Examples of antigen-binding fragments include, but are not limited to, a Fab fragment (a monovalent fragment consisting of the VL, VH, CL, and CH1 domains), a F(ab')$_2$ fragment (a bivalent fragment comprising two Fab fragments linked by a disulfide bridge at the hinge region), a single chain Fv (scFv), a disulfide-linked Fv (dsFv), complementarity determining regions (CDRs), a VL (light chain variable region), and a VH (heavy chain variable region).

As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

As used herein, the term "lyoprotectant" refers to a molecule that prevents or reduces chemical and/or physical instability of a protein or other substance upon lyophilization and subsequent storage. Exemplary lyoprotectants include sugars such as sucrose or trehalose; an amino acid such as monosodium glutamate or histidine; a methylamine such as betaine; a lyotropic salt such as magnesium sulfate: a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. In some embodiments, a lyoprotectant is a non-reducing sugar, such as trehalose or sucrose.

As used herein, the term "soluble" refers to the ability of a therapeutic agent to form a homogenous solution. In some embodiments, the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts). In some embodiments, the pharmaceutical compositions are formulated such that calcium salts are excluded from such compositions. In some embodiments, therapeutic agents are soluble in its corresponding pharmaceutical composition.

As used herein, the term "stable" refers to the ability of the therapeutic agent (e.g., a ETV:IDS protein molecule comprising an IDS-Fc fusion polypeptide) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 2, 3 or 4 weeks; or 1, 3, 6, 12, 18, 24, 30, 36 months or more). In general, pharmaceutical compositions described herein have been formulated such that they are capable of stabilizing, or alternatively slowing or preventing the degradation, of one or more therapeutic agents formulated therewith (e.g., recombinant proteins). In the context of a formulation, a stable formulation is one in which the therapeutic agent therein essentially retains its physical and/or chemical integrity and biological activity upon storage and during processes (such as freeze/thaw, mechanical mixing and lyophilization). For protein stability, it can be measured by, e.g., formation of high molecular weight (HMW) aggregates, formation of low molecular weight particles (indicative of clipping), loss of enzyme activity, generation of peptide fragments, shift of charge profiles or other factors described in the Examples.

The following Examples are intended to be non-limiting.

Example 1

Construction of Fusion Proteins Comprising IDS

Design and Cloning

IDS-Fc fusion proteins were designed that contain (i) a fusion polypeptide where a mature, human IDS enzyme is fused to a human IgG1 fragment that includes the Fc region (an "IDS-Fc fusion polypeptide"), and (ii) a modified human IgG1 fragment which contains mutations in the Fc region that confer transferrin receptor (TfR) binding (a "modified Fc polypeptide"). In particular, IDS-Fc fusion polypeptides were created in which IDS fragments were fused to either the N- or C-terminus of the human IgG1 Fc region. In some cases, a linker was placed between the IDS and IgG1 fragments to alleviate any steric hindrance between the two fragments. In all constructs, the signal peptide from the kappa chain V-III, amino acids 1-20 (UniProtKB ID—P01661) was inserted upstream of the fusion to facilitate secretion, and IDS was truncated to consist of amino acids S26-P550 (UniProtKB ID—P22304). The fragment of the human IgG1 Fc region used corresponds to amino acids D104-K330 of the sequence in UniProtKB ID P01857 (positions 221-447, EU numbering, which includes 10 amino acids of the hinge (positions 221-230)). In some embodiments, another Fc polypeptide derived from human IgG1 residues D104-K330 but lacking the IDS fusion was co-transfected with the IDS-Fc fusion polypeptide in order to generate heterodimeric fusion proteins with one IDS enzyme (a "monozyme"). In some constructs, the IgG1 fragments contained additional mutations to facilitate heterodimerization of the two Fc regions. Control IDS-Fc fusion proteins that lack the mutations that confer TfR binding were designed and constructed analogously, with the difference being that these proteins lacked the mutations that confer TfR binding. As an additional control, an IDS polypeptide (amino acids S26-P550) with a C-terminal hexahistidine tag (SEQ ID NO:38) was generated to facilitate detection and purification.

The TfR-binding protein molecules are dimers formed by an IDS-Fc fusion polypeptide and a modified Fc polypeptide that binds to TfR. For dimers where the IDS enzyme is linked to the N-terminus of the Fc region, the IDS-Fc fusion polypeptide may have the sequence of any one of SEQ ID NOS:4, 5 and 24. In these sequences, the IDS sequence is underlined and contains a cysteine at position 59 (double underlined) modified to formylglycine. The IDS was joined to the Fc polypeptide by a GGGGS linker (SEQ ID NO:36). A portion of an IgG1 hinge region (DKTHTCPPCP; SEQ ID NO:22) was included at the N-terminus of the Fc polypeptide. The CH2 domain sequence starts at position 541 of SEQ ID NOS:4, 5 and 24.

The IDS-Fc fusion protein ETV:IDS 35.21 is a dimer formed by an IDS-Fc fusion polypeptide having the sequence of any one of SEQ ID NOS:4, 5 and 24 and a modified Fc polypeptide that binds to TfR having the sequence of SEQ ID NO:25. The IDS-Fc fusion protein ETV:IDS 35.21 may also be further processed during cell culture production, such that the IDS-Fc fusion polypeptide has the sequence of any one of SEQ ID NOS:39, 40 and 43 and/or the modified Fc polypeptide that binds to TfR has the sequence of SEQ ID NO:44. Thus, as used herein, the term ETV:IDS 35.21 may be used to refer to protein molecules having unprocessed sequences (i.e., SEQ ID NOs:4, 5, 24 and 25); protein molecules comprising one or more processed sequences (i.e., selected from SEQ ID NOs: 39, 40, 43 and 44); or to a mixture comprising processed and unprocessed protein molecules. The first 10 amino acids are a portion of an IgG1 hinge region. The CH2 domain sequence starts at position 11 of SEQ ID NOs:25 and 44, respectively.

The IDS-Fc fusion protein ETV:IDS 35.21.17.2 is a dimer formed by an IDS-Fc fusion polypeptide having the sequence of any one of SEQ ID NOS:4, 5 and 24 and a modified Fc polypeptide that binds to TfR having the sequence of SEQ ID NO:30. The IDS-Fc fusion protein ETV:IDS 35.21.17.2 may also be further processed during cell culture production, such that the IDS-Fc fusion polypeptide has the sequence of any one of SEQ ID NOS:39, 40 and 43 and/or the modified Fc polypeptide that binds to TfR has the sequence of SEQ ID NO:49. Thus, as used herein, the term ETV:IDS 35.21.17.2 may be used to refer to protein molecules having unprocessed sequences (i.e., SEQ ID NOs:4, 5, 24 and 30); protein molecules comprising one or more processed sequences (i.e., selected from SEQ ID NOs: 39, 40, 43 and 49); or to a mixture comprising processed and unprocessed protein molecules. The first 10 amino acids are a portion of an IgG1 hinge region. The CH2 domain sequence starts at position 11 of SEQ ID NOs:30 and 49, respectively.

The IDS-Fc fusion protein ETV:IDS 35.23.2 is a dimer formed by an IDS-Fc fusion polypeptide having the sequence of any one of SEQ ID NOS:4, 5 and 24 and a modified Fc polypeptide that binds to TfR having the sequence of SEQ ID NO:7. The IDS-Fc fusion protein ETV:IDS 35.23.2 may also be further processed during cell culture production, such that the IDS-Fc fusion polypeptide has the sequence of any one of SEQ ID NOS:39, 40 and 43 and/or the modified Fc polypeptide that binds to TfR has the sequence of SEQ ID NO:42. Thus, as used herein, the term ETV:IDS 35.23.2 may be used to refer to protein molecules having unprocessed sequences (i.e., SEQ ID NOs:4, 5, 24 and 7); protein molecules comprising one or more processed sequences (i.e., selected from SEQ ID NOs: 39, 40, 43 and 42); or to a mixture comprising processed and unprocessed protein molecules. The first 10 amino acids are a portion of an IgG1 hinge region. The CH2 domain sequence starts at position 11 of SEQ ID NOs:7 and 42, respectively.

The IDS-Fc fusion protein ETV:IDS 35.21.17 is a dimer formed by an IDS-Fc fusion polypeptide having the sequence of any one of SEQ ID NOS:4, 5 and 24 and a modified Fc polypeptide that binds to TfR having the sequence of SEQ ID NO:6. The IDS-Fc fusion protein ETV:IDS 35.21.17 may also be further processed during cell culture production, such that the IDS-Fc fusion polypeptide has the sequence of any one of SEQ ID NOS:39, 40 and 43 and/or the modified Fc polypeptide that binds to TfR has the sequence of SEQ ID NO:41. Thus, as used herein, the term ETV:IDS 35.21.17 may be used to refer to protein molecules having unprocessed sequences (i.e., SEQ ID NOs:4, 5, 24 and 6); protein molecules comprising one or more processed sequences (i.e., selected from SEQ ID NOs: 39, 40, 43 and 41); or to a mixture comprising processed and unprocessed protein molecules. The N-terminus of the modified Fc polypeptide may include a portion of an IgG1 hinge region (e.g., SEQ ID NO:22).

Protein Expression and Purification

To express recombinant IDS enzyme fused to an Fc region, ExpiCHO cells (Thermo Fisher Scientific) were transfected with relevant DNA constructs using Expifectamine™ CHO transfection kit according to manufacturer's instructions (Thermo Fisher Scientific). Cells were grown in ExpiCHO™ Expression Medium at 37° C., 6% $CO_2$ and 120 rpm in an orbital shaker (Infors HT Multitron). In brief, logarithmic growing ExpiCHO™ cells were transfected at $6 \times 10^6$ cells/ml density with 0.8 µg of DNA plasmid per mL of culture volume. After transfection, cells were returned to 37° C. and transfected cultures were supplemented with feed as indicated 18-22 hrs post transfection. Transfected cell culture supernatants were harvested 120 hrs post transfection by centrifugation at 3,500 rpm from 20 mins. Clarified supernatants were filtered (0.22 µM membrane) and stored at 4° C. Expression of an epitope-tagged IDS enzyme (used as a control) was carried out as described above with minor modifications. In brief, an IDS enzyme harboring a C-terminal hexahistidine tag (SEQ ID NO:38) was expressed in ExpiCHO cells.

IDS-Fc fusion proteins with (or without) engineered Fc regions conferring TfR binding were purified from cell culture supernatants using Protein A affinity chromatography. Supernatants were loaded onto a HiTrap Mab Select SuRe Protein A affinity column (GE Healthcare Life Sciences using an Akta Pure System). The column was then washed with >20 column volumes (CVs) of PBS. Bound proteins were eluted using 100 mM citrate/NaOH buffer pH 3.0 containing 150 mM NaCl. Immediately after elution, fractions were neutralized using 1 M arginine-670 mM succinate buffer pH 5.0 (at a 1:5 dilution). Homogeneity of IDS-Fc fusion proteins in eluted fractions was assessed by reducing and non-reducing SDS-PAGE.

To purify hexahistadine-tagged (SEQ ID NO:38) IDS enzyme, transfected supernatants were exhaustively dialyzed against 15 L of 20 mM HEPES pH 7.4 containing 100 mM NaCl overnight. Dialyzed supernatants were bound to a HisTrap column (GE Healthcare Life Sciences using an Akta Pure System). After binding, the column was washed with 20 CV of PBS. Bound proteins were eluted using PBS containing 500 mM imidazole. Homogeneity of IDS enzyme in eluted fractions was assessed by reducing and non-reducing SDS-PAGE. Pooled fractions containing IDS enzyme were diluted 1:10 in 50 mM Tris pH 7.5 and further purified using Q Sepharose High Performance (GE Healthcare). After binding, the column was washed with 10 CV of 50 mM Tris pH 7.5. Bound proteins were eluted using a linear gradient to 50 mM Tris pH 7.5 and 0.5 M NaCl and collected in 1 CV fractions. Fraction purity was assessed by non-reducing SDS-PAGE. Purification yielded homogeneous IDS-Fc fusion proteins and hexahistidine-tagged (SEQ ID NO:38) IDS enzyme.

Recombinant IDS-Fc fusion protein was also produced by stable cell line pools. Briefly, stable cell lines generated by transfection of CHOK1SV GS-KO™ cells (Lonza Biologics PLC) with relevant DNA constructs were cultured in growth medium in stirred tank 10-L bioreactors. The cell culture medium was harvested two weeks after inoculation and purified in a three-step process that included a Protein A chromatography, ion exchange chromatography, and ultrafiltration/diafiltration before being stored at 2-8° C.

Example 2

Formulation Development and Evaluation

The following formulations and conditions were evaluated as described below. As shown in Table 2.1 various buffer components were tested, including the buffer of commercial comparator Elaprase (test buffer #1). Unless indicated otherwise, 10 mg/mL of a representative ETV:IDS protein (ETV:IDS 35.23.2, Example 1), was used to assess each test buffer.

TABLE 2.1

| | | | | | |
|---|---|---|---|---|---|
| Test Buffer Formulations. | | | | | |
| Test Buffer # | Buffer | pH | NaCl (mM) | Arg-HCl (mM) | kD ranking |
| 1 | 20 mM Na-Phosphate | 6.0 | 137 | | 3 |
| 2 | 20 mM Na-Phosphate | 6.0 | | 100 | 5 |
| 3 | 20 mM K-Phosphate | 7.0 | 137 | | 1 |
| 4 | 20 mM Arg-Succinate | 6.0 | 137 | | 4 |
| 5 | 20 mM His-HCl | 5.0 | 137 | | 6 |
| 6 | 20 mM His-HCl | 6.5 | 137 | 75 | 2 |

As described below, the following properties were assessed: 1) colloidal stability as indicated by diffusion interaction parameter kD, measured by Dynamic Light Scattering (DLS); and 2) conformational stability as indicated by $T_{on}$ and $T_{agg}$, measured by Differential Scanning Fluorimetry (DSF) and Static Light Scattering (SLS).

Evaluation of Test Buffers
Measurement of Colloidal Stability (DLS)

A dilution series of ETV:IDS protein molecule was prepared starting from 10 mg/mL (10, 8, 6, 5, 4, 3, 2 mg/mL). DLS signal was measured using a Wyatt DynaPro Plate Reader II. kD values and standard deviations were calculated after linear regression. A positive kD value indicates repulsive forces (i.e., increased solubility) between protein molecules, whereas a negative kD indicates attractive forces (i.e., increased aggregation). Repulsive forces correlate with increased colloidal stability and are favored. As shown in Table 2.2, test buffers #3 and 6 had the highest kD values, indicating these buffers favored colloidal stability.

TABLE 2.2

| | | |
|---|---|---|
| Colloidal Stability (DLS) | | |
| Test Buffer # | kD (mL/g) | Std. Dev. kD (mL/g) |
| 1 | 0.05 | 0.73 |
| 2 | -2.78 | 0.60 |
| 3 | 3.08 | 0.66 |
| 4 | -2.15 | 0.77 |
| 5 | -7.38 | 0.62 |
| 6 | 3.02 | 0.75 |

Measurement of Conformational Stability (DSF/SLS)

ETV:IDS protein molecule was tested at 5 mg/mL, 9 µl sample volume. The thermal ramp was 15-95° C., with a heating rate of 0.33° C./min. Tm was determined by DSF and $T_{agg}$ was determined by SLS.

As shown in Table 2.3 below, test buffer 5 (His-HCl, pH 5.0) exhibited a significantly lower Tm1 than other buffers. The other buffers showed comparable conformational stability behavior.

TABLE 2.3

| | | | |
|---|---|---|---|
| Conformations Stability (DSF/SLS) | | | |
| Test Buffer # | Tm1 (° C.) | Tm2 (° C.) | Tagg (° C.) |
| 1 | 68.1 | 74.1 | 65.1 |
| 2 | 66.9 | 74.1 | 65.4 |
| 3 | 66.6 | n.t. | 60.8 |
| 4 | 67.5 | 73.1 | 65.4 |
| 5 | 56.4 | 72.1 | 66.7 |
| 6 | 66.5 | 73.3 | 65.9 |

The binding kinetics between ETV:IDS protein molecule and TfR was also assessed in the various test buffers. No significant change was observed across buffer conditions.

In summary, as shown in Table 2.2, colloidal stability of ETV:IDS protein molecule was found to be improved with higher pH buffers 6.5 and 7.0 (slightly positive kD values). While the protein molecule generally showed a good conformational stability, it was found to be significantly impaired at lower pH (about pH 5.0) (Table 2.3). Otherwise, conformational stability was not significantly affected by buffer type in the low range of pH 6.0-7.0. Based on the colloidal and conformational stability behavior, a pH range of 6.0-7.0 appears to be favorable for the protein molecule.

Evaluation of Low and High pH Conditions

To further inform the formulation development, ETV:IDS protein molecule was evaluated in the various test buffers with low and high pH under forced degradation conditions. The sample descriptions and techniques used for each evaluation are summarized in Table 2.4 below.

TABLE 2.4

| Evaluation of Test Buffers | | | |
|---|---|---|---|
| Sample Description | SEC | RP-HPLC (red/non-red) | Caliper (red/non-red) |
| 50 mM Tris pH 8, 2 days, 40° C. | X | | |
| 50 mM Tris pH 8, 2 days, 40° C. Control | | | |
| 50 mM Tris pH 8, 5 days, 40° C. | | | |
| 50 mM Tris pH 8, 5 days, 40° C. Control | | | |
| 50 mM Acetate pH 4, 2 days, 40° C. | | X | X |
| 50 mM Acetate pH 4, 2 days, 40° C. Control | | | |
| 50 mM Acetate pH 4, 5 days, 40° C. | | | |
| 50 mM Acetate pH 4, 5 days, 40° C. Control | | | |
| 0.81 mM AAPH, 24 hours, 25° C. | X | | |
| 24H, 25C Control | | | |
| 0.81 mM AAPH, 24 hours, 40° C. | | | |
| 24H, 40C Control | | | |
| 0.2% H2O2, 24 hours, 25° C. | | | |
| 0.2% H2O2, 24 hours, 40° C. | | | |
| T0 Control | | | T0 control |

SEC Assay

The protein molecule was evaluated by SEC at various pH conditions at time 0, 2 days and 5 days (see, Table 2.5). Control refers to protein in 20 mM sodium phosphate, pH 6.

As shown in Table 2.5, aggregates increased in a pH dependent manner in all stressed samples, with the highest aggregate levels observed at pH 4 and pH 8. However, a slight increase in aggregation at pH 7 was also observed. In the tables below, UMW indicates high molecular weight content, and LMW indicates low molecular weight content.

TABLE 2.5.

| SEC Results of Forced Degradation Conditions | | | | |
|---|---|---|---|---|
| | | Relative peak area percent | | |
| | Sample name | Total HMW | Main Peak | LMW |
| Control pH 6 | T0 | 1.3 | 97.8 | 0.9 |
| Deamidation in 50 mM Tris, pH 8 | T0 | 1.2 | 97.8 | 1.0 |
| | 2d | 10.0 | 89.0 | 1.0 |
| | 2d control | 1.3 | 97.7 | 1.1 |
| | 5d | 21.1 | 77.7 | 1.2 |
| | 5d control | 1.5 | 97.3 | 1.2 |

TABLE 2.5.-continued

| SEC Results of Forced Degradation Conditions | | | | |
|---|---|---|---|---|
| | | Relative peak area percent | | |
| | Sample name | Total HMW | Main Peak | LMW |
| Clipping in 50 mM Acetate, pH 4 | T0 | 15.1 | 80.3 | 4.6 |
| | 2d | 56.9 | 33.6 | 9.5 |
| | 2d control | 1.3 | 97.6 | 1.1 |
| | 5d | — | — | — |
| | 5d control | 1.5 | 97.3 | 1.2 |
| AAPH Oxidation pH 6 | 24h 25° C. | 1.6 | 97.5 | 1.0 |
| | 24h 25° C. control | 1.3 | 97.8 | 1.0 |
| | 24h 40° C. | 6.7 | 92.1 | 1.2 |
| | 24h 40° C. control | 1.3 | 97.7 | 1.0 |
| H2O2 Oxidation pH 6 | 24h 25° C. | 1.4 | 96.9 | 1.7 |
| | 24h 40° C. | 21.4 | 76.6 | 2.1 |
| Control pH 6 | T0 | 1.2 | 97.87 | 0.95 |

RP-HPLC Assay

RP-HPLC was used to assess forced clipping and oxidation of the ETV:IDS protein molecule in non-reduced samples. As summarized in Table 2.6 below, significant fragmentation in stressed samples was observed, while controls (protein in 20 mM sodium phosphate, pH 6) remained stable. Clipping was also observed in non-reduced stressed samples, which may be related to oxidation. In particular, stress conditions for clipping at pH 4 resulted in substantial reduction of the main peak and a temperature-dependent reduction in the main peak was observed for oxidation stress conditions. Reduced samples confirmed findings of significant fragmentation at low pH (data not shown).

TABLE 2.6

| Forced clipping and oxidation assay results from RP-HPLC samples | | | | |
|---|---|---|---|---|
| | Sample name | Sum Pre-Peaks | Main Peak | Sum Post-Peaks |
| Control | T0 | 2.62 | 92.63 | 4.75 |
| Clipping in 50 mM Acetate, pH 4 | T0 | 3.64 | 92.16 | 4.20 |
| | 2d | 22.00 | 42.74 | 34.43 |
| | 2d control | 3.39 | 92.15 | 4.41 |
| | 5d | 24.66 | 25.59 | 48.75 |
| | 5d control | 3.02 | 92.14 | 4.84 |
| AAPH Oxidation pH 6 | 24 h 25° C. | 2.54 | 93.10 | 4.36 |
| | 24 h 25° C. control | 3.13 | 92.54 | 4.33 |
| | 24 h 40° C. | 2.60 | 90.18 | 7.22 |
| | 24 h 40° C. control | 2.59 | 93.68 | 3.73 |
| H2O2 Oxidation pH 6 | 24 h 25° C. | 2.93 | 91.98 | 5.09 |
| | 24 h 40° C. | 3.74 | 89.71 | 6.54 |

Caliper Assay

Caliper samples were used to assess forced clipping of the ETV:IDS protein molecule. Results on non-reduced samples indicated that the protein molecule was sensitive to clipping under stressed conditions (40° C.), and the protein was fully degraded after 5 days in 50 mM acetate, pH 4 (Table 2.7).

Controls were composed of ETV:IDS protein in 20 mM sodium phosphate, pH 6. Results on reduced samples indicated that fragmentation of molecule was occurring.

TABLE 2.7

| Forced clipping assay results from Caliper samples | |
| --- | --- |
| Sample | % Intact |
| T0 | 96.7 |
| 2d control | 97.3 |
| 2d | 48.7 |
| 5d control | 97.0 |
| 5d | 2.3 |

In summary, the forced degradation stress panel on the protein molecule indicates 1) a strong risk for clipping at low pH; 2) significant pH-dependent aggregation; and 3) a likely disposition towards oxidation.

Example 3

Evaluation of Storage Conditions

A pH/buffer screen was carried out on three buffer systems in pH range 5.5-6.5. The concentration of a representative ETV:IDS protein (ETV:IDS 35.23.2, Example 1) was tested at 10 mg/mL. A matrix of the buffers that were tested and the specific formulations are shown in Tables 3.1 and 3.2, respectively. The relevant storage conditions are shown Table 3.3. Samples were evaluated as follows: 1) Clarity/Opalescence; 2) pH; 3) Size-exclusion (SE)-HPLC; 4) CE-SDS (Caliper); and 5) RP-HPLC.

TABLE 3.1

| Matrix of Buffers Tested | | | | | |
| --- | --- | --- | --- | --- | --- |
| 20 mM Na-Phosphate | | 20 mM Histidine-HCl | | 20 mM Na-Acetate | |
| pH | NaCl (mM) | pH | NaCl (mM) | pH | NaCl (mM) |
| | | 5.5 | 50 | 5.5 | 50 |
| 6.0 | 137/50 | 6.0 | 50 | 6.0 | 50 |
| 6.5 | 50 | 6.5 | 50 | | |

TABLE 3.2

| Specific Formulations | |
| --- | --- |
| Formulation Number | Sample Description |
| F1 | 20 mM Na-Phosphate pH 6.0, 137 mM NaCl |
| F2 | 20 mM Na-Phosphate pH 6.0, 50 mM NaCl |
| F3 | 20 mM Na-Phosphate pH 6.5, 50 mM NaCl |
| F4 | 20 mM Histidine-HCl pH 5.5, 50 mM NaCl |
| F5 | 20 mM Histidine-HCl pH 6.0, 50 mM NaCl |
| F6 | 20 mM Histidine-HCl pH 6.5, 50 mM NaCl |
| F7 | 20 mM Na-Acetate pH 5.5, 50 mM NaCl |
| F8 | 20 mM Na-Acetate pH 6.0, 50 mM NaCl |

TABLE 3.3

| Storage Conditions | | |
| --- | --- | --- |
| | Timepoint (weeks) | |
| Temperature | 0 | 2 |
| +2-8° C. | X | X |
| +25° C./60% RH | N/A | X |
| +40° C./75% RH | N/A | X |

X = Samples taken for analysis pH Assessment

The impact of storage conditions on the pH of the various formulations was assessed. As shown in Tables 3.4 and 3.5, no significant pH deviations were observed under the conditions tested.

TABLE 3.4

| Protein Content and Osmolarity | |
| --- | --- |
| Formulation | T0 |
| Protein content (mg/ml) | |
| F1 | 10.8 |
| F2 | 10.3 |
| F3 | 10.2 |
| F4 | 10.5 |
| F5 | 10.1 |
| F6 | 10.0 |
| F7 | 9.6 |
| F8 | 9.9 |
| Osmolarity (mOsm/kg) | |
| F1 | 307 |
| F2 | 138 |
| F3 | 141 |
| F4 | 132 |
| F5 | 128 |
| F6 | 123 |
| F7 | 135 |
| F8 | 136 |

TABLE 3.5

| Impact of Storage Conditions on pH | | | | |
| --- | --- | --- | --- | --- |
| | | pH | | |
| Formulation | T0 | 2-8° C. | 25° C. | 40° C. |
| F1 | 6.0 | 6.0 | 6.0 | 6.1 |
| F2 | 6.0 | 6.1 | 6.1 | 6.1 |
| F3 | 6.5 | 6.5 | 6.5 | 6.6 |
| F4 | 5.5 | 5.5 | 5.5 | 5.6 |
| F5 | 6.0 | 5.9 | 6.0 | 6.0 |
| F6 | 6.5 | 6.4 | 6.5 | 6.5 |
| F7 | 5.5 | 5.5 | 5.6 | 5.6 |
| F8 | 6.0 | 6.0 | 6.1 | 6.1 |

Turbidity Analysis

The impact of the various storage conditions on turbidity was evaluated for each of the formulations. Turbidity was low and stable for most of the systems that were tested; however, there was an increase in turbidity in the buffer systems at pH 5.5 (Table 3.6) for the 40° C. storage condition.

TABLE 3.6

| Buffer | pH | NaCl (mM) | | Formulation | T0 | 2-8° C. | 25° C. | 40° C. |
|---|---|---|---|---|---|---|---|---|
| | | | Impact of Storage Conditions on Turbidity | | | | | |
| 20 mM Na-Phosphate | 6 | 137 | Turbidity (NTU) | F1 | 5 | 5 | 5 | 5 |
| 20 mM Na-Phosphate | 6 | 50 | | F2 | 5 | 4 | 5 | 4 |
| 20 mM Na-Phosphate | 6.5 | 50 | | F3 | 4 | 4 | 4 | 5 |
| 20 mM His-HCl | 5.5 | 50 | | F4 | 5 | 5 | 5 | 7 |
| 20 mM His-HCl | 6 | 50 | | F5 | 5 | 5 | 4 | 5 |
| 20 mM His-HCl | 6.5 | 50 | | F6 | 4 | 4 | 4 | 4 |
| 20 mM Na-Acetate | 5.5 | 50 | | F7 | 5 | 5 | 5 | 8 |
| 20 mM Na-Acetate | 6 | 50 | | F8 | 5 | 5 | 5 | 5 |

SE-HPLC Analysis

SE-HPLC was used to assess forced clipping of the ETV:IDS protein molecule (Table 3.7). The ETV:IDS protein molecule itself was used as a baseline for comparisons with formulations F1-F8 at 2-8° C.

No effect from elevated NaCl concentration was observed as illustrated by comparing F1 and F2 buffer systems. Higher LMW (clipping) was observed at pH 6 relative to pH 6.5 in phosphate buffer systems at both 25° C. and 40° C. (e.g. F2 and F3 buffer systems). Additionally, a pH-dependent clip-ping effect was observed in the His-HCl buffer system across F4, F5, and F6 (less clipping observed at higher pH values tested). Similarly, high LMW levels were observed at lower pH in the Na-Acetate buffer system comparing F7 relative to F8. A slight pH dependence on HMW species is observed at 40 C over 2 weeks, but is not observed over 2 weeks at 2-8° C. and 25° C. Overall, a higher pH (6.5) provides more favorable conditions for the protein molecule and F6 and F3 buffer systems appear to yield the most favorable results.

TABLE 3.7

| | | | | | | | |
|---|---|---|---|---|---|---|---|
| | SE-HPLC Analysis | | | | | | |
| | Relative peak area percent | | | | Relative peak area percent | | |
| Sample name | Total HMW | Main Peak | LMW Skim | Sample name | Total HMW | Main Peak | LMW Skim |
| | T0 | | | | 2 weeks @ 2-8° C. | | |
| | | | | ETV: IDS (control) | 1.66 | 97.37 | 0.97 |
| F1 | 1.50 | 97.54 | 0.97 | F1 | 1.63 | 97.37 | 1.01 |
| F2 | 1.46 | 97.59 | 0.95 | F2 | 1.58 | 97.41 | 1.01 |
| F3 | 1.50 | 97.54 | 0.96 | F3 | 1.59 | 97.46 | 0.96 |
| F4 | 1.49 | 97.48 | 1.03 | F4 | 1.58 | 97.35 | 1.08 |
| F5 | 1.50 | 97.52 | 0.98 | F5 | 1.59 | 97.46 | 0.95 |
| F6 | 1.50 | 97.53 | 0.97 | F6 | 1.58 | 97.48 | 0.94 |
| F7 | 1.50 | 97.49 | 1.00 | F7 | 1.63 | 97.20 | 1.17 |
| F8 | 1.53 | 97.51 | 0.96 | F8 | 1.66 | 97.37 | 0.97 |
| | 2 weeks @ 25° C. | | | | 2 weeks @ 40° C. | | |
| F1 | 1.69 | 96.75 | 1.56 | F1 | 2.27 | 94.23 | 3.52 |
| F2 | 1.67 | 96.75 | 1.57 | F2 | 2.32 | 94.07 | 3.61 |
| F3 | 1.66 | 97.31 | 1.03 | F3 | 2.95 | 95.81 | 1.23 |
| F4 | 1.63 | 94.83 | 3.53 | F4 | 2.62 | 72.77 | 22.79 |
| F5 | 1.61 | 97.01 | 1.38 | F5 | 2.44 | 92.29 | 5.26 |
| F6 | 1.62 | 97.36 | 1.02 | F6 | 2.53 | 96.11 | 1.36 |
| F7 | 1.72 | 95.13 | 3.15 | F7 | 2.74 | 86.49 | 10.77 |
| F8 | 1.73 | 96.99 | 1.28 | F8 | 2.35 | 95.26 | 2.39 |

CE-SDS (Caliper) Analysis

CE-SDS (Caliper) was used to assess stability of the ETV:IDS protein molecule in reduced and non-reduced samples.

For non-reduced samples, the protein molecule appears more stable at higher pH, with F3 and F6 buffer systems yielding the most favorable results (Table 3.8). For reduced samples, a pH-dependent degradation of species IDS-Fc fusion polypeptide (indicated by A1%) was observed (Table 3.8).

TABLE 3.8

| | CE-SDS (Caliper) Analysis | | | | | | | |
|---|---|---|---|---|---|---|---|---|
| | Non-reduced | Reduced | | | Non-reduced | Reduced | | |
| | Intact % | A1 % | A2 % | Sum A1 + A2 | Intact % | A1 % | A2 % | Sum A1 + A2 |
| | T0 | | | | 2 weeks @ 2-8° C. | | | |
| F1 | 98.00 | 44.98 | 54.64 | 99.62 | 97.25 | 65.68 | 33.86 | 99.54 |
| F2 | 98.06 | 45.25 | 54.37 | 99.62 | 97.20 | 65.26 | 34.22 | 99.48 |
| F3 | 97.95 | 44.09 | 55.53 | 99.62 | 97.04 | 66.18 | 33.34 | 99.52 |
| F4 | 97.97 | 44.64 | 54.78 | 99.42 | 97.07 | 66.08 | 33.43 | 99.51 |
| F5 | 98.18 | 43.51 | 56.03 | 99.53 | 97.26 | 67.45 | 32.07 | 99.52 |
| F6 | 97.95 | 47.38 | 52.22 | 99.60 | 97.19 | 67.34 | 32.16 | 99.50 |
| F7 | 98.14 | 42.60 | 56.82 | 99.43 | 97.31 | 67.58 | 31.96 | 99.54 |
| F8 | 98.20 | 43.79 | 55.80 | 99.60 | 96.92 | 67.03 | 32.49 | 99.53 |
| | 2 weeks @ 25° C. | | | | 2 weeks @ 40° C. | | | |
| F1 | 99.26 | 66.42 | 32.97 | 99.38 | 91.32 | 53.37 | 45.68 | 99.05 |
| F2 | 96.12 | 65.36 | 34.12 | 99.47 | 91.03 | 52.31 | 46.40 | 98.71 |
| F3 | 96.45 | 64.58 | 34.86 | 99.44 | 93.81 | 55.61 | 43.36 | 98.97 |
| F4 | 94.27 | 55.56 | 43.85 | 99.40 | 51.19 | 27.49 | 61.54 | 89.03 |
| F5 | 95.57 | 58.69 | 40.73 | 99.41 | 88.64 | 49.50 | 49.60 | 99.09 |
| F6 | 95.89 | 58.74 | 40.59 | 99.33 | 93.67 | 54.48 | 44.81 | 99.29 |
| F7 | 94.76 | 56.56 | 42.81 | 99.38 | 77.74 | 41.53 | 54.51 | 96.04 |
| F8 | 95.26 | 57.54 | 41.82 | 99.36 | 92.60 | 51.83 | 47.20 | 99.04 |

RP-HPLC Assay

RP-HPLC was used to assess the ETV:IDS protein molecule in non-reduced and reduced samples (Table 3.9). Species A1 refers to the IDS-Fc fusion polypeptide and A2 refers to the modified Fc polypeptide.

As shown in Table 3.9 below, the protein is stable in all buffer systems at 2-8° C. A pH-dependent decrease in the main peak and an increase in pre-peaks indicates that clipping is occurring. A decrease in IDS-Fc fusion polypeptide (A1) is observed at lower pH. F3 and F6 buffer systems appear to show the best environment for maintaining molecule stability.

TABLE 3.9

| | | | | RP-HPLC Analysis | | | | | |
|---|---|---|---|---|---|---|---|---|---|
| | | | | Non-reduced | | | Reduced | | |
| Label | Buffer | pH | NaCl mM | Total post-peaks | Total pre-peaks | Main peak | A1 % | A2 % | Sum A1 + A2 |
| | | | | T0 | | | | | |
| F1 | 20 mM Na-Phosphate | 6 | 137 | 5.6 | 2.3 | 92.2 | 70.3 | 22.1 | 92.5 |
| F2 | 20 mM Na-Phosphate | 6 | 50 | 5.5 | 2.6 | 91.9 | 70.4 | 22.2 | 92.7 |
| F3 | 20 mM Na-Phosphate | 6.5 | 50 | 5.4 | 2.5 | 92.1 | 70.5 | 22.2 | 92.7 |
| F4 | 20 mM His-HCL | 5.5 | 50 | 5.6 | 2.6 | 91.9 | 70.5 | 22.2 | 92.7 |
| F5 | 20 mM His-HCL | 6 | 50 | 5.9 | 3.1 | 91.0 | 70.1 | 22.3 | 92.4 |
| F6 | 20 mM His-HCL | 6.5 | 50 | 5.9 | 3.3 | 90.8 | 70.4 | 22.3 | 92.7 |
| F7 | 20 mM Na-Acetate | 5.5 | 50 | 5.8 | 2.7 | 91.5 | 70.4 | 22.2 | 92.6 |
| F8 | 20 mM Na-Acetate | 6 | 50 | 6.0 | 2.8 | 91.1 | 70.1 | 22.2 | 92.3 |
| Label | Buffer | pH | NaCl mM | 2 weeks @ 2-8° C. | | | | | |
| F1 | 20 mM Na-Phosphate | 6 | 137 | 3.8 | 5.0 | 91.2 | 71.5 | 21.6 | 93.1 |
| F2 | 20 mM Na-Phosphate | 6 | 50 | 3.7 | 4.6 | 91.8 | 71.7 | 21.5 | 93.2 |
| F3 | 20 mM Na- Phosphate | 6.5 | 50 | 3.7 | 4.3 | 91.7 | 71.6 | 21.7 | 93.3 |
| F4 | 20 mM His-HCL | 5.5 | 50 | 3.8 | 4.1 | 92.2 | 71.6 | 21.7 | 93.2 |
| F5 | 20 mM His-HCL | 6 | 50 | 3.8 | 4.1 | 92.0 | 71.7 | 21.5 | 93.2 |

TABLE 3.9-continued

| | | | | Non-reduced | | | Reduced | | |
|---|---|---|---|---|---|---|---|---|---|
| | | | | Total post-peaks | Total pre-peaks | Main peak | A1 % | A2 % | Sum A1 + A2 |
| F6 | 20 mM His-HCL | 6.5 | 50 | 3.8 | 4.1 | 92.1 | 71.6 | 21.6 | 93.1 |
| F7 | 20 mM Na-Acetate | 5.5 | 50 | 4.1 | 5.3 | 90.5 | 71.2 | 21.4 | 92.7 |
| F8 | 20 mM Na-Acetate | 6 | 50 | 4.0 | 3.8 | 92.3 | 71.6 | 21.5 | 93.1 |

| Label | Buffer | pH | NaCl mM | 2 weeks @ 25° C. | | | | | |
|---|---|---|---|---|---|---|---|---|---|
| F1 | 20 mM Na-Phosphate | 6 | 137 | 4.6 | 6.1 | 89.3 | 71.0 | 21.6 | 92.6 |
| F2 | 20 mM Na-Phosphate | 6 | 50 | 4.3 | 5.9 | 89.7 | 71.2 | 21.5 | 92.7 |
| F3 | 20 mM Na-Phosphate | 6.5 | 50 | 4.0 | 5.2 | 90.8 | 71.5 | 21.6 | 93.1 |
| F4 | 20 mM His-HCL | 5.5 | 50 | 6.5 | 7.0 | 86.5 | 70.2 | 21.7 | 91.9 |
| F5 | 20 mM His-HCL | 6 | 50 | 4.1 | 5.5 | 90.4 | 71.5 | 21.7 | 93.2 |
| F6 | 20 mM His-HCL | 6.5 | 50 | 3.8 | 5.4 | 90.8 | 71.4 | 21.5 | 93.0 |
| F7 | 20 mM Na-Acetate | 5.5 | 50 | 5.9 | 6.7 | 87.3 | 70.5 | 21.6 | 92.1 |
| F8 | 20 mM Na-Acetate | 6 | 50 | 4.3 | 5.7 | 90.0 | 71.2 | 21.5 | 92.7 |

| Label | Buffer | pH | NaCl mM | 2 weeks @ 40° C. | | | | | |
|---|---|---|---|---|---|---|---|---|---|
| F1 | 20 mM Na-Phosphate | 6 | 137 | 6.7 | 10.0 | 83.3 | 69.5 | 21.3 | 90.8 |
| F2 | 20 mM Na-Phosphate | 6 | 50 | 7.0 | 8.3 | 84.7 | 62.9 | 21.4 | 84.3 |
| F3 | 20 mM Na-Phosphate | 6.5 | 50 | 4.6 | 6.9 | 88.4 | 70.6 | 21.2 | 91.8 |
| F4 | 20 mM His-HCL | 5.5 | 50 | 26.6 | 27.4 | 46.1 | 60.4 | 21.8 | 82.2 |
| F5 | 20 mM His-HCL | 6 | 50 | 8.7 | 9.2 | 82.0 | 68.4 | 21.5 | 89.9 |
| F6 | 20 mM His-HCL | 6.5 | 50 | 4.6 | 6.6 | 88.8 | 70.6 | 21.5 | 92.0 |
| F7 | 20 mM Na-Acetate | 5.5 | 50 | 14.1 | 14.9 | 71.0 | 65.7 | 21.4 | 87.1 |
| F8 | 20 mM Na-Acetate | 6 | 50 | 5.8 | 7.4 | 86.8 | 67.0 | 21.7 | 88.7 |

Example 4

Surfactant Screen

A surfactant screen was carried out using a buffer system having 20 mM sodium phosphate, 50 mM NaCl, and pH 6.5. The concentration of a representative ETV:IDS protein (ETV:IDS 35.23.2, Example 1) was tested at 30 mg/mL. As shown in Table 4.1, the surfactants tested were Polysorbate 20 (PS-20) at and Polysorbate 80 (PS-80), in varying concentrations.

TABLE 4.1

| Specific Formulations | |
|---|---|
| Formulation Number | Sample Description |
| F1 | PS-20 at 0.5 mg/mL |
| F2 | PS-20 at 0.2 mg/mL |
| F3 | PS-80 at 0.5 mg/mL |
| F4 | PS-80 at 0.2 mg/mL |

These formulations were subjected to shake stress (2-8° C. and ambient temperature, 5 days, 200 RPM horizontal shaking) and freeze/thaw (5× consecutive cycles fluctuating between 25° C. and <65° C.) (Tables 4.2 and 4.3, respectively). Samples were evaluated as follows: 1) Clarity/Opalescence; 2) visible particles; 3) subvisible particles; 4) SE-HPLC; 5) CE-SDS (Caliper); and 6) surfactant content.

TABLE 4.2

| Shake Stress | | |
|---|---|---|
| | Timepoint | |
| Temperature | 0 | After agitation stress |
| +2-8° C. | X | X |
| ambient | | X |

X = samples taken for analysis

TABLE 4.3

| Freeze Thaw | | |
|---|---|---|
| | Timepoint | |
| Temperature | 0 | After F/T stress |
| 5x cycles (+25° C./≤−65° C.) | X | X |

X = samples taken for analysis

Visible Particles and Turbidity

Formulations F1-F4 were evaluated for particle formation (visible and subvisible) and turbidity after stressing. As shown in Table 4.4, no visible particle formation was observed in the stress panel. In addition, as illustrated in Table 4.5, no significant differences were observed in subvisible particles in either shake tests or in freeze-thaw tests. Finally, turbidity remained unchanged in the samples after stressing (Table 4.6).

TABLE 4.4

| Visible Particle Formation | | | | |
| --- | --- | --- | --- | --- |
| | Visible particles | | | |
| | T0 | shake 2-8° C. | shake RT | 5x F/T |
| F1 | 2 | 0 | 0 | 0 |
| F2 | 1 | 0 | 0 | 0 |
| F3 | 2 | 0 | 0 | 0 |
| F4 | 0 | 0 | 0 | 0 |

TABLE 4.5

| Sub-Visible Particle Formation | | | | | | | | | | |
| --- | --- | --- | --- | --- | --- | --- | --- | --- | --- | --- |
| Cumulative Counts/ml | ≥2 μm | ≥5 μm | ≥10 μm | ≥25 μm | | ≥2 μm | ≥5 μm | ≥10 μm | ≥25 μm | |
| | T0 | | | | | 5 d shake 2-8° C. | | | | |
| Sub-visible Particles | F1 291 | 53 | 8 | 2 | F1 | 38 | 13 | 2 | 0 | |
| | F2 193 | 27 | 14 | 1 | F2 | 27 | 10 | 1 | 0 | |
| | F3 699 | 113 | 6 | 1 | F3 | 69 | 13 | 2 | 0 | |
| | F4 241 | 48 | 9 | 0 | F4 | 28 | 8 | 1 | 0 | |
| | 5 d shake RT | | | | | 5 × F/T | | | | |
| Sub-visible Particles | F1 52 | 26 | 8 | 0 | F1 | 24 | 13 | 3 | 0 | |
| | F2 17 | 8 | 0 | 0 | F2 | 34 | 3 | 0 | 0 | |
| | F3 33 | 13 | 3 | 1 | F3 | 19 | 14 | 3 | 0 | |
| | F4 14 | 5 | 4 | 1 | F4 | 53 | 29 | 3 | 0 | |

TABLE 4.6

| Turbidity | | | | |
| --- | --- | --- | --- | --- |
| | Turbidity | | | |
| | T0 | shake 2-8° C. | shake RT | 5x F/T |
| F1 | 12 | 10 | 10 | 10 |
| F2 | 10 | 10 | 10 | 10 |
| F3 | 10 | 10 | 10 | 10 |
| F4 | 10 | 10 | 10 | 10 |

SE-HPLC Analysis

SE-HPLC was used to assess stability of the ETV:IDS protein molecule after agitation and freeze-thaw stress.

All formulations indicated good stability in the shake stress by SEC, with slight better stabilizing properties observed in PS-20 over PS-80 (Table 4.7).

TABLE 4.7

| | SE-HPLC Analysis | | | | | |
| --- | --- | --- | --- | --- | --- | --- |
| | Relative peak area percent | | | Relative peak area percent | | |
| Buffer Sample | Total HMW | Main Peak | LMW Skim | Total HMW | Main Peak | LMW Skim |
| | T0 | | | 5 d shake 2-8° C. | | |
| 0.5 mg/mL PS20 (F1) | 1.8 | 97.3 | 1.0 | 1.8 | 97.3 | 0.9 |
| 0.2 mg/mL PS20 (F2) | 1.8 | 97.3 | 0.9 | 1.8 | 97.3 | 0.9 |
| 0.5 mg/mL PS80 (F3) | 1.8 | 97.3 | 0.9 | 1.8 | 97.3 | 0.9 |
| 0.2 mg/mL PS80 (F4) | 1.8 | 97.2 | 0.9 | 1.9 | 97.2 | 0.9 |
| | 5 d shake RT | | | 5 × FT | | |
| 0.5 mg/mL PS20 (F1) | 1.8 | 97.2 | 1.0 | 2.1 | 97.0 | 1.0 |
| 0.2 mg/mL PS20 (F2) | 1.8 | 97.2 | 1.0 | 2.2 | 96.9 | 1.0 |
| 0.5 mg/mL PS80 (F3) | 1.9 | 97.2 | 1.0 | 2.1 | 97.0 | 1.0 |
| 0.2 mg/mL PS80 (F4) | 1.9 | 97.1 | 1.0 | 2.2 | 96.9 | 1.0 |

CE-SDS (Caliper) Analysis

CE-SDS (Caliper) was used to assess stability of the ETV:IDS protein molecule in reduced and non-reduced samples.

As shown in Table 4.8, the protein molecule appears to be stable in all stress tests. Stable values were observed for both intact (non-reduced) samples as well as sum of fragments (A1=IDS-Fc fusion polypeptide, A2=modified Fc polypeptide).

TABLE 4.8

| | CE-SDS (Caliper) Analysis | | | | | | | | |
| --- | --- | --- | --- | --- | --- | --- | --- | --- | --- |
| | | Reduced | | | | | Reduced | | |
| | Non-reduced Intact % | A1 % | A2 % | Sum A1 + A2 | | Non-reduced Intact % | A1 % | A2 % | Sum A1 + A2 |
| | T0 | | | | | 5 d shake 2-8° C. | | | |
| F1 | 98.1 | 46.4 | 52.9 | 99.3 | F1 | 97.8 | 46.9 | 52.4 | 99.3 |
| F2 | 98.1 | 52.1 | 47.3 | 99.4 | F2 | 98.0 | 50.3 | 49.1 | 99.4 |
| F3 | 98.0 | 49.1 | 50.3 | 99.3 | F3 | 98.3 | 47.0 | 52.3 | 99.3 |
| F4 | 97.8 | 51.0 | 48.6 | 99.5 | F4 | 98.2 | 50.2 | 49.2 | 99.4 |
| | 5 d shake RT | | | | | 5 × FT | | | |
| F1 | 98.0 | 49.2 | 50.2 | 99.3 | F1 | 98.2 | 47.8 | 51.5 | 99.3 |
| F2 | 98.0 | 46.3 | 53.0 | 99.3 | F2 | 98.1 | 48.0 | 51.4 | 99.3 |
| F3 | 98.2 | 48.4 | 50.5 | 98.9 | F3 | 98.1 | 48.7 | 50.8 | 99.4 |
| F4 | 98.0 | 50.7 | 48.7 | 99.4 | F4 | 97.9 | 50.0 | 49.3 | 99.3 |

In certain embodiments, the surfactant amount can be increased up to, e.g., 1 mg/mL (e.g., about 0.6 mg/mL, 0.7 mg/mL, 0.8 mg/mL, 0.9 mg/mL, 1.0 mg/mL) without affecting the stability of the protein in the formulation.

Example 5

Formulation Development and Evaluation of Lyophilized Formulation

For further formulation assessment, the buffer systems listed in Table 5.1 were tested. A lyophilized format was also tested. The concentration of a representative ETV:IDS protein (ETV: ID S 35.23.2, Example 1) was tested at 20 mg/mL. These formulations were subjected to shake stress (room temperature, 5 days, 200 RPM horizontal shaking) and freeze/thaw stress (5x consecutive cycles fluctuating between 25° C. and ≤65° C.). Samples were evaluated as follows: 1) SE-HPLC; 2) CE-SDS (Caliper); and 3) surfactant content.

TABLE 5.1

Formulations tested

| Label | Buffer | pH | NaCl (mM) | PS20 (mg/mL) | Methionine (mM) | Sucrose (mM) | Format |
|---|---|---|---|---|---|---|---|
| F1 | 20 mM Na-Phosphate | 6.5 | 50 | 0.4 | 10 | 175 | Liquid |
| F2 | 20 mM Na-Phosphate | 6.5 | 50 | 0.4 | 0 | 175 | Liquid |
| F3 | 20 mM Na-Phosphate | 6.5 | 150 | 0.4 | 10 | 175 | Liquid |
| F4 | 20 mM His-HCl | 6.5 | 50 | 0.4 | 0 | 175 | Lyo |

SE-HPLC Analysis

SE-HPLC was used to assess stability of the ETV:IDS protein molecule under stress conditions.

Significant BMW and LMW content was observed in liquid formulations F1-F3 at elevated temperature (40° C.); however, the lyophilized formulation F4 remained stable at all storage temperatures (Table 5.2). All formulations performed similarly at lower temperature (⇐25° C.) for up to 1 month.

TABLE 5.2

SE-HPLC Analysis

| Sample Description | Size Exclusion Chromatography UKSL-4485 | | |
|---|---|---|---|
| | HMW (% Area) | Main Peak (% Area) | LMW (% Area) |
| F1, T0, 5° C. | 1.6 | 97.5 | 0.9 |
| F2, T0, 5° C. | 1.6 | 97.5 | 0.9 |
| F3, T0, 5° C. | 1.6 | 97.5 | 0.9 |
| F4, T0, 5° C. | 1.6 | 97.5 | 0.9 |
| F4, T0, lyo recon 5° C. | 1.6 | 97.5 | 0.9 |
| F1, 5d, shake 25° C. | 1.7 | 97.4 | 0.9 |
| F2, 5d, shake 25° C. | 1.7 | 97.4 | 0.9 |
| F3, 5d, shake 25° C. | 1.6 | 97.4 | 1.0 |
| F4, 5d, shake 25° C. | 1.7 | 97.4 | 0.9 |
| F1, 5x, ≤−65° C. 12 h & 25° C. 12 h | 1.7 | 97.4 | 0.9 |
| F2, 5x, ≤−65° C. 12 h & 25° C. 12 h | 1.6 | 97.5 | 0.9 |
| F3, 5x, ≤−65° C. 12 h & 25° C. 12 h | 1.7 | 97.4 | 0.9 |
| F4, 5x, ≤−65° C. 12 h & 25° C. 12 h | 1.7 | 97.4 | 0.9 |
| F1, 1 m, 5° C. | 1.7 | 97.4 | 0.9 |
| F2, 1 m, 5° C. | 1.7 | 97.4 | 0.9 |
| F3, 1 m, 5° C. | 1.7 | 97.4 | 0.9 |
| F4, 1 m, 5° C. | 1.6 | 97.5 | 0.9 |
| Fl, 1 m, 25° C. | 1.7 | 97.3 | 1.1 |
| F2, 1 m, 25° C. | 1.7 | 97.2 | 1.1 |
| F3, 1 m, 25° C. | 1.7 | 97.2 | 1.1 |

TABLE 5.2-continued

SE-HPLC Analysis

| Sample Description | Size Exclusion Chromatography UKSL-4485 | | |
|---|---|---|---|
| | HMW (% Area) | Main Peak (% Area) | LMW (% Area) |
| F4, 1 m, 25° C. | 1.7 | 97.4 | 0.9 |
| F1, 1 m, 40° C. | 4.4 | 94.0 | 1.6 |
| F2, 1 m, 40° C. | 5.1 | 93.2 | 1.7 |
| F3, 1 m, 40° C. | 4.8 | 93.6 | 1.6 |
| F4, 1 m, 40° C. | 1.6 | 97.5 | 0.9 |

RP-HPLC Assay

RP-HPLC was used to assess the ETV:IDS protein molecule in non-reduced and reduced samples. A1 refers to the IDS-Fc fusion polypeptide, and A2 refers to the modified Fc polypeptide.

As shown in Table 5.3 below, at increasing temperatures, a reduction in the main peak was observed as well as an increase in both pre- and post-peaks.

TABLE 5.3

RP-HPLC Analysis

| Sample Description | Non-reduced | | | Reduced Sum |
|---|---|---|---|---|
| | Pre Peak (% Area) | Main Peak (% Area) | Post Peak (% Area) | A1 + A2 (% Area) |
| F1, T0, 5° C. | 3.5 | 92.9 | 3.6 | 94.4 |
| F2, T0, 5° C. | 3.9 | 92.5 | 3.6 | 94.0 |
| F3, T0, 5° C. | 3.7 | 92.9 | 3.4 | 94.2 |
| F4, T0, 5° C. | 3.7 | 92.7 | 3.5 | 94.1 |
| F4, T0, lyo recon 5° C. | 3.8 | 93.0 | 3.2 | 94.1 |
| F1, 5d, shake 25° C. | 3.9 | 92.7 | 3.3 | 94.1 |
| F2, 5d, shake 25° C. | 4.1 | 92.1 | 3.6 | 94.1 |
| F3, 5d, shake 25° C. | 3.9 | 93.1 | 3.0 | 93.9 |
| F4, 5d, shake 25° C. | 3.4 | 93.4 | 3.1 | 93.4 |
| F1, 5x, ≤−65° C. 12 h & 25° C. 12 h | 3.7 | 92.9 | 3.4 | 94.4 |
| F2, 5x, ≤−65° C. 12 h & 25° C. 12 h | 3.9 | 92.5 | 3.4 | 93.9 |
| F3, 5x, ≤−65° C. 12 h & 25° C. 12 h | 3.8 | 92.6 | 3.6 | 94.0 |
| F4, 5x, ≤−65° C. 12 h & 25° C. 12 h | 3.8 | 93.5 | 2.7 | 94.2 |
| F1, 1 m, 5° C. | 2.0 | 94.2 | 3.5 | 94.6 |
| F2, 1 m, 5° C. | 2.5 | 93.7 | 3.8 | 94.6 |
| F3, 1 m, 5° C. | 2.1 | 94.4 | 3.5 | 93.3 |
| F4, 1 m, 5° C. | | | | |
| F1, 1 m, 25° C. | 2.2 | 93.8 | 3.7 | 94.7 |
| F2, 1 m, 25° C. | 3.3 | 92.6 | 4.1 | 95.2 |
| F3, 1 m, 25° C. | 2.7 | 93.2 | 4.1 | 93.5 |
| F4, 1 m, 25° C. | | | | |

TABLE 5.3-continued

| | RP-HPLC Analysis | | | |
|---|---|---|---|---|
| | RP-HPLC | | | Reduced Sum |
| | Non-reduced | | | |
| Sample Description | Pre Peak (% Area) | Main Peak (% Area) | Post Peak (% Area) | A1 + A2 (% Area) |
| F1, 1 m, 40° C. | 4.4 | 89.6 | 5.7 | 93.3 |
| F2, 1 m, 40° C. | 6.0 | 88.2 | 5.8 | 95.1 |
| F3, 1 m, 40° C. | 4.9 | 89.4 | 5.7 | 93.4 |
| F4, 1 m, 40° C. | | | | |
| F4 T0 was tested as a reference (kept frozen for storage stability) | 2.1 | 94.0 | 3.7 | 94.9 |

CE-SDS (Caliper) Analysis

CE-SDS (Caliper) was used to assess stability of the ETV:IDS protein molecule in reduced and non-reduced samples.

As shown in Table 5.4, a significant decrease of intact molecule was observed at storage conditions of 40° C. A1 corresponds to IDS-Fc fusion polypeptide, and A2 corresponds to modified Fc polypeptide.

TABLE 5.4

| | CE-SDS (Caliper) Analysis | | | |
|---|---|---|---|---|
| | Caliper non-reduced | Caliper reduced | | |
| Sample Description | Intact Protein Molecule (% Area) | Sum A1 + A2 (% Area) | A1 (% Area) | A2 (% Area) |
| F1, T0, 5° C. | 98.8 | 99.6 | 40.0 | 59.6 |
| F2, T0, 5° C. | 98.4 | 99.6 | 40.5 | 59.1 |
| F3, T0, 5° C. | 98.5 | 99.6 | 39.0 | 60.6 |
| F4, T0, 5° C. | 98.6 | 99.6 | 40.6 | 59.0 |
| F4, T0, lyo recon 5° C. | 98.4 | 99.6 | 39.5 | 60.1 |
| F1, 5 d, shake 25° C. | 98.3 | 99.6 | 39.0 | 60.6 |
| F2, 5 d, shake 25° C. | 98.3 | 99.6 | 38.0 | 61.6 |
| F3, 5 d, shake 25° C. | 98.3 | 99.3 | 37.5 | 61.8 |
| F4, 5 d, shake 25° C. | 98.2 | 99.6 | 41.3 | 58.3 |
| F1, 5x, ≤−65° C. 12 h & 25° C. 12 h | 95.4 | 99.6 | 39.3 | 60.3 |
| F2, 5x, ≤−65° C. 12 h & 25° C. 12 h | 98.4 | 99.6 | 39.9 | 59.8 |
| F3, 5x, ≤−65° C. 12 h & 25° C. 12 h | 98.2 | 99.6 | 40.3 | 59.3 |
| F4, 5x, ≤−65° C. 12 h & 25° C. 12 h | 98.2 | 99.6 | 41.8 | 57.8 |
| F1, 1 m, 5° C. | 96.1 | 99.3 | 45.1 | 54.2 |
| F2, 1 m, 5° C. | 96.6 | 99.3 | 45.2 | 54.2 |
| F3, 1 m, 5° C. | 96.2 | 99.2 | 46.5 | 52.8 |
| F4, 1 m, 5° C. | n.a. | n.a. | n.a. | n.a. |
| F1, 1 m, 25° C. | 95.4 | 99.2 | 45.8 | 53.4 |
| F2, 1 m, 25° C. | 95.6 | 99.2 | 46.5 | 52.7 |
| F3, 1 m, 25° C. | 97.4 | 99.2 | 47.2 | 52.0 |
| F4, 1 m, 25° C. | n.a. | n.a. | n.a. | n.a. |
| F1, 1 m, 40° C. | 90.3 | 98.8 | 48.4 | 50.4 |
| F2, 1 m, 40° C. | 90.0 | 98.9 | 48.9 | 50.0 |
| F3, 1 m, 40° C. | 90.7 | 98.8 | 49.7 | 49.1 |
| F4, 1 m, 40° C. | n.a. | n.a. | n.a. | n.a. |
| F4 T0 was tested as a reference (kept frozen for storage stability) | 97.5 | 99.3 | 45.5 | 53.8 |

TABLE 5.4-continued — *(CE-SDS (Caliper) Analysis — combined above)*

Example 6

Stability Analysis

For further formulation stability assessment, a formulation containing the following was tested for stability at 5° C. and 40° C.: ETV:IDS protein concentration=30 mg/mL; 20 mM sodium phosphate; 50 mM NaCl; 175 mM sucrose; 0.6 mg/mL polysorbate-20 (PS-20); 10 mM L-methionine; and pH 6.5. The ETV:IDS protein tested in this assessment is represented by ETV:IDS 35.23.2 and described in Example 1. Samples were taken at T=0, T=2 weeks, and T=4 weeks. Samples were evaluated as follows: 1) visible particles; 2) sub-visible particles (e.g. by light obscuration); 3) SE-HPLC; and 4) Polysorbate content (FMA, ELSD).

As shown in Table 6.1, no visible particle formation was observed at the various temperature/time points. The sub-visible particles were observed at a constant low level over the conditions. For the size exclusion chromatography, the sample was stable at 5° C. and an increase in BMW content and slight increase in LMW content was observed at 40° C. The polysorbate content was also found to be stable over all conditions.

TABLE 6.1

| | | | | | | | | | | Surfactant Content |
|---|---|---|---|---|---|---|---|---|---|---|
| | Stability Analysis | | | | | | | | | |
| | Visual Inspection | | Sub-visible particles (Cumulative counts/mL) | | | | Size Exclusion Chromatography Main | | | FMA |
| Sample Description | Seidenader (#/Vial) | B/W (#/Vial) | ≥2 μm | ≥5 μm | ≥10 μm | ≥25 μm | HMW (% Area) | Peak (% Area) | LMW (% Area) | [PS 20] mg/mL |
| LSRT T0 | 0 | 0 | 115 | 72 | 37 | 0 | 0.7 | 99.3 | <LOQ | 0.6 |
| LSRT 2w 5° C. | 0 | 0 | 115 | 65 | 37 | 2 | 0.7 | 99.3 | <LOQ | 0.6 |
| LSRT 2w 40° C. | 0 | 0 | 32 | 5 | 3 | 2 | 1.8 | 97.9 | 0.3 | 0.6 |
| LSRT 4w 5° C. | 0 | 0 | 100 | 65 | 30 | 5 | 0.7 | 99.3 | <LOQ | 0.6 |
| LSRT 4w 40° C. | 0 | 0 | 142 | 67 | 33 | 0 | 2.4 | 97.1 | 0.5 | 0.6 |

Example 7

Formulation Development and Evaluation

A protein molecule comprising an ERT enzyme-Fc fusion polypeptide and a modified Fc polypeptide may be included in a formulation as described in any one of Examples 2-6, wherein the IDS amino acid sequence is replaced with an alternative ERT amino acid sequence. Such formulations may be evaluated using an assay as described in Examples 2-6.

TABLE A

Informal Sequence Listing

| SEQ ID NO: | Sequence | Description |
|---|---|---|
| 1 | TDALNVLLIIVDDLRPSLGCYGDKLVRSPNIDQLASHSLLFQNAFA QQAVCAPSRVSFLTGRRPDTTRLYDFNSYWRVHAGNFSTIPQYFKE NGYVTMSVGKVFHPGISSNHTDDSPYSWSFPPYHPSSEKYENTKTC RGPDGELHANLLCPVDVLDVPEGTLPDKQSTEQAIQLLEKMKTSAS PFFLAVGYHKPHIPFRYPKEFQKLYPLENITLAPDPEVPDGLPPVA YNPWMDIRQREDVQALNISVPYGPIPVDFQRKIRQSYFASVSYLDT QVGRLLSALDDLQLANSTIIAFTSDHGWALGEHGEWAKYSNFDVAT HVPLIFYVPGRTASLPEAGEKLFPYLDPFDSASQLMEPGRQSMDLV ELVSLFPTLAGLAGLQVPPRCPVPSFHVELCREGKNLLKHFRFRDL EEDPYLPGNPRELIAYSQYPRPSDIPQWNSDKPSLKDIKIMGYSIR TIDYRYTVWVGFNPDEFLANFSDIHAGELYFVDSDPLQDHNMYNDS QGGDLFQLLMP | Mature human iduronate sulfatase (IDS) polypeptide sequence |
| 2 | SETQANSTTDALNVLLIIVDDLRPSLGCYGDKLVRSPNIDQLASHS LLFQNAFAQQAVCAPSRVSFLTGRRPDTTRLYDFNSYWRVHAGNFS TIPQYFKENGYVTMSVGKVFHPGISSNHTDDSPYSWSFPPYHPSSE KYENTKTCRGPDGELHANLLCPVDVLDVPEGTLPDKQSTEQAIQLL EKMKTSASPFFLAVGYHKPHIPFRYPKEFQKLYPLENITLAPDPEV PDGLPPVAYNPWMDIRQREDVQALNISVPYGPIPVDFQRKIRQSYF ASVSYLDTQVGRLLSALDDLQLANSTIIAFTSDHGWALGEHGEWAK YSNFDVATHVPLIFYVPGRTASLPEAGEKLFPYLDPFDSASQLMEP GRQSMDLVELVSLFPTLAGLAGLQVPPRCPVPSFHVELCREGKNLL KHFRFRDLEEDPYLPGNPRELIAYSQYPRPSDIPQWNSDKPSLKDI KIMGYSIRTIDYRYTVWVGFNPDEFLANFSDIHAGELYFVDSDPLQ DHNMYNDSQGGDLFQLLMP | IDS sequence |
| 3 | SETQANSTTDALNVLLIIVDDLRPSLGCYGDKLVRSPNIDQLASHS LLFQNAFAQQAVFGAPSRVSFLTGRRPDTTRLYDFNSYWRVHAGNF STIPQYFKENGYVTMSVGKVFHPGISSNHTDDSPYSWSFPPYHPSS EKYENTKTCRGPDGELHANLLCPVDVLDVPEGTLPDKQSTEQAIQL LEKMKTSASPFFLAVGYHKPHIPFRYPKEFQKLYPLENITLAPDPE VPDGLPPVAYNPWMDIRQREDVQALNISVPYGPIPVDFQRKIRQSY FASVSYLDTQVGRLLSALDDLQLANSTIIAFTSDHGWALGEHGEWA KYSNFDVATHVPLIFYVPGRTASLPEAGEKLFPYLDPFDSASQLME PGRQSMDLVELVSLFPTLAGLAGLQVPPRCPVPSFHVELCREGKNL LKHFRFRDLEEDPYLPGNPRELIAYSQYPRPSDIPQWNSDKPSLKD IKIMGYSIRTIDYRYTVWVGFNPDEFLANFSDIHAGELYFVDSDPL QDHNMYNDSQGGDLFQLLMP | IDS sequence with substitution of formylglycine at position 59 (bold with double underline) |
| 4 | SETQANSTTDALNVLLIIVDDLRPSLGCYGDKLVRSPNIDQLASHS LLFQNAFAQQAVCAPSRVSFLTGRRPDTTRLYDFNSYWRVHAGNFS TIPQYFKENGYVTMSVGKVFHPGISSNHTDDSPYSWSFPPYHPSSE KYENTKTCRGPDGELHANLLCPVDVLDVPEGTLPDKQSTEQAIQLL EKMKTSASPFFLAVGYHKPHIPFRYPKEFQKLYPLENITLAPDPEV PDGLPPVAYNPWMDIRQREDVQALNISVPYGPIPVDFQRKIRQSYF ASVSYLDTQVGRLLSALDDLQLANSTIIAFTSDHGWALGEHGEWAK YSNFDVATHVPLIFYVPGRTASLPEAGEKLFPYLDPFDSASQLMEP GRQSMDLVELVSLFPTLAGLAGLQVPPRCPVPSFHVELCREGKNLL KHFRFRDLEEDPYLPGNPRELIAYSQYPRPSDIPQWNSDKPSLKDI KIMGYSIRTIDYRYTVWVGFNPDEFLANFSDIHAGELYFVDSDPLQ DHNMYNDSQGGDLFQLLMPGGGGSDKTHTCPPCPAPEAAGGPSVFL FPPKPKDTLMISRTPEVTCVVVDVSHEDPEVKFNWYVDGVEVHNAK TKPREEQYNSTYRVVSVLTVLHQDWLNGKEYKCKVSNKALPAPIEK TISKAKGQPREPQVYTLPPSRDELTKNQVSLSCAVKGFYPSDIAVE WESNGQPENNYKTTPPVLDSDGSFFLVSKLTVDKSRWQQGNVFSCS VMHEALHNHYTQKSLSLSPGK | IDS-Fc fusion polypeptide, with cysteine at position 59 of IDS (bold with double underline), hole mutation, and LALA mutation |
| 5 | SETQANSTTDALNVLLIIVDDLRPSLGCYGDKLVRSPNIDQLASHS LLFQNAFAQQAVFGAPSRVSFLTGRRPDTTRLYDFNSYWRVHAGNF STIPQYFKENGYVTMSVGKVFHPGISSNHTDDSPYSWSFPPYHPSS EKYENTKTCRGPDGELHANLLCPVDVLDVPEGTLPDKQSTEQAIQL | IDS-Fc fusion polypeptide, with formylglycine at position 59 of IDS |

TABLE A-continued

Informal Sequence Listing

| SEQ ID NO: | Sequence | Description |
|---|---|---|
| | LEKMKTSASPFFLAVGYHKPHIPFRYPKEFQKLYPLENITLAPDPE VPDGLPPVAYNPWMDIRQREDVQALNISVPYGPIPVDFQRKIRQSY FASVSYLDTQVGRLLSALDDLQLANSTIIAFTSDHGWALGEHGEWA KYSNFDVATHVPLIFYVPGRTASLPEAGEKLFPYLDPFDSASQLME PGRQSMDLVELVSLFPTLAGLAGLQVPPRCPVPSFHVELCREGKNL LKHFRFRDLEEDPYLPGNPRELIAYSQYPRPSDIPQWNSDKPSLKD IKIMGYSIRTIDYRYTVWVGFNPDEFLANFSDIHAGELYFVDSDPL QDHNMYNDSQGGDLFQLLMPGGGGSDKTHTCPPCPAPEAAGGPSVF LFPPKPKDTLMISRIPEVTCVVVDVSHEDPEVKFNWYVDGVEVHNA KTKPREEQYNSTYRVVSVLTVLHQDWLNGKEYKCKVSNKALPAPIE KTISKAKGQPREPQVYTLPPSRDELTKNQVSLSCAVKGFYPSDIAV EWESNGQPENNYKITPPVLDSDGSFFLVSKLTVDKSRWQQGNVFSC SVMHEALHNHYTQKSLSLSPGK | (bold with double underline), hole mutation, and LALA mutation |
| 6 | APEAAGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLWCL VKGFYPSDIAVLWESYGTEWSSYKTTPPVLDSDGSFFLYSKLTVTK EEWQQGFVFSCSVMHEALHNHYTQKSLSLSPGK | Clone CH3C.35.21.17 with knob and LALA mutations |
| 7 | DKTHTCPPCPAPEAAGGPSVFLFPPKPKDTLMISRTPEVTAVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLWCLVKGFYPSDIAVEWESYGTEWANYKTTPPVLDSDGSF FLYSKLTVTKEEWQQGFVFSCSVMHEALHNHYTQKSLSLSPGK | Clone CH3C.35.23.2 with knob and LALA mutations + portion of human IgG1 hinge sequence |
| 8 | APELLGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLTCL VKGFYPSDIAVEWESNGQPENNYKTTPPVLDSDGSFFLYSKLTVDK SRWQQGNVFSCSVMHEALHNHYTQKSLSLSPGK | Wild-type human Fc sequence positions 231-447 EU index numbering |
| 9 | APELLGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAK | CH2 domain sequence positions 231-340 EU index numbering |
| 10 | GQPREPQVYTLPPSRDELTKNQVSLTCLVKGFYPSDIAVEWESNGQ PENNYKTTPPVLDSDGSFFLYSKLTVDKSRWQQGNVESCSVMHEAL HNHYTQKSLSLSPGK | CH3 domain sequence Positions 341-447 EU index numbering |
| 11 | MPPPRTGRGLLWLGLVLSSVCVALGSETQANSTTDALNVLLIIVDD LRPSLGCYGDKLVRSPNIDQLASHSLLFQNAFAQQAVCAPSRVSFL TGRRPDTTRLYDENSYWRVHAGNESTIPQYFKENGYVTMSVGKVFH PGISSNHTDDSPYSWSFPPYHPSSEKYENTKTCRGPDGELHANLLC PVDVLDVPEGTLPDKQSTEQAIQLLEKMKTSASPFFLAVGYHKPHI PFRYPKEFQKLYPLENITLAPDPEVPDGLPPVAYNPWMDIRQREDV QALNISVPYGPIPVDFQRKIRQSYFASVSYLDTQVGRLLSALDDLQ LANSTIIAFTSDHGWALGEHGEWAKYSNFDVATHVPLIFYVPGRTA SLPEAGEKLFPYLDPFDSASQLMEPGRQSMDLVELVSLFPTLAGLA GLQVPPRCPVPSFHVELCREGKNLLKHERFRDLEEDPYLPGNPREL TAYSQYPRPSDIPQWNSDKPSLKDIKIMGYSIRTIDYRYTVWVGFN PDEFLANFSDIHAGELYFVDSDPLQDHNMYNDSQGGDLFQLLMP | Full-length human IDS polypeptide sequence |
| 12 | EPKSCDKTHTCPPCP | Human IgG1 hinge amino acid sequence |
| 13 | MMDQARSAFSNLFGGEPLSYTRFSLARQVDGDNSHVEMKLAVDEEE NADNNTKANVTKPKRCSGSICYGTIAVIVFFLIGFMIGYLGYCKGV EPKTECERLAGTESPVREEPGEDFPAARRLYWDDLKRKLSEKLDST DFTGTIKLLNENSYVPREAGSQKDENLALYVENQFREFKLSKVWRD QHFVKIQVKDSAQNSVIIVDKNGRLVYLVENPGGYVAYSKAATVTG KLVHANFGTKKDFEDLYTPVNGSIVIVRAGKITFAEKVANAESLNA IGVLIYMDQTKFPIVNAELSFFGHAHLGTGDPYTPGFPSFNHTQFP PSRSSGLPNIPVQTISRAAAEKLFGNMEGDCPSDWKIDSTCRMVTS ESKNVKLTVSNVLKEIKILNIFGVIKGFVEPDHYVVVGAQRDAWGP GAAKSGVGTALLLKLAQMFSDMVLKDGFQPSRSIIFASWSAGDFGS VGATEWLEGYLSSLHLKAFTYINLDKAVLGTSNFKVSASPLLYTLI EKTMQNVKHPVTGQFLYQDSNWASKVEKLTLDNAAFPFLAYSGIPA VSFCFCEDTDYPYLGTTMDTYKELTERIPELNKVARAAAEVAGQFV IKLTHDVELNLDYERYNSQLLSFVRDLNQYRADIKEMGLSLQWLYS ARGDFFRATSRLTTDFGNAEKTDRFVMKKLNDRVMRVEYHFLSPYV SPKESPFRHVFWGSGSHTLPALLENLKLRKQNNGAFNETLFRNQLA LATWTIQGAANALSGDVWDIDNEF | Human transferrin receptor protein 1 (TFR1) |

TABLE A-continued

Informal Sequence Listing

| SEQ ID NO: | Sequence | Description |
|---|---|---|
| 14 | APELLGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLSCA VKGFYPSDIAVEWESNGQPENNYKTTPPVLDSDGSFFLVSKLTVDK SRWQQGNVFSCSVMHEALHNHYTQKSLSLSPGK | Fc sequence with hole mutations |
| 15 | APEAAGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLSCA VKGFYPSDIAVEWESNGQPENNYKTTPPVLDSDGSFFLVSKLTVDK SRWQQGNVFSCSVMHEALHNHYTQKSLSLSPGK | Fc sequence with hole and LALA mutations |
| 16 | APELLGGPSVFLFPPKPKDTLYITREPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLSCA VKGFYPSDIAVEWESNGQPENNYKTTPPVLDSDGSFFLVSKLTVDK SRWQQGNVFSCSVMHEALHNHYTQKSLSLSPGK | Fc sequence with hole and YTE mutations |
| 17 | APEAAGGPSVFLFPPKPKDTLYITREPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLSCA VKGFYPSDIAVEWSNGQPENNYKTTPPVLDSDGSFFLVSKLTVDK SRWQQGNVFSCSVMHEALHNHYTQKSLSLSPGK | Fc sequence with hole, LALA, and YTE mutations |
| 18 | APELLGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLWCL VKGFYPSDIAVEWESNGQPENNYKTTPPVLDSDGSFFLYSKLTVDK SRWQQGNVFSCSVMHEALHNHYTQKSLSLSPGK | Fc sequence with knob mutation |
| 19 | APEAAGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLWCL VKGFYPSDIAVEWESNGQPENNYKTTPPVLDSDGSFFLYSKLTVDK SRWQQGNVFSCSVMHEALHNHYTQKSLSLSPGK | Fc sequence with knob and LALA mutations |
| 20 | APELLGGPSVFLFPPKPKDTLYITREPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLWCL VKGFYPSDIAVEWESNGQPENNYKTTPPVLDSDGSFFLYSKLTVDK SRWQQGNVFSCSVMHEALHNHYTQKSLSLSPGK | Fc sequence with knob and YTE mutations |
| 21 | APEAAGGPSVFLFPPKPKDTLYITREPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLWCL VKGFYPSDIAVEWESNGQPENNYKTTPPVLDSDGSFFLYSKLTVDK SRWQQGNVFSCSVMHEALHNHYTQKSLSLSPGK | Fc sequence with knob, LALA, and YTE mutations |
| 22 | DKTHTCPPCP | Portion of human IgG1 hinge sequence |
| 23 | SETQANSTTDALNVLLIIVDDLRPSLGCYGDKLVRSPNIDQLASHS LLFQNAFAQQAVCAPSRVSFLTGRRPDTTRLYDFNSYWRVHAGNFS TIPQYFKENGYVTMSVGKVFHPGISSNHTDDSPYSWSFPPYHPSSE KYENTKTCRGPDGELHANLLCPVDVLDVPEGTLPDKQSTEQAIQLL EKMKTSASPFFLAVGYHKPHIPFRYPKEFQKLYPLENITLAPDPEV PDGLPPVAYNPWMDIRQREDVQALNISVPYGPIPVDFQRKIRQSYF ASVSYLDTQVGRLLSALDDLQLANSTIIAFTSDHGWALGEHGEWAK YSNFDVATHVPLIFYVPGRTASLPEAGEKLFPYLDPFDSASQLMEP GRQSMDLVELVSLFPTLAGLAGLQVPPRCPVPSFHVELCREGKNLL KHFRFRDLEEDPYLPGNPRELIAYSQYPRPSDIPQWNSDKPSLKDI KIMGYSIRTIDYRYTVWVGFNPDEFLANFSDIHAGELYFVDSDPLQ DHNMYNDSQGGDLFQLLMP | IDS sequence (cysteine modified to formylglycine double underlined) |
| 24 | SETQANSTTDALNVLLIIVDDLRPSLGCYGDKLVRSPNIDQLASHS LLFQNAFAQQAVCAPSRVSFLTGRRPDTTRLYDFNSYWRVHAGNFS TIPQYFKENGYVTMSVGKVFHPGISSNHTDDSPYSWSFPPYHPSSE KYENTKTCRGPDGELHANLLCPVDVLDVPEGTLPDKQSTEQAIQLL EKMKTSASPFFLAVGYHKPHIPFRYPKEFQKLYPLENITLAPDPEV PDGLPPVAYNPWMDIRQREDVQALNISVPYGPIPVDFQRKIRQSYF ASVSYLDTQVGRLLSALDDLQLANSTIIAFTSDHGWALGEHGEWAK YSNFDVATHVPLIFYVPGRTASLPEAGEKLFPYLDPFDSASQLMEP GRQSMDLVELVSLFPTLAGLAGLQVPPRCPVPSFHVELCREGKNLL KHFRFRDLEEDPYLPGNPRELIAYSQYPRPSDIPQWNSDKPSLKDI KIMGYSIRTIDYRYTVWVGFNPDEFLANFSDIHAGELYFVDSDPLQ | IDS-Fc fusion polypeptide with IDS sequence underlined (cysteine modified to formylglycine double underlined) and hole and LALA mutations |

TABLE A-continued

Informal Sequence Listing

| SEQ ID NO: | Sequence | Description |
|---|---|---|
| | DHNMYNDSQGGDLFQLLMPGGGGSDKTHTCPPCPAPEAAGGPSVFL FPPKPKDTLMISRIPEVTCVVVDVSHEDPEVKFNWYVDGVEVHNAK TKPREEQYNSTYRVVSVLTVLHQDWLNGKEYKCKVSNKALPAPIEK TISKAKGQPREPQVYTLPPSRDELTKNQVSLSCAVKGFYPSDIAVE WESNGQPENNYKTTPPVLDSDGSFFLVSKLTVDKSRWQQGNVFSCS VMHEALHNHYTQKSLSLSPGK | |
| 25 | DKTHTCPPCPAPEAAGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLSWCLVKGFYPSDIAVWWESYGTEWSSYKTTPPVLDSDGSF FLYSKLTVTKEEWQQGFVFSCSVMHEALHNHYTQKSLSLSPGK | Clone CH3C.35.21 with knob and LALA mutations and portion of human IgG1 hinge sequence |
| 26 | SETQANSTTDALNVLLIIVDDLRPSLGCYGDKLVRSPNIDQLASHS LLFQNAFAQQAVCAPSRVSFLTGRRPDTTRLYDFNSYWRVHAGNFS TIPQYFKENGYVTMSVGKVFHPGISSNHTDDSPYSWSFPPYHPSSE KYENTKTCRGPDGELHANLLCPVDVLDVPEGTLPDKQSTEQAIQLL EKMKTSASPFFLAVGYHKPHIPFRYPKEFQKLYPLENITLAPDPEV PDGLPPVAYNPWMDIRQREDVQALNISVPYGPIPVDFQRKIRQSYF ASVSYLDTQVGRLLSALDDLQLANSTIIAFTSDHGWALGEHGEWAK YSNFDVATHVPLIFYVPGRTASLPEAGEKLFPYLDPFDSASQLMEP GRQSMDLVELVSLFPTLAGLAGLQVPPRCPVPSFHVELCREGKNLL KHFRFRDLEEDPYLPGNPRELIAYSQYPRPSDIPQWNSDKPSLKDI KIMGYSIRTIDYRYTVWVGFNPDEFLANFSDIHAGELYFVDSDPLQ DHNMYNDSQGGDLFQLLMPGGGGSDKTHTCPPCPAPELLGGPSVFL FPPKPKDTLMISRTPEVTCVVVDVSHEDPEVKFNWYVDGVEVHNAK TKPREEQYNSTYRVVSVLTVLHQDWLNGKEYKCKVSNKALPAPIEK TISKAKGQPREPQVYTLPPSRDELTKNQVSLSCAVKGFYPSDIAVE WESNGQPENNYKTTPPVLDSDGSFFLVSKLTVDKSRWQQGNVFSCS VMHEALHNHYTQKSLSLSPGK | IDS-Fc fusion polypeptide with IDS sequence underlined (cysteine modified to formylglycine double underlined) and hole mutations |
| 27 | SETQANSTTDALNVLLIIVDDLRPSLGCYGDKLVRSPNIDQLASHS LLFQNAFAQQAVCAPSRVSFLTGRRPDTTRLYDFNSYWRVHAGNFS TIPQYFKENGYVTMSVGKVFHPGISSNHTDDSPYSWSFPPYHPSSE KYENTKTCRGPDGELHANLLCPVDVLDVPEGTLPDKQSTEQAIQLL EKMKTSASPFFLAVGYHKPHIPFRYPKEFQKLYPLENITLAPDPEV PDGLPPVAYNPWMDIRQREDVQALNISVPYGPIPVDFQRKIRQSYF ASVSYLDTQVGRLLSALDDLQLANSTIIAFTSDHGWALGEHGEWAK YSNFDVATHVPLIFYVPGRTASLPEAGEKLFPYLDPFDSASQLMEP GRQSMDLVELVSLFPTLAGLAGLQVPPRCPVPSFHVELCREGKNLL KHFRFRDLEEDPYLPGNPRELIAYSQYPRPSDIPQWNSDKPSLKDI KIMGYSIRTIDYRYTVWVGFNPDEFLANFSDIHAGELYFVDSDPLQ DHNMYNDSQGGDLFQLLMPGGGGSDKTHTCPPCPAPELLGGPSVFL FPPKPKDTLMISRTPEVTCVVVDVSHEDPEVKFNWYVDGVEVHNAK TKPREEQYNSTYRVVSVLTVLHQDWLNGKEYKCKVSNKALPAPIEK TISKAKGQPREPQVYTLPPSRDELTKNQVSLWCLVKGFYPSDIAVE WESNGQPENNYKTTPPVLDSDGSFFLYSKLTVDKSRWQQGNVFSCS VMHEALHNHYTQKSLSLSPGK | IDS-Fc fusion polypeptide with IDS sequence underlined (cysteine modified to formylglycine double underlined) and knob mutation |
| 28 | APEAAGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLWCL VKGFYPSDIAVEWESYGTEWANYKTTPPVLDSDGSFFLYSKLTVTK EEWQQGFVFSCSVMHEALHNHYTQKSLSLSPGK | Clone CH3C.35.23.2 with knob and LALA mutations |
| 29 | APEAAGGPSVFLFPPKPKDTLMISRIPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLWCL VKGFYPSDIAVLWESYGTEWASYKTTPPVLDSDGSFFLYSKLTVTK EEWQQGFVFSCSVMHEALHNHYTQKSLSLSPGK | Clone CH3C.35.21.17.2 with knob and LALA mutations |
| 30 | DKTHTCPPCPAPEAAGGPSVFLFPPKPKDTLMISRTPEVICVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLWCLVKGFYPSDIAVLWESYGTEWASYKTTPPVLDSDGSF FLYSKLTVTKEEWQQGFVFSCSVMHEALHNHYTQKSLSLS | Clone CH3C.35.21.17.2 with knob and LALA mutations and portion PGK of human IgG1 hinge sequence |
| 31 | SETQANSTTDALNVLLIIVDDLRPSLGCYGDKLVRSPNIDQLASHS LLFQNAFAQQAVCAPSRVSFLTGRRPDTTRLYDFNSYWRVHAGNFS TIPQYFKENGYVTMSVGKVFHPGISSNHTDDSPYSWSFPPYHPSSE KYENTKTCRGPDGELHANLLCPVDVLDVPEGTLPDKQSTEQAIQLL EKMKTSASPFFLAVGYHKPHIPFRYPKEFQKLYPLENITLAPDPEV PDGLPPVAYNPWMDIRQREDVQALNISVPYGPIPVDFQRKIRQSYF ASVSYLDTQVGRLLSALDDLQLANSTIIAFTSDHGWALGEHGEWAK | IDS-Fc fusion polypeptide with IDS sequence underlined and hole mutations |

TABLE A-continued

Informal Sequence Listing

| SEQ ID NO: | Sequence | Description |
|---|---|---|
| | YSNFDVATHVPLIFYVPGRTASLPEAGEKLFPYLDPFDSASQLMEP GRQSMDLVELVSLFPTLAGLAGLQVPPRCPVPSFHVELCREGKNLL KHFRFRDLEEDPYLPGNPRELIAYSQYPRPSDIPQWNSDKPSLKDI KIMGYSIRTIDYRYTVWVGFNPDEFLANFSDIHAGELYFVDSDPLQ DHNMYNDSQGGDLFQLLMPGGGGSDKTHTCPPCPAPELLGGPSVFL FPPKPKDTLMISRTPEVTCVVVDVSHEDPEVKFNWYVDGVEVHNAK TKPREEQYNSTYRVVSVLTVLHQDWLNGKEYKCKVSNKALPAPIEK TISKAKGQPREPQVYTLPPSRDELTKNQVSLSCAVKGFYPSDIAVE WESNGQPENNYKTTPPVLDSDGSFFLVSKLTVDKSRWQQGNVFSCS VMHEALHNHYTQKSLSLSPGK | |
| 32 | SETQANSTTDALNVLLIIVDDLRPSLGCYGDKLVRSPNIDQLASHS LLFQNAFAQQAVCAPSRVSFLTGRRPDTTRLYDFNSYWRVHAGNFS TIPQYFKENGYVTMSVGKVFHPGISSNHTDDSPYSWSFPPYHPSSE KYENTKTCRGPDGELHANLLCPVDVLDVPEGTLPDKQSTEQAIQLL EKMKTSASPFFLAVGYHKPHIPFRYPKEFQKLYPLENITLAPDPEV PDGLPPVAYNPWMDIRQREDVQALNISVPYGPIPVDFQRKIRQSYF ASVSYLDTQVGRLLSALDDLQLANSTIIAFTSDHGWALGEHGEWAK YSNFDVATHVPLIFYVPGRTASLPEAGEKLFPYLDPFDSASQLMEP GRQSMDLVELVSLFPTLAGLAGLQVPPRCPVPSFHVELCREGKNLL KHFRFRDLEEDPYLPGNPRELIAYSQYPRPSDIPQWNSDKPSLKDI KIMGYSIRTIDYRYTVWVGFNPDEFLANFSDIHAGELYFVDSDPLQ DHNMYNDSQGGDLFQLLMPGGGGSDKTHTCPPCPAPELLGGPSVFL FPPKPKDTLMISRIPEVTCVVVDVSHEDPEVKFNWYVDGVEVHNAK TKPREEQYNSTYRVVSVLTVLHQDWLNGKEYKCKVSNKALPAPIEK TISKAKGQPREPQVYTLPPSRDELTKNQVSLWCLVKGFYPSDIAVE WESNGQPENNYKTTPPVLDSDGSFFLYSKLTVDKSRWQQGNVFSCS VMHEALHNHYTQKSLSLSPGK | IDS-Fc fusion polypeptide with IDS sequence underlined and knob mutation |
| 33 | SETQANSTTDALNVLLIIVDDLRPSLGCYGDKLVRSPNIDQLASHS LLFQNAFAQQAVfGAPSRVSFLTGRRPDTTRLYDFNSYWRVHAGNF STIPQYFKENGYVTMSVGKVFHPGISSNHTDDSPYSWSFPPYHPSS EKYENTKTCRGPDGELHANLLCPVDVLDVPEGTLPDKQSTEQAIQL LEKMKTSASPFFLAVGYHKPHIPFRYPKEFQKLYPLENITLAPDPE VPDGLPPVAYNPWMDIRQREDVQALNISVPYGPIPVDFQRKIRQSY FASVSYLDTQVGRLLSALDDLQLANSTIIAFTSDHGWALGEHGEWA KYSNFDVATHVPLIFYVPGRTASLPEAGEKLFPYLDPFDSASQLME PGRQSMDLVELVSLFPTLAGLAGLQVPPRCPVPSFHVELCREGKNL LKHFRFRDLEEDPYLPGNPRELIAYSQYPRPSDIPQWNSDKPSLKD IKIMGYSIRTIDYRYTVWVGFNPDEFLANFSDIHAGELYFVDSDPL QDHNMYNDSQGGDLFQLLMPGGGGSDKTHTCPPCPAPELLGGPSVF LFPPKPKDTLMISRTPEVTCVVVDVSHEDPEVKFNWYVDGVEVHNA KTKPREEQYNSTYRVVSVLTVLHQDWLNGKEYKCKVSNKALPAPIE KTISKAKGQPREPQVYTLPPSRDELTKNQVSLSCAVKGFYPSDIAV EWESNGQPENNYKITPPVLDSDGSFFLVSKLTVDKSRWQQGNVFSC SVMHEALHNHYTQKSLSLSPGK | IDS-Fc fusion polypeptide with IDS sequence underlined (formylglycine residue "fG" double underlined) and hole mutations |
| 34 | SETQANSTTDALNVLLIIVDDLRPSLGCYGDKLVRSPNIDQLASHS LLFQNAFAQQAVfGAPSRVSFLTGRRPDTTRLYDFNSYWRVHAGNF STIPQYFKENGYVTMSVGKVFHPGISSNHTDDSPYSWSFPPYHPSS EKYENTKTCRGPDGELHANLLCPVDVLDVPEGTLPDKQSTEQAIQL LEKMKTSASPFFLAVGYHKPHIPFRYPKEFQKLYPLENITLAPDPE VPDGLPPVAYNPWMDIRQREDVQALNISVPYGPIPVDFQRKIRQSY FASVSYLDTQVGRLLSALDDLQLANSTIIAFTSDHGWALGEHGEWA KYSNFDVATHVPLIFYVPGRTASLPEAGEKLFPYLDPFDSASQLME PGRQSMDLVELVSLFPTLAGLAGLQVPPRCPVPSFHVELCREGKNL LKHFRFRDLEEDPYLPGNPRELIAYSQYPRPSDIPQWNSDKPSLKD IKIMGYSIRTIDYRYTVWVGFNPDEFLANFSDIHAGELYFVDSDPL QDHNMYNDSQGGDLFQLLMPGGGGSDKTHTCPPCPAPELLGGPSVF LFPPKPKDTLMISRTPEVTCVVVDVSHEDPEVKFNWYVDGVEVHNA KTKPREEQYNSTYRVVSVLTVLHQDWLNGKEYKCKVSNKALPAPIE KTISKAKGQPREPQVYTLPPSRDELTKNQVSLWCLVKGFYPSDIAV EWESNGQPENNYKITPPVLDSDGSFFLYSKLTVDKSRWQQGNVFSC SVMHEALHNHYTQKSLSLSPGK | IDS-Fc fusion polypeptide with IDS sequence underlined (formylglycine residue "fG" double underlined) and knob mutation |
| 35 | NSVIIVDKNGRLVYLVENPGGYVAYSKAATVTGKLVHANFGTKKDF EDLYTPVNGSIVIVRAGKITFAEKVANAESLNAIGVLIYMDQTKFP IVNAELSFFGHAHLGTGDPYTPGFPSFNHTQFPPSRSSGLPNIPVQ TISRAAAEKLFGNMEGDCPSDWKTDSTCRMVTSESKNVKLTVS | Human TfR apical domain |
| 36 | GGGGS | Glycine-rich linker |
| 37 | GGGGSGGGGS | Glycine-rich linker |
| 38 | HHHHHH | Hexahistidine tag |

TABLE A-continued

Informal Sequence Listing

| SEQ ID NO: | Sequence | Description |
|---|---|---|
| 39 | SETQANSTTDALNVLLIIVDDLRPSLGCYGDKLVRSPNIDQLASHS LLFQNAFAQQA**VCAPSRVSFLTGRRPDTTRLYDFNSYWRVHAGNFS TIPQYFKENGYVTMSVGKVFHPGISSNHTDDSPYSWSFPPYHPSSE KYENTKTCRGPDGELHANLLCPVDVLDVPEGTLPDKQSTEQAIQLL EKMKTSASPFFLAVGYHKPHIPFRYPKEFQKLYPLENITLAPDPEV PDGLPPVAYNPWMDIRQREDVQALNISVPYGPIPVDFQRKIRQSYF ASVSYLDTQVGRLLSALDDLQLANSTIIAFTSDHGWALGEHGEWAK YSNFDVATHVPLIFYVPGRTASLPEAGEKLFPYLDPFDSASQLMEP GRQSMDLVELVSLFPTLAGLAGLQVPPRCPVPSFHVELCREGKNLL KHFRFRDLEEDPYLPGNPRELIAYSQYPRPSDIPQWNSDKPSLKDI KIMGYSIRTIDYRYTVWVGFNPDEFLANFSDIHAGELYFVDSDPLQ DHNMYNDSQGGDLFQLLMPGGGGSDKTHTCPPCPAPEAAGGPSVFL FPPPKPKDTLMISRIPEVTCVVVDVSHEDPEVKFNWYVDGVEVHNAK TKPREEQYNSTYRVVSVLTVLHQDWLNGKEYKCKVSNKALPAPIEK TISKAKGQPREPQVYTLPPSRDELTKNQVSLSCAVKGFYPSDIAVE WESNGQPENNYKTTPPVLDSDGSFFLVSKLTVDKSRWQQGNVFSCS VMHEALHNHYTQKSLSLSPG | IDS-Fc fusion polypeptide, with cysteine at position 59 of IDS (bold with double underline), hole mutation, and LALA mutation |
| 40 | SETQANSTTDALNVLLIIVDDLRPSLGCYGDKLVRSPNIDQLASHS LLFQNAFAQQAVFGAPSRVSFLTGRRPDTTRLYDFNSYWRVHAGNF STIPQYFKENGYVTMSVGKVFHPGISSNHTDDSPYSWSFPPYHPSS EKYENTKTCRGPDGELHANLLCPVDVLDVPEGTLVDKQSTEQATQL LEKMKTSASPFFLAVGYHKPHIPFRYPKEFQKLYPLENITLAPDPE VPDGLPPVAYNPWMDIRQREDVQALNISVPYGPIPVDFQRKIRQSY FASVSYLDTQVGRLLSALDDLQLANSTIIAFTSDHGWALGEHGEWA KYSNFDVATHVPLIFYVPGRTASLPEAGEKLFPYLDPFDSASQLME PGRQSMDLVELVSLFPTLAGLAGLQVPPRCPVPSFHVELCREGKNL LKHFRFRDLEEDPYLPGNPRELIAYSQYPRPSDIPQWNSDKPSLKD IKIMGYSIRTIDYRYTVWVGFNPDEFLANFSDIHAGELYFVDSDPL QDHNMYNDSQGGDLFQLLMPGGGGSDKTHTCPPCPAPEAAGGPSVF LFPPPKPKDILMISRIPEVTCVVVDVSHEDPEVKFNWYVDGVEVHNA KTKPREEQYNSTYRVVSVLTVLHQDWLNGKEYKCKVSNKALPAPIE KTISKAKGQPREPQVYTLPPSRDELTKNQVSLSCAVKGFYPSDIAV EWESNGQPENNYKTIPPVLDSDGSFFLVSKLTVDKSRWQQGNVFSC SVMHEALHNHYTQKSLSLSPG | IDS-Fc fusion polypeptide, with formylglycine at position 59 of IDS (bold with double underline), hole mutation, and LALA mutation |
| 41 | APEAAGGPSVFLFPPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLWCL VKGFYPSDIAVLWESYGTEWSSYKTTPPVLDSDGSFFLYSKLTVTK EEWQQGFVFSCSVMHEALHNHYTQKSLSLSPG | Clone CH3C.35.21.17 with knob and LALA mutations |
| 42 | DKTHTCPPCPAPEAAGGPSVFLFPPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLWCLVKGFYPSDIAVEWESYGTEWANYKTTPPVLDSDGSF FLYSKLTVTKEEWQQGFVFSCSVMHEALHNHYTQKSLSLSPG | Clone CH3C.35.23.2 with knob and LALA mutations + portion of human IgG1 hinge sequence |
| 43 | SETQANSTTDALNVLLIIVDDLRPSLGCYGDKLVRSPNIDQLASHS LLFQNAFAQQAVCAPSRVSFLTGRRPDTTRLYDFNSYWRVHAGNFS TIPQYFKENGYVTMSVGKVFHPGISSNHTDDSPYSWSFPPYHPSSE KYENTKTCRGPDGELHANLLCPVDVLDVPEGTLPDKQSTEQATQLL EKMKTSASPFFLAVGYHKPHIPFRYPKEFQKLYPLENITLAPDPEV PDGLPPVAYNPWMDIRQREDVQALNISVPYGPIPVDFQRKIRQSYF ASVSYLDTQVGRLLSALDDLQLANSTIIAFTSDHGWALGEHGEWAK YSNFDVATHVPLIFYVPGRTASLPEAGEKLFPYLDPFDSASQLMEP GRQSMDLVELVSLFPTLAGLAGLQVPPRCPVPSFHVELCREGKNLL KHFRFRDLEEDPYLPGNPRELIAYSQYPRPSDIPQWNSDKPSLKDI KIMGYSIRTIDYRYTVWVGFNPDEFLANFSDIHAGELYFVDSDPLQ DHNMYNDSQGGDLFQLLMPGGGGSDKTHTCPPCPAPEAAGGPSVFL FPPPKPKDILMISRTPEVTCVVVDVSHEDPEVKFNWYVDGVEVHNAK TKPREEQYNSTYRVVSVLTVLHQDWLNGKEYKCKVSNKALPAPIEK TISKAKGQPREPQVYTLPPSRDELTKNQVSLSCAVKGFYPSDIAVE WESNGQPENNYKTIPPVLDSDGSFFLVSKLTVDKSRWQQGNVFSCS VMHEALHNHYTQKSLSLSPG | IDS-Fc fusion polypeptide with IDS sequence underlined (cysteine modified to formylglycine double underlined) and hole and LALA mutations |
| 44 | DKTHTCPPCPAPEAAGGPSVFLFPPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLWCLVKGFYPSDIAVWWESYGTEWSSYKTTPPVLDSDGSF FLYSKLTVTKEEWQQGFVFSCSVMHEALHNHYTQKSLSLSPG | Clone CH3C.35.21 with knob and LALA mutations and portion of human IgG1 hinge sequence |

TABLE A-continued

Informal Sequence Listing

| SEQ ID NO: | Sequence | Description |
|---|---|---|
| 45 | SETQANSTTDALNVLLIIVDDLRPSLGCYGDKLVRSPNIDQLASHS LLFQNAFAQQAVCAPSRVSFLTGRRPDTTRLYDFNSYWRVHAGNFS TIPQYFKENGYVTMSVGKVFHPGISSNHTDDSPYSWSFPPYHPSSE KYENTKTCRGPDGELHANLLCPVDVLDVPEGTLPDKQSTEQAIQLL EKMKTSASPFFLAVGYHKPHIPFRYPKEFQKLYPLENITLAPDPEV PDGLPPVAYNPWMDIRQREDVQALNISVPYGPIPVDFQRKIRQSYF ASVSYLDTQVGRLLSALDDLQLANSTIIAFTSDHGWALGEHGEWAK YSNFDVATHVPLIFYVPGRTASLPEAGEKLFPYLDPFDSASQLMEP GRQSMDLVELVSLFPTLAGLAGLQVPPRCPVPSFHVELCREGKNLL KHFRFRDLEEDPYLPGNPRELIAYSQYPRPSDIPQWNSDKPSLKDI KIMGYSIRTIDYRYTVWVGFNPDEFLANFSDIHAGELYFVDSDPLQ DHNMYNDSQGGDLFQLLMPGGGGSDKTHTCPPCPAPELLGGPSVFL FPPKPKDTLMISRTPEVTCVVVDVSHEDPEVKFNWYVDGVEVHNAK TKPREEQYNSTYRVVSVLTVLHQDWLNGKEYKCKVSNKALPAPIEK TISKAKGQPREPQVYTLPPSRDELTKNQVSLSCAVKGFYPSDIAVE WESNGQPENNYKTTPPVLDSDGSFFLVSKLTVDKSRWQQGNVFSCS VMHEALHNHYTQKSLSLSPG | IDS-Fc fusion polypeptide with IDS sequence underlined (cysteine modified to formylglycine double underlined) and hole mutations |
| 46 | SETQANSTTDALNVLLIIVDDLRPSLGCYGDKLVRSPNIDQLASHS LLFQNAFAQQAVCAPSRVSFLTGRRPDTTRLYDFNSYWRVHAGNFS TIPQYFKENGYVTMSVGKVFHPGISSNHTDDSPYSWSFPPYHPSSE KYENTKTCRGPDGELHANLLCPVDVLDVPEGTLPDKQSTEQAIQLL EKMKTSASPFFLAVGYHKPHIPFRYPKEFQKLYPLENITLAPDPEV PDGLPPVAYNPWMDIRQREDVQALNISVPYGPIPVDFQRKIRQSYF ASVSYLDTQVGRLLSALDDLQLANSTIIAFTSDHGWALGEHGEWAK YSNFDVATHVPLIFYVPGRTASLPEAGEKLFPYLDPFDSASQLMEP GRQSMDLVELVSLFPTLAGLAGLQVPPRCPVPSFHVELCREGKNLL KHFRFRDLEEDPYLPGNPRELIAYSQYPRPSDIPQWNSDKPSLKDI KIMGYSIRTIDYRYTVWVGFNPDEFLANFSDIHAGELYFVDSDPLQ DHNMYNDSQGGDLFQLLMPGGGGSDKTHTCPPCPAPELLGGPSVFL FPPKPKDTLMISRTPEVTCVVVDVSHEDPEVKFNWYVDGVEVHNAK TKPREEQYNSTYRVVSVLTVLHQDWLNGKEYKCKVSNKALPAPIEK TISKAKGQPREPQVYTLPPSRDELTKNQVSLWCLVKGFYPSDIAVE WESNGQPENNYKTTPPVLDSDGSFFLYSKLTVDKSRWQQGNVFSCS VMHEALHNHYTQKSLSLSPG | IDS-Fc fusion polypeptide with IDS sequence underlined (cysteine modified to formylglycine double underlined) and knob mutation |
| 47 | APEAAGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLWCL VKGFYPSDIAVEWESYGTEWANYKTTPPVLDSDGSFFLYSKLTVTK EEWQQGFVFSCSVMHEALHNHYTQKSLSLSPG | Clone CH3C.35.23.2 with knob and LALA mutations |
| 48 | APEAAGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLWCL VKGFYPSDIAVLWESYGTEWASYKTTPPVLDSDGSFFLYSKLTVTK EEWQQGFVFSCSVMHEALHNHYTQKSLSLSPG | Clone CH3C.35.21.17.2 with knob and LALA mutations |
| 49 | DKTHTCPPCPAPEAAGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLWCLVKGFYPSDIAVLWESYGTEWASYKTTPPVLDSDGSF FLYSKLTVTKEEWQQGFVFSCSVMHEALHNHYTQKSLSLSPG | Clone CH3C.35.21.17.2 with knob and LALA mutations and portion of human IgG1 hinge sequence |
| 50 | SETQANSTTDALNVLLIIVDDLRPSLGCYGDKLVRSPNIDQLASHS LLFQNAFAQQAVCAPSRVSFLTGRRPDTTRLYDFNSYWRVHAGNFS TIPQYFKENGYVTMSVGKVFHPGISSNHTDDSPYSWSFPPYHPSSE KYENTKTCRGPDGELHANLLCPVDVLDVPEGTLPDKQSTEQAIQLL EKMKTSASPFFLAVGYHKPHIPFRYPKEFQKLYPLENITLAPDPEV PDGLPPVAYNPWMDIRQREDVQALNISVPYGPIPVDFQRKIRQSYF ASVSYLDTQVGRLLSALDDLQLANSTIIAFTSDHGWALGEHGEWAK YSNFDVATHVPLIFYVPGRTASLPEAGEKLFPYLDPFDSASQLMEP GRQSMDLVELVSLFPTLAGLAGLQVPPRCPVPSFHVELCREGKNLL KHFRFRDLEEDPYLPGNPRELIAYSQYPRPSDIPQWNSDKPSLKDI KIMGYSIRTIDYRYTVWVGFNPDEFLANFSDIHAGELYFVDSDPLQ DHNMYNDSQGGDLFQLLMPGGGGSDKTHTCPPCPAPELLGGPSVFL FPPKPKDTLMISRTPEVTCVVVDVSHEDPEVKFNWYVDGVEVHNAK TKPREEQYNSTYRVVSVLTVLHQDWLNGKEYKCKVSNKALPAPIEK TISKAKGQPREPQVYTLPPSRDELTKNQVSLSCAVKGFYPSDIAVE WESNGQPENNYKTTPPVLDSDGSFFLVSKLTVDKSRWQQGNVFSCS VMHEALHNHYTQKSLSLSPG | IDS-Fc fusion polypeptide with IDS sequence underlined and hole mutations |

TABLE A-continued

Informal Sequence Listing

| SEQ ID NO: | Sequence | Description |
|---|---|---|
| 51 | SETQANSTTDALNVLLIIVDDLRPSLGCYGDKLVRSPNIDQLASHS<br>LLFQNAFAQQAVCAPSRVSFLTGRRPDTTRLYDFNSYWRVHAGNFS<br>TIPQYFKENGYVTMSVGKVFHPGISSNHTDDSPYSWSFPPYHPSSE<br>KYENTKTCRGPDGELHANLLCPVDVLDVPEGTLPDKQSTEQAIQLL<br>EKMKTSASPFFLAVGYHKPHIPFRYPKEFQKLYPLENITLAPDPEV<br>PDGLPPVAYNPWMDIRQREDVQALNISVPYGPIPVDFQRKIRQSYF<br>ASVSYLDTQVGRLLSALDDLQLANSTIIAFTSDHGWALGEHGEWAK<br>YSNFDVATHVPLIFYVPGRTASLPEAGEKLFPYLDPFDSASQLMEP<br>GRQSMDLVELVSLFPTLAGLAGLQVPPRCPVPSFHVELCREGKNLL<br>KHFRFRDLEEDPYLPGNPRELIAYSQYPRPSDIPQWNSDKPSLKDI<br>KIMGYSIRTIDYRYTVWVGFNPDEFLANFSDIHAGELYFVDSDPLQ<br>DHNMYNDSQGGDLFQLLMPGGGGSDKTHTCPPCPAPELLGGPSVFL<br>FPPKPKDTLMISRTPEVTCVVVDVSHEDPEVKFNWYVDGVEVHNAK<br>TKPREEQYNSTYRVVSVLTVLHQDWLNGKEYKCKVSNKALPAPIEK<br>TISKAKGQPREPQVYTLPPSRDELTKNQVSLWCLVKGFYPSDIAVE<br>WESNGQPENNYKTTPPVLDSDGSFFLYSKLTVDKSRWQQGNVFSCS<br>VMHEALHNHYTQKSLSLSPG | IDS-Fc fusion polypeptide with IDS sequence underlined and knob mutation |
| 52 | SETQANSTTDALNVLLIIVDDLRPSLGCYGDKLVRSPNIDQLASHS<br>LLFQNAFAQQAVfGAPSRVSFLTGRRPDTTRLYDFNSYWRVHAGNF<br>STIPQYFKENGYVTMSVGKVFHPGISSNHTDDSPYSWSFPPYHPSS<br>EKYENTKTCRGPDGELHANLLCPVDVLDVPEGTLPDKQSTEQAIQL<br>LEKMKTSASPFFLAVGYHKPHIPFRYPKEFQKLYPLENITLAPDPE<br>VPDGLPPVAYNPWMDIRQREDVQALNISVPYGPIPVDFQRKIRQSY<br>FASVSYLDTQVGRLLSALDDLQLANSTIIAFTSDHGWALGEHGEWA<br>KYSNFDVATHVPLIFYVPGRTASLPEAGEKLFPYLDPFDSASQLME<br>PGRQSMDLVELVSLFPTLAGLAGLQVPPRCPVPSFHVELCREGKNL<br>LKHFRFRDLEEDPYLPGNPRELIAYSQYPRPSDIPQWNSDKPSLKD<br>IKIMGYSIRTIDYRYTVWVGFNPDEFLANFSDIHAGELYFVDSDPL<br>QDHNMYNDSQGGDLFQLLMPGGGGSDKTHTCPPCPAPELLGGPSVF<br>LFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIE<br>KTISKAKGQPREPQVYTLPPSRDELTKNQVSLSCAVKGFYPSDIAV<br>EWESNGQPENNYKITPPVLDSDGSFFLVSKLTVDKSRWQQGNVFSC<br>SVMHEALHNHYTQKSLSLSPG | IDS-Fc fusion polypeptide with IDS sequence underlined (formylglycine residue "fG" double underlined) and hole mutations |
| 53 | SETQANSTTDALNVLLIIVDDLRPSLGCYGDKLVRSPNIDQLASHS<br>LLFQNAFAQQAVfGAPSRVSFLTGRRPDTTRLYDFNSYWRVHAGNF<br>STIPQYFKENGYVTMSVGKVFHPGISSNHTDDSPYSWSFPPYHPSS<br>EKYENTKTCRGPDGELHANLLCPVDVLDVPEGTLPDKQSTEQAIQL<br>LEKMKTSASPFFLAVGYHKPHIPFRYPKEFQKLYPLENITLAPDPE<br>VPDGLPPVAYNPWMDIRQREDVQALNISVPYGPIPVDFQRKIRQSY<br>FASVSYLDTQVGRLLSALDDLQLANSTIIAFTSDHGWALGEHGEWA<br>KYSNFDVATHVPLIFYVPGRTASLPEAGEKLFPYLDPFDSASQLME<br>PGRQSMDLVELVSLFPTLAGLAGLQVPPRCPVPSFHVELCREGKNL<br>LKHFRFRDLEEDPYLPGNPRELIAYSQYPRPSDIPQWNSDKPSLKD<br>IKIMGYSIRTIDYRYTVWVGFNPDEFLANFSDIHAGELYFVDSDPL<br>QDHNMYNDSQGGDLFQLLMPGGGGSDKTHTCPPCPAPELLGGPSVF<br>LFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIE<br>KTISKAKGQPREPQVYTLPPSRDELTKNQVSLWCLVKGFYPSDIAV<br>EWESNGQPENNYKITPPVLDSDGSFFLYSKLTVDKSRWQQGNVFSC<br>SVMHEALHNHYTQKSLSLSPG | IDS-Fc fusion polypeptide with IDS sequence underlined (formylglycine residue "fG" double underlined) and knob mutation |
| 54 | APELLGGPSVFLFPPKPKDTLMISRTPEVTCVVVDVSHEDPEVKFN<br>WYVDGVEVHNAKTKPREEQYNSTYRVVSVLTVLHQDWLNGKEYKCK<br>VSNKALPAPIEKTISKAKGQPREPQVYTLPPSRDELTKNQVSLSCA<br>VKGFYPSDIAVEWESNGQPENNYKTTPPVLDSDGSFFLVSKLTVDK<br>SRWQQGNVFSCSVMHEALHNHYTQKSLSLSPG | Fc sequence with hole mutations |
| 55 | APEAAGGPSVFLFPPKPKDTLMISRTPEVTCVVVDVSHEDPEVKFN<br>WYVDGVEVHNAKTKPREEQYNSTYRVVSVLTVLHQDWLNGKEYKCK<br>VSNKALPAPIEKTISKAKGQPREPQVYTLPPSRDELTKNQVSLSCA<br>VKGFYPSDIAVEWESNGQPENNYKTTPPVLDSDGSFFLVSKLTVDK<br>SRWQQGNVFSCSVMHEALHNHYTQKSLSLSPG | Fc sequence with hole and LALA mutations |
| 56 | APELLGGPSVFLFPPKPKDTLYITREPEVTCVVVDVSHEDPEVKFN<br>WYVDGVEVHNAKTKPREEQYNSTYRVVSVLTVLHQDWLNGKEYKCK<br>VSNKALPAPIEKTISKAKGQPREPQVYTLPPSRDELTKNQVSLSCA<br>VKGFYPSDIAVEWESNGQPENNYKTTPPVLDSDGSFFLVSKLTVDK<br>SRWQQGNVFSCSVMHEALHNHYTQKSLSLSPG | Fc sequence with hole and YTE mutations |
| 57 | APEAAGGPSVFLFPPKPKDTLYITREPEVTCVVVDVSHEDPEVKFN<br>WYVDGVEVHNAKTKPREEQYNSTYRVVSVLTVLHQDWLNGKEYKCK<br>VSNKALPAPIEKTISKAKGQPREPQVYTLPPSRDELTKNQVSLSCA | Fc sequence with hole, LALA, and YTE mutations |

TABLE A-continued

Informal Sequence Listing

| SEQ ID NO: | Sequence | Description |
|---|---|---|
| | VKGFYPSDIAVEWESNGQPENNYKTTPPVLDSDGSFFLVSKLTVDK SRWQQGNVFSCSVMHEALHNHYTQKSLSLSPG | |
| 58 | APELLGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLWCL VKGFYPSDIAVEWESNGQPENNYKTTPPVLDSDGSFFLYSKLTVDK SRWQQGNVFSCSVMHEALHNHYTQKSLSLSPG | Fc sequence with knob mutation |
| 59 | APEAAGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLWCL VKGFYPSDIAVEWESNGQPENNYKTTPPVLDSDGSFFLYSKLTVDK SRWQQGNVFSCSVMHEALHNHYTQKSLSLSPG | Fc sequence with knob and LALA mutations |
| 60 | APELLGGPSVFLFPPKPKDTLYITREPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLWCL VKGFYPSDIAVEWESNGQPENNYKTTPPVLDSDGSFFLYSKLTVDK SRWQQGNVFSCSVMHEALHNHYTQKSLSLSPG | Fc sequence with knob and YTE mutations |
| 61 | APEAAGGPSVFLFPPKPKDTLYITREPEVTCVVVDVSHEDPEVKFN WYVDGVEVHNAKTKPREEQYNSTYRVVSVLTVLHQDWLNGKEYKCK VSNKALPAPIEKTISKAKGQPREPQVYTLPPSRDELTKNQVSLWCL VKGFYPSDIAVEWESNGQPENNYKTTPPVLDSDGSFFLYSKLTVDK SRWQQGNVFSCSVMHEALHNHYTQKSLSLSPG | Fc sequence with knob, LALA, and YTE mutations |

All publications, patents, and patent documents are incorporated by reference herein, as though individually incorporated by reference. The present disclosure has been described with reference to various specific and preferred embodiments and techniques. However, it should be understood that many variations and modifications may be made while remaining within the spirit and scope of the invention.

What is claimed is:

1. A pharmaceutical composition comprising:

a. (i) a protein molecule comprising: a first Fc polypeptide comprising the amino acid sequence of SEQ ID NO:42; and a fusion polypeptide comprising the amino acid sequence of SEQ ID NO: 40; and (ii) a protein molecule comprising: a first Fc polypeptide comprising the amino acid sequence of SEQ ID NO:42; and a fusion polypeptide comprising the amino acid sequence of SEQ ID NO: 39;

b. a buffer; and c. a salt;

wherein the pH of the pharmaceutical composition is about 5.5 to 7.0.

2. The pharmaceutical composition of claim 1, wherein the buffer is selected from the group consisting of: a phosphate buffer, an acetate buffer, an arginine buffer, and a histidine buffer.

3. The pharmaceutical composition of claim 2, wherein the buffer is a phosphate buffer, and wherein the phosphate buffer is a sodium phosphate buffer or a potassium phosphate buffer.

4. The pharmaceutical composition of claim 1, wherein the salt is a sodium salt selected from the group consisting of: sodium chloride, sodium sulfate, and sodium phosphate.

5. The pharmaceutical composition of claim 1, wherein the pharmaceutical composition further comprises a surfactant.

6. The pharmaceutical composition of claim 1, wherein the pharmaceutical composition further comprises a stabilizer comprising a sugar.

7. The pharmaceutical composition of claim 1, wherein the protein molecule concentration is about 5-50 mg/mL.

8. The pharmaceutical composition of claim 1, wherein the buffer concentration is about 5-50 mM.

9. The pharmaceutical composition of claim 1, wherein the salt concentration is about 30-150 mM.

10. The pharmaceutical composition of claim 5, wherein the surfactant concentration is about 0.1-1.0 mg/mL.

11. The pharmaceutical composition of claim 5, wherein the surfactant comprises polysorbate.

12. The pharmaceutical composition of claim 11, wherein the surfactant is selected from the group consisting of: polysorbate-20 (PS-20) and polysorbate-80 (PS-80).

13. The pharmaceutical composition of claim 6, wherein the stabilizer comprises a sugar selected from sucrose or trehalose.

14. The pharmaceutical composition of claim 6, wherein the sugar concentration is about 100-250 mM.

15. The pharmaceutical composition of claim 1, wherein the composition further comprises methionine.

16. The pharmaceutical composition of claim 15, wherein the methionine concentration is about 5-20 mM.

17. The pharmaceutical composition of claim 1, wherein the pH of the pharmaceutical composition is about 6.5±0.5.

18. A method of treating Hunter syndrome in a subject in need thereof, comprising providing and administering the pharmaceutical composition of claim 1 to the subject.

19. The pharmaceutical composition of claim 1, further comprising:

a. (iii) a protein molecule comprising: a first Fc polypeptide comprising the amino acid sequence of SEQ ID NO:7; and a fusion polypeptide comprising the amino acid sequence of SEQ ID NO: 5; and/or a. (iv) a protein molecule comprising: a first Fc polypeptide comprising the amino acid sequence of SEQ ID NO:7; and a fusion polypeptide comprising the amino acid sequence of SEQ ID NO: 4.

20. The pharmaceutical composition of claim 1, comprising: a buffer comprising sodium phosphate; sodium chloride; a surfactant; and a stabilizer comprising a sugar.

21. A pharmaceutical composition comprising:

a. (i) a protein molecule comprising: a first Fc polypeptide comprising the amino acid sequence of SEQ ID NO:42; and a fusion polypeptide comprising the amino acid sequence of SEQ ID NO: 40; and (ii) a protein molecule comprising: a first Fc polypeptide comprising the amino acid sequence of SEQ ID NO:42; and a fusion polypeptide comprising the amino acid sequence of SEQ ID NO: 39;

b. about 10-30 mM of sodium phosphate buffer;

c. about 30-100 mM sodium chloride;

d. about 0.4-0.7 mg/mL of a polysorbate surfactant;

e. about 150-200 mM of sucrose; and f. about 5-25 mM methionine;

wherein the pH of the pharmaceutical composition is 6.5±0.5.

22. The pharmaceutical composition of claim 21, further comprising:

a. (iii) a protein molecule comprising: a first Fc polypeptide comprising the amino acid sequence of SEQ ID NO:7; and a fusion polypeptide comprising the amino acid sequence of SEQ ID NO: 5; and/or (iv) a protein molecule comprising: a first Fc polypeptide comprising the amino acid sequence of SEQ ID NO:7; and a fusion polypeptide comprising the amino acid sequence of SEQ ID NO: 4.

23. The pharmaceutical composition of claim 21, wherein the sodium phosphate buffer concentration is about 15-25 mM.

24. The pharmaceutical composition of claim 21, wherein the sodium phosphate buffer concentration is about 20 mM.

25. The pharmaceutical composition of claim 21, wherein the sodium chloride concentration is about 40-100 mM.

26. The pharmaceutical composition of claim 21, wherein the sodium chloride concentration is about 50 mM.

27. The pharmaceutical composition of claim 21, wherein the polysorbate surfactant concentration is about 0.6 mg/mL.

28. The pharmaceutical composition of claim 21, wherein the polysorbate surfactant is polysorbate-20 (PS-20).

29. The pharmaceutical composition of claim 21, wherein the sucrose concentration is about 175 mM.

30. The pharmaceutical composition of claim 21, wherein the methionine concentration is about 5-15 mM.

31. The pharmaceutical composition of claim 21, wherein the methionine concentration is about 10 mM.

32. The pharmaceutical composition of claim 21, wherein the protein molecule concentration is about 5-50 mg/mL.

33. The pharmaceutical composition of claim 21, wherein the protein molecule concentration is about 10-40 mg/mL.

34. The pharmaceutical composition of claim 21, wherein the protein molecule concentration is about 30 mg/mL.

35. The pharmaceutical composition of claim 22, comprising:

b. about 20 mM of sodium phosphate buffer;

c. about 50 mM sodium chloride;

d. about 0.6 mg/mL of polysorbate-20 (PS-20);

e. about 175 mM of sucrose; and f. about 10 mM methionine;

wherein the protein molecule concentration is about 5-50 mg/mL; and wherein the pH of the pharmaceutical composition is 6.5±0.2.

36. The pharmaceutical composition of claim 35, wherein the protein molecule concentration is about 10-40 mg/mL.

37. The pharmaceutical composition of claim 35, wherein the protein molecule concentration is about 30 mg/mL.

\* \* \* \* \*